US011103576B1

(12) United States Patent
Duprex

(10) Patent No.: US 11,103,576 B1
(45) Date of Patent: Aug. 31, 2021

(54) MEASLES VIRUS VACCINE EXPRESSING SARS-COV-2 PROTEIN(S)

(71) Applicant: University of Pittsburgh—Of the Commonwealth System of Higher Education, Pittsburgh, PA (US)

(72) Inventor: William Paul Duprex, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/010,591

(22) Filed: Sep. 2, 2020

Related U.S. Application Data

(60) Provisional application No. 63/071,479, filed on Aug. 28, 2020, provisional application No. 63/039,275, filed on Jun. 15, 2020.

(51) Int. Cl.

| | |
|---|---|
| ***A61K 39/00*** | (2006.01) |
| ***A61K 39/12*** | (2006.01) |
| ***C12N 7/00*** | (2006.01) |
| ***C07K 16/10*** | (2006.01) |
| ***A61K 39/155*** | (2006.01) |
| ***A61K 39/215*** | (2006.01) |
| ***C07K 14/005*** | (2006.01) |

(52) U.S. Cl.
CPC .......... *A61K 39/215* (2013.01); *C07K 14/005* (2013.01); *C12N 7/00* (2013.01); *A61K 2039/5256* (2013.01); *A61K 2039/575* (2013.01); *C12N 2760/18434* (2013.01); *C12N 2760/18443* (2013.01); *C12N 2770/20034* (2013.01)

(58) Field of Classification Search
CPC ...... A61K 39/12; A61K 2039/53; C12N 7/00; C07K 2317/76; Y02A 50/30
See application file for complete search history.

(56) References Cited

FOREIGN PATENT DOCUMENTS

| | | | |
|---|---|---|---|
| WO | WO 98/13501 | A2 | 4/1998 |
| WO | WO 2009/032954 | A1 | 3/2009 |

OTHER PUBLICATIONS

Liniger et al., "Induction of neutralizing antibodies and cellular immune responses against SARS coronavirus by recombinant measles viruses", Vaccine, 2008, 26:2164-2174.*

Padron-Regalado, "Vaccines for SARS-CoV-2: Lessons from other coronavirus strains", Infect Dis Ther, 2020, 9:255-274.*

Bankamp et al., "Genetic characterization of measles vaccine strains," *J. Infect. Dis.*, 204 Suppl. 1: 5533-5548 (2011).

Case et al., "Neutralizing antibody and soluble ACE2 inhibition of a replication-competent VSV-SARS-CoV-2 and a clinical isolate of SARS-CoV-2," *bioRxiv*, doi:10.1101/2020.05.18.102038 (2020).

Duckert et al., "Prediction of proprotein convertase cleavage sites," *Protein Engineering, Design & Selection*, 17(1): 107-112 (2004).

Rennick et al., "Live-attenuated measles virus vaccine targets dendritic cells and macrophages in muscle of nonhuman primates," *J. Virol.* 89(4): 2192-2200 (2015).

Wrapp et al., "Cryo-EM structure of the 2019-nCoV spike in the prefusion conformation," *Science*, 13: 1260-1263 (2020).

* cited by examiner

*Primary Examiner* — Barry A Chestnut
(74) *Attorney, Agent, or Firm* — Leydig, Voit & Mayer, Ltd.

(57) ABSTRACT

A recombinant measles viral vector comprising a nucleic acid sequence encoding a Severe Acute Respiratory Syndrome Coronavirus 2 (SARS-CoV-2) spike glycoprotein is provided. Polypeptides comprising the SARS-CoV-2 spike glycoprotein also are provided, as well as related nucleic acids, vectors, and compositions. The polypeptides, nucleic acids, vectors, and compositions can be used in methods of preventing, inhibiting, reducing, eliminating, protecting, or delaying the onset of an infection or an infectious clinical condition caused by coronavirus and methods for inducing an immune response against a coronavirus.

10 Claims, 15 Drawing Sheets

Specification includes a Sequence Listing.

rMV$^{EZ}$SARSCoV2-S6

$10^{-6}$ $10^{-7}$ rMV$^{EZ}$SARSCoV2-S6

| | 1:20 | 1:40 | 1:80 | 1:160 | 1:320 | 1:640 |
|---|---|---|---|---|---|---|
| rMV$^{EZ}$SARSCoV-2-S-CO | + | + | +/- | - | - | - |
| rMV$^{EZ}$SARSCoV2-S-COAA | + | + | + | +/- | - | - |
| rMV$^{EZ}$SARSCoV2-S6 | + | + | + | +/- | - | - |
| rMV$^{EZ}$ | - | - | - | - | - | - |

| | measles virus neutralization (pre-challenge) | | | | | | SARS-CoV-2 neutralization (pre-challenge) | | | | | |
|---|---|---|---|---|---|---|---|---|---|---|---|---|
| | 1:20 | 1:40 | 1:80 | 1:160 | 1:320 | 1:640 | 1:20 | 1:40 | 1:80 | 1:160 | 1:320 | 1:640 |
| $rMV^{EZ}$SARS-CoV-2-S-CO | + | + | + | + | - | - | + | + | +/- | + | - | - |
| $rMV^{EZ}$SARS-CoV-2-S-CO | + | + | + | + | - | - | + | + | + | + | + | + |
| $rMV^{EZ}$SARS-CoV-2-S-CO | + | - | - | - | - | - | + | + | - | - | - | - |
| $rMV^{EZ}$ | + | + | + | + | - | - | - | - | - | - | - | - |
| $rMV^{EZ}$ | + | + | + | + | - | - | - | - | - | - | - | - |

SEQUENCE LISTING

```
<160> NUMBER OF SEQ ID NOS: 26

<210> SEQ ID NO 1
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Non-codon optimized SARS-CoV-2 Spike
      from rMV-EZ-SARS-CoV-2-S clone 6
<220> FEATURE:
<221> NAME/KEY: misc_feature
<222> LOCATION: (118)..(118)
<223> OTHER INFORMATION: mutation that arose during cloning
<220> FEATURE:
<221> NAME/KEY: misc_feature
<222> LOCATION: (1088)..(1088)
<223> OTHER INFORMATION: mutation that arose during cloning
<220> FEATURE:
<221> NAME/KEY: misc_feature
<222> LOCATION: (1239)..(1239)
<223> OTHER INFORMATION: mutation that arose during cloning
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal

<400> SEQUENCE: 1

atgtttgttt ttcttgtttt attgccacta gtctctagtc agtgtgttaa tcttacaacc      60

agaactcaat taccccctgc atacactaat tctttcacac gtggtgttta ttacccttac     120

aaagttttca gatcctcagt tttacattca actcaggact tgttcttacc tttcttttcc     180

aatgttactt ggttccatgc tatacatgtc tctgggacca atggtactaa gaggtttgat     240

aaccctgtcc taccatttaa tgatggtgtt tattttgctt ccactgagaa gtctaacata     300

ataagaggct ggatttttgg tactacttta gattcgaaga cccagtccct acttattgtt     360
```

-continued

```
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgttg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccaggtc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
```

-continued aaattgattg ccaaccaatt taatagtgct attggcaaaa ttcaagactc actttcttcc 2820
acagcaagtg cacttggaaa acttcaagat gtggtcaacc aaaatgcaca agctttaaac 2880
acgcttgtta aacaacttag ctccaatttt ggtgcaattt caagtgtttt aaatgatatc 2940
ctttcacgtc ttgacaaagt tgaggctgaa gtgcaaattg ataggttgat cacaggcaga 3000
cttcaaagtt tgcagacata tgtgactcaa caattaatta gagctgcaga aatcagagct 3060
tctgctaatc ttgctgctac taaaatgtca gagtgtgtac ttggacaatc aaaaagagtt 3120
gatttttgtg gaaagggcta tcatcttatg tccttccctc agtcagcacc tcatggtgta 3180
gtcttcttgc atgtgactta tgtccctgca caagaaaaga acttcacaac tgctcctgcc 3240
atttgtcatg atggaaaagc acactttcct cgtgaaggtg tctttgtttc aaatggcaca 3300
cactggtttg taacacaaag gaatttttat gaaccacaaa tcattactac agacaacaca 3360
tttgtgtctg gtaactgtga tgttgtaata ggaattgtca acaacacagt ttatgatcct 3420
ttgcaacctg aattagactc attcaaggag gagttagata aatattttaa gaatcataca 3480
tcaccagatg ttgatttagg tgacatctct ggcattaatg cttcagttgt aaacattcaa 3540
aaagaaattg accgcctcaa tgaggttgcc aagaatttaa atgaatctct catcgatctc 3600
caagaacttg gaaagtatga gcagtatata aaatggccat ggtacatttg gctaggtttt 3660
atagctggct tgattgccat agtaatggtg acaattatgc tttgctgtat gaccagttgc 3720
tgtagttgtc tcaagggctg ttgttcttgt ggatcctgct gcaaatttga tgaagacgac 3780
tctgagccag tgctcaaagg agtcgcatta gcttacacat aa 3822

<210> SEQ ID NO 2
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: Human codon optimized SARS-CoV-2 Spike
from rMV-EZ-SARS-CoV-2-S-CO

<400> SEQUENCE: 2
atgttcgtct tcctggtcct gctgcctctg gtctcctcac agtgcgtcaa tctgacaact 60
cggactcagc tgccacctgc ttatactaat agcttcacca gaggcgtgta ctatcctgac 120
aaggtgttta gaagctccgt gctgcactct acacaggatc tgtttctgcc attctttagc 180
aacgtgacct ggttccacgc catccacgtg agcggcacca atggcacaaa gcggttcgac 240
aatcccgtgc tgccttttaa cgatggcgtg tacttcgcct ctaccgagaa gagcaacatc 300
atcagaggct ggatctttgg caccacactg gactccaaga cacagtctct gctgatcgtg 360
aacaatgcca ccaacgtggt catcaaggtg tgcgagttcc agttttgtaa tgatcccttc 420
ctgggcgtgt actatcacaa gaacaataag agctggatgg agtccgagtt tagagtgtat 480
tctagcgcca acaactgcac atttgagtac gtgagccagc ctttcctgat ggacctggag 540
ggcaagcagg gcaatttcaa gaacctgagg gagttcgtgt ttaagaatat cgacggctac 600
ttcaaaatct actctaagca cacccccatc aacctggtgc gcgacctgcc tcagggcttc 660
agcgccctgg agcccctggt ggatctgcct atcggcatca acatcacccg gtttcagaca 720
ctgctggccc tgcacagaag ctacctgaca cccggcgact cctctagcgg atggaccgcc 780
ggcgctgccg cctactatgt gggctacctc cagccccgga ccttcctgct gaagtacaac 840

-continued

```
gagaatggca ccatcacaga cgcagtggat tgcgccctgg accccctgag cgagacaaag    900
tgtacactga agtcctttac cgtggagaag ggcatctatc agacatccaa tttcagggtg    960
cagccaaccg agtctatcgt gcgctttcct aatatcacaa acctgtgccc atttggcgag   1020
gtgttcaacg caacccgctt cgccagcgtg tacgcctgga ataggaagcg gatcagcaac   1080
tgcgtggccg actatagcgt gctgtacaac tccgcctctt tcagcacctt taagtgctat   1140
ggcgtgtccc ccacaaagct gaatgacctg tgctttacca acgtctacgc cgattctttc   1200
gtgatcaggg gcgacgaggt gcgccagatc gcccccggcc agacaggcaa gatcgcagac   1260
tacaattata agctgccaga cgatttcacc ggctgcgtga tcgcctggaa cagcaacaat   1320
ctggattcca aagtgggcgg caactacaat tatctgtacc ggctgtttag aaagagcaat   1380
ctgaagccct tcgagaggga catctctaca gaaatctacc aggccggcag caccccttgc   1440
aatggcgtgg agggctttaa ctgttatttc ccactccagt cctacggctt ccagcccaca   1500
aacggcgtgg gctatcagcc ttaccgcgtg gtggtgctga gctttgagct gctgcacgcc   1560
ccagcaacag tgtgcggccc caagaagtcc accaatctgg tgaagaacaa gtgcgtgaac   1620
ttcaacttca acggcctgac cggcacaggc gtgctgaccg agtccaacaa gaagttcctg   1680
ccatttcagc agttcggcag ggacatcgca gataccacag acgccgtgcg cgacccacag   1740
accctggaga tcctggacat cacaccctgc tctttcggcg gcgtgagcgt gatcacaccc   1800
ggcaccaata caagcaacca ggtggccgtg ctgtatcagg acgtgaattg taccgaggtg   1860
cccgtggcta tccacgccga tcagctgacc ccaacatggc gggtgtacag caccggctcc   1920
aacgtcttcc agacaagagc cggatgcctg atcggagcag agcacgtgaa caattcctat   1980
gagtgcgaca tcccaatcgg cgccggcatc tgtgcctctt accagaccca gacaaactct   2040
cccagaagag cccggagcgt ggcctcccag tctatcatcg cctataccat gtccctgggc   2100
gccgagaaca gcgtggccta ctctaacaat agcatcgcca tcccaaccaa cttcacaatc   2160
tctgtgacca cagagatcct gcccgtgtcc atgaccaaga catctgtgga ctgcacaatg   2220
tatatctgtg gcgattctac cgagtgcagc aacctgctgc tccagtacgg cagcttttgt   2280
acccagctga atagagccct gacaggcatc gccgtggagc aggataagaa cacacaggag   2340
gtgttcgccc aggtgaagca aatctacaag accccccccta tcaaggactt tggcggcttc   2400
aatttttccc agatcctgcc tgatccatcc aagccttcta agcggagctt tatcgaggac   2460
ctgctgttca acaaggtgac cctggccgat gccggcttca tcaagcagta tggcgattgc   2520
ctgggcgaca tcgcagccag ggacctgatc tgcgcccaga agtttaatgg cctgaccgtg   2580
ctgccacccc tgctgacaga tgagatgatc gcacagtaca caagcgccct gctggccggc   2640
accatcacat ccggatggac cttcggcgca ggagccgccc tccagatccc ctttgccatg   2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga agcagctgag cagcaacttc ggcgccatct ctagcgtgct gaatgacatc   2940
ctgagccggc tggacaaggt ggaggcagag gtgcagatcg accggctgat caccggccgg   3000
ctccagagcc tccagaccta tgtgacacag cagctgatca gggccgccga gatcagggcc   3060
agcgccaatc tggcagcaac caagatgtcc gagtgcgtgc tgggccagtc taagagagtg   3120
gacttttgtg gcaagggcta tcacctgatg tccttccctc agtctgcccc acacggcgtg   3180
```

gtgtttctgc acgtgaccta cgtgcccgcc caggagaaga acttcaccac agcccctgcc 3240
atctgccacg atggcaaggc ccactttcca agggagggcg tgttcgtgtc caacggcacc 3300
cactggtttg tgacacagcg caatttctac gagccccaga tcatcaccac agacaacacc 3360
ttcgtgagcg gcaactgtga cgtggtcatc ggcatcgtga acaataccgt gtatgatcca 3420
ctccagcccg agctggacag ctttaaggag gagctggata agtatttcaa gaatcacacc 3480
tcccctgacg tggatctggg cgacatcagc ggcatcaatg cctccgtggt gaacatccag 3540
aaggagatcg accgcctgaa cgaggtggct aagaatctga acgagagcct gatcgacctc 3600
caggagctgg gcaagtatga gcagtacatc aagtggccct ggtacatctg gctgggcttc 3660
atcgccggcc tgatcgccat cgtgatggtg accatcatgc tgtgctgtat gacatcctgc 3720
tgttcttgcc tgaagggctg ctgtagctgt ggctcctgct gtaagtttga cgaggatgac 3780
tctgaacctg tgctgaaggg cgtgaagctg cattacacct aa 3822

<210> SEQ ID NO 3
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Human codon optimized SARS-CoV-2 Spike
from rMV-EZ-SARS-CoV-2-S-CO-AA
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 3
atgttcgtct tcctggtcct gctgcctctg gtctcctcac agtgcgtcaa tctgacaact 60
cggactcagc tgccacctgc ttatactaat agcttcacca gaggcgtgta ctatcctgac 120
aaggtgttta gaagctccgt gctgcactct acacaggatc tgtttctgcc attctttagc 180
aacgtgacct ggttccacgc catccacgtg agcggcacca atggcacaaa gcggttcgac 240
aatcccgtgc tgccttttaa cgatggcgtg tacttcgcct ctaccgagaa gagcaacatc 300
atcagaggct ggatctttgg caccacactg gactccaaga cacagtctct gctgatcgtg 360
aacaatgcca ccaacgtggt catcaaggtg tgcgagttcc agttttgtaa tgatcccttc 420
ctgggcgtgt actatcacaa gaacaataag agctggatgg agtccgagtt tagagtgtat 480
tctagcgcca acaactgcac atttgagtac gtgagccagc ctttcctgat ggacctggag 540
ggcaagcagg gcaatttcaa gaacctgagg gagttcgtgt ttaagaatat cgacggctac 600
ttcaaaatct actctaagca cacccccatc aacctggtgc gcgacctgcc tcagggcttc 660
agcgccctgg agcccctggt ggatctgcct atcggcatca acatcacccg gtttcagaca 720
ctgctggccc tgcacagaag ctacctgaca cccggcgact cctctagcgg atggaccgcc 780
ggcgctgccg cctactatgt gggctacctc cagccccgga ccttcctgct gaagtacaac 840
gagaatggca ccatcacaga cgcagtggat tgcgccctgg accccctgag cgagacaaag 900
tgtacactga agtcctttac cgtggagaag ggcatctatc agacatccaa tttcagggtg 960
cagccaaccg agtctatcgt gcgctttcct aatatcacaa acctgtgccc atttggcgag 1020
gtgttcaacg caacccgctt cgccagcgtg tacgcctgga ataggaagcg gatcagcaac 1080

-continued

```
tgcgtggccg actatagcgt gctgtacaac tccgcctctt tcagcacctt taagtgctat   1140
ggcgtgtccc ccacaaagct gaatgacctg tgctttacca acgtctacgc cgattctttc   1200
gtgatcaggg gcgacgaggt gcgccagatc gcccccggcc agacaggcaa gatcgcagac   1260
tacaattata agctgccaga cgatttcacc ggctgcgtga tcgcctggaa cagcaacaat   1320
ctggattcca aagtgggcgg caactacaat tatctgtacc ggctgtttag aaagagcaat   1380
ctgaagccct tcgagaggga catctctaca gaaatctacc aggccggcag cacccccttgc   1440
aatggcgtgg agggctttaa ctgttatttc ccactccagt cctacggctt ccagcccaca   1500
aacggcgtgg gctatcagcc ttaccgcgtg gtggtgctga gctttgagct gctgcacgcc   1560
ccagcaacag tgtgcggccc caagaagtcc accaatctgg tgaagaacaa gtgcgtgaac   1620
ttcaacttca acggcctgac cggcacaggc gtgctgaccg agtccaacaa gaagttcctg   1680
ccatttcagc agttcggcag ggacatcgca gataccacag acgccgtgcg cgacccacag   1740
accctggaga tcctggacat cacaccctgc tctttcggcg gcgtgagcgt gatcacaccc   1800
ggcaccaata caagcaacca ggtggccgtg ctgtatcagg acgtgaattg taccgaggtg   1860
cccgtggcta tccacgccga tcagctgacc ccaacatggc gggtgtacag caccggctcc   1920
aacgtcttcc agacaagagc cggatgcctg atcggagcag agcacgtgaa caattcctat   1980
gagtgcgaca tcccaatcgg cgccggcatc tgtgcctctt accagaccca gacaaactct   2040
cccagaagag cccggagcgt ggcctcccag tctatcatcg cctataccat gtccctgggc   2100
gccgagaaca gcgtggccta ctctaacaat agcatcgcca tcccaaccaa cttcacaatc   2160
tctgtgacca cagagatcct gcccgtgtcc atgaccaaga catctgtgga ctgcacaatg   2220
tatatctgtg gcgattctac cgagtgcagc aacctgctgc tccagtacgg cagcttttgt   2280
acccagctga atagagccct gacaggcatc gccgtggagc aggataagaa cacacaggag   2340
gtgttcgccc aggtgaagca aatctacaag acccccccta tcaaggactt tggcggcttc   2400
aatttttccc agatcctgcc tgatccatcc aagccttcta agcggagctt tatcgaggac   2460
ctgctgttca acaaggtgac cctggccgat gccggcttca tcaagcagta tggcgattgc   2520
ctgggcgaca tcgcagccag ggacctgatc tgcgcccaga agtttaatgg cctgaccgtg   2580
ctgccacccc tgctgacaga tgagatgatc gcacagtaca caagcgccct gctggccggc   2640
accatcacat ccggatggac cttcggcgca ggagccgccc tccagatccc ctttgccatg   2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga agcagctgag cagcaacttc ggcgccatct ctagcgtgct gaatgacatc   2940
ctgagccggc tggacaaggt ggaggcagag gtgcagatcg accggctgat caccggccgg   3000
ctccagagcc tccagaccta tgtgacacag cagctgatca gggccgccga gatcagggcc   3060
agcgccaatc tggcagcaac caagatgtcc gagtgcgtgc tgggccagtc taagagagtg   3120
gacttttgtg gcaagggcta tcacctgatg tccttccctc agtctgcccc acacggcgtg   3180
gtgtttctgc acgtgaccta cgtgcccgcc caggagaaga acttcaccac agcccctgcc   3240
atctgccacg atggcaaggc ccactttcca agggagggcg tgttcgtgtc caacggcacc   3300
cactggtttg tgacacagcg caatttctac gagccccaga tcatcaccac agacaacacc   3360
ttcgtgagcg gcaactgtga cgtggtcatc ggcatcgtga acaataccgt gtatgatcca   3420
```

-continued

```
ctccagcccg agctggacag ctttaaggag gagctggata agtatttcaa gaatcacacc   3480

tcccctgacg tggatctggg cgacatcagc ggcatcaatg cctccgtggt gaacatccag   3540

aaggagatcg accgcctgaa cgaggtggct aagaatctga acgagagcct gatcgacctc   3600

caggagctgg gcaagtatga gcagtacatc aagtggccct ggtacatctg gctgggcttc   3660

atcgccggcc tgatcgccat cgtgatggtg accatcatgc tgtgctgtat gacatcctgc   3720

tgttcttgcc tgaagggctg ctgtagctgt ggctcctgct gtaagtttga cgaggatgac   3780

tctgaacctg tgctgaaggg cgtggcgctg gcttacacct aa                      3822
```

<210> SEQ ID NO 4
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Non-codon optimized SARS-CoV-2 Spike from rMV-EZ-SARS-CoV-2-S
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal

<400> SEQUENCE: 4

```
atgtttgttt ttcttgtttt attgccacta gtctctagtc agtgtgttaa tcttacaacc     60

agaactcaat tacccccctgc atacactaat tctttcacac gtggtgttta ttaccctgac   120

aaagttttca gatcctcagt tttacattca actcaggact tgttcttacc tttcttttcc   180

aatgttactt ggttccatgc tatacatgtc tctgggacca atggtactaa gaggtttgat   240

aaccctgtcc taccatttaa tgatggtgtt tattttgctt ccactgagaa gtctaacata   300

ataagaggct ggatttttgg tactacttta gattcgaaga cccagtccct acttattgtt   360

aataacgcta ctaatgttgt tattaaagtc tgtgaatttc aattttgtaa tgatccattt   420

ttgggtgttt attaccacaa aaacaacaaa agttggatgg aaagtgagtt cagagtttat   480

tctagtgcga ataattgcac ttttgaatat gtctctcagc cttttcttat ggaccttgaa   540

ggaaaacagg gtaatttcaa aaatcttagg gaatttgtgt ttaagaatat tgatggttat   600

tttaaaatat attctaagca cacgcctatt aatttagtgc gtgatctccc tcagggtttt   660

tcggctttag aaccattggt agatttgcca ataggtatta acatcactag gtttcaaact   720

ttacttgctt tacatagaag ttatttgact cctggtgatt cttcttcagg ttggacagct   780

ggtgctgcag cttattatgt gggttatctt caacctagga cttttctatt aaaatataat   840

gaaaatggaa ccattacaga tgctgtagac tgtgcacttg accctctctc agaaacaaag   900

tgtacgttga aatccttcac tgtagaaaaa ggaatctatc aaacttctaa ctttagagtc   960

caaccaacag aatctattgt tagatttcct aatattacaa acttgtgccc ttttggtgaa  1020

gtttttaacg ccaccagatt tgcatctgtt tatgcttgga acaggaagag aatcagcaac  1080

tgtgttgctg attattctgt cctatataat tccgcatcat tttccacttt taagtgttat  1140

ggagtgtctc ctactaaatt aaatgatctc tgctttacta atgtctatgc agattcattt  1200

gtaattagag gtgatgaagt cagacaaatc gctccagggc aaactggaaa gattgctgat  1260

tataattata aattaccaga tgattttaca ggctgcgtta tagcttggaa ttctaacaat  1320
```

-continued

```
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
```

-continued

```
atagctggct tgattgccat agtaatggtg acaattatgc tttgctgtat gaccagttgc   3720

tgtagttgtc tcaagggctg ttgttcttgt ggatcctgct gcaaatttga tgaagacgac   3780

tctgagccag tgctcaaagg agtcgcatta gcttacacat aa                      3822
```

<210> SEQ ID NO 5
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S sequence from rMV-EZ-SARS-CoV-2-S-CO-AA-PPP
<220> FEATURE:
<221> NAME/KEY: misc_feature
<222> LOCATION: (2956)..(2961)
<223> OTHER INFORMATION: mutation to lock in the prefusion conformation
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 5

```
atgttcgtct tcctggtcct gctgcctctg gtctcctcac agtgcgtcaa tctgacaact     60

cggactcagc tgccacctgc ttatactaat agcttcacca gaggcgtgta ctatcctgac    120

aaggtgttta gaagctccgt gctgcactct acacaggatc tgtttctgcc attctttagc    180

aacgtgacct ggttccacgc catccacgtg agcggcacca atggcacaaa gcggttcgac    240

aatcccgtgc tgccttttaa cgatggcgtg tacttcgcct ctaccgagaa gagcaacatc    300

atcagaggct ggatctttgg caccacactg gactccaaga cacagtctct gctgatcgtg    360

aacaatgcca ccaacgtggt catcaaggtg tgcgagttcc agttttgtaa tgatcccttc    420

ctgggcgtgt actatcacaa gaacaataag agctggatgg agtccgagtt tagagtgtat    480

tctagcgcca acaactgcac atttgagtac gtgagccagc ctttcctgat ggacctggag    540

ggcaagcagg gcaatttcaa gaacctgagg gagttcgtgt ttaagaatat cgacggctac    600

ttcaaaatct actctaagca cacccccatc aacctggtgc gcgacctgcc tcagggcttc    660

agcgccctgg agcccctggt ggatctgcct atcggcatca acatcacccg gtttcagaca    720

ctgctggccc tgcacagaag ctacctgaca cccggcgact cctctagcgg atggaccgcc    780

ggcgctgccg cctactatgt gggctacctc cagccccgga ccttcctgct gaagtacaac    840

gagaatggca ccatcacaga cgcagtggat tgcgccctgg accccctgag cgagacaaag    900

tgtacactga agtcctttac cgtggagaag ggcatctatc agacatccaa tttcagggtg    960

cagccaaccg agtctatcgt gcgctttcct aatatcacaa acctgtgccc atttggcgag   1020

gtgttcaacg caacccgctt cgccagcgtg tacgcctgga ataggaagcg gatcagcaac   1080

tgcgtggccg actatagcgt gctgtacaac tccgcctctt tcagcacctt taagtgctat   1140

ggcgtgtccc ccacaaagct gaatgacctg tgctttacca acgtctacgc cgattctttc   1200

gtgatcaggg gcgacgaggt gcgccagatc gcccccggcc agacaggcaa gatcgcagac   1260

tacaattata agctgccaga cgatttcacc ggctgcgtga tcgcctggaa cagcaacaat   1320

ctggattcca aagtgggcgg caactacaat tatctgtacc ggctgtttag aaagagcaat   1380
```

-continued

```
ctgaagccct tcgagaggga catctctaca gaaatctacc aggccggcag cacccccttgc   1440
aatggcgtgg agggctttaa ctgttatttc ccactccagt cctacggctt ccagcccaca   1500
aacggcgtgg gctatcagcc ttaccgcgtg gtggtgctga gctttgagct gctgcacgcc   1560
ccagcaacag tgtgcggccc caagaagtcc accaatctgg tgaagaacaa gtgcgtgaac   1620
ttcaacttca acggcctgac cggcacaggc gtgctgaccg agtccaacaa gaagttcctg   1680
ccatttcagc agttcggcag ggacatcgca gataccacag acgccgtgcg cgacccacag   1740
accctggaga tcctggacat cacaccctgc tctttcggcg gcgtgagcgt gatcacaccc   1800
ggcaccaata caagcaacca ggtggccgtg ctgtatcagg acgtgaattg taccgaggtg   1860
cccgtggcta tccacgccga tcagctgacc ccaacatggc gggtgtacag caccggctcc   1920
aacgtcttcc agacaagagc cggatgcctg atcggagcag agcacgtgaa caattcctat   1980
gagtgcgaca tcccaatcgg cgccggcatc tgtgcctctt accagaccca gacaaactct   2040
cccagaagag cccggagcgt ggcctcccag tctatcatcg cctataccat gtccctgggc   2100
gccgagaaca gcgtggccta ctctaacaat agcatcgcca tcccaaccaa cttcacaatc   2160
tctgtgacca cagagatcct gcccgtgtcc atgaccaaga catctgtgga ctgcacaatg   2220
tatatctgtg gcgattctac cgagtgcagc aacctgctgc tccagtacgg cagcttttgt   2280
acccagctga atagagccct gacaggcatc gccgtggagc aggataagaa cacacaggag   2340
gtgttcgccc aggtgaagca aatctacaag acccccccta tcaaggactt tggcggcttc   2400
aatttttccc agatcctgcc tgatccatcc aagccttcta agcggagctt tatcgaggac   2460
ctgctgttca acaaggtgac cctggccgat gccggcttca tcaagcagta tggcgattgc   2520
ctgggcgaca tcgcagccag ggacctgatc tgcgcccaga agtttaatgg cctgaccgtg   2580
ctgccacccc tgctgacaga tgagatgatc gcacagtaca caagcgccct gctggccggc   2640
accatcacat ccggatggac cttcggcgca ggagccgccc tccagatccc ctttgccatg   2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga agcagctgag cagcaacttc ggcgccatct ctagcgtgct gaatgacatc   2940
ctgagccggc tggaccctcc tgaggcagag gtgcagatcg accggctgat caccggccgg   3000
ctccagagcc tccagaccta tgtgacacag cagctgatca gggccgccga gatcagggcc   3060
agcgccaatc tggcagcaac caagatgtcc gagtgcgtgc tgggccagtc taagagagtg   3120
gacttttgtg gcaagggcta tcacctgatg tccttccctc agtctgcccc acacggcgtg   3180
gtgtttctgc acgtgaccta cgtgcccgcc caggagaaga acttcaccac agcccctgcc   3240
atctgccacg atggcaaggc ccactttcca agggagggcg tgttcgtgtc caacggcacc   3300
cactggtttg tgacacagcg caatttctac gagccccaga tcatcaccac agacaacacc   3360
ttcgtgagcg gcaactgtga cgtggtcatc ggcatcgtga acaataccgt gtatgatcca   3420
ctccagcccg agctggacag ctttaaggag gagctggata agtatttcaa gaatcacacc   3480
tcccctgacg tggatctggg cgacatcagc ggcatcaatg cctccgtggt gaacatccag   3540
aaggagatcg accgcctgaa cgaggtggct aagaatctga acgagagcct gatcgacctc   3600
caggagctgg gcaagtatga gcagtacatc aagtggccct ggtacatctg gctgggcttc   3660
atcgccggcc tgatcgccat cgtgatggtg accatcatgc tgtgctgtat gacatcctgc   3720
tgttcttgcc tgaagggctg ctgtagctgt ggctcctgct gtaagtttga cgaggatgac   3780
```

tctgaacctg tgctgaaggg cgtggcgctg gcttacacct aa 3822

<210> SEQ ID NO 6
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S sequence
from rMV-EZ-SARS-CoV-2-S-CO-AA-fneg-PP
<220> FEATURE:
<221> NAME/KEY: misc_feature
<222> LOCATION: (2044)..(2045)
<223> OTHER INFORMATION: mutation to ablate the furin cleavage signal
<220> FEATURE:
<221> NAME/KEY: misc_feature
<222> LOCATION: (2047)..(2049)
<223> OTHER INFORMATION: mutation to ablate the furin cleavage signal
<220> FEATURE:
<221> NAME/KEY: misc_feature
<222> LOCATION: (2051)..(2053)
<223> OTHER INFORMATION: mutation to ablate the furin cleavage signal
<220> FEATURE:
<221> NAME/KEY: misc_feature
<222> LOCATION: (2055)..(2055)
<223> OTHER INFORMATION: mutation to ablate the furin cleavage signal
<220> FEATURE:
<221> NAME/KEY: misc_feature
<222> LOCATION: (2956)..(2961)
<223> OTHER INFORMATION: mutation to lock in the prefusion conformation
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 6
atgttcgtct tcctggtcct gctgcctctg gtctcctcac agtgcgtcaa tctgacaact 60
cggactcagc tgccacctgc ttatactaat agcttcacca gaggcgtgta ctatcctgac 120
aaggtgttta gaagctccgt gctgcactct acacaggatc tgtttctgcc attctttagc 180
aacgtgacct ggttccacgc catccacgtg agcggcacca atggcacaaa gcggttcgac 240
aatcccgtgc tgccttttaa cgatggcgtg tacttcgcct ctaccgagaa gagcaacatc 300
atcagaggct ggatctttgg caccacactg gactccaaga cacagtctct gctgatcgtg 360
aacaatgcca ccaacgtggt catcaaggtg tgcgagttcc agttttgtaa tgatcccttc 420
ctgggcgtgt actatcacaa gaacaataag agctggatgg agtccgagtt tagagtgtat 480
tctagcgcca acaactgcac atttgagtac gtgagccagc ctttcctgat ggacctggag 540
ggcaagcagg gcaatttcaa gaacctgagg gagttcgtgt ttaagaatat cgacggctac 600
ttcaaaatct actctaagca cacccccatc aacctggtgc gcgacctgcc tcagggcttc 660
agcgccctgg agcccctggt ggatctgcct atcggcatca acatcacccg gtttcagaca 720
ctgctggccc tgcacagaag ctacctgaca cccggcgact cctctagcgg atggaccgcc 780
ggcgctgccg cctactatgt gggctacctc cagccccgga ccttcctgct gaagtacaac 840
gagaatggca ccatcacaga cgcagtggat tgcgccctgg accccctgag cgagacaaag 900
tgtacactga agtcctttac cgtggagaag ggcatctatc agacatccaa tttcagggtg 960
cagccaaccg agtctatcgt gcgctttcct aatatcacaa acctgtgccc atttggcgag 1020

-continued gtgttcaacg caacccgctt cgccagcgtg tacgcctgga ataggaagcg gatcagcaac 1080
tgcgtggccg actatagcgt gctgtacaac tccgcctctt tcagcacctt taagtgctat 1140
ggcgtgtccc ccacaaagct gaatgacctg tgctttacca acgtctacgc cgattctttc 1200
gtgatcaggg gcgacgaggt gcgccagatc gcccccggcc agacaggcaa gatcgcagac 1260
tacaattata agctgccaga cgatttcacc ggctgcgtga tcgcctggaa cagcaacaat 1320
ctggattcca aagtgggcgg caactacaat tatctgtacc ggctgtttag aaagagcaat 1380
ctgaagccct tcgagaggga catctctaca gaaatctacc aggccggcag caccccttgc 1440
aatggcgtgg agggctttaa ctgttatttc ccactccagt cctacggctt ccagcccaca 1500
aacggcgtgg gctatcagcc ttaccgcgtg gtggtgctga gctttgagct gctgcacgcc 1560
ccagcaacag tgtgcggccc caagaagtcc accaatctgg tgaagaacaa gtgcgtgaac 1620
ttcaacttca acggcctgac cggcacaggc gtgctgaccg agtccaacaa gaagttcctg 1680
ccatttcagc agttcggcag ggacatcgca gataccacag acgccgtgcg cgacccacag 1740
accctggaga tcctggacat cacaccctgc tctttcggcg gcgtgagcgt gatcacaccc 1800
ggcaccaata caagcaacca ggtggccgtg ctgtatcagg acgtgaattg taccgaggtg 1860
cccgtggcta tccacgccga tcagctgacc ccaacatggc gggtgtacag caccggctcc 1920
aacgtcttcc agacaagagc cggatgcctg atcggagcag agcacgtgaa caattcctat 1980
gagtgcgaca tcccaatcgg cgccggcatc tgtgcctctt accagaccca gacaaactct 2040
cccgcatctg tgggcagcgt ggcctcccag tctatcatcg cctataccat gtccctgggc 2100
gccgagaaca gcgtggccta ctctaacaat agcatcgcca tcccaaccaa cttcacaatc 2160
tctgtgacca cagagatcct gcccgtgtcc atgaccaaga catctgtgga ctgcacaatg 2220
tatatctgtg gcgattctac cgagtgcagc aacctgctgc tccagtacgg cagcttttgt 2280
acccagctga atagagccct gacaggcatc gccgtggagc aggataagaa cacacaggag 2340
gtgttcgccc aggtgaagca aatctacaag acccccccta tcaaggactt tggcggcttc 2400
aatttttccc agatcctgcc tgatccatcc aagccttcta agcggagctt tatcgaggac 2460
ctgctgttca acaaggtgac cctggccgat gccggcttca tcaagcagta tggcgattgc 2520
ctgggcgaca tcgcagccag ggacctgatc tgcgcccaga agtttaatgg cctgaccgtg 2580
ctgccacccc tgctgacaga tgagatgatc gcacagtaca caagcgccct gctggccggc 2640
accatcacat ccggatggac cttcggcgca ggagccgccc tccagatccc ctttgccatg 2700
cagatggcct ataggttcaa cggcatcggc gtgacccaga atgtgctgta cgagaaccag 2760
aagctgatcg ccaatcagtt taactccgcc atcggcaaga tccaggacag cctgtcctct 2820
acagccagcg ccctgggcaa gctccaggat gtggtgaatc agaacgccca ggccctgaat 2880
accctggtga agcagctgag cagcaacttc ggcgccatct ctagcgtgct gaatgacatc 2940
ctgagccggc tggaccctcc tgaggcagag gtgcagatcg accggctgat caccggccgg 3000
ctccagagcc tccagaccta tgtgacacag cagctgatca gggccgccga gatcagggcc 3060
agcgccaatc tggcagcaac caagatgtcc gagtgcgtgc tgggccagtc taagagagtg 3120
gacttttgtg gcaagggcta tcacctgatg tccttccctc agtctgcccc acacggcgtg 3180
gtgtttctgc acgtgaccta cgtgcccgcc caggagaaga acttcaccac agcccctgcc 3240
atctgccacg atggcaaggc ccactttcca agggagggcg tgttcgtgtc caacggcacc 3300
cactggtttg tgacacagcg caatttctac gagccccaga tcatcaccac agacaacacc 3360

-continued ttcgtgagcg gcaactgtga cgtggtcatc ggcatcgtga acaataccgt gtatgatcca 3420
ctccagcccg agctggacag ctttaaggag gagctggata agtatttcaa gaatcacacc 3480
tcccctgacg tggatctggg cgacatcagc ggcatcaatg cctccgtggt gaacatccag 3540
aaggagatcg accgcctgaa cgaggtggct aagaatctga acgagagcct gatcgacctc 3600
caggagctgg gcaagtatga gcagtacatc aagtggccct ggtacatctg gctgggcttc 3660
atcgccggcc tgatcgccat cgtgatggtg accatcatgc tgtgctgtat gacatcctgc 3720
tgttcttgcc tgaagggctg ctgtagctgt ggctcctgct gtaagtttga cgaggatgac 3780
tctgaacctg tgctgaaggg cgtggcgctg gcttacacct aa 3822

<210> SEQ ID NO 7
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: codon optimized SARS-CoV-2 S
from rMV-EZ-SARS-CoV-2-S-CO-AA-fneg
<220> FEATURE:
<221> NAME/KEY: misc_feature
<222> LOCATION: (2044)..(2045)
<223> OTHER INFORMATION: mutation to ablate the furin cleavage signal
<220> FEATURE:
<221> NAME/KEY: misc_feature
<222> LOCATION: (2047)..(2049)
<223> OTHER INFORMATION: mutation to ablate the furin cleavage signal
<220> FEATURE:
<221> NAME/KEY: misc_feature
<222> LOCATION: (2051)..(2053)
<223> OTHER INFORMATION: mutation to ablate the furin cleavage signal
<220> FEATURE:
<221> NAME/KEY: misc_feature
<222> LOCATION: (2055)..(2055)
<223> OTHER INFORMATION: mutation to ablate the furin cleavage signal
<220> FEATURE:
<221> NAME/KEY: misc_feature
<222> LOCATION: (3805)..(3806)
<223> OTHER INFORMATION: mutation that disrupts ER retention signal
<220> FEATURE:
<221> NAME/KEY: misc_feature
<222> LOCATION: (3811)..(3812)
<223> OTHER INFORMATION: mutation that disrupts ER retention signal

<400> SEQUENCE: 7
atgttcgtct tcctggtcct gctgcctctg gtctcctcac agtgcgtcaa tctgacaact 60
cggactcagc tgccacctgc ttatactaat agcttcacca gaggcgtgta ctatcctgac 120
aaggtgttta gaagctccgt gctgcactct acacaggatc tgtttctgcc attctttagc 180
aacgtgacct ggttccacgc catccacgtg agcggcacca atggcacaaa gcggttcgac 240
aatcccgtgc tgccttttaa cgatggcgtg tacttcgcct ctaccgagaa gagcaacatc 300
atcagaggct ggatctttgg caccacactg gactccaaga cacagtctct gctgatcgtg 360
aacaatgcca ccaacgtggt catcaaggtg tgcgagttcc agttttgtaa tgatcccttc 420
ctgggcgtgt actatcacaa gaacaataag agctggatgg agtccgagtt tagagtgtat 480
tctagcgcca acaactgcac atttgagtac gtgagccagc ctttcctgat ggacctggag 540
ggcaagcagg gcaatttcaa gaacctgagg gagttcgtgt ttaagaatat cgacggctac 600
ttcaaaatct actctaagca cacccccatc aacctggtgc gcgacctgcc tcagggcttc 660
agcgccctgg agcccctggt ggatctgcct atcggcatca acatcacccg gtttcagaca 720

-continued

```
ctgctggccc tgcacagaag ctacctgaca cccggcgact cctctagcgg atggaccgcc    780
ggcgctgccg cctactatgt gggctacctc cagccccgga ccttcctgct gaagtacaac    840
gagaatggca ccatcacaga cgcagtggat tgcgccctgg accccctgag cgagacaaag    900
tgtacactga agtcctttac cgtggagaag ggcatctatc agacatccaa tttcagggtg    960
cagccaaccg agtctatcgt gcgctttcct aatatcacaa acctgtgccc atttggcgag   1020
gtgttcaacg caacccgctt cgccagcgtg tacgcctgga ataggaagcg gatcagcaac   1080
tgcgtggccg actatagcgt gctgtacaac tccgcctctt tcagcacctt taagtgctat   1140
ggcgtgtccc ccacaaagct gaatgacctg tgctttacca acgtctacgc cgattctttc   1200
gtgatcaggg gcgacgaggt gcgccagatc gcccccggcc agacaggcaa gatcgcagac   1260
tacaattata agctgccaga cgatttcacc ggctgcgtga tcgcctggaa cagcaacaat   1320
ctggattcca aagtgggcgg caactacaat tatctgtacc ggctgtttag aaagagcaat   1380
ctgaagccct tcgagaggga catctctaca gaaatctacc aggccggcag cacccccttgc   1440
aatggcgtgg agggctttaa ctgttatttc ccactccagt cctacggctt ccagcccaca   1500
aacggcgtgg gctatcagcc ttaccgcgtg gtggtgctga gctttgagct gctgcacgcc   1560
ccagcaacag tgtgcggccc caagaagtcc accaatctgg tgaagaacaa gtgcgtgaac   1620
ttcaacttca acggcctgac cggcacaggc gtgctgaccg agtccaacaa gaagttcctg   1680
ccatttcagc agttcggcag ggacatcgca gataccacag acgccgtgcg cgacccacag   1740
accctggaga tcctggacat cacaccctgc tctttcggcg gcgtgagcgt gatcacaccc   1800
ggcaccaata caagcaacca ggtggccgtg ctgtatcagg acgtgaattg taccgaggtg   1860
cccgtggcta tccacgccga tcagctgacc ccaacatggc gggtgtacag caccggctcc   1920
aacgtcttcc agacaagagc cggatgcctg atcggagcag agcacgtgaa caattcctat   1980
gagtgcgaca tcccaatcgg cgccggcatc tgtgcctctt accagaccca gacaaactct   2040
cccgcatctg tgggcagcgt ggcctcccag tctatcatcg cctataccat gtccctgggc   2100
gccgagaaca gcgtggccta ctctaacaat agcatcgcca tcccaaccaa cttcacaatc   2160
tctgtgacca cagagatcct gcccgtgtcc atgaccaaga catctgtgga ctgcacaatg   2220
tatatctgtg gcgattctac cgagtgcagc aacctgctgc tccagtacgg cagcttttgt   2280
acccagctga atagagccct gacaggcatc gccgtggagc aggataagaa cacacaggag   2340
gtgttcgccc aggtgaagca aatctacaag accccccccta tcaaggactt tggcggcttc   2400
aatttttccc agatcctgcc tgatccatcc aagccttcta agcggagctt tatcgaggac   2460
ctgctgttca acaaggtgac cctggccgat gccggcttca tcaagcagta tggcgattgc   2520
ctgggcgaca tcgcagccag ggacctgatc tgcgcccaga agtttaatgg cctgaccgtg   2580
ctgccacccc tgctgacaga tgagatgatc gcacagtaca caagcgccct gctggccggc   2640
accatcacat ccggatggac cttcggcgca ggagccgccc tccagatccc ctttgccatg   2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga agcagctgag cagcaacttc ggcgccatct ctagcgtgct gaatgacatc   2940
ctgagccggc tggacaaggt ggaggcagag gtgcagatcg accggctgat caccggccgg   3000
ctccagagcc tccagaccta tgtgacacag cagctgatca gggccgccga gatcagggcc   3060
agcgccaatc tggcagcaac caagatgtcc gagtgcgtgc tgggccagtc taagagagtg   3120
```

```
gacttttgtg gcaagggcta tcacctgatg tccttccctc agtctgcccc acacggcgtg   3180

gtgtttctgc acgtgaccta cgtgcccgcc caggagaaga acttcaccac agcccctgcc   3240

atctgccacg atggcaaggc ccactttcca agggagggcg tgttcgtgtc caacggcacc   3300

cactggtttg tgacacagcg caatttctac gagccccaga tcatcaccac agacaacacc   3360

ttcgtgagcg gcaactgtga cgtggtcatc ggcatcgtga acaataccgt gtatgatcca   3420

ctccagcccg agctggacag ctttaaggag gagctggata agtatttcaa gaatcacacc   3480

tcccctgacg tggatctggg cgacatcagc ggcatcaatg cctccgtggt gaacatccag   3540

aaggagatcg accgcctgaa cgaggtggct aagaatctga acgagagcct gatcgacctc   3600

caggagctgg gcaagtatga gcagtacatc aagtggccct ggtacatctg gctgggcttc   3660

atcgccggcc tgatcgccat cgtgatggtg accatcatgc tgtgctgtat gacatcctgc   3720

tgttcttgcc tgaagggctg ctgtagctgt ggctcctgct gtaagtttga cgaggatgac   3780

tctgaacctg tgctgaaggg cgtggcgctg gcttacacct aa                      3822
```

```
<210> SEQ ID NO 8
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3822)
<223> OTHER INFORMATION: Non-codon optimized SARS-CoV-2 Spike
      from rMV-EZ-SARS-CoV-2-S clone 6
<220> FEATURE:
<221> NAME/KEY: MISC_FEATURE
<222> LOCATION: (40)..(40)
<223> OTHER INFORMATION: residue differs from designed sequence
<220> FEATURE:
<221> NAME/KEY: MISC_FEATURE
<222> LOCATION: (363)..(363)
<223> OTHER INFORMATION: residue differs from designed sequence
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 8

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Tyr Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125
```

-continued

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys
325 330 335

Pro Phe Gly Glu Val Phe Asn Ala Thr Arg Phe Ala Ser Val Tyr Ala
340 345 350

Trp Asn Arg Lys Arg Ile Ser Asn Cys Val Val Asp Tyr Ser Val Leu
355 360 365

Tyr Asn Ser Ala Ser Phe Ser Thr Phe Lys Cys Tyr Gly Val Ser Pro
370 375 380

Thr Lys Leu Asn Asp Leu Cys Phe Thr Asn Val Tyr Ala Asp Ser Phe
385 390 395 400

Val Ile Arg Gly Asp Glu Val Arg Gln Ile Ala Pro Gly Gln Thr Gly
405 410 415

Lys Ile Ala Asp Tyr Asn Tyr Lys Leu Pro Asp Asp Phe Thr Gly Cys
420 425 430

Val Ile Ala Trp Asn Ser Asn Asn Leu Asp Ser Lys Val Gly Gly Asn
435 440 445

Tyr Asn Tyr Leu Tyr Arg Leu Phe Arg Lys Ser Asn Leu Lys Pro Phe
450 455 460

Glu Arg Asp Ile Ser Thr Glu Ile Tyr Gln Ala Gly Ser Thr Pro Cys
465 470 475 480

Asn Gly Val Glu Gly Phe Asn Cys Tyr Phe Pro Leu Gln Ser Tyr Gly
485 490 495

Phe Gln Pro Thr Asn Gly Val Gly Tyr Gln Pro Tyr Arg Val Val Val
500 505 510

Leu Ser Phe Glu Leu Leu His Ala Pro Ala Thr Val Cys Gly Pro Lys
515 520 525

Lys Ser Thr Asn Leu Val Lys Asn Lys Cys Val Asn Phe Asn Phe Asn
530 535 540

-continued

```
Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
```

-continued

```
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Ala Leu  Ala Tyr Thr
    1265                 1270


<210> SEQ ID NO 9
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: Human codon optimized SARS-CoV-2 Spike
      from rMV-EZ-SARS-CoV-2-S-CO

<400> SEQUENCE: 9

Met Phe Val Phe Leu Val Leu Leu Pro Leu Val Ser Ser Gln Cys Val
1               5                   10                  15
```

-continued

```
Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430
```

-continued

```
Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
```

-continued

```
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260
```

Val Leu Lys Gly Val Lys Leu His Tyr Thr
1265 1270

<210> SEQ ID NO 10
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: Human codon optimized SARS-CoV-2 Spike from rMV-EZ-SARS-CoV-2-S-CO-AA
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 10

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala

-continued

```
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700
```

-continued

```
Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110
```

```
Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Ala Leu  Ala Tyr Thr
    1265                 1270


<210> SEQ ID NO 11
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: SARS-CoV-2 Spike from rMV-EZ-SARS-CoV-2-S-CO-S
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 11

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125
```

-continued

```
Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
```

-continued

```
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975
```

-continued

```
Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Ala Leu  Ala Tyr Thr
    1265                 1270
```

<210> SEQ ID NO 12
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S sequence
      from rMV-EZ-SARS-CoV-2-S-CO-AA-PP
<220> FEATURE:
<221> NAME/KEY: MISC_FEATURE
<222> LOCATION: (986)..(987)
<223> OTHER INFORMATION: mutation to lock in the prefusion conformation
<220> FEATURE:
<221> NAME/KEY: MISC_FEATURE

```
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 12

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
```

-continued

```
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800
```

-continued

```
Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200
```

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Ala Leu Ala Tyr Thr
    1265                1270

<210> SEQ ID NO 13
<211> LENGTH: 1281
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S sequence
      from rMV-EZ-SARS-CoV-2-S-CO-AA-fneg-PP
<220> FEATURE:
<221> NAME/KEY: MISC_FEATURE
<222> LOCATION: (682)..(685)
<223> OTHER INFORMATION: mutation to ablate the furin cleavage signal
<220> FEATURE:
<221> NAME/KEY: MISC_FEATURE
<222> LOCATION: (986)..(987)
<223> OTHER INFORMATION: mutation to lock in the prefusion conformation
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 13

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

-continued

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
```

-continued

```
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ala Ser Val Gly Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020
```

```
Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Ala Leu  Ala Tyr Thr Arg Arg  Ala Arg Ser
    1265                 1270                 1275

Val Ala  Ser
    1280
```

<210> SEQ ID NO 14
<211> LENGTH: 1273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1273)
<223> OTHER INFORMATION: codon optimized SARS-CoV-2 S
      from rMV-EZ-SARS-CoV-2-S-CO-AA-fneg
<220> FEATURE:
<221> NAME/KEY: MISC_FEATURE
<222> LOCATION: (682)..(685)
<223> OTHER INFORMATION: mutation to ablate the furin cleavage signal
<220> FEATURE:
<221> NAME/KEY: MISC_FEATURE
<222> LOCATION: (1269)..(1269)
<223> OTHER INFORMATION: mutation that disrupts ER retention signal
<220> FEATURE:
<221> NAME/KEY: MISC_FEATURE
<222> LOCATION: (1271)..(1271)
<223> OTHER INFORMATION: mutation that disrupts ER retention signal

<400> SEQUENCE: 14

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly

-continued

```
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Ala Ser Val Gly Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830
```

```
Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230
```

```
Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Ala Leu  Ala Tyr Thr
    1265                1270
```

<210> SEQ ID NO 15
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-clone 6

<400> SEQUENCE: 15

```
accaaacaaa gttgggtaag gatagttcaa tcaatgatca ttttctagtg cacttaggat     60

tcaagatcct attatcaggg acaagagcag gattaaggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtcaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540

gatggttcga gaacaaggaa atctcagata ttgaagtgca agaccctgag ggattcaaca    600

tgattctggg taccatccta gctcaaattt gggtcttgct cgcaaaggcg gttacggccc    660

cagacacggc agctgattcg gagctaagaa ggtggataaa gtacacccaa caaagaaggg    720

tagttggtga atttagattg gagagaaaat ggttggatgt ggtgaggaac aggattgccg    780

aggacctctc cttacgccga ttcatggtcg ctctaatcct ggatatcaag agaacacccg    840

gaaacaaacc caggattgct gaaatgatat gtgacattga tacatatatc gtagaggcag    900

gattagccag ttttatcctg actattaagt ttgggataga aactatgtat cctgctcttg    960

gactgcatga atttgctggt gagttatcca cacttgagtc cttgatgaac ctttaccagc   1020

aaatggggga aactgcaccc tacatggtaa tcctggagaa ctcaattcag aacaagttca   1080

gtgcaggatc ataccctctg ctctggagct atgccatggg agtaggagtg gaacttgaaa   1140

actccatggg aggtttgaac tttggccgat cttactttga tccagcatat tttagattag   1200

ggcaagagat ggtaaggagg tcagctggaa aggtcagttc cacattggca tctgaactcg   1260

gtatcactgc cgaggatgca aggcttgttt cagagattgc aatgcatact actgaggaca   1320

agatcagtag agcggttgga cccagacaag cccaagtatc atttctacac ggtgatcaaa   1380

gtgagaatga gctaccgaga ttgggggggca aggaagatag gagggtcaaa cagagtcgag   1440

gagaagccag ggagagctac agagaaaccg ggcccagcag agcaagtgat gcgagagctg   1500

cccatcttcc aaccggcaca cccctagaca ttgacactgc atcggagtcc agccaagatc   1560

cgcaggacag tcgaaggtca gctgacgccc tgcttaggct gcaagccatg gcaggaatct   1620

cggaagaaca aggctcagac acggacaccc ctatagtgta caatgacaga aatcttctag   1680
```

-continued

```
actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag ttccacaggc gcgccatgtt tgtttttctt gttttattgc cactagtctc   3480
tagtcagtgt gttaatctta caaccagaac tcaattaccc cctgcataca ctaattcttt   3540
cacacgtggt gtttattacc cttacaaagt tttcagatcc tcagttttac attcaactca   3600
ggacttgttc ttacctttct tttccaatgt tacttggttc catgctatac atgtctctgg   3660
gaccaatggt actaagaggt ttgataaccc tgtcctacca tttaatgatg gtgtttattt   3720
tgcttccact gagaagtcta acataataag aggctggatt tttggtacta ctttagattc   3780
gaagacccag tccctactta ttgttaataa cgctactaat gttgttatta aagtctgtga   3840
atttcaattt tgtaatgatc catttttggg tgtttattac cacaaaaaca acaaaagttg   3900
gatggaaagt gagttcagag tttattctag tgcgaataat tgcacttttg aatatgtctc   3960
tcagcctttt cttatggacc ttgaaggaaa acagggtaat ttcaaaaatc ttagggaatt   4020
tgtgtttaag aatattgatg gttattttaa aatatattct aagcacacgc ctattaattt   4080
```

-continued agtgcgtgat ctccctcagg gtttttcggc tttagaacca ttggtagatt tgccaatagg 4140
tattaacatc actaggtttc aaactttact tgctttacat agaagttatt tgactcctgg 4200
tgattcttct tcaggttgga cagctggtgc tgcagcttat tatgtgggtt atcttcaacc 4260
taggactttt ctattaaaat ataatgaaaa tggaaccatt acagatgctg tagactgtgc 4320
acttgaccct ctctcagaaa caaagtgtac gttgaaatcc ttcactgtag aaaaaggaat 4380
ctatcaaact tctaacttta gagtccaacc aacagaatct attgttagat ttcctaatat 4440
tacaaacttg tgcccttttg gtgaagtttt taacgccacc agatttgcat ctgtttatgc 4500
ttggaacagg aagagaatca gcaactgtgt tgttgattat tctgtcctat ataattccgc 4560
atcattttcc acttttaagt gttatggagt gtctcctact aaattaaatg atctctgctt 4620
tactaatgtc tatgcagatt catttgtaat tagaggtgat gaagtcagac aaatcgctcc 4680
aggtcaaact ggaaagattg ctgattataa ttataaatta ccagatgatt ttacaggctg 4740
cgttatagct tggaattcta acaatcttga ttctaaggtt ggtggtaatt ataattacct 4800
gtatagattg tttaggaagt ctaatctcaa accttttgag agagatattt caactgaaat 4860
ctatcaggcc ggtagcacac cttgtaatgg tgttgaaggt tttaattgtt actttccttt 4920
acaatcatat ggtttccaac ccactaatgg tgttggttac caaccataca gagtagtagt 4980
actttctttt gaacttctac atgcaccagc aactgtttgt ggacctaaaa agtctactaa 5040
tttggttaaa aacaaatgtg tcaatttcaa cttcaatggt ttaacaggca caggtgttct 5100
tactgagtct aacaaaaagt ttctgccttt ccaacaattt ggcagagaca ttgctgacac 5160
tactgatgct gtccgtgatc cacagacact tgagattctt gacattacac catgttcttt 5220
tggtggtgtc agtgttataa caccaggaac aaatacttct aaccaggttg ctgttcttta 5280
tcaggatgtt aactgcacag aagtccctgt tgctattcat gcagatcaac ttactcctac 5340
ttggcgtgtt tattctacag gttctaatgt ttttcaaaca cgtgcaggct gtttaatagg 5400
ggctgaacat gtcaacaact catatgagtg tgacataccc attggtgcag gtatatgcgc 5460
tagttatcag actcagacta attctcctcg gcgggcacgt agtgtagcta gtcaatccat 5520
cattgcctac actatgtcac ttggtgcaga aaattcagtt gcttactcta ataactctat 5580
tgccataccc acaaatttta ctattagtgt taccacagaa attctaccag tgtctatgac 5640
caagacatca gtagattgta caatgtacat ttgtggtgat tcaactgaat gcagcaatct 5700
tttgttgcaa tatggcagtt tttgtacaca attaaaccgt gctttaactg gaatagctgt 5760
tgaacaagac aaaaacaccc aagaagtttt tgcacaagtc aaacaaattt acaaaacacc 5820
accaattaaa gattttggtg gttttaattt ttcacaaata ttaccagatc catcaaaacc 5880
aagcaagagg tcatttattg aagatctact tttcaacaaa gtgacacttg cagatgctgg 5940
cttcatcaaa caatatggtg attgccttgg tgatattgct gctagagacc tcatttgtgc 6000
acaaaagttt aacggcctta ctgttttgcc acctttgctc acagatgaaa tgattgctca 6060
atacacttct gcactgttag cgggtacaat cacttctggt tggacctttg gtgcaggtgc 6120
tgcattacaa ataccatttg ctatgcaaat ggcttatagg tttaatggta ttggagttac 6180
acagaatgtt ctctatgaga accaaaaatt gattgccaac caatttaata gtgctattgg 6240
caaaattcaa gactcacttt cttccacagc aagtgcactt ggaaaacttc aagatgtggt 6300
caaccaaaat gcacaagctt taaacacgct tgttaaacaa cttagctcca attttggtgc 6360
aatttcaagt gttttaaatg atatcctttc acgtcttgac aaagttgagg ctgaagtgca 6420

-continued

```
aattgatagg ttgatcacag gcagacttca aagtttgcag acatatgtga ctcaacaatt   6480
aattagagct gcagaaatca gagcttctgc taatcttgct gctactaaaa tgtcagagtg   6540
tgtacttgga caatcaaaaa gagttgattt ttgtggaaag ggctatcatc ttatgtcctt   6600
ccctcagtca gcacctcatg gtgtagtctt cttgcatgtg acttatgtcc ctgcacaaga   6660
aaagaacttc acaactgctc ctgccatttg tcatgatgga aaagcacact ttcctcgtga   6720
aggtgtcttt gtttcaaatg gcacacactg gtttgtaaca caaaggaatt tttatgaacc   6780
acaaatcatt actacagaca acacatttgt gtctggtaac tgtgatgttg taataggaat   6840
tgtcaacaac acagtttatg atcctttgca acctgaatta gactcattca aggaggagtt   6900
agataaatat tttaagaatc atacatcacc agatgttgat ttaggtgaca tctctggcat   6960
taatgcttca gttgtaaaca ttcaaaaaga aattgaccgc ctcaatgagg ttgccaagaa   7020
tttaaatgaa tctctcatcg atctccaaga acttggaaag tatgagcagt atataaaatg   7080
gccatggtac atttggctag gttttatagc tggcttgatt gccatagtaa tggtgacaat   7140
tatgctttgc tgtatgacca gttgctgtag ttgtctcaag ggctgttgtt cttgtggatc   7200
ctgctgcaaa tttgatgaag acgactctga gccagtgctc aaaggagtcg cattagctta   7260
cacataacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatcccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgataccc gcagaggttc cgtgttgttt   7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gatagggggc accagtcttc   8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccct cacaatgaca gccagaaggc ccggacaaaa   8460
aagcccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggacccccg aggaccaacc cccaaggctg cccccgatcc   8640
aaaccaccaa ccgcatcccc accacccccg ggaaagaaac ccccagcaat tggaaggccc   8700
ctccccctct tcctcaacac aagaactcca caaccgaacc gcacaagcga ccgaggtgac   8760
ccaaccgcag gcatccgact ccctagacag atcctctctc cccggcaaac taaacaaaac   8820
```

-continued ttagggccaa ggaacataca cacccaacag aacccagacc ccggcccacg gcgccgcgcc 8880
cccaaccccc gacaaccaga gggagccccc aaccaatccc gccggctccc ccggtgccca 8940
caggcaggga caccaacccc cgaacagacc cagcacccaa ccatcgacaa tccaagacgg 9000
gggggccccc ccaaaaaaag gcccccaggg gccgacagcc agcaccgcga ggaagcccac 9060
ccaccccaca cacgaccacg gcaaccaaac cagaacccag accaccctgg gccaccagct 9120
cccagactcg gccatcaccc cgcagaaagg aaaggccaca acccgcgcac cccagccccg 9180
atccggcggg gagccaccca acccgaacca gcacccaaga gcgatccccg aaggaccccc 9240
gaaccgcaaa ggacatcagt atcccacagc ctctccaagt cccccggtct cctccccttc 9300
tcgaagggac caaaagatca atccaccaca cccgacgaca ctcaactccc cacccctaaa 9360
ggagacaccg ggaatcccag aatcaagact catccaatgt ccatcatggg tctcaaggtg 9420
aacgtctctg ccatattcat ggcagtactg ttaactctcc aaacacccac cggtcaaatc 9480
cattggggca atctctctaa gataggggtg gtaggaatag gaagtgcaag ctacaaagtt 9540
atgactcgtt ccagccatca atcattagtc ataaaattaa tgcccaatat aactctcctc 9600
aataactgca cgagggtaga gattgcagaa tacaggagac tactgagaac agttttggaa 9660
ccaattagag atgcacttaa tgcaatgacc cagaatataa gaccggttca gagtgtagct 9720
tcaagtagga gacacaagag atttgcggga gtagtcctgg caggtgcggc cctaggcgtc 9780
gccacagctg ctcagataac agccggcatt gcacttcacc agtccatgct gaactctcaa 9840
gccatcgaca atctgagagc gagcctggaa actactaatc aggcaattga ggcaatcaga 9900
caagcagggc aggagatgat attggctgtt cagggtgtcc aagactacat caataatgag 9960
ctgataccgt ctatgaacca actatcttgt gatttaatcg gccagaagct cgggctcaaa 10020
ttgctcagat actatacaga aatcctgtca ttatttggcc ccagcttacg ggaccccata 10080
tctgcggaga tatctatcca ggctttgagc tatgcgcttg gaggagacat caataaggtg 10140
ttagaaaagc tcggatacag tggaggtgat ttactgggca tcttagagag cagaggaata 10200
aaggcccgga taactcacgt cgacacagag tcctacttca ttgtcctcag tatagcctat 10260
ccgacgctgt ccgagattaa gggggtgatt gtccaccggc tagaggggt ctcgtacaac 10320 ataggctctc aagagtggta taccactgtg cccaagtatg ttgcaaccca agggtacctt 10380
atctcgaatt ttgatgagtc atcgtgtact ttcatgccag aggggactgt gtgcagccaa 10440
aatgccttgt acccgatgag tcctctgctc caagaatgcc tccgggggtc caccaagtcc 10500
tgtgctcgta cactcgtatc cgggtctttt gggaaccggt tcattttatc acaagggaac 10560
ctaatagcca attgtgcatc aatcctttgc aagtgttaca caacaggaac gatcattaat 10620
caagaccctg acaagatcct aacatacatt gctgccgatc actgcccggt agtcgaggtg 10680
aacggcgtga ccatccaagt cgggagcagg aggtatccag atgctgtgta cttgcacaga 10740
attgacctcg gtcctcccat atcattggag aggttggacg tagggacaaa tctggggaat 10800
gcaattgcta agttggagga tgccaaggaa ttgttggagt catcggacca gatattgagg 10860
agtatgaaag gtttatcgag cactagcata gtctacatcc tgattgcagt gtgtcttgga 10920
gggttgatag ggatccccgc tttaatatgt tgctgcaggg ggcgttgtaa caaaaaggga 10980
gaacaagttg gtatgtcaag accaggccta aagcctgatc ttacgggaac atcaaaatcc 11040
tatgtaaggt cgctctgatc ctctacaact cttgaaacac aaatgtccca caagtctcct 11100
cttcgtcatc aagcaaccac cgcacccagc atcaagccca cctgaaatta tctccggctt 11160

-continued

```
ccctctggcc gaacaatatc ggtagttaat taaaacttag ggtgcaagat catccacaat  11220
gtcaccacaa cgagaccgga taaatgcctt ctacaaagat aacccccatc ccaagggaag  11280
taggatagtc attaacagag aacatcttat gattgataga ccttatgttt tgctggctgt  11340
tctgtttgtc atgtttctga gcttgatcgg gttgctagcc attgcaggca ttagacttca  11400
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
tgaagtgggc ctgaggacac ctcagagatt cactgaccta gtgaaattca tctctgacaa  11580
gattaaattc cttaatccgg atagggagta cgacttcaga gatctcactt ggtgtatcaa  11640
cccgccagag agaatcaaat tggattatga tcaatactgt gcagatgtgg ctgctgaaga  11700
gctcatgaat gcattggtga actcaactct actggagacc agaacaacca atcagttcct  11760
agctgtctca aagggaaact gctcagggcc cactacaatc agaggtcaat tctcaaacat  11820
gtcgctgtcc ctgttagact tgtatttagg tcgaggttac aatgtgtcat ctatagtcac  11880
tatgacatcc cagggaatgt atgggggaac ttacctagtg gaaaagccta atctgagcag  11940
caaaaggtca gagttgtcac aactgagcat gtaccgagtg tttgaagtag gtgttatcag  12000
aaatccgggt ttgggggctc cggtgttcca tatgacaaac tatcttgagc aaccagccag  12060
taatgatctc agcaactgta tggtggcttt gggggagctc aaactcgcag ccctttgtca  12120
cggggaagat tctatcacaa ttccctatca gggatcaggg aaaggtgtca gcttccagct  12180
cgtcaagcta ggtgtctgga aatccccaac cgacatgcaa tcctgggtcc ccttatcaac  12240
ggatgatcca gtgatagaca ggctttacct ctcatctcac agaggtgtta tcgctgacaa  12300
tcaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
cctagcctta ggtgtaatca acacattgga gtggataccg agattcaagg ttagtcccta  12660
cctcttcaat gtcccaatta aggaagcagg cgaagactgc catgccccaa catacctacc  12720
tgcggaggtg gatggtgatg tcaaactcag ttccaatctg gtgattctac ctggtcaaga  12780
tctccaatat gttttggcaa cctacgatac ttccagggtt gaacatgctg tggtttatta  12840
cgtttacagc ccaggccgct cattttctta cttttatcct tttaggttgc ctataaaggg  12900
ggtccccatc gaattacaag tggaatgctt cacatgggac caaaaactct ggtgccgtca  12960
cttctgtgtg cttgcggact cagaatctgg tggacatatc actcactctg ggatggtggg  13020
catgggagtc agctgcacag tcacccggga agatggaacc aatcgcagat agggctgcta  13080
gtgaaccaat ctcatgatgt cacccagaca tcaggcatac ccactagtgt gaaatagaca  13140
tcagaattaa gaaaaacgta gggtccaagt ggttccccgt tatggactcg ctatctgtca  13200
accagatctt ataccctgaa gttcacctag atagcccgat agttaccaat aagatagtag  13260
ccatcctgga gtatgctcga gtccctcacg cttacagcct ggaggaccct acactgtgtc  13320
agaacatcaa gcaccgccta aaaaacggat tttccaacca aatgattata aacaatgtgg  13380
aagttgggaa tgtcatcaag tccaagctta ggagttatcc ggcccactct catattccat  13440
atccaaattg taatcaggat ttatttaaca tagaagacaa agagtcaacg aggaagatcc  13500
gtgaactcct caaaaagggg aattcgctgt actccaaagt cagtgataag gttttccaat  13560
```

```
gcttaaggga cactaactca cggcttggcc taggctccga attgagggag gacatcaagg  13620
agaaagttat taacttggga gtttacatgc acagctccca gtggtttgag ccctttctgt  13680
tttggtttac agtcaagact gagatgaggt cagtgattaa atcacaaacc catacttgcc  13740
ataggaggag acacacacct gtattcttca ctggtagttc agttgagttg ctaatctctc  13800
gtgaccttgt tgctataatc agtaaagagt ctcaacatgt atattacctg acatttgaac  13860
tggttttgat gtattgtgat gtcatagagg ggaggttaat gacagagacc gctatgacta  13920
ttgatgctag gtatacagag cttctaggaa gagtcagata catgtggaaa ctgatagatg  13980
gtttcttccc tgcactcggg aatccaactt atcaaattgt agccatgctg gagcctcttt  14040
cacttgctta cctgcagctg agggatataa cagtagaact cagaggtgct ttccttaacc  14100
actgctttac tgaaatacat gatgttcttg accaaaacgg gttttctgat gaaggtactt  14160
atcatgagtt aattgaagct ctagattaca ttttcataac tgatgacata catctgacag  14220
gggagatttt ctcatttttc agaagtttcg gccaccccag acttgaagca gtaacggctg  14280
ctgaaaatgt taggaaatac atgaatcagc ctaaagtcat tgtgtatgag actctgatga  14340
aaggtcatgc catattttgt ggaatcataa tcaacggcta tcgtgacagg cacggaggca  14400
gttggccacc gctgaccctc cccctgcatg ctgcagacac aatccggaat gctcaagctt  14460
caggtgaagg gttaacacat gagcagtgcg ttgataactg gagatctttt gctggagtga  14520
aatttggctg ctttatgcct cttagcctgg atagtgatct gacaatgtac ctaaaggaca  14580
aggcacttgc tgctctccaa agggaatggg attcagttta cccgaaagag ttcctgcgtt  14640
acgaccctcc caagggaacc gggtcacgga ggcttgtaga tgttttcctt aatgattcga  14700
gctttgaccc atatgatgtg ataatgtatg ttgtaagtgg agcttacctc catgaccctg  14760
agttcaacct gtcttacagc ctgaaagaaa aggagatcaa ggaaacaggt agactttttg  14820
ctaaaatgac ttacaaaatg agggcatgcc aagtgattgc tgaaaatcta atctcaaacg  14880
ggattggcaa atattttaag gacaatggga tggccaagga tgagcacgat ttgactaagg  14940
cactccacac tctagctgtc tcaggagtcc ccaaagatct caaagaaagt cacagggggg  15000
ggccagtctt aaaaacctac tcccgaagcc cagtccacac aagtaccagg aacgtgagag  15060
cagcaaaagg gtttataggg ttccctcaag taattcggca ggaccaagac actgatcatc  15120
cggagaatat ggaagcttac gagacagtca gtgcatttat cacgactgat ctcaagaagt  15180
actgccttaa ttggagatat gagaccatca gcttgtttgc acagaggcta aatgagattt  15240
acggattgcc ctcatttttc cagtggctgc ataagaggct tgagacctct gtcctgtatg  15300
taagtgaccc tcattgcccc cccgaccttg acgcccatat cccgttatat aaagtcccca  15360
atgatcaaat cttcattaag taccctatgg gaggtataga agggtattgt cagaagctgt  15420
ggaccatcag caccattccc tatctatacc tggctgctta tgagagcgga gtaaggattg  15480
cttcgttagt gcaaggggac aatcagacca tagccgtaac aaaaagggta cccagcacat  15540
ggccctacaa ccttaagaaa cgggaagctg ctagagtaac tagagattac tttgtaattc  15600
ttaggcaaag gctacatgat attggccatc acctcaaggc aaatgagaca attgtttcat  15660
cacatttttt tgtctattca aaaggaatat attatgatgg gctacttgtg tcccaatcac  15720
tcaagagcat cgcaagatgt gtattctggt cagagactat agttgatgaa acaagggcag  15780
catgcagtaa tattgctaca acaatggcta aaagcatcga gagaggttat gaccgttacc  15840
ttgcatattc cctgaacgtc ctaaaagtga tacagcaaat tctgatctct cttggcttca  15900
```

caatcaattc aaccatgacc cgggatgtag tcatacccct cctcacgaac aacgacctct 15960
taataaggat ggcactgttg cccgctccta ttggggggat gaattatctg aatatgagca 16020
ggctgtttgt cagaaacatc ggtgatccag taacatcatc aattgctgat ctcaagagaa 16080
tgattctcgc ctcactaatg cctgaagaga ccctccatca agtaatgaca caacaaccgg 16140
gggactcttc attcctagac tgggctagcg acccttactc agcaaatctt gtatgtgtcc 16200
agagcatcac tagactcctc aagaacataa ctgcaaggtt tgtcctgatc catagtccaa 16260
acccaatgtt aaaaggatta ttccatgatg acagtaaaga agaggacgag ggactggcgg 16320
cattcctcat ggacaggcat attatagtac ctagggcagc tcatgaaatc ctggatcata 16380
gtgtcacagg ggcaagagag tctattgcag gcatgctgga taccacaaaa ggcctgattc 16440
gagccagcat gaggaagggg gggttaacct ctcgagtgat aaccagattg tccaattatg 16500
actatgaaca attcagagca gggatggtgc tattgacagg aagaaagaga aatgtcctca 16560
ttgacaaaga gtcatgttca gtgcagctgg cgagagctct aagaagccat atgtgggcga 16620
ggctagctcg aggacggcct atttacggcc ttgaggtccc tgatgtacta gaatctatgc 16680
gaggccacct tattcggcgt catgagacat gtgtcatctg cgagtgtgga tcagtcaact 16740
acggatggtt ttttgtcccc tcgggttgcc aactggatga tattgacaag gaaacatcat 16800
ccttgagagt cccatatatt ggttctacca ctgatgagag aacagacatg aagcttgcct 16860
tcgtaagagc cccaagtcga tccttgcgat ctgctgttag aatagcaaca gtgtactcat 16920
gggcttacgg tgatgatgat agctcttgga acgaagcctg gttgttggct aggcaaaggg 16980
ccaatgtgag cctggaggag ctaagggtga tcactcccat ctcaacttcg actaatttag 17040
cgcataggtt gagggatcgt agcactcaag tgaaatactc aggtacatcc cttgtccgag 17100
tggcgaggta taccacaatc tccaacgaca atctctcatt tgtcatatca gataagaagg 17160
ttgatactaa ctttatatac caacaaggaa tgcttctagg gttgggtgtt ttagaaacat 17220
tgtttcgact cgagaaagat accggatcat ctaacacggt attacatctt cacgtcgaaa 17280
cagattgttg cgtgatcccg atgatagatc atcccaggat acccagctcc cgcaagctag 17340
agctgagggc agagctatgt accaacccat tgatatatga taatgcacct ttaattgaca 17400
gagatacaac aaggctatac acccagagcc ataggaggca ccttgtggaa tttgttacat 17460
ggtccacacc ccaactatat cacattttag ctaagtccac agcactatct atgattgacc 17520
tggtaacaaa atttgagaag gaccatatga atgaaatttc agctctcata ggggatgacg 17580
atatcaatag tttcataact gagtttctgc tcatagagcc aagattattc actatctact 17640
tgggccagtg tgcggccatc aattgggcat ttgatgtaca ttatcataga ccatcaggga 17700
aatatcagat gggtgagctg ttgtcatcgt tcctttctag aatgagcaaa ggagtgttta 17760
aggtgcttgt caatgctcta agccacccaa agatctacaa gaaattctgg cattgtggta 17820
ttatagagcc tatccatggt ccttcacttg atgctcaaaa cttgcacaca actgtgtgca 17880
acatggttta cacatgctat atgacctacc tcgacctgtt gttgaatgaa gagttagaag 17940
agttcacatt tctcttgtgt gaaagcgacg aggatgtagt accggacaga ttcgacaaca 18000
tccaggcaaa acacttatgt gttctggcag atttgtactg tcaaccaggg acctgcccac 18060
caattcgagg tctaagaccg gtagagaaat gtgcagttct aaccgaccat atcaaggcag 18120
aggctaggtt atctccagca ggatcttcgt ggaacataaa tccaattatt gtagaccatt 18180
actcatgctc tctgacttat ctccggcgag gatcgatcaa acagataaga ttgagagttg 18240
atccaggatt cattttcgac gccctcgctg aggtaaatgt cagtcagcca aagatcggca 18300

-continued

```
gcaacaacat ctcaaatatg agcatcaagg ctttcagacc cccacacgat gatgttgcaa  18360
aattgctcaa agatatcaac acaagcaagc acaatcttcc catttcaggg ggcaatctcg  18420
ccaattatga aatccatgct ttccgcagaa tcgggttgaa ctcatctgct tgctacaaag  18480
ctgttgagat atcaacatta attaggagat gccttgagcc aggggaggac ggcttgttct  18540
tgggtgaggg atcgggttcc atgttgatca cttataagga gatacttaaa ctaaacaagt  18600
gcttctataa tagtggggtt tccgccaatt ctagatctgg tcaaagggaa ttagcaccct  18660
atccctccga agttggcctt gtcgaacaca gaatgggagt aggtaatatt gtcaaagtgc  18720
tctttaacgg gaggcccgaa gtcacgtggg taggcagtgt agattgcttc aatttcatag  18780
ttagtaatat ccctacctct agtgtggggt ttatccattc agatatagag accttgccta  18840
acaaagatac tatagagaag ctagaggaat tggcagccat cttatcgatg gctctgctcc  18900
tgggcaaaat aggatcaata ctggtgatta agcttatgcc tttcagcggg gattttgttc  18960
agggatttat aagttatgta gggtcccatt atagagaagt gaaccttgta taccctagat  19020
acagcaactt catatctact gaatcttatt tggttatgac agatctcaag gctaaccggc  19080
taatgaatcc tgaaaagatt aagcagcaga taattgaatc atctgtgagg acttcacctg  19140
gacttatagg tcacatccta tccattaagc aactaagctg catacaagca attgtgggag  19200
acgcagttag tagaggtgat atcaatccta ctctgaaaaa acttacacct atagagcagg  19260
tgctgatcaa ttgcgggttg gcaattaacg gacctaagct gtgcaaagaa ttgatccacc  19320
atgatgttgc ctcagggcaa gatggattgc ttaattctat actcatcctc tacagggagt  19380
tggcaagatt caaagacaac caaagaagtc aacaagggat gttccacgct taccccgtat  19440
tggtaagtag caggcaacga gaacttatat ctaggatcac ccgcaaattt tgggggcaca  19500
ttcttcttta ctccgggaac agaaagttga taaataagtt tatccagaat ctcaagtccg  19560
gctatctgat actagactta caccagaata tcttcgttaa gaatctatcc aagtcagaga  19620
aacagattat tatgacgggg ggtttgaaac gtgagtgggt ttttaaggta acagtcaagg  19680
agaccaaaga atggtataag ttagtcggat acagtgccct gattaaggac taattggttg  19740
aactccggaa ccctaatcct gccctaggtg gttaggcatt atttgcaata gattaaagaa  19800
aactttgaaa atacgaagtt tctattccca gctttgtctg gtggccggca tggtcccagc  19860
ctcctcgctg gcgccggctg ggcaacattc cgaggggacc gtcccctcgg taatggcgaa  19920
tgggacgcgg ccgatccggc tgctaacaaa gcccgaaagg aagctgagtt ggctgctgcc  19980
accgctgagc aataactagc ataacccctt ggggcctcta aacgggtctt gaggggtttt  20040
ttgctgaaag gaggaactat atccggatgc ggccgatccg gctgctaaca aagcccgaaa  20100
ggaagctgag ttggctgctg ccaccgctga gcaataacta gcataacccc ttggggcctc  20160
taaacgggtc ttgaggggtt ttttgctgaa aggaggaact atatccggat ggccgccacc  20220
ggccggtggg ccttgcagca catccccctt tcgccagctg gcgtaatagc gaagaggccc  20280
gcaccgatcg cccttcccaa cagttgcgca gcctgaatgg cgaatgggac gcgccctgta  20340
gcggcgcatt aagcgcggcg ggtgtggtgg ttacgcgcag cgtgaccgct acacttgcca  20400
gcgccctagc gcccgctcct ttcgctttct tcccttcctt tctcgccacg ttcgccggct  20460
ttccccgtca agctctaaat cgggggctcc ctttagggtt ccgatttagt gctttacggc  20520
acctcgaccc caaaaaactt gattagggtg atggttcacg tgggccatcg ccctgataga  20580
cggtttttcg ccctttgacg ttggagtcca cgttctttaa tagtggactc ttgttccaaa  20640
```

```
ctggaacaac actcaaccct atctcggtct attcttttga tttataaggg attttgccga  20700
tttcggccta ttggttaaaa aatgagctga tttaacaaaa atttaacgcg aattttaaca  20760
aaatattaac gcttacaatt taggtggcac ttttcgggga aatgtgcgcg gaacccctat  20820
ttgtttattt ttctaaatac attcaaatat gtatccgctc atgagacaat aaccctgata  20880
aatgcttcaa taatattgaa aaaggaagag tatgagtatt caacatttcc gtgtcgccct  20940
tattcccttt tttgcggcat tttgccttcc tgtttttgct cacccagaaa cgctggtgaa  21000
agtaaaagat gctgaagatc agttgggtgc acgagtgggt tacatcgaac tggatctcaa  21060
cagcggtaag atccttgaga gttttcgccc cgaagaacgt tttccaatga tgagcacttt  21120
taaagttctg ctatgtggcg cggtattatc ccgtattgac gccgggcaag agcaactcgg  21180
tcgccgcata cactattctc agaatgactt ggttgagtac tcaccagtca cagaaaagca  21240
tcttacggat ggcatgacag taagagaatt atgcagtgct gccataacca tgagtgataa  21300
cactgcggcc aacttacttc tgacaacgat cggaggaccg aaggagctaa ccgctttttt  21360
gcacaacatg ggggatcatg taactcgcct tgatcgttgg gaaccggagc tgaatgaagc  21420
cataccaaac gacgagcgtg acaccacgat gcctgtagca atggcaacaa cgttgcgcaa  21480
actattaact ggcgaactac ttacactagc ttcccggcaa caattaatag actggatgga  21540
ggcggataaa gttgcaggac cacttctgcg ctcggccctt ccggctggct ggtttattgc  21600
tgataaatct ggagccggtg agcgtgggtc tcgcggtatc attgcagcac tggggccaga  21660
tggtaagccc tcccgtatcg tagttatcta cacgacgggg agtcaggcaa ctatggatga  21720
acgaaataga cagatcgctg agataggtgc ctcactgatt aagcattggt aactgtcaga  21780
ccaagtttac tcatatatac tttagattga tttaaaactt catttttaat ttaaaaggat  21840
ctaggtgaag atcctttttg ataatctcat gaccaaaatc ccttaacgtg agttttcgtt  21900
ccactgagcg tcagaccccg tagaaaagat caaaggatct tcttgagatc ctttttttct  21960
gcgcgtaatc tgctgcttgc aaacaaaaaa accaccgcta ccagcggtgg tttgtttgcc  22020
ggatcaagag ctaccaactc tttttccgaa ggtaactggc ttcagcagag cgcagatacc  22080
aaatactgtt cttctagtgt agccgtagtt aggccaccac ttcaagaact ctgtagcacc  22140
gcctacatac ctcgctctgc taatcctgtt accagtggct gctgccagtg gcgataagtc  22200
gtgtcttacc gggttggact caagacgata gttaccggat aaggcgcagc ggtcgggctg  22260
aacggggggt tcgtgcacac agcccagctt ggagcgaacg acctacaccg aactgagata  22320
cctacagcgt gagctatgag aaagcgccac gcttcccgaa gggagaaagg cggacaggta  22380
tccggtaagc ggcagggtcg gaacaggaga gcgcacgagg gagcttccag ggggaaacgc  22440
ctggtatctt tatagtcctg tcgggtttcg ccacctctga cttgagcgtc gatttttgtg  22500
atgctcgtca ggggggcgga gcctatggaa aaacgccagc aacgcggcct ttttacggtt  22560
cctggccttt tgctggcctt ttgctcacat gttctttcct gcgttatccc ctgattctgt  22620
ggataaccgt attaccgcct ttgagtgagc tgataccgct cgccgcagcc gaacgaccga  22680
gcgcagcgag tcagtgagcg aggaagcgga agagcgccca atacgcaaac cgcctctccc  22740
cgcgcgttgg ccgattcatt aatgcagctg gcacgacagg tttcccgact ggaaagcggg  22800
cagtgagcgc aacgcaatta atgtgagtta gctcactcat taggcacccc aggctttaca  22860
ctttatgctt ccggctcgta tgttgtgtgg aattgtgagc ggacaacaat ttcacacagg  22920
aaacagctat gaccatgatt acgccaagct cgggcggccg cttgtaatac gactcactat  22980
a                                                                   22981
```

<210> SEQ ID NO 16
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO

<400> SEQUENCE: 16
accaaacaaa gttgggtaag gatagttcaa tcaatgatca ttttctagtg cacttaggat 60
tcaagatcct attatcaggg acaagagcag gattaaggat atccgagatg gccacacttt 120
taaggagctt agcattgttc aaaagaaaca aggacaaacc acccattaca tcaggatccg 180
gtggagccat cagaggaatc aaacacatta ttatagtacc aatccctgga gattcctcaa 240
ttaccactcg atccagactt ctggaccggt tggtcaggtt aattggaaac ccggatgtga 300
gcgggcccaa actaacaggg gcactaatag gtatattatc cttatttgtg gagtctccag 360
gtcaattgat tcagaggatc accgatgacc ctgacgttag cataaggctg ttagaggttg 420
tccagagtga ccagtcacaa tctggcctta ccttcgcatc aagaggtacc aacatggagg 480
atgaggcgga ccaatacttt tcacatgatg atccaattag tagtgatcaa tccaggttcg 540
gatggttcga gaacaaggaa atctcagata ttgaagtgca agaccctgag ggattcaaca 600
tgattctggg taccatccta gctcaaattt gggtcttgct cgcaaaggcg gttacggccc 660
cagacacggc agctgattcg gagctaagaa ggtggataaa gtacacccaa caaagaaggg 720
tagttggtga atttagattg gagagaaaat ggttggatgt ggtgaggaac aggattgccg 780
aggacctctc cttacgccga ttcatggtcg ctctaatcct ggatatcaag agaacacccg 840
gaaacaaacc caggattgct gaaatgatat gtgacattga tacatatatc gtagaggcag 900
gattagccag ttttatcctg actattaagt ttgggataga aactatgtat cctgctcttg 960
gactgcatga atttgctggt gagttatcca cacttgagtc cttgatgaac ctttaccagc 1020
aaatggggga aactgcaccc tacatggtaa tcctggagaa ctcaattcag aacaagttca 1080
gtgcaggatc ataccctctg ctctggagct atgccatggg agtaggagtg gaacttgaaa 1140
actccatggg aggtttgaac tttggccgat cttactttga tccagcatat tttagattag 1200
ggcaagagat ggtaaggagg tcagctggaa aggtcagttc cacattggca tctgaactcg 1260
gtatcactgc cgaggatgca aggcttgttt cagagattgc aatgcatact actgaggaca 1320
agatcagtag agcggttgga cccagacaag cccaagtatc atttctacac ggtgatcaaa 1380
gtgagaatga gctaccgaga ttgggggggca aggaagatag gagggtcaaa cagagtcgag 1440
gagaagccag ggagagctac agagaaaccg ggcccagcag agcaagtgat gcgagagctg 1500
cccatcttcc aaccggcaca cccctagaca ttgacactgc atcggagtcc agccaagatc 1560
cgcaggacag tcgaaggtca gctgacgccc tgcttaggct gcaagccatg gcaggaatct 1620
cggaagaaca aggctcagac acggacaccc ctatagtgta caatgacaga aatcttctag 1680
actaggtgcg agaggccgag gaccagaaca acatccgcct accctccatc attgttataa 1740
aaaacttagg aaccaggtcc acacagccgc cagcccatca accatccact cccacgattg 1800
gagccgatgg cagaagagca ggcacgccat gtcaaaaacg gactggaatg catccgggct 1860
ctcaaggccg agcccatcgg ctcactggcc atcgaggaag ctatggcagc atggtcagaa 1920

-continued

```
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag ttccacaggc gcgccatgtt cgtcttcctg gtcctgctgc ctctggtctc   3480
ctcacagtgc gtcaatctga caactcggac tcagctgcca cctgcttata ctaatagctt   3540
caccagaggc gtgtactatc ctgacaaggt gtttagaagc tccgtgctgc actctacaca   3600
ggatctgttt ctgccattct ttagcaacgt gacctggttc cacgccatcc acgtgagcgg   3660
caccaatggc acaaagcggt tcgacaatcc cgtgctgcct tttaacgatg gcgtgtactt   3720
cgcctctacc gagaagagca acatcatcag aggctggatc tttggcacca cactggactc   3780
caagacacag tctctgctga tcgtgaacaa tgccaccaac gtggtcatca aggtgtgcga   3840
gttccagttt tgtaatgatc ccttcctggg cgtgtactat cacaagaaca ataagagctg   3900
gatggagtcc gagtttagag tgtattctag cgccaacaac tgcacatttg agtacgtgag   3960
ccagcctttc ctgatggacc tggagggcaa gcagggcaat ttcaagaacc tgagggagtt   4020
cgtgtttaag aatatcgacg gctacttcaa aatctactct aagcacaccc ccatcaacct   4080
ggtgcgcgac ctgcctcagg gcttcagcgc cctggagccc ctggtggatc tgcctatcgg   4140
catcaacatc acccggtttc agacactgct ggccctgcac agaagctacc tgacacccgg   4200
cgactcctct agcggatgga ccgccggcgc tgccgcctac tatgtgggct acctccagcc   4260
ccggaccttc ctgctgaagt acaacgagaa tggcaccatc acagacgcag tggattgcgc   4320
```

-continued

```
cctggacccc ctgagcgaga caaagtgtac actgaagtcc tttaccgtgg agaagggcat   4380
ctatcagaca tccaatttca gggtgcagcc aaccgagtct atcgtgcgct ttcctaatat   4440
cacaaacctg tgcccatttg gcgaggtgtt caacgcaacc cgcttcgcca gcgtgtacgc   4500
ctggaatagg aagcggatca gcaactgcgt ggccgactat agcgtgctgt acaactccgc   4560
ctctttcagc acctttaagt gctatggcgt gtcccccaca aagctgaatg acctgtgctt   4620
taccaacgtc tacgccgatt ctttcgtgat caggggcgac gaggtgcgcc agatcgcccc   4680
cggccagaca ggcaagatcg cagactacaa ttataagctg ccagacgatt tcaccggctg   4740
cgtgatcgcc tggaacagca acaatctgga ttccaaagtg ggcggcaact acaattatct   4800
gtaccggctg tttagaaaga gcaatctgaa gcccttcgag agggacatct ctacagaaat   4860
ctaccaggcc ggcagcaccc cttgcaatgg cgtggagggc tttaactgtt atttcccact   4920
ccagtcctac ggcttccagc ccacaaacgg cgtgggctat cagccttacc gcgtggtggt   4980
gctgagcttt gagctgctgc acgccccagc aacagtgtgc ggccccaaga agtccaccaa   5040
tctggtgaag aacaagtgcg tgaacttcaa cttcaacggc ctgaccggca caggcgtgct   5100
gaccgagtcc aacaagaagt tcctgccatt tcagcagttc ggcagggaca tcgcagatac   5160
cacagacgcc gtgcgcgacc cacagaccct ggagatcctg gacatcacac cctgctcttt   5220
cggcggcgtg agcgtgatca cacccggcac caatacaagc aaccaggtgg ccgtgctgta   5280
tcaggacgtg aattgtaccg aggtgcccgt ggctatccac gccgatcagc tgaccccaac   5340
atggcgggtg tacagcaccg gctccaacgt cttccagaca agagccggat gcctgatcgg   5400
agcagagcac gtgaacaatt cctatgagtg cgacatccca atcggcgccg gcatctgtgc   5460
ctcttaccag acccagacaa actctcccag aagagcccgg agcgtggcct cccagtctat   5520
catcgcctat accatgtccc tgggcgccga gaacagcgtg gcctactcta acaatagcat   5580
cgccatccca accaacttca caatctctgt gaccacagag atcctgcccg tgtccatgac   5640
caagacatct gtggactgca caatgtatat ctgtggcgat tctaccgagt gcagcaacct   5700
gctgctccag tacggcagct tttgtaccca gctgaataga gccctgacag gcatcgccgt   5760
ggagcaggat aagaacacac aggaggtgtt cgcccaggtg aagcaaatct acaagacccc   5820
ccctatcaag gactttggcg gcttcaattt ttcccagatc ctgcctgatc catccaagcc   5880
ttctaagcgg agctttatcg aggacctgct gttcaacaag gtgaccctgg ccgatgccgg   5940
cttcatcaag cagtatggcg attgcctggg cgacatcgca gccagggacc tgatctgcgc   6000
ccagaagttt aatggcctga ccgtgctgcc accccctgctg acagatgaga tgatcgcaca   6060
gtacacaagc gccctgctgg ccggcaccat cacatccgga tggaccttcg gcgcaggagc   6120
cgccctccag atcccctttg ccatgcagat ggcctatagg ttcaacggca tcggcgtgac   6180
ccagaatgtg ctgtacgaga accagaagct gatcgccaat cagtttaact ccgccatcgg   6240
caagatccag gacagcctgt cctctacagc cagcgccctg ggcaagctcc aggatgtggt   6300
gaatcagaac gcccaggccc tgaataccct ggtgaagcag ctgagcagca acttcggcgc   6360
catctctagc gtgctgaatg acatcctgag ccggctggac aaggtggagg cagaggtgca   6420
gatcgaccgg ctgatcaccg gccggctcca gagcctccag acctatgtga cacagcagct   6480
gatcagggcc gccgagatca gggccagcgc caatctggca gcaaccaaga tgtccgagtg   6540
cgtgctgggc cagtctaaga gagtggactt ttgtggcaag ggctatcacc tgatgtcctt   6600
ccctcagtct gccccacacg gcgtggtgtt tctgcacgtg acctacgtgc ccgcccagga   6660
```

-continued

```
gaagaacttc accacagccc ctgccatctg ccacgatggc aaggcccact ttccaaggga   6720
gggcgtgttc gtgtccaacg gcacccactg gtttgtgaca cagcgcaatt tctacgagcc   6780
ccagatcatc accacagaca acaccttcgt gagcggcaac tgtgacgtgg tcatcggcat   6840
cgtgaacaat accgtgtatg atccactcca gcccgagctg gacagcttta aggaggagct   6900
ggataagtat ttcaagaatc acacctcccc tgacgtggat ctgggcgaca tcagcggcat   6960
caatgcctcc gtggtgaaca tccagaagga gatcgaccgc ctgaacgagg tggctaagaa   7020
tctgaacgag agcctgatcg acctccagga gctgggcaag tatgagcagt acatcaagtg   7080
gccctggtac atctggctgg gcttcatcgc cggcctgatc gccatcgtga tggtgaccat   7140
catgctgtgc tgtatgacat cctgctgttc ttgcctgaag ggctgctgta gctgtggctc   7200
ctgctgtaag tttgacgagg atgactctga acctgtgctg aagggcgtga agctgcatta   7260
cacctaacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatccccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgataccc gcagaggttc cgtgttgttt   7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gatagggggc accagtcttc   8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgacccccct cacaatgaca gccagaaggc ccggacaaaa   8460
aagcccccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggacccccg aggaccaacc cccaaggctg cccccgatcc   8640
aaaccaccaa ccgcatcccc accacccccg ggaaagaaac ccccagcaat tggaaggccc   8700
ctccccctct tcctcaacac aagaactcca caaccgaacc gcacaagcga ccgaggtgac   8760
ccaaccgcag gcatccgact ccctagacag atcctctctc cccggcaaac taaacaaaac   8820
ttagggccaa ggaacataca cacccaacag aacccagacc ccggcccacg gcgccgcgcc   8880
cccaaccccc gacaaccaga gggagccccc aaccaatccc gccggctccc ccggtgccca   8940
caggcaggga caccaacccc cgaacagacc cagcacccaa ccatcgacaa tccaagacgg   9000
gggggccccc ccaaaaaaag gcccccaggg gccgacagcc agcaccgcga ggaagcccac   9060
```

-continued

```
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggaccccc   9240
gaaccgcaaa ggacatcagt atcccacagc ctctccaagt cccccggtct cctccccttc   9300
tcgaagggac caaaagatca atccaccaca cccgacgaca ctcaactccc cacccctaaa   9360
ggagacaccg ggaatcccag aatcaagact catccaatgt ccatcatggg tctcaaggtg   9420
aacgtctctg ccatattcat ggcagtactg ttaactctcc aaacacccac cggtcaaatc   9480
cattggggca atctctctaa gataggggtg gtaggaatag gaagtgcaag ctacaaagtt   9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa gaccggttca gagtgtagct   9720
tcaagtagga gacacaagag atttgcggga gtagtcctgg caggtgcggc cctaggcgtc   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg gccagaagct cgggctcaaa  10020
ttgctcagat actatacaga aatcctgtca ttatttggcc ccagcttacg ggaccccata  10080
tctgcggaga tatctatcca ggctttgagc tatgcgcttg gaggagacat caataaggtg  10140
ttagaaaagc tcggatacag tggaggtgat ttactgggca tcttagagag cagaggaata  10200
aaggcccgga taactcacgt cgacacagag tcctacttca ttgtcctcag tatagcctat  10260
ccgacgctgt ccgagattaa gggggtgatt gtccaccggc tagagggggt ctcgtacaac  10320
ataggctctc aagagtggta taccactgtg cccaagtatg ttgcaaccca agggtacctt  10380
atctcgaatt ttgatgagtc atcgtgtact ttcatgccag aggggactgt gtgcagccaa  10440
aatgccttgt acccgatgag tcctctgctc caagaatgcc tccgggggtc caccaagtcc  10500
tgtgctcgta cactcgtatc cgggtctttt gggaaccggt tcattttatc acaagggaac  10560
ctaatagcca attgtgcatc aatcctttgc aagtgttaca caacaggaac gatcattaat  10620
caagaccctg acaagatcct aacatacatt gctgccgatc actgcccggt agtcgaggtg  10680
aacggcgtga ccatccaagt cgggagcagg aggtatccag atgctgtgta cttgcacaga  10740
attgacctcg gtcctcccat atcattggag aggttggacg tagggacaaa tctggggaat  10800
gcaattgcta agttggagga tgccaaggaa ttgttggagt catcggacca gatattgagg  10860
agtatgaaag gtttatcgag cactagcata gtctacatcc tgattgcagt gtgtcttgga  10920
gggttgatag ggatccccgc tttaatatgt tgctgcaggg ggcgttgtaa caaaaaggga  10980
gaacaagttg gtatgtcaag accaggccta aagcctgatc ttacgggaac atcaaaatcc  11040
tatgtaaggt cgctctgatc ctctacaact cttgaaacac aaatgtccca caagtctcct  11100
cttcgtcatc aagcaaccac cgcacccagc atcaagccca cctgaaatta tctccggctt  11160
ccctctggcc gaacaatatc ggtagttaat taaaacttag ggtgcaagat catccacaat  11220
gtcaccacaa cgagaccgga taaatgcctt ctacaaagat aacccccatc ccaagggaag  11280
taggatagtc attaacagag aacatcttat gattgataga ccttatgttt tgctggctgt  11340
tctgtttgtc atgtttctga gcttgatcgg gttgctagcc attgcaggca ttagacttca  11400
```

```
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
tgaagtgggc ctgaggacac ctcagagatt cactgaccta gtgaaattca tctctgacaa  11580
gattaaattc cttaatccgg atagggagta cgacttcaga gatctcactt ggtgtatcaa  11640
cccgccagag agaatcaaat tggattatga tcaatactgt gcagatgtgg ctgctgaaga  11700
gctcatgaat gcattggtga actcaactct actggagacc agaacaacca atcagttcct  11760
agctgtctca aagggaaact gctcagggcc cactacaatc agaggtcaat tctcaaacat  11820
gtcgctgtcc ctgttagact tgtatttagg tcgaggttac aatgtgtcat ctatagtcac  11880
tatgacatcc cagggaatgt atgggggaac ttacctagtg gaaaagccta atctgagcag  11940
caaaaggtca gagttgtcac aactgagcat gtaccgagtg tttgaagtag gtgttatcag  12000
aaatccgggt ttgggggctc cggtgttcca tatgacaaac tatcttgagc aaccagccag  12060
taatgatctc agcaactgta tggtggcttt gggggagctc aaactcgcag ccctttgtca  12120
cggggaagat tctatcacaa ttccctatca gggatcaggg aaaggtgtca gcttccagct  12180
cgtcaagcta ggtgtctgga aatccccaac cgacatgcaa tcctgggtcc ccttatcaac  12240
ggatgatcca gtgatagaca ggctttacct ctcatctcac agaggtgtta tcgctgacaa  12300
tcaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
cctagcctta ggtgtaatca acacattgga gtggataccg agattcaagg ttagtcccta  12660
cctcttcaat gtcccaatta aggaagcagg cgaagactgc catgccccaa catacctacc  12720
tgcggaggtg gatggtgatg tcaaactcag ttccaatctg gtgattctac ctggtcaaga  12780
tctccaatat gttttggcaa cctacgatac ttccagggtt gaacatgctg tggtttatta  12840
cgtttacagc ccaggccgct cattttctta cttttatcct tttaggttgc ctataaaggg  12900
ggtccccatc gaattacaag tggaatgctt cacatgggac caaaaactct ggtgccgtca  12960
cttctgtgtg cttgcggact cagaatctgg tggacatatc actcactctg ggatggtggg  13020
catgggagtc agctgcacag tcacccggga agatggaacc aatcgcagat agggctgcta  13080
gtgaaccaat ctcatgatgt cacccagaca tcaggcatac ccactagtgt gaaatagaca  13140
tcagaattaa gaaaaacgta gggtccaagt ggttccccgt tatggactcg ctatctgtca  13200
accagatctt ataccctgaa gttcacctag atagcccgat agttaccaat aagatagtag  13260
ccatcctgga gtatgctcga gtccctcacg cttacagcct ggaggaccct acactgtgtc  13320
agaacatcaa gcaccgccta aaaaacggat tttccaacca aatgattata aacaatgtgg  13380
aagttgggaa tgtcatcaag tccaagctta ggagttatcc ggcccactct catattccat  13440
atccaaattg taatcaggat ttatttaaca tagaagacaa agagtcaacg aggaagatcc  13500
gtgaactcct caaaaagggg aattcgctgt actccaaagt cagtgataag gttttccaat  13560
gcttaaggga cactaactca cggcttggcc taggctccga attgagggag gacatcaagg  13620
agaaagttat taacttggga gtttacatgc acagctccca gtggtttgag ccctttctgt  13680
tttggtttac agtcaagact gagatgaggt cagtgattaa atcacaaacc catacttgcc  13740
ataggaggag acacacacct gtattcttca ctggtagttc agttgagttg ctaatctctc  13800
```

gtgaccttgt tgctataatc agtaaagagt ctcaacatgt atattacctg acatttgaac 13860
tggttttgat gtattgtgat gtcatagagg ggaggttaat gacagagacc gctatgacta 13920
ttgatgctag gtatacagag cttctaggaa gagtcagata catgtggaaa ctgatagatg 13980
gtttcttccc tgcactcggg aatccaactt atcaaattgt agccatgctg gagcctcttt 14040
cacttgctta cctgcagctg agggatataa cagtagaact cagaggtgct ttccttaacc 14100
actgctttac tgaaatacat gatgttcttg accaaaacgg gttttctgat gaaggtactt 14160
atcatgagtt aattgaagct ctagattaca ttttcataac tgatgacata catctgacag 14220
gggagatttt ctcatttttc agaagtttcg gccaccccag acttgaagca gtaacggctg 14280
ctgaaaatgt taggaaatac atgaatcagc ctaaagtcat tgtgtatgag actctgatga 14340
aaggtcatgc catattttgt ggaatcataa tcaacggcta tcgtgacagg cacggaggca 14400
gttggccacc gctgaccctc cccctgcatg ctgcagacac aatccggaat gctcaagctt 14460
caggtgaagg gttaacacat gagcagtgcg ttgataactg gagatctttt gctggagtga 14520
aatttggctg ctttatgcct cttagcctgg atagtgatct gacaatgtac ctaaaggaca 14580
aggcacttgc tgctctccaa agggaatggg attcagttta cccgaaagag ttcctgcgtt 14640
acgaccctcc caagggaacc gggtcacgga ggcttgtaga tgttttcctt aatgattcga 14700
gctttgaccc atatgatgtg ataatgtatg ttgtaagtgg agcttacctc catgaccctg 14760
agttcaacct gtcttacagc ctgaaagaaa aggagatcaa ggaaacaggt agactttttg 14820
ctaaaatgac ttacaaaatg agggcatgcc aagtgattgc tgaaaatcta atctcaaacg 14880
ggattggcaa atattttaag gacaatggga tggccaagga tgagcacgat ttgactaagg 14940
cactccacac tctagctgtc tcaggagtcc ccaaagatct caaagaaagt cacagggggg 15000
ggccagtctt aaaaacctac tcccgaagcc cagtccacac aagtaccagg aacgtgagag 15060
cagcaaaagg gtttataggg ttccctcaag taattcggca ggaccaagac actgatcatc 15120
cggagaatat ggaagcttac gagacagtca gtgcatttat cacgactgat ctcaagaagt 15180
actgccttaa ttggagatat gagaccatca gcttgtttgc acagaggcta aatgagattt 15240
acggattgcc ctcatttttc cagtggctgc ataagaggct tgagacctct gtcctgtatg 15300
taagtgaccc tcattgcccc cccgaccttg acgcccatat cccgttatat aaagtcccca 15360
atgatcaaat cttcattaag taccctatgg gaggtataga agggtattgt cagaagctgt 15420
ggaccatcag caccattccc tatctatacc tggctgctta tgagagcgga gtaaggattg 15480
cttcgttagt gcaaggggac aatcagacca tagccgtaac aaaaagggta cccagcacat 15540
ggccctacaa ccttaagaaa cgggaagctg ctagagtaac tagagattac tttgtaattc 15600
ttaggcaaag gctacatgat attggccatc acctcaaggc aaatgagaca attgtttcat 15660
cacatttttt tgtctattca aaaggaatat attatgatgg gctacttgtg tcccaatcac 15720
tcaagagcat cgcaagatgt gtattctggt cagagactat agttgatgaa acaagggcag 15780
catgcagtaa tattgctaca acaatggcta aaagcatcga gagaggttat gaccgttacc 15840
ttgcatattc cctgaacgtc ctaaaagtga tacagcaaat tctgatctct cttggcttca 15900
caatcaattc aaccatgacc cgggatgtag tcatacccct cctcacgaac aacgacctct 15960
taataaggat ggcactgttg cccgctccta ttgggggggat gaattatctg aatatgagca 16020
ggctgtttgt cagaaacatc ggtgatccag taacatcatc aattgctgat ctcaagagaa 16080
tgattctcgc ctcactaatg cctgaagaga ccctccatca agtaatgaca caacaaccgg 16140

-continued

```
gggactcttc attcctagac tgggctagcg acccttactc agcaaatctt gtatgtgtcc  16200
agagcatcac tagactcctc aagaacataa ctgcaaggtt tgtcctgatc catagtccaa  16260
acccaatgtt aaaaggatta ttccatgatg acagtaaaga agaggacgag ggactggcgg  16320
cattcctcat ggacaggcat attatagtac ctagggcagc tcatgaaatc ctggatcata  16380
gtgtcacagg ggcaagagag tctattgcag gcatgctgga taccacaaaa ggcctgattc  16440
gagccagcat gaggaagggg gggttaacct ctcgagtgat aaccagattg tccaattatg  16500
actatgaaca attcagagca gggatggtgc tattgacagg aagaaagaga aatgtcctca  16560
ttgacaaaga gtcatgttca gtgcagctgg cgagagctct aagaagccat atgtgggcga  16620
ggctagctcg aggacggcct atttacggcc ttgaggtccc tgatgtacta gaatctatgc  16680
gaggccacct tattcggcgt catgagacat gtgtcatctg cgagtgtgga tcagtcaact  16740
acggatggtt ttttgtcccc tcgggttgcc aactggatga tattgacaag gaaacatcat  16800
ccttgagagt cccatatatt ggttctacca ctgatgagag aacagacatg aagcttgcct  16860
tcgtaagagc cccaagtcga tccttgcgat ctgctgttag aatagcaaca gtgtactcat  16920
gggcttacgg tgatgatgat agctcttgga acgaagcctg gttgttggct aggcaaaggg  16980
ccaatgtgag cctggaggag ctaagggtga tcactcccat ctcaacttcg actaatttag  17040
cgcataggtt gagggatcgt agcactcaag tgaaatactc aggtacatcc cttgtccgag  17100
tggcgaggta taccacaatc tccaacgaca atctctcatt tgtcatatca gataagaagg  17160
ttgatactaa ctttatatac caacaaggaa tgcttctagg gttgggtgtt ttagaaacat  17220
tgtttcgact cgagaaagat accggatcat ctaacacggt attacatctt cacgtcgaaa  17280
cagattgttg cgtgatcccg atgatagatc atcccaggat acccagctcc cgcaagctag  17340
agctgagggc agagctatgt accaacccat tgatatatga taatgcacct ttaattgaca  17400
gagatacaac aaggctatac acccagagcc ataggaggca ccttgtggaa tttgttacat  17460
ggtccacacc ccaactatat cacattttag ctaagtccac agcactatct atgattgacc  17520
tggtaacaaa atttgagaag gaccatatga atgaaatttc agctctcata ggggatgacg  17580
atatcaatag tttcataact gagtttctgc tcatagagcc aagattattc actatctact  17640
tgggccagtg tgcggccatc aattgggcat ttgatgtaca ttatcataga ccatcaggga  17700
aatatcagat gggtgagctg ttgtcatcgt tcctttctag aatgagcaaa ggagtgttta  17760
aggtgcttgt caatgctcta agccacccaa agatctacaa gaaattctgg cattgtggta  17820
ttatagagcc tatccatggt ccttcacttg atgctcaaaa cttgcacaca actgtgtgca  17880
acatggttta cacatgctat atgacctacc tcgacctgtt gttgaatgaa gagttagaag  17940
agttcacatt tctcttgtgt gaaagcgacg aggatgtagt accggacaga ttcgacaaca  18000
tccaggcaaa acacttatgt gttctggcag atttgtactg tcaaccaggg acctgcccac  18060
caattcgagg tctaagaccg gtagagaaat gtgcagttct aaccgaccat atcaaggcag  18120
aggctaggtt atctccagca ggatcttcgt ggaacataaa tccaattatt gtagaccatt  18180
actcatgctc tctgacttat ctccggcgag gatcgatcaa acagataaga ttgagagttg  18240
atccaggatt cattttcgac gccctcgctg aggtaaatgt cagtcagcca aagatcggca  18300
gcaacaacat ctcaaatatg agcatcaagg ctttcagacc cccacacgat gatgttgcaa  18360
aattgctcaa agatatcaac acaagcaagc acaatcttcc catttcaggg ggcaatctcg  18420
ccaattatga aatccatgct ttccgcagaa tcgggttgaa ctcatctgct tgctacaaag  18480
ctgttgagat atcaacatta attaggagat gccttgagcc aggggaggac ggcttgttct  18540
```

tgggtgaggg atcgggttcc atgttgatca cttataagga gatacttaaa ctaaacaagt 18600
gcttctataa tagtggggtt tccgccaatt ctagatctgg tcaaagggaa ttagcaccct 18660
atccctccga agttggcctt gtcgaacaca gaatgggagt aggtaatatt gtcaaagtgc 18720
tctttaacgg gaggcccgaa gtcacgtggg taggcagtgt agattgcttc aatttcatag 18780
ttagtaatat ccctacctct agtgtggggt ttatccattc agatatagag accttgccta 18840
acaaagatac tatagagaag ctagaggaat tggcagccat cttatcgatg gctctgctcc 18900
tgggcaaaat aggatcaata ctggtgatta agcttatgcc tttcagcggg gattttgttc 18960
agggatttat aagttatgta gggtcccatt atagagaagt gaaccttgta taccctagat 19020
acagcaactt catatctact gaatcttatt tggttatgac agatctcaag gctaaccggc 19080
taatgaatcc tgaaaagatt aagcagcaga taattgaatc atctgtgagg acttcacctg 19140
gacttatagg tcacatccta tccattaagc aactaagctg catacaagca attgtgggag 19200
acgcagttag tagaggtgat atcaatccta ctctgaaaaa acttacacct atagagcagg 19260
tgctgatcaa ttgcgggttg gcaattaacg gacctaagct gtgcaaagaa ttgatccacc 19320
atgatgttgc ctcagggcaa gatggattgc ttaattctat actcatcctc tacagggagt 19380
tggcaagatt caaagacaac caaagaagtc aacaagggat gttccacgct taccccgtat 19440
tggtaagtag caggcaacga gaacttatat ctaggatcac ccgcaaattt tgggggcaca 19500
ttcttcttta ctccgggaac agaaagttga taaataagtt tatccagaat ctcaagtccg 19560
gctatctgat actagactta caccagaata tcttcgttaa gaatctatcc aagtcagaga 19620
aacagattat tatgacgggg ggtttgaaac gtgagtgggt ttttaaggta acagtcaagg 19680
agaccaaaga atggtataag ttagtcggat acagtgccct gattaaggac taattggttg 19740
aactccggaa ccctaatcct gccctaggtg gttaggcatt atttgcaata gattaaagaa 19800
aactttgaaa atacgaagtt tctattccca gctttgtctg gtggccggca tggtcccagc 19860
ctcctcgctg gcgccggctg ggcaacattc cgaggggacc gtcccctcgg taatggcgaa 19920
tgggacgcgg ccgatccggc tgctaacaaa gcccgaaagg aagctgagtt ggctgctgcc 19980
accgctgagc aataactagc ataacccctt ggggcctcta aacgggtctt gaggggtttt 20040
ttgctgaaag gaggaactat atccggatgc ggccgatccg gctgctaaca aagcccgaaa 20100
ggaagctgag ttggctgctg ccaccgctga gcaataacta gcataacccc ttggggcctc 20160
taaacgggtc ttgaggggtt ttttgctgaa aggaggaact atatccggat ggccgccacc 20220
ggccggtggg ccttgcagca catccccctt tcgccagctg gcgtaatagc gaagaggccc 20280
gcaccgatcg cccttcccaa cagttgcgca gcctgaatgg cgaatgggac gcgccctgta 20340
gcggcgcatt aagcgcggcg ggtgtggtgg ttacgcgcag cgtgaccgct acacttgcca 20400
gcgccctagc gcccgctcct ttcgctttct tcccttcctt tctcgccacg ttcgccggct 20460
ttccccgtca agctctaaat cgggggctcc ctttagggtt ccgatttagt gctttacggc 20520
acctcgaccc caaaaaactt gattagggtg atggttcacg tgggccatcg ccctgataga 20580
cggtttttcg ccctttgacg ttggagtcca cgttctttaa tagtggactc ttgttccaaa 20640
ctggaacaac actcaaccct atctcggtct attcttttga tttataaggg attttgccga 20700
tttcggccta ttggttaaaa aatgagctga tttaacaaaa atttaacgcg aattttaaca 20760
aaatattaac gcttacaatt taggtggcac ttttcgggga aatgtgcgcg gaacccctat 20820
ttgtttattt ttctaaatac attcaaatat gtatccgctc atgagacaat aaccctgata 20880

-continued

```
aatgcttcaa taatattgaa aaaggaagag tatgagtatt caacatttcc gtgtcgccct  20940
tattcccttt tttgcggcat tttgccttcc tgtttttgct cacccagaaa cgctggtgaa  21000
agtaaaagat gctgaagatc agttgggtgc acgagtgggt tacatcgaac tggatctcaa  21060
cagcggtaag atccttgaga gttttcgccc cgaagaacgt tttccaatga tgagcacttt  21120
taaagttctg ctatgtggcg cggtattatc ccgtattgac gccgggcaag agcaactcgg  21180
tcgccgcata cactattctc agaatgactt ggttgagtac tcaccagtca cagaaaagca  21240
tcttacggat ggcatgacag taagagaatt atgcagtgct gccataacca tgagtgataa  21300
cactgcggcc aacttacttc tgacaacgat cggaggaccg aaggagctaa ccgctttttt  21360
gcacaacatg ggggatcatg taactcgcct tgatcgttgg gaaccggagc tgaatgaagc  21420
cataccaaac gacgagcgtg acaccacgat gcctgtagca atggcaacaa cgttgcgcaa  21480
actattaact ggcgaactac ttacactagc ttcccggcaa caattaatag actggatgga  21540
ggcggataaa gttgcaggac cacttctgcg ctcggccctt ccggctggct ggtttattgc  21600
tgataaatct ggagccggtg agcgtgggtc tcgcggtatc attgcagcac tggggccaga  21660
tggtaagccc tcccgtatcg tagttatcta cacgacgggg agtcaggcaa ctatggatga  21720
acgaaataga cagatcgctg agataggtgc ctcactgatt aagcattggt aactgtcaga  21780
ccaagtttac tcatatatac tttagattga tttaaaactt catttttaat ttaaaaggat  21840
ctaggtgaag atcctttttg ataatctcat gaccaaaatc ccttaacgtg agttttcgtt  21900
ccactgagcg tcagaccccg tagaaaagat caaaggatct tcttgagatc cttttttct  21960
gcgcgtaatc tgctgcttgc aaacaaaaaa accaccgcta ccagcggtgg tttgtttgcc  22020
ggatcaagag ctaccaactc tttttccgaa ggtaactggc ttcagcagag cgcagatacc  22080
aaatactgtt cttctagtgt agccgtagtt aggccaccac ttcaagaact ctgtagcacc  22140
gcctacatac ctcgctctgc taatcctgtt accagtggct gctgccagtg gcgataagtc  22200
gtgtcttacc gggttggact caagacgata gttaccggat aaggcgcagc ggtcgggctg  22260
aacggggggt tcgtgcacac agcccagctt ggagcgaacg acctacaccg aactgagata  22320
cctacagcgt gagctatgag aaagcgccac gcttcccgaa gggagaaagg cggacaggta  22380
tccggtaagc ggcagggtcg gaacaggaga gcgcacgagg gagcttccag ggggaaacgc  22440
ctggtatctt tatagtcctg tcgggtttcg ccacctctga cttgagcgtc gatttttgtg  22500
atgctcgtca ggggggcgga gcctatggaa aaacgccagc aacgcggcct ttttacggtt  22560
cctggccttt tgctggcctt ttgctcacat gttctttcct gcgttatccc ctgattctgt  22620
ggataaccgt attaccgcct ttgagtgagc tgataccgct cgccgcagcc gaacgaccga  22680
gcgcagcgag tcagtgagcg aggaagcgga agagcgccca atacgcaaac cgcctctccc  22740
cgcgcgttgg ccgattcatt aatgcagctg gcacgacagg tttcccgact ggaaagcggg  22800
cagtgagcgc aacgcaatta atgtgagtta gctcactcat taggcacccc aggctttaca  22860
ctttatgctt ccggctcgta tgttgtgtgg aattgtgagc ggacaacaat ttcacacagg  22920
aaacagctat gaccatgatt acgccaagct cgggcggccg cttgtaatac gactcactat  22980
a                                                                  22981
```

<210> SEQ ID NO 17
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA

<400> SEQUENCE: 17

```
accaaacaaa gttgggtaag gatagttcaa tcaatgatca ttttctagtg cacttaggat     60

tcaagatcct attatcaggg acaagagcag gattaaggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtcaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540

gatggttcga gaacaaggaa atctcagata ttgaagtgca agaccctgag ggattcaaca    600

tgattctggg taccatccta gctcaaattt gggtcttgct cgcaaaggcg gttacggccc    660

cagacacggc agctgattcg gagctaagaa ggtggataaa gtacacccaa caaagaaggg    720

tagttggtga atttagattg gagagaaaat ggttggatgt ggtgaggaac aggattgccg    780

aggacctctc cttacgccga ttcatggtcg ctctaatcct ggatatcaag agaacacccg    840

gaaacaaacc caggattgct gaaatgatat gtgacattga tacatatatc gtagaggcag    900

gattagccag ttttatcctg actattaagt ttgggataga aactatgtat cctgctcttg    960

gactgcatga atttgctggt gagttatcca cacttgagtc cttgatgaac ctttaccagc   1020

aaatggggga aactgcaccc tacatggtaa tcctggagaa ctcaattcag aacaagttca   1080

gtgcaggatc ataccctctg ctctggagct atgccatggg agtaggagtg gaacttgaaa   1140

actccatggg aggtttgaac tttggccgat cttactttga tccagcatat tttagattag   1200

ggcaagagat ggtaaggagg tcagctggaa aggtcagttc cacattggca tctgaactcg   1260

gtatcactgc cgaggatgca aggcttgttt cagagattgc aatgcatact actgaggaca   1320

agatcagtag agcggttgga cccagacaag cccaagtatc atttctacac ggtgatcaaa   1380

gtgagaatga gctaccgaga ttgggggggca aggaagatag gagggtcaaa cagagtcgag   1440

gagaagccag ggagagctac agagaaaccg ggcccagcag agcaagtgat gcgagagctg   1500

cccatcttcc aaccggcaca cccctagaca ttgacactgc atcggagtcc agccaagatc   1560

cgcaggacag tcgaaggtca gctgacgccc tgcttaggct gcaagccatg gcaggaatct   1620

cggaagaaca aggctcagac acggacaccc ctatagtgta caatgacaga aatcttctag   1680

actaggtgcg agaggccgag gaccagaaca acatccgcct accctccatc attgttataa   1740

aaaacttagg aaccaggtcc acacagccgc cagcccatca accatccact cccacgattg   1800

gagccgatgg cagaagagca ggcacgccat gtcaaaaacg gactggaatg catccgggct   1860

ctcaaggccg agcccatcgg ctcactggcc atcgaggaag ctatggcagc atggtcagaa   1920

atatcagaca acccaggaca ggagcgagcc acctgcaggg aagagaaggc aggcagttcg   1980

ggtctcagca aaccatgcct ctcagcaatt ggatcaactg aaggcggtgc acctcgcatc   2040

cgcggtcagg gacctggaga gagcgatgac gacgctgaaa ctttgggaat ccccccaaga   2100

aatctccagg catcaagcac tgggttacag tgttattatg tttatgatca cagcggtgaa   2160
```

-continued

```
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag ttccacaggc gcgccatgtt cgtcttcctg gtcctgctgc ctctggtctc   3480
ctcacagtgc gtcaatctga caactcggac tcagctgcca cctgcttata ctaatagctt   3540
caccagaggc gtgtactatc ctgacaaggt gtttagaagc tccgtgctgc actctacaca   3600
ggatctgttt ctgccattct ttagcaacgt gacctggttc cacgccatcc acgtgagcgg   3660
caccaatggc acaaagcggt tcgacaatcc cgtgctgcct tttaacgatg gcgtgtactt   3720
cgcctctacc gagaagagca acatcatcag aggctggatc tttggcacca cactggactc   3780
caagacacag tctctgctga tcgtgaacaa tgccaccaac gtggtcatca aggtgtgcga   3840
gttccagttt tgtaatgatc ccttcctggg cgtgtactat cacaagaaca ataagagctg   3900
gatggagtcc gagtttagag tgtattctag cgccaacaac tgcacatttg agtacgtgag   3960
ccagcctttc ctgatggacc tggagggcaa gcagggcaat ttcaagaacc tgagggagtt   4020
cgtgtttaag aatatcgacg gctacttcaa aatctactct aagcacaccc ccatcaacct   4080
ggtgcgcgac ctgcctcagg gcttcagcgc cctggagccc ctggtggatc tgcctatcgg   4140
catcaacatc acccggtttc agacactgct ggccctgcac agaagctacc tgacacccgg   4200
cgactcctct agcggatgga ccgccggcgc tgccgcctac tatgtgggct acctccagcc   4260
ccggaccttc ctgctgaagt acaacgagaa tggcaccatc acagacgcag tggattgcgc   4320
cctggacccc ctgagcgaga caaagtgtac actgaagtcc tttaccgtgg agaagggcat   4380
ctatcagaca tccaatttca gggtgcagcc aaccgagtct atcgtgcgct ttcctaatat   4440
cacaaacctg tgcccatttg gcgaggtgtt caacgcaacc cgcttcgcca gcgtgtacgc   4500
ctggaatagg aagcggatca gcaactgcgt ggccgactat agcgtgctgt acaactccgc   4560
```

-continued

```
ctctttcagc acctttaagt gctatggcgt gtcccccaca aagctgaatg acctgtgctt   4620
taccaacgtc tacgccgatt ctttcgtgat caggggcgac gaggtgcgcc agatcgcccc   4680
cggccagaca ggcaagatcg cagactacaa ttataagctg ccagacgatt tcaccggctg   4740
cgtgatcgcc tggaacagca acaatctgga ttccaaagtg ggcggcaact acaattatct   4800
gtaccggctg tttagaaaga gcaatctgaa gcccttcgag agggacatct ctacagaaat   4860
ctaccaggcc ggcagcaccc cttgcaatgg cgtggagggc tttaactgtt atttcccact   4920
ccagtcctac ggcttccagc ccacaaacgg cgtgggctat cagccttacc gcgtggtggt   4980
gctgagcttt gagctgctgc acgccccagc aacagtgtgc ggccccaaga agtccaccaa   5040
tctggtgaag aacaagtgcg tgaacttcaa cttcaacggc ctgaccggca caggcgtgct   5100
gaccgagtcc aacaagaagt tcctgccatt tcagcagttc ggcagggaca tcgcagatac   5160
cacagacgcc gtgcgcgacc cacagaccct ggagatcctg gacatcacac cctgctcttt   5220
cggcggcgtg agcgtgatca cacccggcac caatacaagc aaccaggtgg ccgtgctgta   5280
tcaggacgtg aattgtaccg aggtgcccgt ggctatccac gccgatcagc tgaccccaac   5340
atggcgggtg tacagcaccg gctccaacgt cttccagaca agagccggat gcctgatcgg   5400
agcagagcac gtgaacaatt cctatgagtg cgacatccca atcggcgccg gcatctgtgc   5460
ctcttaccag acccagacaa actctcccag aagagcccgg agcgtggcct cccagtctat   5520
catcgcctat accatgtccc tgggcgccga gaacagcgtg gcctactcta acaatagcat   5580
cgccatccca accaacttca caatctctgt gaccacagag atcctgcccg tgtccatgac   5640
caagacatct gtggactgca caatgtatat ctgtggcgat tctaccgagt gcagcaacct   5700
gctgctccag tacggcagct tttgtaccca gctgaataga gccctgacag gcatcgccgt   5760
ggagcaggat aagaacacac aggaggtgtt cgcccaggtg aagcaaatct acaagacccc   5820
ccctatcaag gactttggcg gcttcaattt ttcccagatc ctgcctgatc catccaagcc   5880
ttctaagcgg agctttatcg aggacctgct gttcaacaag gtgaccctgg ccgatgccgg   5940
cttcatcaag cagtatggcg attgcctggg cgacatcgca gccagggacc tgatctgcgc   6000
ccagaagttt aatggcctga ccgtgctgcc acccctgctg acagatgaga tgatcgcaca   6060
gtacacaagc gccctgctgg ccggcaccat cacatccgga tggaccttcg gcgcaggagc   6120
cgccctccag atcccctttg ccatgcagat ggcctatagg ttcaacggca tcggcgtgac   6180
ccagaatgtg ctgtacgaga accagaagct gatcgccaat cagtttaact ccgccatcgg   6240
caagatccag gacagcctgt cctctacagc cagcgccctg ggcaagctcc aggatgtggt   6300
gaatcagaac gcccaggccc tgaataccct ggtgaagcag ctgagcagca acttcggcgc   6360
catctctagc gtgctgaatg acatcctgag ccggctggac aaggtggagg cagaggtgca   6420
gatcgaccgg ctgatcaccg gccggctcca gagcctccag acctatgtga cacagcagct   6480
gatcagggcc gccgagatca gggccagcgc caatctggca gcaaccaaga tgtccgagtg   6540
cgtgctgggc cagtctaaga gagtggactt ttgtggcaag ggctatcacc tgatgtcctt   6600
ccctcagtct gccccacacg gcgtggtgtt tctgcacgtg acctacgtgc ccgcccagga   6660
gaagaacttc accacagccc ctgccatctg ccacgatggc aaggcccact ttccaaggga   6720
gggcgtgttc gtgtccaacg gcacccactg gtttgtgaca cagcgcaatt tctacgagcc   6780
ccagatcatc accacagaca acaccttcgt gagcggcaac tgtgacgtgg tcatcggcat   6840
cgtgaacaat accgtgtatg atccactcca gcccgagctg gacagcttta aggaggagct   6900
```

-continued

```
ggataagtat ttcaagaatc acacctcccc tgacgtggat ctgggcgaca tcagcggcat   6960
caatgcctcc gtggtgaaca tccagaagga gatcgaccgc ctgaacgagg tggctaagaa   7020
tctgaacgag agcctgatcg acctccagga gctgggcaag tatgagcagt acatcaagtg   7080
gccctggtac atctggctgg gcttcatcgc cggcctgatc gccatcgtga tggtgaccat   7140
catgctgtgc tgtatgacat cctgctgttc ttgcctgaag ggctgctgta gctgtggctc   7200
ctgctgtaag tttgacgagg atgactctga acctgtgctg aagggcgtgg cgctggctta   7260
cacctaacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctggggggttg   7560
ttgaggacag cgatcccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgatacccc gcagaggttc cgtgttgttt   7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gatagggggc accagtcttc   8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccccct cacaatgaca gccagaaggc ccggacaaaa   8460
aagcccccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggacccccg aggaccaacc cccaaggctg cccccgatcc   8640
aaaccaccaa ccgcatcccc accacccccg ggaaagaaac ccccagcaat tggaaggccc   8700
ctccccctct tcctcaacac aagaactcca caaccgaacc gcacaagcga ccgaggtgac   8760
ccaaccgcag gcatccgact ccctagacag atcctctctc cccggcaaac taaacaaaac   8820
ttagggccaa ggaacataca cacccaacag aacccagacc ccggcccacg gcgccgcgcc   8880
cccaaccccc gacaaccaga gggagccccc aaccaatccc gccggctccc ccggtgccca   8940
caggcaggga caccaacccc cgaacagacc cagcacccaa ccatcgacaa tccaagacgg   9000
gggggccccc ccaaaaaaag gcccccaggg gccgacagcc agcaccgcga ggaagcccac   9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggaccccc   9240
gaaccgcaaa ggacatcagt atcccacagc ctctccaagt cccccggtct cctccccttc   9300
```

```
tcgaagggac caaaagatca atccaccaca cccgacgaca ctcaactccc cacccctaaa   9360
ggagacaccg ggaatcccag aatcaagact catccaatgt ccatcatggg tctcaaggtg   9420
aacgtctctg ccatattcat ggcagtactg ttaactctcc aaacacccac cggtcaaatc   9480
cattggggca atctctctaa gataggggtg gtaggaatag gaagtgcaag ctacaaagtt   9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa gaccggttca gagtgtagct   9720
tcaagtagga gacacaagag atttgcggga gtagtcctgg caggtgcggc cctaggcgtc   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg gccagaagct cgggctcaaa  10020
ttgctcagat actatacaga aatcctgtca ttatttggcc ccagcttacg ggaccccata  10080
tctgcggaga tatctatcca ggctttgagc tatgcgcttg gaggagacat caataaggtg  10140
ttagaaaagc tcggatacag tggaggtgat ttactgggca tcttagagag cagaggaata  10200
aaggcccgga taactcacgt cgacacagag tcctacttca ttgtcctcag tatagcctat  10260
ccgacgctgt ccgagattaa gggggtgatt gtccaccggc tagagggggt ctcgtacaac  10320
ataggctctc aagagtggta taccactgtg cccaagtatg ttgcaaccca agggtacctt  10380
atctcgaatt ttgatgagtc atcgtgtact ttcatgccag aggggactgt gtgcagccaa  10440
aatgccttgt acccgatgag tcctctgctc caagaatgcc tccgggggtc caccaagtcc  10500
tgtgctcgta cactcgtatc cggtctttt gggaaccggt tcattttatc acaagggaac  10560
ctaatagcca attgtgcatc aatcctttgc aagtgttaca caacaggaac gatcattaat  10620
caagaccctg acaagatcct aacatacatt gctgccgatc actgcccggt agtcgaggtg  10680
aacggcgtga ccatccaagt cgggagcagg aggtatccag atgctgtgta cttgcacaga  10740
attgacctcg gtcctcccat atcattggag aggttggacg tagggacaaa tctggggaat  10800
gcaattgcta agttggagga tgccaaggaa ttgttggagt catcggacca gatattgagg  10860
agtatgaaag gtttatcgag cactagcata gtctacatcc tgattgcagt gtgtcttgga  10920
gggttgatag ggatccccgc tttaatatgt tgctgcaggg ggcgttgtaa caaaaaggga  10980
gaacaagttg gtatgtcaag accaggccta aagcctgatc ttacgggaac atcaaaatcc  11040
tatgtaaggt cgctctgatc ctctacaact cttgaaacac aaatgtccca caagtctcct  11100
cttcgtcatc aagcaaccac cgcacccagc atcaagccca cctgaaatta tctccggctt  11160
ccctctggcc gaacaatatc ggtagttaat taaaacttag ggtgcaagat catccacaat  11220
gtcaccacaa cgagaccgga taaatgcctt ctacaaagat aacccccatc ccaagggaag  11280
taggatagtc attaacagag aacatcttat gattgataga ccttatgttt tgctggctgt  11340
tctgtttgtc atgtttctga gcttgatcgg gttgctagcc attgcaggca ttagacttca  11400
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
tgaagtgggc ctgaggacac ctcagagatt cactgaccta gtgaaattca tctctgacaa  11580
gattaaattc cttaatccgg atagggagta cgacttcaga gatctcactt ggtgtatcaa  11640
```

-continued

```
cccgccagag agaatcaaat tggattatga tcaatactgt gcagatgtgg ctgctgaaga  11700
gctcatgaat gcattggtga actcaactct actggagacc agaacaacca atcagttcct  11760
agctgtctca aagggaaact gctcagggcc cactacaatc agaggtcaat tctcaaacat  11820
gtcgctgtcc ctgttagact tgtatttagg tcgaggttac aatgtgtcat ctatagtcac  11880
tatgacatcc cagggaatgt atgggggaac ttacctagtg gaaaagccta atctgagcag  11940
caaaaggtca gagttgtcac aactgagcat gtaccgagtg tttgaagtag gtgttatcag  12000
aaatccgggt ttgggggctc cggtgttcca tatgacaaac tatcttgagc aaccagccag  12060
taatgatctc agcaactgta tggtggcttt gggggagctc aaactcgcag ccctttgtca  12120
cggggaagat tctatcacaa ttccctatca gggatcaggg aaaggtgtca gcttccagct  12180
cgtcaagcta ggtgtctgga aatccccaac cgacatgcaa tcctgggtcc ccttatcaac  12240
ggatgatcca gtgatagaca ggctttacct ctcatctcac agaggtgtta tcgctgacaa  12300
tcaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
cctagcctta ggtgtaatca acacattgga gtggataccg agattcaagg ttagtcccta  12660
cctcttcaat gtcccaatta aggaagcagg cgaagactgc catgccccaa catacctacc  12720
tgcggaggtg gatggtgatg tcaaactcag ttccaatctg gtgattctac ctggtcaaga  12780
tctccaatat gttttggcaa cctacgatac ttccagggtt gaacatgctg tggtttatta  12840
cgtttacagc ccaggccgct cattttctta cttttatcct tttaggttgc ctataaaggg  12900
ggtccccatc gaattacaag tggaatgctt cacatgggac caaaaactct ggtgccgtca  12960
cttctgtgtg cttgcggact cagaatctgg tggacatatc actcactctg ggatggtggg  13020
catgggagtc agctgcacag tcacccggga agatggaacc aatcgcagat agggctgcta  13080
gtgaaccaat ctcatgatgt cacccagaca tcaggcatac ccactagtgt gaaatagaca  13140
tcagaattaa gaaaaacgta gggtccaagt ggttccccgt tatggactcg ctatctgtca  13200
accagatctt ataccctgaa gttcacctag atagcccgat agttaccaat aagatagtag  13260
ccatcctgga gtatgctcga gtccctcacg cttacagcct ggaggaccct acactgtgtc  13320
agaacatcaa gcaccgccta aaaaacggat tttccaacca aatgattata aacaatgtgg  13380
aagttgggaa tgtcatcaag tccaagctta ggagttatcc ggcccactct catattccat  13440
atccaaattg taatcaggat ttatttaaca tagaagacaa agagtcaacg aggaagatcc  13500
gtgaactcct caaaaagggg aattcgctgt actccaaagt cagtgataag gttttccaat  13560
gcttaaggga cactaactca cggcttggcc taggctccga attgagggag gacatcaagg  13620
agaaagttat taacttggga gtttacatgc acagctccca gtggtttgag ccctttctgt  13680
tttggtttac agtcaagact gagatgaggt cagtgattaa atcacaaacc catacttgcc  13740
ataggaggag acacacacct gtattcttca ctggtagttc agttgagttg ctaatctctc  13800
gtgaccttgt tgctataatc agtaaagagt ctcaacatgt atattacctg acatttgaac  13860
tggttttgat gtattgtgat gtcatagagg ggaggttaat gacagagacc gctatgacta  13920
ttgatgctag gtatacagag cttctaggaa gagtcagata catgtggaaa ctgatagatg  13980
gtttcttccc tgcactcggg aatccaactt atcaaattgt agccatgctg gagcctcttt  14040
```

```
cacttgctta cctgcagctg agggatataa cagtagaact cagaggtgct ttccttaacc  14100
actgctttac tgaaatacat gatgttcttg accaaaacgg gttttctgat gaaggtactt  14160
atcatgagtt aattgaagct ctagattaca ttttcataac tgatgacata catctgacag  14220
gggagatttt ctcatttttc agaagtttcg gccaccccag acttgaagca gtaacggctg  14280
ctgaaaatgt taggaaatac atgaatcagc ctaaagtcat tgtgtatgag actctgatga  14340
aaggtcatgc catattttgt ggaatcataa tcaacggcta tcgtgacagg cacggaggca  14400
gttggccacc gctgaccctc cccctgcatg ctgcagacac aatccggaat gctcaagctt  14460
caggtgaagg gttaacacat gagcagtgcg ttgataactg gagatctttt gctggagtga  14520
aatttggctg ctttatgcct cttagcctgg atagtgatct gacaatgtac ctaaaggaca  14580
aggcacttgc tgctctccaa agggaatggg attcagttta cccgaaagag ttcctgcgtt  14640
acgaccctcc caagggaacc gggtcacgga ggcttgtaga tgttttcctt aatgattcga  14700
gctttgaccc atatgatgtg ataatgtatg ttgtaagtgg agcttacctc catgaccctg  14760
agttcaacct gtcttacagc ctgaaagaaa aggagatcaa ggaaacaggt agactttttg  14820
ctaaaatgac ttacaaaatg agggcatgcc aagtgattgc tgaaaatcta atctcaaacg  14880
ggattggcaa atattttaag gacaatggga tggccaagga tgagcacgat ttgactaagg  14940
cactccacac tctagctgtc tcaggagtcc ccaaagatct caaagaaagt cacagggggg  15000
ggccagtctt aaaaacctac tcccgaagcc cagtccacac aagtaccagg aacgtgagag  15060
cagcaaaagg gtttataggg ttccctcaag taattcggca ggaccaagac actgatcatc  15120
cggagaatat ggaagcttac gagacagtca gtgcatttat cacgactgat ctcaagaagt  15180
actgccttaa ttggagatat gagaccatca gcttgtttgc acagaggcta aatgagattt  15240
acggattgcc ctcatttttc cagtggctgc ataagaggct tgagacctct gtcctgtatg  15300
taagtgaccc tcattgcccc cccgaccttg acgcccatat cccgttatat aaagtcccca  15360
atgatcaaat cttcattaag taccctatgg gaggtataga agggtattgt cagaagctgt  15420
ggaccatcag caccattccc tatctatacc tggctgctta tgagagcgga gtaaggattg  15480
cttcgttagt gcaaggggac aatcagacca tagccgtaac aaaaagggta cccagcacat  15540
ggccctacaa ccttaagaaa cgggaagctg ctagagtaac tagagattac tttgtaattc  15600
ttaggcaaag gctacatgat attggccatc acctcaaggc aaatgagaca attgtttcat  15660
cacatttttt tgtctattca aaaggaatat attatgatgg gctacttgtg tcccaatcac  15720
tcaagagcat cgcaagatgt gtattctggt cagagactat agttgatgaa acaagggcag  15780
catgcagtaa tattgctaca acaatggcta aaagcatcga gagaggttat gaccgttacc  15840
ttgcatattc cctgaacgtc ctaaaagtga tacagcaaat tctgatctct cttggcttca  15900
caatcaattc aaccatgacc cgggatgtag tcatacccct cctcacgaac aacgacctct  15960
taataaggat ggcactgttg cccgctccta ttggggggat gaattatctg aatatgagca  16020
ggctgtttgt cagaaacatc ggtgatccag taacatcatc aattgctgat ctcaagagaa  16080
tgattctcgc ctcactaatg cctgaagaga ccctccatca agtaatgaca caacaaccgg  16140
gggactcttc attcctagac tggggctagcg accccttactc agcaaatctt gtatgtgtcc  16200
agagcatcac tagactcctc aagaacataa ctgcaaggtt tgtcctgatc catagtccaa  16260
acccaatgtt aaaaggatta ttccatgatg acagtaaaga agaggacgag ggactggcgg  16320
cattcctcat ggacaggcat attatagtac ctagggcagc tcatgaaatc ctggatcata  16380
```

-continued gtgtcacagg ggcaagagag tctattgcag gcatgctgga taccacaaaa ggcctgattc 16440
gagccagcat gaggaagggg gggttaacct ctcgagtgat aaccagattg tccaattatg 16500
actatgaaca attcagagca gggatggtgc tattgacagg aagaaagaga aatgtcctca 16560
ttgacaaaga gtcatgttca gtgcagctgg cgagagctct aagaagccat atgtgggcga 16620
ggctagctcg aggacggcct atttacggcc ttgaggtccc tgatgtacta gaatctatgc 16680
gaggccacct tattcggcgt catgagacat gtgtcatctg cgagtgtgga tcagtcaact 16740
acggatggtt ttttgtcccc tcgggttgcc aactggatga tattgacaag gaaacatcat 16800
ccttgagagt cccatatatt ggttctacca ctgatgagag aacagacatg aagcttgcct 16860
tcgtaagagc cccaagtcga tccttgcgat ctgctgttag aatagcaaca gtgtactcat 16920
gggcttacgg tgatgatgat agctcttgga acgaagcctg gttgttggct aggcaaaggg 16980
ccaatgtgag cctggaggag ctaagggtga tcactcccat ctcaacttcg actaatttag 17040
cgcataggtt gagggatcgt agcactcaag tgaaatactc aggtacatcc cttgtccgag 17100
tggcgaggta taccacaatc tccaacgaca atctctcatt tgtcatatca gataagaagg 17160
ttgatactaa ctttatatac caacaaggaa tgcttctagg gttgggtgtt ttagaaacat 17220
tgtttcgact cgagaaagat accggatcat ctaacacggt attacatctt cacgtcgaaa 17280
cagattgttg cgtgatcccg atgatagatc atcccaggat acccagctcc cgcaagctag 17340
agctgagggc agagctatgt accaacccat tgatatatga taatgcacct ttaattgaca 17400
gagatacaac aaggctatac acccagagcc ataggaggca ccttgtggaa tttgttacat 17460
ggtccacacc ccaactatat cacattttag ctaagtccac agcactatct atgattgacc 17520
tggtaacaaa atttgagaag gaccatatga atgaaatttc agctctcata ggggatgacg 17580
atatcaatag tttcataact gagtttctgc tcatagagcc aagattattc actatctact 17640
tgggccagtg tgcggccatc aattgggcat ttgatgtaca ttatcataga ccatcaggga 17700
aatatcagat gggtgagctg ttgtcatcgt tcctttctag aatgagcaaa ggagtgttta 17760
aggtgcttgt caatgctcta agccacccaa agatctacaa gaaattctgg cattgtggta 17820
ttatagagcc tatccatggt ccttcacttg atgctcaaaa cttgcacaca actgtgtgca 17880
acatggttta cacatgctat atgacctacc tcgacctgtt gttgaatgaa gagttagaag 17940
agttcacatt tctcttgtgt gaaagcgacg aggatgtagt accggacaga ttcgacaaca 18000
tccaggcaaa acacttatgt gttctggcag atttgtactg tcaaccaggg acctgcccac 18060
caattcgagg tctaagaccg gtagagaaat gtgcagttct aaccgaccat atcaaggcag 18120
aggctaggtt atctccagca ggatcttcgt ggaacataaa tccaattatt gtagaccatt 18180
actcatgctc tctgacttat ctccggcgag gatcgatcaa acagataaga ttgagagttg 18240
atccaggatt cattttcgac gccctcgctg aggtaaatgt cagtcagcca aagatcggca 18300
gcaacaacat ctcaaatatg agcatcaagg ctttcagacc cccacacgat gatgttgcaa 18360
aattgctcaa agatatcaac acaagcaagc acaatcttcc catttcaggg ggcaatctcg 18420
ccaattatga aatccatgct ttccgcagaa tcgggttgaa ctcatctgct tgctacaaag 18480
ctgttgagat atcaacatta attaggagat gccttgagcc aggggaggac ggcttgttct 18540
tgggtgaggg atcgggttcc atgttgatca cttataagga gatacttaaa ctaaacaagt 18600
gcttctataa tagtggggtt tccgccaatt ctagatctgg tcaaagggaa ttagcaccct 18660
atccctccga agttggcctt gtcgaacaca gaatgggagt aggtaatatt gtcaaagtgc 18720
tctttaacgg gaggcccgaa gtcacgtggg taggcagtgt agattgcttc aatttcatag 18780

-continued ttagtaatat ccctacctct agtgtggggt ttatccattc agatatagag accttgccta 18840
acaaagatac tatagagaag ctagaggaat tggcagccat cttatcgatg gctctgctcc 18900
tgggcaaaat aggatcaata ctggtgatta agcttatgcc tttcagcggg gattttgttc 18960
agggatttat aagttatgta gggtcccatt atagagaagt gaaccttgta taccctagat 19020
acagcaactt catatctact gaatcttatt tggttatgac agatctcaag gctaaccggc 19080
taatgaatcc tgaaaagatt aagcagcaga taattgaatc atctgtgagg acttcacctg 19140
gacttatagg tcacatccta tccattaagc aactaagctg catacaagca attgtgggag 19200
acgcagttag tagaggtgat atcaatccta ctctgaaaaa acttacacct atagagcagg 19260
tgctgatcaa ttgcgggttg gcaattaacg gacctaagct gtgcaaagaa ttgatccacc 19320
atgatgttgc ctcagggcaa gatggattgc ttaattctat actcatcctc tacagggagt 19380
tggcaagatt caaagacaac caaagaagtc aacaagggat gttccacgct taccccgtat 19440
tggtaagtag caggcaacga gaacttatat ctaggatcac ccgcaaattt tgggggcaca 19500
ttcttcttta ctccgggaac agaaagttga taaataagtt tatccagaat ctcaagtccg 19560
gctatctgat actagactta caccagaata tcttcgttaa gaatctatcc aagtcagaga 19620
aacagattat tatgacgggg ggtttgaaac gtgagtgggt ttttaaggta acagtcaagg 19680
agaccaaaga atggtataag ttagtcggat acagtgccct gattaaggac taattggttg 19740
aactccggaa ccctaatcct gccctaggtg gttaggcatt atttgcaata gattaaagaa 19800
aactttgaaa atacgaagtt tctattccca gctttgtctg gtggccggca tggtcccagc 19860
ctcctcgctg gcgccggctg ggcaacattc cgaggggacc gtcccctcgg taatggcgaa 19920
tgggacgcgg ccgatccggc tgctaacaaa gcccgaaagg aagctgagtt ggctgctgcc 19980
accgctgagc aataactagc ataacccctt ggggcctcta aacgggtctt gaggggtttt 20040
ttgctgaaag gaggaactat atccggatgc ggccgatccg gctgctaaca aagcccgaaa 20100
ggaagctgag ttggctgctg ccaccgctga gcaataacta gcataacccc ttggggcctc 20160
taaacgggtc ttgaggggtt ttttgctgaa aggaggaact atatccggat ggccgccacc 20220
ggccggtggg ccttgcagca catccccctt tcgccagctg gcgtaatagc gaagaggccc 20280
gcaccgatcg cccttcccaa cagttgcgca gcctgaatgg cgaatgggac gcgccctgta 20340
gcggcgcatt aagcgcggcg ggtgtggtgg ttacgcgcag cgtgaccgct acacttgcca 20400
gcgccctagc gcccgctcct ttcgctttct tcccttcctt tctcgccacg ttcgccggct 20460
ttccccgtca agctctaaat cgggggctcc ctttagggtt ccgatttagt gctttacggc 20520
acctcgaccc caaaaaactt gattagggtg atggttcacg tgggccatcg ccctgataga 20580
cggtttttcg ccctttgacg ttggagtcca cgttctttaa tagtggactc ttgttccaaa 20640
ctggaacaac actcaaccct atctcggtct attcttttga tttataaggg attttgccga 20700
tttcggccta ttggttaaaa aatgagctga tttaacaaaa atttaacgcg aattttaaca 20760
aaatattaac gcttacaatt taggtggcac ttttcgggga aatgtgcgcg gaacccctat 20820
ttgtttattt ttctaaatac attcaaatat gtatccgctc atgagacaat aaccctgata 20880
aatgcttcaa taatattgaa aaaggaagag tatgagtatt caacatttcc gtgtcgccct 20940
tattcccttt tttgcggcat tttgccttcc tgtttttgct cacccagaaa cgctggtgaa 21000
agtaaaagat gctgaagatc agttgggtgc acgagtgggt tacatcgaac tggatctcaa 21060
cagcggtaag atccttgaga gttttcgccc cgaagaacgt tttccaatga tgagcacttt 21120

-continued taaagttctg ctatgtggcg cggtattatc ccgtattgac gccgggcaag agcaactcgg 21180
tcgccgcata cactattctc agaatgactt ggttgagtac tcaccagtca cagaaaagca 21240
tcttacggat ggcatgacag taagagaatt atgcagtgct gccataacca tgagtgataa 21300
cactgcggcc aacttacttc tgacaacgat cggaggaccg aaggagctaa ccgctttttt 21360
gcacaacatg ggggatcatg taactcgcct tgatcgttgg gaaccggagc tgaatgaagc 21420
cataccaaac gacgagcgtg acaccacgat gcctgtagca atggcaacaa cgttgcgcaa 21480
actattaact ggcgaactac ttacactagc ttcccggcaa caattaatag actggatgga 21540
ggcggataaa gttgcaggac cacttctgcg ctcggccctt ccggctggct ggtttattgc 21600
tgataaatct ggagccggtg agcgtgggtc tcgcggtatc attgcagcac tggggccaga 21660
tggtaagccc tcccgtatcg tagttatcta cacgacgggg agtcaggcaa ctatggatga 21720
acgaaataga cagatcgctg agataggtgc ctcactgatt aagcattggt aactgtcaga 21780
ccaagtttac tcatatatac tttagattga tttaaaactt catttttaat ttaaaaggat 21840
ctaggtgaag atcctttttg ataatctcat gaccaaaatc ccttaacgtg agttttcgtt 21900
ccactgagcg tcagaccccg tagaaaagat caaaggatct tcttgagatc cttttttct 21960 gcgcgtaatc tgctgcttgc aaacaaaaaa accaccgcta ccagcggtgg tttgtttgcc 22020
ggatcaagag ctaccaactc tttttccgaa ggtaactggc ttcagcagag cgcagatacc 22080
aaatactgtt cttctagtgt agccgtagtt aggccaccac ttcaagaact ctgtagcacc 22140
gcctacatac ctcgctctgc taatcctgtt accagtggct gctgccagtg gcgataagtc 22200
gtgtcttacc gggttggact caagacgata gttaccggat aaggcgcagc ggtcgggctg 22260
aacggggggt tcgtgcacac agcccagctt ggagcgaacg acctacaccg aactgagata 22320
cctacagcgt gagctatgag aaagcgccac gcttcccgaa gggagaaagg cggacaggta 22380
tccggtaagc ggcagggtcg gaacaggaga gcgcacgagg gagcttccag ggggaaacgc 22440
ctggtatctt tatagtcctg tcgggtttcg ccacctctga cttgagcgtc gatttttgtg 22500
atgctcgtca ggggggcgga gcctatggaa aaacgccagc aacgcggcct ttttacggtt 22560
cctggccttt tgctggcctt ttgctcacat gttctttcct gcgttatccc ctgattctgt 22620
ggataaccgt attaccgcct ttgagtgagc tgataccgct cgccgcagcc gaacgaccga 22680
gcgcagcgag tcagtgagcg aggaagcgga agagcgccca atacgcaaac cgcctctccc 22740
cgcgcgttgg ccgattcatt aatgcagctg gcacgacagg tttcccgact ggaaagcggg 22800
cagtgagcgc aacgcaatta atgtgagtta gctcactcat taggcacccc aggctttaca 22860
ctttatgctt ccggctcgta tgttgtgtgg aattgtgagc ggacaacaat ttcacacagg 22920
aaacagctat gaccatgatt acgccaagct cgggcggccg cttgtaatac gactcactat 22980
a 22981

<210> SEQ ID NO 18
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S

<400> SEQUENCE: 18
accaaacaaa gttgggtaag gatagttcaa tcaatgatca ttttctagtg cacttaggat 60

```
tcaagatcct attatcaggg acaagagcag gattaaggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gctcaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
```

-continued agaggcaaca actttccgaa gcttgggaaa actctcaatg ttcctccgcc tccggacccc 2460
ggtagggcca gcacttccgg gacacccatt aaaaagggca cagacgcgag attagcctca 2520
tttggaacgg agatcgcgtc tttattgaca ggtggtgcaa cccaatgtgc tcgaaagtca 2580
ccctcggaac catcagggcc aggtgcacct gcggggaatg tccccgagtg tgtgagcaat 2640
gccgcactga tacaggagtg gacacccgaa tctggtacca caatctcccc gagatcccag 2700
aataatgaag aagggggaga ctattatgat gatgagctgt tctctgatgt ccaagatatt 2760
aaaacagcct tggccaaaat acacgaggat aatcagaaga taatctccaa gctagaatca 2820
ctgctgttat tgaagggaga agttgagtca attaagaagc agatcaacag gcaaaatatc 2880
agcatatcca ccctggaagg acacctctca agcatcatga tcgccattcc tggacttggg 2940
aaggatccca acgaccccac tgcagatgtc gaaatcaatc ccgacttgaa acccatcata 3000
ggcagagatt caggccgagc actggccgaa gttctcaaga aacccgttgc cagccgacaa 3060
ctccaaggaa tgacaaatgg acggaccagt tccagaggac agctgctgaa ggaatttcag 3120
ctaaagccga tcgggaaaaa gatgagctca gccgtcgggt ttgttcctga caccggccct 3180
gcatcacgca gtgtaatccg ctccattata aaatccagcc ggctagagga ggatcggaag 3240
cgttacctga tgactctcct tgatgatatc aaaggagcca atgatcttgc caagttccac 3300
cagatgctga tgaagataat aatgaagtag ctacagctca acttacctgc caaccccatg 3360
ccagtcgacc caactagtac aacctaaatc cattataaaa aacttaggag caaagtgatt 3420
gcctcccaag ttccacaggc gcgccatgtt tgtttttctt gttttattgc cactagtctc 3480
tagtcagtgt gttaatctta caaccagaac tcaattaccc cctgcataca ctaattcttt 3540
cacacgtggt gtttattacc ctgacaaagt tttcagatcc tcagttttac attcaactca 3600
ggacttgttc ttacctttct tttccaatgt tacttggttc catgctatac atgtctctgg 3660
gaccaatggt actaagaggt ttgataaccc tgtcctacca tttaatgatg gtgtttattt 3720
tgcttccact gagaagtcta acataataag aggctggatt tttggtacta ctttagattc 3780
gaagacccag tccctactta ttgttaataa cgctactaat gttgttatta aagtctgtga 3840
atttcaattt tgtaatgatc catttttggg tgtttattac cacaaaaaca acaaaagttg 3900
gatggaaagt gagttcagag tttattctag tgcgaataat tgcacttttg aatatgtctc 3960
tcagcctttt cttatggacc ttgaaggaaa acagggtaat ttcaaaaatc ttagggaatt 4020
tgtgtttaag aatattgatg gttattttaa aatatattct aagcacacgc ctattaattt 4080
agtgcgtgat ctccctcagg gtttttcggc tttagaacca ttggtagatt tgccaatagg 4140
tattaacatc actaggtttc aaactttact tgctttacat agaagttatt tgactcctgg 4200
tgattcttct tcaggttgga cagctggtgc tgcagcttat tatgtgggtt atcttcaacc 4260
taggactttt ctattaaaat ataatgaaaa tggaaccatt acagatgctg tagactgtgc 4320
acttgaccct ctctcagaaa caaagtgtac gttgaaatcc ttcactgtag aaaaaggaat 4380
ctatcaaact tctaacttta gagtccaacc aacagaatct attgttagat ttcctaatat 4440
tacaaacttg tgcccttttg gtgaagtttt taacgccacc agatttgcat ctgtttatgc 4500
ttggaacagg aagagaatca gcaactgtgt tgctgattat tctgtcctat ataattccgc 4560
atcattttcc acttttaagt gttatggagt gtctcctact aaattaaatg atctctgctt 4620
tactaatgtc tatgcagatt catttgtaat tagaggtgat gaagtcagac aaatcgctcc 4680
agggcaaact ggaaagattg ctgattataa ttataaatta ccagatgatt ttacaggctg 4740
cgttatagct tggaattcta acaatcttga ttctaaggtt ggtggtaatt ataattacct 4800

-continued gtatagattg tttaggaagt ctaatctcaa accttttgag agagatattt caactgaaat 4860
ctatcaggcc ggtagcacac cttgtaatgg tgttgaaggt tttaattgtt actttccttt 4920
acaatcatat ggtttccaac ccactaatgg tgttggttac caaccataca gagtagtagt 4980
actttctttt gaacttctac atgcaccagc aactgtttgt ggacctaaaa agtctactaa 5040
tttggttaaa aacaaatgtg tcaatttcaa cttcaatggt ttaacaggca caggtgttct 5100
tactgagtct aacaaaaagt ttctgccttt ccaacaattt ggcagagaca ttgctgacac 5160
tactgatgct gtccgtgatc cacagacact tgagattctt gacattacac catgttcttt 5220
tggtggtgtc agtgttataa caccaggaac aaatacttct aaccaggttg ctgttcttta 5280
tcaggatgtt aactgcacag aagtccctgt tgctattcat gcagatcaac ttactcctac 5340
ttggcgtgtt tattctacag gttctaatgt ttttcaaaca cgtgcaggct gtttaatagg 5400
ggctgaacat gtcaacaact catatgagtg tgacataccc attggtgcag gtatatgcgc 5460
tagttatcag actcagacta attctcctcg gcgggcacgt agtgtagcta gtcaatccat 5520
cattgcctac actatgtcac ttggtgcaga aaattcagtt gcttactcta ataactctat 5580
tgccataccc acaaatttta ctattagtgt taccacagaa attctaccag tgtctatgac 5640
caagacatca gtagattgta caatgtacat ttgtggtgat tcaactgaat gcagcaatct 5700
tttgttgcaa tatggcagtt tttgtacaca attaaaccgt gctttaactg gaatagctgt 5760
tgaacaagac aaaaacaccc aagaagtttt tgcacaagtc aaacaaattt acaaaacacc 5820
accaattaaa gattttggtg gttttaattt ttcacaaata ttaccagatc catcaaaacc 5880
aagcaagagg tcatttattg aagatctact tttcaacaaa gtgacacttg cagatgctgg 5940
cttcatcaaa caatatggtg attgccttgg tgatattgct gctagagacc tcatttgtgc 6000
acaaaagttt aacggcctta ctgttttgcc acctttgctc acagatgaaa tgattgctca 6060
atacacttct gcactgttag cgggtacaat cacttctggt tggacctttg gtgcaggtgc 6120
tgcattacaa ataccatttg ctatgcaaat ggcttatagg tttaatggta ttggagttac 6180
acagaatgtt ctctatgaga accaaaaatt gattgccaac caatttaata gtgctattgg 6240
caaaattcaa gactcacttt cttccacagc aagtgcactt ggaaaacttc aagatgtggt 6300
caaccaaaat gcacaagctt taaacacgct tgttaaacaa cttagctcca attttggtgc 6360
aatttcaagt gttttaaatg atatcctttc acgtcttgac aaagttgagg ctgaagtgca 6420
aattgatagg ttgatcacag gcagacttca aagtttgcag acatatgtga ctcaacaatt 6480
aattagagct gcagaaatca gagcttctgc taatcttgct gctactaaaa tgtcagagtg 6540
tgtacttgga caatcaaaaa gagttgattt ttgtggaaag ggctatcatc ttatgtcctt 6600
ccctcagtca gcacctcatg gtgtagtctt cttgcatgtg acttatgtcc ctgcacaaga 6660
aaagaacttc acaactgctc ctgccatttg tcatgatgga aaagcacact ttcctcgtga 6720
aggtgtcttt gtttcaaatg gcacacactg gtttgtaaca caaaggaatt tttatgaacc 6780
acaaatcatt actacagaca acacatttgt gtctggtaac tgtgatgttg taataggaat 6840
tgtcaacaac acagtttatg atcctttgca acctgaatta gactcattca aggaggagtt 6900
agataaatat tttaagaatc atacatcacc agatgttgat ttaggtgaca tctctggcat 6960
taatgcttca gttgtaaaca ttcaaaaaga aattgaccgc ctcaatgagg ttgccaagaa 7020
tttaaatgaa tctctcatcg atctccaaga acttggaaag tatgagcagt atataaaatg 7080
gccatggtac atttggctag gttttatagc tggcttgatt gccatagtaa tggtgacaat 7140

-continued

```
tatgctttgc tgtatgacca gttgctgtag ttgtctcaag ggctgttgtt cttgtggatc   7200
ctgctgcaaa tttgatgaag acgactctga gccagtgctc aaaggagtcg cattagctta   7260
cacataacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatcccct a gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgatacccc gcagaggttc cgtgttgttt   7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gatagggggc accagtcttc   8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccct cacaatgaca gccagaaggc ccggacaaaa   8460
aagcccccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggacccccg aggaccaacc cccaaggctg cccccgatcc   8640
aaaccaccaa ccgcatcccc accacccccg ggaaagaaac cccagcaat tggaaggccc   8700
ctccccctct tcctcaacac aagaactcca caaccgaacc gcacaagcga ccgaggtgac   8760
ccaaccgcag gcatccgact ccctagacag atcctctctc cccggcaaac taaacaaaac   8820
ttagggccaa ggaacataca cacccaacag aacccagacc ccggcccacg gcgccgcgcc   8880
cccaaccccc gacaaccaga gggagccccc aaccaatccc gccggctccc ccggtgccca   8940
caggcaggga caccaacccc cgaacagacc cagcacccaa ccatcgacaa tccaagacgg   9000
gggggccccc ccaaaaaaag gcccccaggg gccgacagcc agcaccgcga ggaagcccac   9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggaccccc   9240
gaaccgcaaa ggacatcagt atcccacagc ctctccaagt cccccggtct cctccccttc   9300
tcgaagggac caaaagatca atccaccaca cccgacgaca ctcaactccc cacccctaaa   9360
ggagacaccg ggaatcccag aatcaagact catccaatgt ccatcatggg tctcaaggtg   9420
aacgtctctg ccatattcat ggcagtactg ttaactctcc aaacacccac cggtcaaatc   9480
cattggggca atctctctaa gataggggtg gtaggaatag gaagtgcaag ctacaaagtt   9540
```

-continued

```
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa gaccggttca gagtgtagct   9720
tcaagtagga gacacaagag atttgcggga gtagtcctgg caggtgcggc cctaggcgtc   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg gccagaagct cgggctcaaa  10020
ttgctcagat actatacaga aatcctgtca ttatttggcc ccagcttacg ggaccccata  10080
tctgcggaga tatctatcca ggctttgagc tatgcgcttg gaggagacat caataaggtg  10140
ttagaaaagc tcggatacag tggaggtgat ttactgggca tcttagagag cagaggaata  10200
aaggcccgga taactcacgt cgacacagag tcctacttca ttgtcctcag tatagcctat  10260
ccgacgctgt ccgagattaa gggggtgatt gtccaccggc tagagggggt ctcgtacaac  10320
ataggctctc aagagtggta taccactgtg cccaagtatg ttgcaaccca agggtacctt  10380
atctcgaatt ttgatgagtc atcgtgtact ttcatgccag aggggactgt gtgcagccaa  10440
aatgccttgt acccgatgag tcctctgctc caagaatgcc tccgggggtc caccaagtcc  10500
tgtgctcgta cactcgtatc cgggtctttt gggaaccggt tcattttatc acaagggaac  10560
ctaatagcca attgtgcatc aatcctttgc aagtgttaca caacaggaac gatcattaat  10620
caagaccctg acaagatcct aacatacatt gctgccgatc actgcccggt agtcgaggtg  10680
aacggcgtga ccatccaagt cgggagcagg aggtatccag atgctgtgta cttgcacaga  10740
attgacctcg gtcctcccat atcattggag aggttggacg tagggacaaa tctggggaat  10800
gcaattgcta agttggagga tgccaaggaa ttgttggagt catcggacca gatattgagg  10860
agtatgaaag gtttatcgag cactagcata gtctacatcc tgattgcagt gtgtcttgga  10920
gggttgatag ggatccccgc tttaatatgt tgctgcaggg ggcgttgtaa caaaaaggga  10980
gaacaagttg gtatgtcaag accaggccta aagcctgatc ttacgggaac atcaaaatcc  11040
tatgtaaggt cgctctgatc ctctacaact cttgaaacac aaatgtccca caagtctcct  11100
cttcgtcatc aagcaaccac cgcacccagc atcaagccca cctgaaatta tctccggctt  11160
ccctctggcc gaacaatatc ggtagttaat taaaacttag ggtgcaagat catccacaat  11220
gtcaccacaa cgagaccgga taaatgcctt ctacaaagat aacccccatc ccaagggaag  11280
taggatagtc attaacagag aacatcttat gattgataga ccttatgttt tgctggctgt  11340
tctgtttgtc atgtttctga gcttgatcgg gttgctagcc attgcaggca ttagacttca  11400
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
tgaagtgggc ctgaggacac ctcagagatt cactgaccta gtgaaattca tctctgacaa  11580
gattaaattc cttaatccgg atagggagta cgacttcaga gatctcactt ggtgtatcaa  11640
cccgccagag agaatcaaat tggattatga tcaatactgt gcagatgtgg ctgctgaaga  11700
gctcatgaat gcattggtga actcaactct actggagacc agaacaacca atcagttcct  11760
agctgtctca aagggaaact gctcagggcc cactacaatc agaggtcaat tctcaaacat  11820
gtcgctgtcc ctgttagact tgtatttagg tcgaggttac aatgtgtcat ctatagtcac  11880
```

-continued tatgacatcc cagggaatgt atgggggaac ttacctagtg gaaaagccta atctgagcag 11940
caaaaggtca gagttgtcac aactgagcat gtaccgagtg tttgaagtag gtgttatcag 12000
aaatccgggt ttgggggctc cggtgttcca tatgacaaac tatcttgagc aaccagccag 12060
taatgatctc agcaactgta tggtggcttt gggggagctc aaactcgcag ccctttgtca 12120
cggggaagat tctatcacaa ttccctatca gggatcaggg aaaggtgtca gcttccagct 12180
cgtcaagcta ggtgtctgga aatccccaac cgacatgcaa tcctgggtcc ccttatcaac 12240
ggatgatcca gtgatagaca ggctttacct ctcatctcac agaggtgtta tcgctgacaa 12300
tcaagcaaaa tgggctgtcc cgacaacacg aacagatgac aagttgcgaa tggagacatg 12360
cttccaacag gcgtgtaagg gtaaaatcca agcactctgc gagaatcccg agtgggcacc 12420
attgaaggat aacaggattc cttcatacgg ggtcttgtct gttgatctga gtctgacagt 12480
tgagcttaaa atcaaaattg cttcgggatt cgggccattg atcacacacg gttcagggat 12540
ggacctatac aaatccaacc acaacaatgt gtattggctg actatcccgc caatgaagaa 12600
cctagcctta ggtgtaatca acacattgga gtggataccg agattcaagg ttagtcccta 12660
cctcttcaat gtcccaatta aggaagcagg cgaagactgc catgccccaa catacctacc 12720
tgcggaggtg gatggtgatg tcaaactcag ttccaatctg gtgattctac ctggtcaaga 12780
tctccaatat gttttggcaa cctacgatac ttccagggtt gaacatgctg tggtttatta 12840
cgtttacagc ccaggccgct cattttctta cttttatcct tttaggttgc ctataaaggg 12900
ggtccccatc gaattacaag tggaatgctt cacatgggac caaaaactct ggtgccgtca 12960
cttctgtgtg cttgcggact cagaatctgg tggacatatc actcactctg ggatggtggg 13020
catgggagtc agctgcacag tcacccggga agatggaacc aatcgcagat agggctgcta 13080
gtgaaccaat ctcatgatgt cacccagaca tcaggcatac ccactagtgt gaaatagaca 13140
tcagaattaa gaaaaacgta gggtccaagt ggttccccgt tatggactcg ctatctgtca 13200
accagatctt ataccctgaa gttcacctag atagcccgat agttaccaat aagatagtag 13260
ccatcctgga gtatgctcga gtccctcacg cttacagcct ggaggaccct acactgtgtc 13320
agaacatcaa gcaccgccta aaaaacggat tttccaacca aatgattata aacaatgtgg 13380
aagttgggaa tgtcatcaag tccaagctta ggagttatcc ggcccactct catattccat 13440
atccaaattg taatcaggat ttatttaaca tagaagacaa agagtcaacg aggaagatcc 13500
gtgaactcct caaaaagggg aattcgctgt actccaaagt cagtgataag gttttccaat 13560
gcttaaggga cactaactca cggcttggcc taggctccga attgagggag gacatcaagg 13620
agaaagttat taacttggga gtttacatgc acagctccca gtggtttgag ccctttctgt 13680
tttggtttac agtcaagact gagatgaggt cagtgattaa atcacaaacc catacttgcc 13740
ataggaggag acacacacct gtattcttca ctggtagttc agttgagttg ctaatctctc 13800
gtgaccttgt tgctataatc agtaaagagt ctcaacatgt atattacctg acatttgaac 13860
tggttttgat gtattgtgat gtcatagagg ggaggttaat gacagagacc gctatgacta 13920
ttgatgctag gtatacagag cttctaggaa gagtcagata catgtggaaa ctgatagatg 13980
gtttcttccc tgcactcggg aatccaactt atcaaattgt agccatgctg gagcctcttt 14040
cacttgctta cctgcagctg agggatataa cagtagaact cagaggtgct ttccttaacc 14100
actgctttac tgaaatacat gatgttcttg accaaaacgg gttttctgat gaaggtactt 14160
atcatgagtt aattgaagct ctagattaca ttttcataac tgatgacata catctgacag 14220
gggagatttt ctcatttttc agaagtttcg gccaccccag acttgaagca gtaacggctg 14280
ctgaaaatgt taggaaatac atgaatcagc ctaaagtcat tgtgtatgag actctgatga 14340
aaggtcatgc catattttgt ggaatcataa tcaacggcta tcgtgacagg cacggaggca 14400
gttggccacc gctgaccctc cccctgcatg ctgcagacac aatccggaat gctcaagctt 14460
caggtgaagg gttaacacat gagcagtgcg ttgataactg gagatctttt gctggagtga 14520
aatttggctg ctttatgcct cttagcctgg atagtgatct gacaatgtac ctaaaggaca 14580
aggcacttgc tgctctccaa agggaatggg attcagttta cccgaaagag ttcctgcgtt 14640
acgaccctcc caagggaacc gggtcacgga ggcttgtaga tgttttcctt aatgattcga 14700
gctttgaccc atatgatgtg ataatgtatg ttgtaagtgg agcttacctc catgaccctg 14760
agttcaacct gtcttacagc ctgaaagaaa aggagatcaa ggaaacaggt agactttttg 14820
ctaaaatgac ttacaaaatg agggcatgcc aagtgattgc tgaaaatcta atctcaaacg 14880
ggattggcaa atattttaag gacaatggga tggccaagga tgagcacgat ttgactaagg 14940
cactccacac tctagctgtc tcaggagtcc ccaaagatct caaagaaagt cacagggggg 15000
ggccagtctt aaaaacctac tcccgaagcc cagtccacac aagtaccagg aacgtgagag 15060
cagcaaaagg gtttataggg ttccctcaag taattcggca ggaccaagac actgatcatc 15120
cggagaatat ggaagcttac gagacagtca gtgcatttat cacgactgat ctcaagaagt 15180
actgccttaa ttggagatat gagaccatca gcttgtttgc acagaggcta aatgagattt 15240
acggattgcc ctcatttttc cagtggctgc ataagaggct tgagacctct gtcctgtatg 15300
taagtgaccc tcattgcccc cccgaccttg acgcccatat cccgttatat aaagtcccca 15360
atgatcaaat cttcattaag taccctatgg gaggtataga agggtattgt cagaagctgt 15420
ggaccatcag caccattccc tatctatacc tggctgctta tgagagcgga gtaaggattg 15480
cttcgttagt gcaaggggac aatcagacca tagccgtaac aaaaagggta cccagcacat 15540
ggccctacaa ccttaagaaa cgggaagctg ctagagtaac tagagattac tttgtaattc 15600
ttaggcaaag gctacatgat attggccatc acctcaaggc aaatgagaca attgtttcat 15660
cacatttttt tgtctattca aaaggaatat attatgatgg gctacttgtg tcccaatcac 15720
tcaagagcat cgcaagatgt gtattctggt cagagactat agttgatgaa acaagggcag 15780
catgcagtaa tattgctaca acaatggcta aaagcatcga gagaggttat gaccgttacc 15840
ttgcatattc cctgaacgtc ctaaaagtga tacagcaaat tctgatctct cttggcttca 15900
caatcaattc aaccatgacc cggg atgtag tcatacccct cctcacgaac aacgacctct 15960
taataaggat ggcactgttg cccgctccta ttggggggat gaattatctg aatatgagca 16020
ggctgtttgt cagaaacatc ggtgatccag taacatcatc aattgctgat ctcaagagaa 16080
tgattctcgc ctcactaatg cctgaagaga ccctccatca agtaatgaca caacaaccgg 16140
gggactcttc attcctagac tgggctagcg acccttactc agcaaatctt gtatgtgtcc 16200
agagcatcac tagactcctc aagaacataa ctgcaaggtt tgtcctgatc catagtccaa 16260
acccaatgtt aaaaggatta ttccatgatg acagtaaaga agaggacgag ggactggcgg 16320
cattcctcat ggacaggcat attatagtac ctagggcagc tcatgaaatc ctggatcata 16380
gtgtcacagg ggcaagagag tctattgcag gcatgctgga taccacaaaa ggcctgattc 16440
gagccagcat gaggaagggg gggttaacct ctcgagtgat aaccagattg tccaattatg 16500
actatgaaca attcagagca gggatggtgc tattgacagg aagaaagaga aatgtcctca 16560
ttgacaaaga gtcatgttca gtgcagctgg cgagagctct aagaagccat atgtgggcga 16620

-continued

```
ggctagctcg aggacggcct atttacggcc ttgaggtccc tgatgtacta gaatctatgc  16680
gaggccacct tattcggcgt catgagacat gtgtcatctg cgagtgtgga tcagtcaact  16740
acggatggtt ttttgtcccc tcgggttgcc aactggatga tattgacaag gaaacatcat  16800
ccttgagagt cccatatatt ggttctacca ctgatgagag aacagacatg aagcttgcct  16860
tcgtaagagc cccaagtcga tccttgcgat ctgctgttag aatagcaaca gtgtactcat  16920
gggcttacgg tgatgatgat agctcttgga acgaagcctg gttgttggct aggcaaaggg  16980
ccaatgtgag cctggaggag ctaagggtga tcactcccat ctcaacttcg actaatttag  17040
cgcataggtt gagggatcgt agcactcaag tgaaatactc aggtacatcc cttgtccgag  17100
tggcgaggta taccacaatc tccaacgaca atctctcatt tgtcatatca gataagaagg  17160
ttgatactaa ctttatatac caacaaggaa tgcttctagg gttgggtgtt ttagaaacat  17220
tgtttcgact cgagaaagat accggatcat ctaacacggt attacatctt cacgtcgaaa  17280
cagattgttg cgtgatcccg atgatagatc atcccaggat acccagctcc cgcaagctag  17340
agctgagggc agagctatgt accaacccat tgatatatga taatgcacct ttaattgaca  17400
gagatacaac aaggctatac acccagagcc ataggaggca ccttgtggaa tttgttacat  17460
ggtccacacc ccaactatat cacattttag ctaagtccac agcactatct atgattgacc  17520
tggtaacaaa atttgagaag gaccatatga atgaaatttc agctctcata ggggatgacg  17580
atatcaatag tttcataact gagtttctgc tcatagagcc aagattattc actatctact  17640
tgggccagtg tgcggccatc aattgggcat ttgatgtaca ttatcataga ccatcaggga  17700
aatatcagat gggtgagctg ttgtcatcgt tcctttctag aatgagcaaa ggagtgttta  17760
aggtgcttgt caatgctcta agccacccaa agatctacaa gaaattctgg cattgtggta  17820
ttatagagcc tatccatggt ccttcacttg atgctcaaaa cttgcacaca actgtgtgca  17880
acatggttta cacatgctat atgacctacc tcgacctgtt gttgaatgaa gagttagaag  17940
agttcacatt tctcttgtgt gaaagcgacg aggatgtagt accggacaga ttcgacaaca  18000
tccaggcaaa acacttatgt gttctggcag atttgtactg tcaaccaggg acctgcccac  18060
caattcgagg tctaagaccg gtagagaaat gtgcagttct aaccgaccat atcaaggcag  18120
aggctaggtt atctccagca ggatcttcgt ggaacataaa tccaattatt gtagaccatt  18180
actcatgctc tctgacttat ctccggcgag gatcgatcaa acagataaga ttgagagttg  18240
atccaggatt cattttcgac gccctcgctg aggtaaatgt cagtcagcca aagatcggca  18300
gcaacaacat ctcaaatatg agcatcaagg ctttcagacc ccacacgat gatgttgcaa  18360
aattgctcaa agatatcaac acaagcaagc acaatcttcc catttcaggg ggcaatctcg  18420
ccaattatga aatccatgct ttccgcagaa tcgggttgaa ctcatctgct tgctacaaag  18480
ctgttgagat atcaacatta attaggagat gccttgagcc aggggaggac ggcttgttct  18540
tgggtgaggg atcgggttcc atgttgatca cttataagga gatacttaaa ctaaacaagt  18600
gcttctataa tagtggggtt tccgccaatt ctagatctgg tcaaagggaa ttagcaccct  18660
atccctccga agttggcctt gtcgaacaca gaatgggagt aggtaatatt gtcaaagtgc  18720
tctttaacgg gaggcccgaa gtcacgtggg taggcagtgt agattgcttc aatttcatag  18780
ttagtaatat ccctacctct agtgtggggt ttatccattc agatatagag accttgccta  18840
acaaagatac tatagagaag ctagaggaat tggcagccat cttatcgatg gctctgctcc  18900
tgggcaaaat aggatcaata ctggtgatta agcttatgcc tttcagcggg gattttgttc  18960
agggatttat aagttatgta gggtcccatt atagagaagt gaaccttgta taccctagat  19020
```

acagcaactt catatctact gaatcttatt tggttatgac agatctcaag gctaaccggc 19080
taatgaatcc tgaaaagatt aagcagcaga taattgaatc atctgtgagg acttcacctg 19140
gacttatagg tcacatccta tccattaagc aactaagctg catacaagca attgtgggag 19200
acgcagttag tagaggtgat atcaatccta ctctgaaaaa acttacacct atagagcagg 19260
tgctgatcaa ttgcgggttg gcaattaacg gacctaagct gtgcaaagaa ttgatccacc 19320
atgatgttgc ctcagggcaa gatggattgc ttaattctat actcatcctc tacagggagt 19380
tggcaagatt caaagacaac caaagaagtc aacaagggat gttccacgct taccccgtat 19440
tggtaagtag caggcaacga gaacttatat ctaggatcac ccgcaaattt tgggggcaca 19500
ttcttcttta ctccgggaac agaaagttga taaataagtt tatccagaat ctcaagtccg 19560
gctatctgat actagactta caccagaata tcttcgttaa gaatctatcc aagtcagaga 19620
aacagattat tatgacgggg ggtttgaaac gtgagtgggt ttttaaggta acagtcaagg 19680
agaccaaaga atggtataag ttagtcggat acagtgccct gattaaggac taattggttg 19740
aactccggaa ccctaatcct gccctaggtg gttaggcatt atttgcaata gattaaagaa 19800
aactttgaaa atacgaagtt tctattccca gctttgtctg gtggccggca tggtcccagc 19860
ctcctcgctg gcgccggctg ggcaacattc cgaggggacc gtcccctcgg taatggcgaa 19920
tgggacgcgg ccgatccggc tgctaacaaa gcccgaaagg aagctgagtt ggctgctgcc 19980
accgctgagc aataactagc ataacccctt ggggcctcta aacgggtctt gaggggtttt 20040
ttgctgaaag gaggaactat atccggatgc ggccgatccg gctgctaaca aagcccgaaa 20100
ggaagctgag ttggctgctg ccaccgctga gcaataacta gcataacccc ttggggcctc 20160
taaacgggtc ttgaggggtt ttttgctgaa aggaggaact atatccggat ggccgccacc 20220
ggccggtggg ccttgcagca catccccctt tcgccagctg gcgtaatagc gaagaggccc 20280
gcaccgatcg cccttcccaa cagttgcgca gcctgaatgg cgaatgggac gcgccctgta 20340
gcggcgcatt aagcgcggcg ggtgtggtgg ttacgcgcag cgtgaccgct acacttgcca 20400
gcgccctagc gcccgctcct ttcgctttct tcccttcctt tctcgccacg ttcgccggct 20460
ttccccgtca agctctaaat cgggggctcc ctttagggtt ccgatttagt gctttacggc 20520
acctcgaccc caaaaaactt gattagggtg atggttcacg tgggccatcg ccctgataga 20580
cggtttttcg ccctttgacg ttggagtcca cgttctttaa tagtggactc ttgttccaaa 20640
ctggaacaac actcaaccct atctcggtct attcttttga tttataaggg attttgccga 20700
tttcggccta ttggttaaaa aatgagctga tttaacaaaa atttaacgcg aattttaaca 20760
aaatattaac gcttacaatt taggtggcac ttttcgggga aatgtgcgcg gaacccctat 20820
ttgtttattt ttctaaatac attcaaatat gtatccgctc atgagacaat aaccctgata 20880
aatgcttcaa taatattgaa aaaggaagag tatgagtatt caacatttcc gtgtcgccct 20940
tattcccttt tttgcggcat tttgccttcc tgtttttgct cacccagaaa cgctggtgaa 21000
agtaaaagat gctgaagatc agttgggtgc acgagtgggt tacatcgaac tggatctcaa 21060
cagcggtaag atccttgaga gttttcgccc cgaagaacgt tttccaatga tgagcacttt 21120
taaagttctg ctatgtggcg cggtattatc ccgtattgac gccgggcaag agcaactcgg 21180
tcgccgcata cactattctc agaatgactt ggttgagtac tcaccagtca cagaaaagca 21240
tcttacggat ggcatgacag taagagaatt atgcagtgct gccataacca tgagtgataa 21300
cactgcggcc aacttacttc tgacaacgat cggaggaccg aaggagctaa ccgctttttt 21360

-continued

```
gcacaacatg gggatcatg taactcgcct tgatcgttgg gaaccggagc tgaatgaagc  21420

cataccaaac gacgagcgtg acaccacgat gcctgtagca atggcaacaa cgttgcgcaa  21480

actattaact ggcgaactac ttacactagc ttcccggcaa caattaatag actggatgga  21540

ggcggataaa gttgcaggac cacttctgcg ctcggccctt ccggctggct ggtttattgc  21600

tgataaatct ggagccggtg agcgtgggtc tcgcggtatc attgcagcac tggggccaga  21660

tggtaagccc tcccgtatcg tagttatcta cacgacgggg agtcaggcaa ctatggatga  21720

acgaaataga cagatcgctg agataggtgc ctcactgatt aagcattggt aactgtcaga  21780

ccaagtttac tcatatatac tttagattga tttaaaactt catttttaat ttaaaaggat  21840

ctaggtgaag atcctttttg ataatctcat gaccaaaatc ccttaacgtg agttttcgtt  21900

ccactgagcg tcagaccccg tagaaaagat caaaggatct tcttgagatc cttttttct  21960

gcgcgtaatc tgctgcttgc aaacaaaaaa accaccgcta ccagcggtgg tttgtttgcc  22020

ggatcaagag ctaccaactc tttttccgaa ggtaactggc ttcagcagag cgcagatacc  22080

aaatactgtt cttctagtgt agccgtagtt aggccaccac ttcaagaact ctgtagcacc  22140

gcctacatac ctcgctctgc taatcctgtt accagtggct gctgccagtg gcgataagtc  22200

gtgtcttacc gggttggact caagacgata gttaccggat aaggcgcagc ggtcgggctg  22260

aacgggggt tcgtgcacac agcccagctt ggagcgaacg acctacaccg aactgagata  22320

cctacagcgt gagctatgag aaagcgccac gcttcccgaa gggagaaagg cggacaggta  22380

tccggtaagc ggcagggtcg gaacaggaga gcgcacgagg gagcttccag gggaaacgc  22440

ctggtatctt tatagtcctg tcgggtttcg ccacctctga cttgagcgtc gatttttgtg  22500

atgctcgtca gggggcgga gcctatggaa aaacgccagc aacgcggcct ttttacggtt  22560

cctggccttt tgctggcctt ttgctcacat gttctttcct gcgttatccc ctgattctgt  22620

ggataaccgt attaccgcct ttgagtgagc tgataccgct cgccgcagcc gaacgaccga  22680

gcgcagcgag tcagtgagcg aggaagcgga agagcgccca atacgcaaac cgcctctccc  22740

cgcgcgttgg ccgattcatt aatgcagctg gcacgacagg tttcccgact ggaaagcggg  22800

cagtgagcgc aacgcaatta atgtgagtta gctcactcat taggcacccc aggctttaca  22860

ctttatgctt ccggctcgta tgttgtgtgg aattgtgagc ggacaacaat ttcacacagg  22920

aaacagctat gaccatgatt acgccaagct cgggcggccg cttgtaatac gactcactat  22980

a                                                                 22981
```

```
<210> SEQ ID NO 19
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-PP

<400> SEQUENCE: 19
```

```
accaaacaaa gttgggtaag gatagttcaa tcaatgatca ttttctagtg cacttaggat     60

tcaagatcct attatcaggg acaagagcag gattaaggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtcaggtt aattggaaac ccggatgtga    300
```

```
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gctcaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
```

-continued

```
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagtac aacctaaatc cattataaaa aacttaggag caaagtgatt   3420
gcctcccaag ttccacaggc gcgccatgtt cgtcttcctg gtcctgctgc ctctggtctc   3480
ctcacagtgc gtcaatctga caactcggac tcagctgcca cctgcttata ctaatagctt   3540
caccagaggc gtgtactatc ctgacaaggt gtttagaagc tccgtgctgc actctacaca   3600
ggatctgttt ctgccattct ttagcaacgt gacctggttc cacgccatcc acgtgagcgg   3660
caccaatggc acaaagcggt tcgacaatcc cgtgctgcct tttaacgatg gcgtgtactt   3720
cgcctctacc gagaagagca acatcatcag aggctggatc tttggcacca cactggactc   3780
caagacacag tctctgctga tcgtgaacaa tgccaccaac gtggtcatca aggtgtgcga   3840
gttccagttt tgtaatgatc ccttcctggg cgtgtactat cacaagaaca ataagagctg   3900
gatggagtcc gagtttagag tgtattctag cgccaacaac tgcacatttg agtacgtgag   3960
ccagcctttc ctgatggacc tggagggcaa gcagggcaat ttcaagaacc tgagggagtt   4020
cgtgtttaag aatatcgacg gctacttcaa aatctactct aagcacaccc ccatcaacct   4080
ggtgcgcgac ctgcctcagg gcttcagcgc cctggagccc ctggtggatc tgcctatcgg   4140
catcaacatc acccggtttc agacactgct ggccctgcac agaagctacc tgacacccgg   4200
cgactcctct agcggatgga ccgccggcgc tgccgcctac tatgtgggct acctccagcc   4260
ccggaccttc ctgctgaagt acaacgagaa tggcaccatc acagacgcag tggattgcgc   4320
cctggacccc ctgagcgaga caaagtgtac actgaagtcc tttaccgtgg agaagggcat   4380
ctatcagaca tccaatttca gggtgcagcc aaccgagtct atcgtgcgct ttcctaatat   4440
cacaaacctg tgcccatttg gcgaggtgtt caacgcaacc cgcttcgcca gcgtgtacgc   4500
ctggaatagg aagcggatca gcaactgcgt ggccgactat agcgtgctgt acaactccgc   4560
ctctttcagc acctttaagt gctatggcgt gtcccccaca aagctgaatg acctgtgctt   4620
taccaacgtc tacgccgatt ctttcgtgat caggggcgac gaggtgcgcc agatcgcccc   4680
cggccagaca ggcaagatcg cagactacaa ttataagctg ccagacgatt tcaccggctg   4740
cgtgatcgcc tggaacagca acaatctgga ttccaaagtg ggcggcaact acaattatct   4800
gtaccggctg tttagaaaga gcaatctgaa gcccttcgag agggacatct ctacagaaat   4860
ctaccaggcc ggcagcaccc cttgcaatgg cgtggagggc tttaactgtt atttcccact   4920
ccagtcctac ggcttccagc ccacaaacgg cgtgggctat cagccttacc gcgtggtggt   4980
gctgagcttt gagctgctgc acgccccagc aacagtgtgc ggccccaaga agtccaccaa   5040
```

-continued

```
tctggtgaag aacaagtgcg tgaacttcaa cttcaacggc ctgaccggca caggcgtgct   5100
gaccgagtcc aacaagaagt tcctgccatt tcagcagttc ggcagggaca tcgcagatac   5160
cacagacgcc gtgcgcgacc cacagaccct ggagatcctg gacatcacac cctgctcttt   5220
cggcggcgtg agcgtgatca cacccggcac caatacaagc aaccaggtgg ccgtgctgta   5280
tcaggacgtg aattgtaccg aggtgcccgt ggctatccac gccgatcagc tgaccccaac   5340
atggcgggtg tacagcaccg gctccaacgt cttccagaca agagccggat gcctgatcgg   5400
agcagagcac gtgaacaatt cctatgagtg cgacatccca atcggcgccg gcatctgtgc   5460
ctcttaccag acccagacaa actctcccag aagagcccgg agcgtggcct cccagtctat   5520
catcgcctat accatgtccc tgggcgccga gaacagcgtg gcctactcta acaatagcat   5580
cgccatccca accaacttca caatctctgt gaccacagag atcctgcccg tgtccatgac   5640
caagacatct gtggactgca caatgtatat ctgtggcgat tctaccgagt gcagcaacct   5700
gctgctccag tacggcagct tttgtaccca gctgaataga gccctgacag gcatcgccgt   5760
ggagcaggat aagaacacac aggaggtgtt cgcccaggtg aagcaaatct acaagacccc   5820
ccctatcaag gactttggcg gcttcaattt ttcccagatc ctgcctgatc catccaagcc   5880
ttctaagcgg agctttatcg aggacctgct gttcaacaag gtgaccctgg ccgatgccgg   5940
cttcatcaag cagtatggcg attgcctggg cgacatcgca gccagggacc tgatctgcgc   6000
ccagaagttt aatggcctga ccgtgctgcc acccctgctg acagatgaga tgatcgcaca   6060
gtacacaagc gccctgctgg ccggcaccat cacatccgga tggaccttcg gcgcaggagc   6120
cgccctccag atcccctttg ccatgcagat ggcctatagg ttcaacggca tcggcgtgac   6180
ccagaatgtg ctgtacgaga accagaagct gatcgccaat cagtttaact ccgccatcgg   6240
caagatccag gacagcctgt cctctacagc cagcgccctg ggcaagctcc aggatgtggt   6300
gaatcagaac gcccaggccc tgaataccct ggtgaagcag ctgagcagca acttcggcgc   6360
catctctagc gtgctgaatg acatcctgag ccggctggac cctcctgagg cagaggtgca   6420
gatcgaccgg ctgatcaccg gccggctcca gagcctccag acctatgtga cacagcagct   6480
gatcagggcc gccgagatca gggccagcgc caatctggca gcaaccaaga tgtccgagtg   6540
cgtgctgggc cagtctaaga gagtggactt ttgtggcaag ggctatcacc tgatgtcctt   6600
ccctcagtct gccccacacg gcgtggtgtt tctgcacgtg acctacgtgc ccgcccagga   6660
gaagaacttc accacagccc ctgccatctg ccacgatggc aaggcccact ttccaaggga   6720
gggcgtgttc gtgtccaacg gcacccactg gtttgtgaca cagcgcaatt tctacgagcc   6780
ccagatcatc accacagaca acaccttcgt gagcggcaac tgtgacgtgg tcatcggcat   6840
cgtgaacaat accgtgtatg atccactcca gcccgagctg gacagcttta aggaggagct   6900
ggataagtat ttcaagaatc acacctcccc tgacgtggat ctgggcgaca tcagcggcat   6960
caatgcctcc gtggtgaaca tccagaagga gatcgaccgc ctgaacgagg tggctaagaa   7020
tctgaacgag agcctgatcg acctccagga gctgggcaag tatgagcagt acatcaagtg   7080
gccctggtac atctggctgg gcttcatcgc cggcctgatc gccatcgtga tggtgaccat   7140
catgctgtgc tgtatgacat cctgctgttc ttgcctgaag ggctgctgta gctgtggctc   7200
ctgctgtaag tttgacgagg atgactctga acctgtgctg aagggcgtgg cgctggctta   7260
cacctaacgc gcgacgtcct acagctcaac ttacctgcca accccatgcc agtcgaccca   7320
actagtacaa cctaaatcca ttataaaaaa cttaggagca aagtgattgc ctcccaagtt   7380
```

-continued ccacaatgac agagatctac gacttcgaca agtcggcatg ggacatcaaa gggttgatcg 7440
ctccgataca acccaccacc tacagtgatg gcaggctggt gccccaggtc agagtcatag 7500
atcctggtct aggcgacagg aaggatgaat gctttatgta catgtttctg ctgggggttg 7560
ttgaggacag cgatccccta gggcctccaa tcgggcgagc atttgggtcc ctgcccttag 7620
gtgttggcag atccacagca aagcccgaaa aactcctcaa agaggccact gagcttgaca 7680
tagttgttag acgtacagca gggctcaatg aaaaactggt gttctacaac aacaccccac 7740
taactctcct cacaccttgg agaaaggtcc taacaacagg gagtgtcttc aacgcaaacc 7800
aagtgtgcaa tgcggttaat ctgataccgc tcgataccccc gcagaggttc cgtgttgttt 7860
atatgagcat cacccgtctt tcggataacg ggtattacac cgttcctaga agaatgctgg 7920
aattcagatc ggtcaatgca gtggccttca acctgctggt gacccttagg attgacaagg 7980
cgataggccc tgggaagatc atcgacaata cagagcaact tcctgaggca acatttatgg 8040
tccacatcgg gaacttcagg agaaagaaga gtgaagtcta ctctgccgat tattgcaaaa 8100
tgaaaatcga aaagatgggc ctggtttttg cacttggtgg gatagggggc accagtcttc 8160
acattagaag cacaggcaaa atgagcaaga ctctccatgc acaactcggg ttcaagaaga 8220
ccttatgtta cccgctgata gatatcaatg aagaccttaa tcgattactc tggaggagca 8280
gatgcaagat agtaagaatc caggcagttt tgcagccatc agttcctcaa gaattccgca 8340
tttacgacga cgtgatcata aatgatgacc aaggactatt caaagttctg tagaccgtag 8400
tgcccagcaa tgcccgaaaa cgaccccct cacaatgaca gccagaaggc ccggacaaaa 8460
aagccccctc cgaaagactc cacggaccaa gcgagaggcc agccagcagc cgacggcaag 8520
cgcgaacacc aggcggcccc agcacagaac agccctgata caaggccacc accagccacc 8580
ccaatctgca tcctcctcgt gggacccccg aggaccaacc cccaaggctg cccccgatcc 8640
aaaccaccaa ccgcatcccc accaccccg ggaaagaaac cccagcaat tggaaggccc 8700 ctcccctct tcctcaacac aagaactcca caaccgaacc gcacaagcga ccgaggtgac 8760
ccaaccgcag gcatccgact ccctagacag atcctctctc cccggcaaac taaacaaaac 8820
ttagggccaa ggaacataca cacccaacag aacccagacc ccggcccacg gcgccgcgcc 8880
cccaaccccc gacaaccaga gggagccccc aaccaatccc gccggctccc ccggtgccca 8940
caggcaggga caccaacccc cgaacagacc cagcacccaa ccatcgacaa tccaagacgg 9000
gggggccccc ccaaaaaaag gcccccaggg gccgacagcc agcaccgcga ggaagcccac 9060
ccaccccaca cacgaccacg gcaaccaaac cagaacccag accaccctgg gccaccagct 9120
cccagactcg gccatcaccc cgcagaaagg aaaggccaca acccgcgcac cccagccccg 9180
atccggcggg gagccaccca acccgaacca gcacccaaga gcgatccccg aaggaccccc 9240
gaaccgcaaa ggacatcagt atcccacagc ctctccaagt cccccggtct cctccccttc 9300
tcgaagggac caaaagatca atccaccaca cccgacgaca ctcaactccc caccccctaaa 9360 ggagacaccg ggaatcccag aatcaagact catccaatgt ccatcatggg tctcaaggtg 9420
aacgtctctg ccatattcat ggcagtactg ttaactctcc aaacacccac cggtcaaatc 9480
cattggggca atctctctaa gatagggggtg gtaggaatag gaagtgcaag ctacaaagtt 9540
atgactcgtt ccagccatca atcattagtc ataaaattaa tgcccaatat aactctcctc 9600
aataactgca cgagggtaga gattgcagaa tacaggagac tactgagaac agttttggaa 9660
ccaattagag atgcacttaa tgcaatgacc cagaatataa gaccggttca gagtgtagct 9720
tcaagtagga gacacaagag atttgcggga gtagtcctgg caggtgcggc cctaggcgtc 9780
gccacagctg ctcagataac agccggcatt gcacttcacc agtccatgct gaactctcaa 9840
gccatcgaca atctgagagc gagcctggaa actactaatc aggcaattga ggcaatcaga 9900
caagcagggc aggagatgat attggctgtt cagggtgtcc aagactacat caataatgag 9960
ctgataccgt ctatgaacca actatcttgt gatttaatcg gccagaagct cgggctcaaa 10020
ttgctcagat actatacaga aatcctgtca ttatttggcc ccagcttacg ggaccccata 10080
tctgcggaga tatctatcca ggctttgagc tatgcgcttg gaggagacat caataaggtg 10140
ttagaaaagc tcggatacag tggaggtgat ttactgggca tcttagagag cagaggaata 10200
aaggcccgga taactcacgt cgacacagag tcctacttca ttgtcctcag tatagcctat 10260
ccgacgctgt ccgagattaa gggggtgatt gtccaccggc tagagggggt ctcgtacaac 10320
ataggctctc aagagtggta taccactgtg cccaagtatg ttgcaaccca agggtacctt 10380
atctcgaatt ttgatgagtc atcgtgtact ttcatgccag aggggactgt gtgcagccaa 10440
aatgccttgt acccgatgag tcctctgctc caagaatgcc tccgggggtc caccaagtcc 10500
tgtgctcgta cactcgtatc cgggtctttt gggaaccggt tcattttatc acaagggaac 10560
ctaatagcca attgtgcatc aatcctttgc aagtgttaca caacaggaac gatcattaat 10620
caagaccctg acaagatcct aacatacatt gctgccgatc actgcccggt agtcgaggtg 10680
aacggcgtga ccatccaagt cgggagcagg aggtatccag atgctgtgta cttgcacaga 10740
attgacctcg gtcctcccat atcattggag aggttggacg tagggacaaa tctggggaat 10800
gcaattgcta agttggagga tgccaaggaa ttgttggagt catcggacca gatattgagg 10860
agtatgaaag gtttatcgag cactagcata gtctacatcc tgattgcagt gtgtcttgga 10920
gggttgatag ggatccccgc tttaatatgt tgctgcaggg ggcgttgtaa caaaaaggga 10980
gaacaagttg gtatgtcaag accaggccta aagcctgatc ttacgggaac atcaaaatcc 11040
tatgtaaggt cgctctgatc ctctacaact cttgaaacac aaatgtccca caagtctcct 11100
cttcgtcatc aagcaaccac cgcacccagc atcaagccca cctgaaatta tctccggctt 11160
ccctctggcc gaacaatatc ggtagttaat taaaacttag ggtgcaagat catccacaat 11220
gtcaccacaa cgagaccgga taaatgcctt ctacaaagat aacccccatc ccaagggaag 11280
taggatagtc attaacagag aacatcttat gattgataga ccttatgttt tgctggctgt 11340
tctgtttgtc atgtttctga gcttgatcgg gttgctagcc attgcaggca ttagacttca 11400
tcgggcagcc atctacaccg cagagatcca taaaagcctc agcaccaatc tagatgtaac 11460
taactcaatc gagcatcagg tcaaggacgt gctgacacca ctcttcaaaa tcatcggtga 11520
tgaagtgggc ctgaggacac ctcagagatt cactgaccta gtgaaattca tctctgacaa 11580
gattaaattc cttaatccgg atagggagta cgacttcaga gatctcactt ggtgtatcaa 11640
cccgccagag agaatcaaat tggattatga tcaatactgt gcagatgtgg ctgctgaaga 11700
gctcatgaat gcattggtga actcaactct actggagacc agaacaacca atcagttcct 11760
agctgtctca aagggaaact gctcagggcc cactacaatc agaggtcaat tctcaaacat 11820
gtcgctgtcc ctgttagact tgtatttagg tcgaggttac aatgtgtcat ctatagtcac 11880
tatgacatcc cagggaatgt atgggggaac ttacctagtg gaaaagccta atctgagcag 11940
caaaaggtca gagttgtcac aactgagcat gtaccgagtg tttgaagtag gtgttatcag 12000
aaatccgggt ttgggggctc cggtgttcca tatgacaaac tatcttgagc aaccagccag 12060
taatgatctc agcaactgta tggtggcttt gggggagctc aaactcgcag ccctttgtca 12120

-continued cggggaagat tctatcacaa ttccctatca gggatcaggg aaaggtgtca gcttccagct 12180
cgtcaagcta ggtgtctgga aatccccaac cgacatgcaa tcctgggtcc ccttatcaac 12240
ggatgatcca gtgatagaca ggctttacct ctcatctcac agaggtgtta tcgctgacaa 12300
tcaagcaaaa tgggctgtcc cgacaacacg aacagatgac aagttgcgaa tggagacatg 12360
cttccaacag gcgtgtaagg gtaaaatcca agcactctgc gagaatcccg agtgggcacc 12420
attgaaggat aacaggattc cttcatacgg ggtcttgtct gttgatctga gtctgacagt 12480
tgagcttaaa atcaaaattg cttcgggatt cgggccattg atcacacacg gttcagggat 12540
ggacctatac aaatccaacc acaacaatgt gtattggctg actatcccgc caatgaagaa 12600
cctagcctta ggtgtaatca acacattgga gtggataccg agattcaagg ttagtcccta 12660
cctcttcaat gtcccaatta aggaagcagg cgaagactgc catgccccaa catacctacc 12720
tgcggaggtg gatggtgatg tcaaactcag ttccaatctg gtgattctac ctggtcaaga 12780
tctccaatat gttttggcaa cctacgatac ttccagggtt gaacatgctg tggtttatta 12840
cgtttacagc ccaggccgct cattttctta cttttatcct tttaggttgc ctataaaggg 12900
ggtccccatc gaattacaag tggaatgctt cacatgggac caaaaactct ggtgccgtca 12960
cttctgtgtg cttgcggact cagaatctgg tggacatatc actcactctg ggatggtggg 13020
catgggagtc agctgcacag tcacccggga agatggaacc aatcgcagat agggctgcta 13080
gtgaaccaat ctcatgatgt cacccagaca tcaggcatac ccactagtgt gaaatagaca 13140
tcagaattaa gaaaaacgta gggtccaagt ggttccccgt tatggactcg ctatctgtca 13200
accagatctt ataccctgaa gttcacctag atagcccgat agttaccaat aagatagtag 13260
ccatcctgga gtatgctcga gtccctcacg cttacagcct ggaggaccct acactgtgtc 13320
agaacatcaa gcaccgccta aaaaacggat tttccaacca aatgattata aacaatgtgg 13380
aagttgggaa tgtcatcaag tccaagctta ggagttatcc ggcccactct catattccat 13440
atccaaattg taatcaggat ttatttaaca tagaagacaa agagtcaacg aggaagatcc 13500
gtgaactcct caaaaagggg aattcgctgt actccaaagt cagtgataag gttttccaat 13560
gcttaaggga cactaactca cggcttggcc taggctccga attgagggag gacatcaagg 13620
agaaagttat taacttggga gtttacatgc acagctccca gtggtttgag ccctttctgt 13680
tttggtttac agtcaagact gagatgaggt cagtgattaa atcacaaacc catacttgcc 13740
ataggaggag acacacacct gtattcttca ctggtagttc agttgagttg ctaatctctc 13800
gtgaccttgt tgctataatc agtaaagagt ctcaacatgt atattacctg acatttgaac 13860
tggttttgat gtattgtgat gtcatagagg ggaggttaat gacagagacc gctatgacta 13920
ttgatgctag gtatacagag cttctaggaa gagtcagata catgtggaaa ctgatagatg 13980
gtttcttccc tgcactcggg aatccaactt atcaaattgt agccatgctg gagcctcttt 14040
cacttgctta cctgcagctg agggatataa cagtagaact cagaggtgct ttccttaacc 14100
actgctttac tgaaatacat gatgttcttg accaaaacgg gttttctgat gaaggtactt 14160
atcatgagtt aattgaagct ctagattaca ttttcataac tgatgacata catctgacag 14220
gggagatttt ctcatttttc agaagtttcg gccaccccag acttgaagca gtaacggctg 14280
ctgaaaatgt taggaaatac atgaatcagc ctaaagtcat tgtgtatgag actctgatga 14340
aaggtcatgc catattttgt ggaatcataa tcaacggcta tcgtgacagg cacggaggca 14400
gttggccacc gctgaccctc cccctgcatg ctgcagacac aatccggaat gctcaagctt 14460
caggtgaagg gttaacacat gagcagtgcg ttgataactg gagatctttt gctggagtga 14520

-continued

```
aatttggctg ctttatgcct cttagcctgg atagtgatct gacaatgtac ctaaaggaca  14580
aggcacttgc tgctctccaa agggaatggg attcagttta cccgaaagag ttcctgcgtt  14640
acgaccctcc caagggaacc gggtcacgga ggcttgtaga tgttttcctt aatgattcga  14700
gctttgaccc atatgatgtg ataatgtatg ttgtaagtgg agcttacctc catgaccctg  14760
agttcaacct gtcttacagc ctgaaagaaa aggagatcaa ggaaacaggt agactttttg  14820
ctaaaatgac ttacaaaatg agggcatgcc aagtgattgc tgaaaatcta atctcaaacg  14880
ggattggcaa atattttaag gacaatggga tggccaagga tgagcacgat ttgactaagg  14940
cactccacac tctagctgtc tcaggagtcc ccaaagatct caaagaaagt cacagggggg  15000
ggccagtctt aaaaacctac tcccgaagcc cagtccacac aagtaccagg aacgtgagag  15060
cagcaaaagg gtttataggg ttccctcaag taattcggca ggaccaagac actgatcatc  15120
cggagaatat ggaagcttac gagacagtca gtgcatttat cacgactgat ctcaagaagt  15180
actgccttaa ttggagatat gagaccatca gcttgtttgc acagaggcta aatgagattt  15240
acggattgcc ctcatttttc cagtggctgc ataagaggct tgagacctct gtcctgtatg  15300
taagtgaccc tcattgcccc cccgaccttg acgcccatat cccgttatat aaagtcccca  15360
atgatcaaat cttcattaag taccctatgg gaggtataga agggtattgt cagaagctgt  15420
ggaccatcag caccattccc tatctatacc tggctgctta tgagagcgga gtaaggattg  15480
cttcgttagt gcaaggggac aatcagacca tagccgtaac aaaaagggta cccagcacat  15540
ggccctacaa ccttaagaaa cgggaagctg ctagagtaac tagagattac tttgtaattc  15600
ttaggcaaag gctacatgat attggccatc acctcaaggc aaatgagaca attgtttcat  15660
cacatttttt tgtctattca aaaggaatat attatgatgg gctacttgtg tcccaatcac  15720
tcaagagcat cgcaagatgt gtattctggt cagagactat agttgatgaa acaagggcag  15780
catgcagtaa tattgctaca acaatggcta aaagcatcga gagaggttat gaccgttacc  15840
ttgcatattc cctgaacgtc ctaaaagtga tacagcaaat tctgatctct cttggcttca  15900
caatcaattc aaccatgacc cgggatgtag tcatacccct cctcacgaac aacgacctct  15960
taataaggat ggcactgttg cccgctccta ttggggggat gaattatctg aatatgagca  16020
ggctgtttgt cagaaacatc ggtgatccag taacatcatc aattgctgat ctcaagagaa  16080
tgattctcgc ctcactaatg cctgaagaga ccctccatca agtaatgaca caacaaccgg  16140
gggactcttc attcctagac tgggctagcg acccttactc agcaaatctt gtatgtgtcc  16200
agagcatcac tagactcctc aagaacataa ctgcaaggtt tgtcctgatc catagtccaa  16260
acccaatgtt aaaaggatta ttccatgatg acagtaaaga agaggacgag ggactggcgg  16320
cattcctcat ggacaggcat attatagtac ctagggcagc tcatgaaatc ctggatcata  16380
gtgtcacagg ggcaagagag tctattgcag gcatgctgga taccacaaaa ggcctgattc  16440
gagccagcat gaggaagggg gggttaacct ctcgagtgat aaccagattg tccaattatg  16500
actatgaaca attcagagca gggatggtgc tattgacagg aagaaagaga aatgtcctca  16560
ttgacaaaga gtcatgttca gtgcagctgg cgagagctct aagaagccat atgtgggcga  16620
ggctagctcg aggacggcct atttacggcc ttgaggtccc tgatgtacta gaatctatgc  16680
gaggccacct tattcggcgt catgagacat gtgtcatctg cgagtgtgga tcagtcaact  16740
acggatggtt ttttgtcccc tcgggttgcc aactggatga tattgacaag gaaacatcat  16800
ccttgagagt cccatatatt ggttctacca ctgatgagag aacagacatg aagcttgcct  16860
```

-continued

```
tcgtaagagc cccaagtcga tccttgcgat ctgctgttag aatagcaaca gtgtactcat  16920
gggcttacgg tgatgatgat agctcttgga acgaagcctg gttgttggct aggcaaaggg  16980
ccaatgtgag cctggaggag ctaagggtga tcactcccat ctcaacttcg actaatttag  17040
cgcataggtt gagggatcgt agcactcaag tgaaatactc aggtacatcc cttgtccgag  17100
tggcgaggta taccacaatc tccaacgaca atctctcatt tgtcatatca gataagaagg  17160
ttgatactaa ctttatatac caacaaggaa tgcttctagg gttgggtgtt ttagaaacat  17220
tgtttcgact cgagaaagat accggatcat ctaacacggt attacatctt cacgtcgaaa  17280
cagattgttg cgtgatcccg atgatagatc atcccaggat acccagctcc cgcaagctag  17340
agctgagggc agagctatgt accaacccat tgatatatga taatgcacct ttaattgaca  17400
gagatacaac aaggctatac acccagagcc ataggaggca ccttgtggaa tttgttacat  17460
ggtccacacc ccaactatat cacattttag ctaagtccac agcactatct atgattgacc  17520
tggtaacaaa atttgagaag gaccatatga atgaaatttc agctctcata ggggatgacg  17580
atatcaatag tttcataact gagtttctgc tcatagagcc aagattattc actatctact  17640
tgggccagtg tgcggccatc aattgggcat ttgatgtaca ttatcataga ccatcaggga  17700
aatatcagat gggtgagctg ttgtcatcgt tcctttctag aatgagcaaa ggagtgttta  17760
aggtgcttgt caatgctcta agccacccaa agatctacaa gaaattctgg cattgtggta  17820
ttatagagcc tatccatggt ccttcacttg atgctcaaaa cttgcacaca actgtgtgca  17880
acatggttta cacatgctat atgacctacc tcgacctgtt gttgaatgaa gagttagaag  17940
agttcacatt tctcttgtgt gaaagcgacg aggatgtagt accggacaga ttcgacaaca  18000
tccaggcaaa acacttatgt gttctggcag atttgtactg tcaaccaggg acctgcccac  18060
caattcgagg tctaagaccg gtagagaaat gtgcagttct aaccgaccat atcaaggcag  18120
aggctaggtt atctccagca ggatcttcgt ggaacataaa tccaattatt gtagaccatt  18180
actcatgctc tctgacttat ctccggcgag gatcgatcaa acagataaga ttgagagttg  18240
atccaggatt cattttcgac gccctcgctg aggtaaatgt cagtcagcca aagatcggca  18300
gcaacaacat ctcaaatatg agcatcaagg ctttcagacc cccacacgat gatgttgcaa  18360
aattgctcaa agatatcaac acaagcaagc acaatcttcc catttcaggg ggcaatctcg  18420
ccaattatga aatccatgct ttccgcagaa tcgggttgaa ctcatctgct tgctacaaag  18480
ctgttgagat atcaacatta attaggagat gccttgagcc aggggaggac ggcttgttct  18540
tgggtgaggg atcgggttcc atgttgatca cttataagga gatacttaaa ctaaacaagt  18600
gcttctataa tagtggggtt tccgccaatt ctagatctgg tcaaagggaa ttagcaccct  18660
atccctccga agttggcctt gtcgaacaca gaatgggagt aggtaatatt gtcaaagtgc  18720
tctttaacgg gaggcccgaa gtcacgtggg taggcagtgt agattgcttc aatttcatag  18780
ttagtaatat ccctacctct agtgtggggt ttatccattc agatatagag accttgccta  18840
acaaagatac tatagagaag ctagaggaat tggcagccat cttatcgatg gctctgctcc  18900
tgggcaaaat aggatcaata ctggtgatta agcttatgcc tttcagcggg gattttgttc  18960
agggatttat aagttatgta gggtcccatt atagagaagt gaaccttgta taccctagat  19020
acagcaactt catatctact gaatcttatt tggttatgac agatctcaag gctaaccggc  19080
taatgaatcc tgaaaagatt aagcagcaga taattgaatc atctgtgagg acttcacctg  19140
gacttatagg tcacatccta tccattaagc aactaagctg catacaagca attgtgggag  19200
acgcagttag tagaggtgat atcaatccta ctctgaaaaa acttacacct atagagcagg  19260
```

tgctgatcaa ttgcgggttg gcaattaacg gacctaagct gtgcaaagaa ttgatccacc 19320
atgatgttgc ctcagggcaa gatggattgc ttaattctat actcatcctc tacagggagt 19380
tggcaagatt caaagacaac caaagaagtc aacaagggat gttccacgct taccccgtat 19440
tggtaagtag caggcaacga gaacttatat ctaggatcac ccgcaaattt tgggggcaca 19500
ttcttcttta ctccgggaac agaaagttga taaataagtt tatccagaat ctcaagtccg 19560
gctatctgat actagactta caccagaata tcttcgttaa gaatctatcc aagtcagaga 19620
aacagattat tatgacgggg ggtttgaaac gtgagtgggt ttttaaggta acagtcaagg 19680
agaccaaaga atggtataag ttagtcggat acagtgccct gattaaggac taattggttg 19740
aactccggaa ccctaatcct gccctaggtg gttaggcatt atttgcaata gattaaagaa 19800
aactttgaaa atacgaagtt tctattccca gctttgtctg gtggccggca tggtcccagc 19860
ctcctcgctg gcgccggctg ggcaacattc cgaggggacc gtcccctcgg taatggcgaa 19920
tgggacgcgg ccgatccggc tgctaacaaa gcccgaaagg aagctgagtt ggctgctgcc 19980
accgctgagc aataactagc ataacccctt ggggcctcta aacgggtctt gaggggtttt 20040
ttgctgaaag gaggaactat atccggatgc ggccgatccg gctgctaaca aagcccgaaa 20100
ggaagctgag ttggctgctg ccaccgctga gcaataacta gcataacccc ttggggcctc 20160
taaacgggtc ttgaggggtt ttttgctgaa aggaggaact atatccggat ggccgccacc 20220
ggccggtggg ccttgcagca catccccctt tcgccagctg gcgtaatagc gaagaggccc 20280
gcaccgatcg cccttcccaa cagttgcgca gcctgaatgg cgaatgggac gcgccctgta 20340
gcggcgcatt aagcgcggcg ggtgtggtgg ttacgcgcag cgtgaccgct acacttgcca 20400
gcgccctagc gcccgctcct ttcgctttct tcccttcctt tctcgccacg ttcgccggct 20460
ttccccgtca agctctaaat cgggggctcc ctttagggtt ccgatttagt gctttacggc 20520
acctcgaccc caaaaaactt gattagggtg atggttcacg tgggccatcg ccctgataga 20580
cggtttttcg ccctttgacg ttggagtcca cgttctttaa tagtggactc ttgttccaaa 20640
ctggaacaac actcaaccct atctcggtct attcttttga tttataaggg attttgccga 20700
tttcggccta ttggttaaaa aatgagctga tttaacaaaa atttaacgcg aattttaaca 20760
aaatattaac gcttacaatt taggtggcac ttttcgggga aatgtgcgcg gaacccctat 20820
ttgtttattt ttctaaatac attcaaatat gtatccgctc atgagacaat aaccctgata 20880
aatgcttcaa taatattgaa aaaggaagag tatgagtatt caacatttcc gtgtcgccct 20940
tattcccttt tttgcggcat tttgccttcc tgtttttgct cacccagaaa cgctggtgaa 21000
agtaaaagat gctgaagatc agttgggtgc acgagtgggt tacatcgaac tggatctcaa 21060
cagcggtaag atccttgaga gttttcgccc cgaagaacgt tttccaatga tgagcacttt 21120
taaagttctg ctatgtggcg cggtattatc ccgtattgac gccgggcaag agcaactcgg 21180
tcgccgcata cactattctc agaatgactt ggttgagtac tcaccagtca cagaaaagca 21240
tcttacggat ggcatgacag taagagaatt atgcagtgct gccataacca tgagtgataa 21300
cactgcggcc aacttacttc tgacaacgat cggaggaccg aaggagctaa ccgctttttt 21360
gcacaacatg ggggatcatg taactcgcct tgatcgttgg gaaccggagc tgaatgaagc 21420
cataccaaac gacgagcgtg acaccacgat gcctgtagca atggcaacaa cgttgcgcaa 21480
actattaact ggcgaactac ttacactagc ttcccggcaa caattaatag actggatgga 21540
ggcggataaa gttgcaggac cacttctgcg ctcggccctt ccggctggct ggtttattgc 21600

```
tgataaatct ggagccggtg agcgtgggtc tcgcggtatc attgcagcac tggggccaga  21660

tggtaagccc tcccgtatcg tagttatcta cacgacgggg agtcaggcaa ctatggatga  21720

acgaaataga cagatcgctg agataggtgc ctcactgatt aagcattggt aactgtcaga  21780

ccaagtttac tcatatatac tttagattga tttaaaactt catttttaat ttaaaaggat  21840

ctaggtgaag atcctttttg ataatctcat gaccaaaatc ccttaacgtg agttttcgtt  21900

ccactgagcg tcagaccccg tagaaaagat caaaggatct tcttgagatc cttttttct  21960

gcgcgtaatc tgctgcttgc aaacaaaaaa accaccgcta ccagcggtgg tttgtttgcc  22020

ggatcaagag ctaccaactc tttttccgaa ggtaactggc ttcagcagag cgcagatacc  22080

aaatactgtt cttctagtgt agccgtagtt aggccaccac ttcaagaact ctgtagcacc  22140

gcctacatac ctcgctctgc taatcctgtt accagtggct gctgccagtg gcgataagtc  22200

gtgtcttacc gggttggact caagacgata gttaccggat aaggcgcagc ggtcgggctg  22260

aacggggggt tcgtgcacac agcccagctt ggagcgaacg acctacaccg aactgagata  22320

cctacagcgt gagctatgag aaagcgccac gcttcccgaa gggagaaagg cggacaggta  22380

tccggtaagc ggcagggtcg gaacaggaga gcgcacgagg gagcttccag ggggaaacgc  22440

ctggtatctt tatagtcctg tcgggtttcg ccacctctga cttgagcgtc gatttttgtg  22500

atgctcgtca ggggggcgga gcctatggaa aaacgccagc aacgcggcct ttttacggtt  22560

cctggccttt tgctggcctt ttgctcacat gttctttcct gcgttatccc ctgattctgt  22620

ggataaccgt attaccgcct ttgagtgagc tgataccgct cgccgcagcc gaacgaccga  22680

gcgcagcgag tcagtgagcg aggaagcgga agagcgccca atacgcaaac cgcctctccc  22740

cgcgcgttgg ccgattcatt aatgcagctg gcacgacagg tttcccgact ggaaagcggg  22800

cagtgagcgc aacgcaatta atgtgagtta gctcactcat taggcacccc aggctttaca  22860

ctttatgctt ccggctcgta tgttgtgtgg aattgtgagc ggacaacaat ttcacacagg  22920

aaacagctat gaccatgatt acgccaagct cgggcggccg cttgtaatac gactcactat  22980

a                                                                  22981
```

<210> SEQ ID NO 20
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-fneg-PP

<400> SEQUENCE: 20

```
accaaacaaa gttgggtaag gatagttcaa tcaatgatca ttttctagtg cacttaggat     60

tcaagatcct attatcaggg acaagagcag gattaaggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtcaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540
```

```
gatggttcga gaacaaggaa atctcagata ttgaagtgca agaccctgag ggattcaaca     600
tgattctggg taccatccta gctcaaattt gggtcttgct cgcaaaggcg gttacggccc     660
cagacacggc agctgattcg gagctaagaa ggtggataaa gtacacccaa caaagaaggg     720
tagttggtga atttagattg gagagaaaat ggttggatgt ggtgaggaac aggattgccg     780
aggacctctc cttacgccga ttcatggtcg ctctaatcct ggatatcaag agaacacccg     840
gaaacaaacc caggattgct gaaatgatat gtgacattga tacatatatc gtagaggcag     900
gattagccag ttttatcctg actattaagt ttgggataga aactatgtat cctgctcttg     960
gactgcatga atttgctggt gagttatcca cacttgagtc cttgatgaac ctttaccagc    1020
aaatggggga aactgcaccc tacatggtaa tcctggagaa ctcaattcag aacaagttca    1080
gtgcaggatc ataccctctg ctctggagct atgccatggg agtaggagtg gaacttgaaa    1140
actccatggg aggtttgaac tttggccgat cttactttga tccagcatat tttagattag    1200
ggcaagagat ggtaaggagg tcagctggaa aggtcagttc cacattggca tctgaactcg    1260
gtatcactgc cgaggatgca aggcttgttt cagagattgc aatgcatact actgaggaca    1320
agatcagtag agcggttgga cccagacaag cccaagtatc atttctacac ggtgatcaaa    1380
gtgagaatga gctaccgaga ttgggggggca aggaagatag gagggtcaaa cagagtcgag    1440
gagaagccag ggagagctac agagaaaccg ggcccagcag agcaagtgat gcgagagctg    1500
cccatcttcc aaccggcaca cccctagaca ttgacactgc atcggagtcc agccaagatc    1560
cgcaggacag tcgaaggtca gctgacgccc tgcttaggct gcaagccatg gcaggaatct    1620
cggaagaaca aggctcagac acggacaccc ctatagtgta caatgacaga aatcttctag    1680
actaggtgcg agaggccgag gaccagaaca acatccgcct accctccatc attgttataa    1740
aaaacttagg aaccaggtcc acacagccgc cagcccatca accatccact cccacgattg    1800
gagccgatgg cagaagagca ggcacgccat gtcaaaaacg gactggaatg catccgggct    1860
ctcaaggccg agcccatcgg ctcactggcc atcgaggaag ctatggcagc atggtcagaa    1920
atatcagaca acccaggaca ggagcgagcc acctgcaggg aagagaaggc aggcagttcg    1980
ggtctcagca aaccatgcct ctcagcaatt ggatcaactg aaggcggtgc acctcgcatc    2040
cgcggtcagg gacctggaga gagcgatgac gacgctgaaa ctttgggaat ccccccaaga    2100
aatctccagg catcaagcac tgggttacag tgttattatg tttatgatca cagcggtgaa    2160
gcggttaagg gaatccaaga tgctgactct atcatggttc aatcaggcct tgatggtgat    2220
agcaccctct caggaggaga caatgaatct gaaaacagcg atgtggatat tggcgaacct    2280
gataccgagg gatatgctat cactgaccgg ggatctgctc ccatctctat ggggttcagg    2340
gcttctgatg ttgaaactgc agaaggaggg gagatccacg agctcctgag actccaatcc    2400
agaggcaaca actttccgaa gcttgggaaa actctcaatg ttcctccgcc tccggacccc    2460
ggtagggcca gcacttccgg gacacccatt aaaaagggca cagacgcgag attagcctca    2520
tttggaacgg agatcgcgtc tttattgaca ggtggtgcaa cccaatgtgc tcgaaagtca    2580
ccctcggaac catcagggcc aggtgcacct gcggggaatg tccccgagtg tgtgagcaat    2640
gccgcactga tacaggagtg gacacccgaa tctggtacca caatctcccc gagatcccag    2700
aataatgaag aagggggaga ctattatgat gatgagctgt tctctgatgt ccaagatatt    2760
aaaacagcct tggccaaaat acacgaggat aatcagaaga taatctccaa gctagaatca    2820
ctgctgttat tgaagggaga agttgagtca attaagaagc agatcaacag gcaaaatatc    2880
```

-continued agcatatcca ccctggaagg acacctctca agcatcatga tcgccattcc tggacttggg 2940
aaggatccca acgaccccac tgcagatgtc gaaatcaatc ccgacttgaa acccatcata 3000
ggcagagatt caggccgagc actggccgaa gttctcaaga aacccgttgc cagccgacaa 3060
ctccaaggaa tgacaaatgg acggaccagt tccagaggac agctgctgaa ggaatttcag 3120
ctaaagccga tcgggaaaaa gatgagctca gccgtcgggt ttgttcctga caccggccct 3180
gcatcacgca gtgtaatccg ctccattata aaatccagcc ggctagagga ggatcggaag 3240
cgttacctga tgactctcct tgatgatatc aaaggagcca atgatcttgc caagttccac 3300
cagatgctga tgaagataat aatgaagtag ctacagctca acttacctgc caaccccatg 3360
ccagtcgacc caactagtac aacctaaatc cattataaaa aacttaggag caaagtgatt 3420
gcctcccaag ttccacaggc gcgccatgtt cgtcttcctg gtcctgctgc ctctggtctc 3480
ctcacagtgc gtcaatctga caactcggac tcagctgcca cctgcttata ctaatagctt 3540
caccagaggc gtgtactatc ctgacaaggt gtttagaagc tccgtgctgc actctacaca 3600
ggatctgttt ctgccattct ttagcaacgt gacctggttc cacgccatcc acgtgagcgg 3660
caccaatggc acaaagcggt tcgacaatcc cgtgctgcct tttaacgatg gcgtgtactt 3720
cgcctctacc gagaagagca acatcatcag aggctggatc tttggcacca cactggactc 3780
caagacacag tctctgctga tcgtgaacaa tgccaccaac gtggtcatca aggtgtgcga 3840
gttccagttt tgtaatgatc ccttcctggg cgtgtactat cacaagaaca ataagagctg 3900
gatggagtcc gagtttagag tgtattctag cgccaacaac tgcacatttg agtacgtgag 3960
ccagcctttc ctgatggacc tggagggcaa gcagggcaat ttcaagaacc tgagggagtt 4020
cgtgtttaag aatatcgacg gctacttcaa aatctactct aagcacaccc ccatcaacct 4080
ggtgcgcgac ctgcctcagg gcttcagcgc cctggagccc ctggtggatc tgcctatcgg 4140
catcaacatc acccggtttc agacactgct ggccctgcac agaagctacc tgacacccgg 4200
cgactcctct agcggatgga ccgccggcgc tgccgcctac tatgtgggct acctccagcc 4260
ccggaccttc ctgctgaagt acaacgagaa tggcaccatc acagacgcag tggattgcgc 4320
cctggacccc ctgagcgaga caaagtgtac actgaagtcc tttaccgtgg agaagggcat 4380
ctatcagaca tccaatttca gggtgcagcc aaccgagtct atcgtgcgct ttcctaatat 4440
cacaaacctg tgcccatttg gcgaggtgtt caacgcaacc cgcttcgcca gcgtgtacgc 4500
ctggaatagg aagcggatca gcaactgcgt ggccgactat agcgtgctgt acaactccgc 4560
ctctttcagc acctttaagt gctatggcgt gtcccccaca aagctgaatg acctgtgctt 4620
taccaacgtc tacgccgatt ctttcgtgat caggggcgac gaggtgcgcc agatcgcccc 4680
cggccagaca ggcaagatcg cagactacaa ttataagctg ccagacgatt tcaccggctg 4740
cgtgatcgcc tggaacagca acaatctgga ttccaaagtg ggcggcaact acaattatct 4800
gtaccggctg tttagaaaga gcaatctgaa gcccttcgag agggacatct ctacagaaat 4860
ctaccaggcc ggcagcaccc cttgcaatgg cgtggagggc tttaactgtt atttcccact 4920
ccagtcctac ggcttccagc ccacaaacgg cgtgggctat cagccttacc gcgtggtggt 4980
gctgagcttt gagctgctgc acgccccagc aacagtgtgc ggccccaaga agtccaccaa 5040
tctggtgaag aacaagtgcg tgaacttcaa cttcaacggc ctgaccggca caggcgtgct 5100
gaccgagtcc aacaagaagt tcctgccatt tcagcagttc ggcagggaca tcgcagatac 5160
cacagacgcc gtgcgcgacc cacagaccct ggagatcctg gacatcacac cctgctcttt 5220
cggcggcgtg agcgtgatca cacccggcac caatacaagc aaccaggtgg ccgtgctgta 5280

-continued

```
tcaggacgtg aattgtaccg aggtgcccgt ggctatccac gccgatcagc tgaccccaac   5340
atggcgggtg tacagcaccg gctccaacgt cttccagaca agagccggat gcctgatcgg   5400
agcagagcac gtgaacaatt cctatgagtg cgacatccca atcggcgccg gcatctgtgc   5460
ctcttaccag acccagacaa actctcccgc atctgtgggc agcgtggcct cccagtctat   5520
catcgcctat accatgtccc tgggcgccga gaacagcgtg gcctactcta acaatagcat   5580
cgccatccca accaacttca caatctctgt gaccacagag atcctgcccg tgtccatgac   5640
caagacatct gtggactgca caatgtatat ctgtggcgat tctaccgagt gcagcaacct   5700
gctgctccag tacggcagct ttgtacccca gctgaataga gccctgacag gcatcgccgt   5760
ggagcaggat aagaacacac aggaggtgtt cgcccaggtg aagcaaatct acaagacccc   5820
ccctatcaag gactttggcg gcttcaattt ttcccagatc ctgcctgatc catccaagcc   5880
ttctaagcgg agctttatcg aggacctgct gttcaacaag gtgaccctgg ccgatgccgg   5940
cttcatcaag cagtatggcg attgcctggg cgacatcgca gccagggacc tgatctgcgc   6000
ccagaagttt aatggcctga ccgtgctgcc acccctgctg acagatgaga tgatcgcaca   6060
gtacacaagc gccctgctgg ccggcaccat cacatccgga tggaccttcg gcgcaggagc   6120
cgccctccag atcccctttg ccatgcagat ggcctatagg ttcaacggca tcggcgtgac   6180
ccagaatgtg ctgtacgaga accagaagct gatcgccaat cagtttaact ccgccatcgg   6240
caagatccag gacagcctgt cctctacagc cagcgccctg ggcaagctcc aggatgtggt   6300
gaatcagaac gcccaggccc tgaataccct ggtgaagcag ctgagcagca acttcggcgc   6360
catctctagc gtgctgaatg acatcctgag ccggctggac cctcctgagg cagaggtgca   6420
gatcgaccgg ctgatcaccg gccggctcca gagcctccag acctatgtga cacagcagct   6480
gatcagggcc gccgagatca gggccagcgc caatctggca gcaaccaaga tgtccgagtg   6540
cgtgctgggc cagtctaaga gagtggactt ttgtggcaag ggctatcacc tgatgtcctt   6600
ccctcagtct gccccacacg gcgtggtgtt tctgcacgtg acctacgtgc ccgcccagga   6660
gaagaacttc accacagccc ctgccatctg ccacgatggc aaggcccact ttccaaggga   6720
gggcgtgttc gtgtccaacg gcacccactg gtttgtgaca cagcgcaatt tctacgagcc   6780
ccagatcatc accacagaca acaccttcgt gagcggcaac tgtgacgtgg tcatcggcat   6840
cgtgaacaat accgtgtatg atccactcca gcccgagctg gacagcttta aggaggagct   6900
ggataagtat ttcaagaatc acacctcccc tgacgtggat ctgggcgaca tcagcggcat   6960
caatgcctcc gtggtgaaca tccagaagga gatcgaccgc ctgaacgagg tggctaagaa   7020
tctgaacgag agcctgatcg acctccagga gctgggcaag tatgagcagt acatcaagtg   7080
gccctggtac atctggctgg gcttcatcgc cggcctgatc gccatcgtga tggtgaccat   7140
catgctgtgc tgtatgacat cctgctgttc ttgcctgaag ggctgctgta gctgtggctc   7200
ctgctgtaag tttgacgagg atgactctga acctgtgctg aagggcgtgg cgctggctta   7260
cacctaacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatccccta gggcctccaa tcgggcgagc atttgggtcc ctgcccttag   7620
```

-continued

```
gtgttggcag atccacagca aagcccgaaa aactcctcaa agaggccact gagcttgaca   7680
tagttgttag acgtacagca gggctcaatg aaaaactggt gttctacaac aacaccccac   7740
taactctcct cacaccttgg agaaaggtcc taacaacagg gagtgtcttc aacgcaaacc   7800
aagtgtgcaa tgcggttaat ctgataccgc tcgatacccc gcagaggttc cgtgttgttt   7860
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gatagggggc accagtcttc   8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgaccccct cacaatgaca gccagaaggc ccggacaaaa   8460
aagcccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggacccccg aggaccaacc cccaaggctg cccccgatcc   8640
aaaccaccaa ccgcatcccc accaccccg ggaaagaaac ccccagcaat tggaaggccc   8700
ctcccctct tcctcaacac aagaactcca caaccgaacc gcacaagcga ccgaggtgac   8760
ccaaccgcag gcatccgact ccctagacag atcctctctc cccggcaaac taaacaaaac   8820
ttagggccaa ggaacataca cacccaacag aacccagacc ccggcccacg gcgccgcgcc   8880
cccaaccccc gacaaccaga gggagccccc aaccaatccc gccggctccc ccggtgccca   8940
caggcaggga caccaacccc cgaacagacc cagcacccaa ccatcgacaa tccaagacgg   9000
gggggccccc ccaaaaaaag gcccccaggg gccgacagcc agcaccgcga ggaagcccac   9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggaccccc   9240
gaaccgcaaa ggacatcagt atcccacagc ctctccaagt cccccggtct cctccccttc   9300
tcgaagggac caaaagatca atccaccaca cccgacgaca ctcaactccc cacccctaaa   9360
ggagacaccg ggaatcccag aatcaagact catccaatgt ccatcatggg tctcaaggtg   9420
aacgtctctg ccatattcat ggcagtactg ttaactctcc aaacacccac cggtcaaatc   9480
cattggggca atctctctaa gataggggtg gtaggaatag gaagtgcaag ctacaaagtt   9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa gaccggttca gagtgtagct   9720
tcaagtagga gacacaagag atttgcggga gtagtcctgg caggtgcggc cctaggcgtc   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg gccagaagct cgggctcaaa  10020
```

ttgctcagat actatacaga aatcctgtca ttatttggcc ccagcttacg ggaccccata 10080
tctgcggaga tatctatcca ggctttgagc tatgcgcttg gaggagacat caataaggtg 10140
ttagaaaagc tcggatacag tggaggtgat ttactgggca tcttagagag cagaggaata 10200
aaggcccgga taactcacgt cgacacagag tcctacttca ttgtcctcag tatagcctat 10260
ccgacgctgt ccgagattaa gggggtgatt gtccaccggc tagagggggt ctcgtacaac 10320
ataggctctc aagagtggta taccactgtg cccaagtatg ttgcaaccca agggtacctt 10380
atctcgaatt ttgatgagtc atcgtgtact ttcatgccag aggggactgt gtgcagccaa 10440
aatgccttgt acccgatgag tcctctgctc caagaatgcc tccgggggtc caccaagtcc 10500
tgtgctcgta cactcgtatc cgggtctttt gggaaccggt tcattttatc acaagggaac 10560
ctaatagcca attgtgcatc aatcctttgc aagtgttaca caacaggaac gatcattaat 10620
caagaccctg acaagatcct aacatacatt gctgccgatc actgcccggt agtcgaggtg 10680
aacggcgtga ccatccaagt cgggagcagg aggtatccag atgctgtgta cttgcacaga 10740
attgacctcg gtcctcccat atcattggag aggttggacg tagggacaaa tctggggaat 10800
gcaattgcta agttggagga tgccaaggaa ttgttggagt catcggacca gatattgagg 10860
agtatgaaag gtttatcgag cactagcata gtctacatcc tgattgcagt gtgtcttgga 10920
gggttgatag ggatccccgc tttaatatgt tgctgcaggg ggcgttgtaa caaaaaggga 10980
gaacaagttg gtatgtcaag accaggccta aagcctgatc ttacgggaac atcaaaatcc 11040
tatgtaaggt cgctctgatc ctctacaact cttgaaacac aaatgtccca caagtctcct 11100
cttcgtcatc aagcaaccac cgcacccagc atcaagccca cctgaaatta tctccggctt 11160
ccctctggcc gaacaatatc ggtagttaat taaaacttag ggtgcaagat catccacaat 11220
gtcaccacaa cgagaccgga taaatgcctt ctacaaagat aacccccatc ccaagggaag 11280
taggatagtc attaacagag aacatcttat gattgataga ccttatgttt tgctggctgt 11340
tctgtttgtc atgtttctga gcttgatcgg gttgctagcc attgcaggca ttagacttca 11400
tcgggcagcc atctacaccg cagagatcca taaaagcctc agcaccaatc tagatgtaac 11460
taactcaatc gagcatcagg tcaaggacgt gctgacacca ctcttcaaaa tcatcggtga 11520
tgaagtgggc ctgaggacac ctcagagatt cactgaccta gtgaaattca tctctgacaa 11580
gattaaattc cttaatccgg atagggagta cgacttcaga gatctcactt ggtgtatcaa 11640
cccgccagag agaatcaaat tggattatga tcaatactgt gcagatgtgg ctgctgaaga 11700
gctcatgaat gcattggtga actcaactct actggagacc agaacaacca atcagttcct 11760
agctgtctca aagggaaact gctcagggcc cactacaatc agaggtcaat tctcaaacat 11820
gtcgctgtcc ctgttagact tgtatttagg tcgaggttac aatgtgtcat ctatagtcac 11880
tatgacatcc cagggaatgt atgggggaac ttacctagtg gaaaagccta atctgagcag 11940
caaaaggtca gagttgtcac aactgagcat gtaccgagtg tttgaagtag gtgttatcag 12000
aaatccgggt ttgggggctc cggtgttcca tatgacaaac tatcttgagc aaccagccag 12060
taatgatctc agcaactgta tggtggcttt gggggagctc aaactcgcag ccctttgtca 12120
cggggaagat tctatcacaa ttccctatca gggatcaggg aaaggtgtca gcttccagct 12180
cgtcaagcta ggtgtctgga aatccccaac cgacatgcaa tcctgggtcc ccttatcaac 12240
ggatgatcca gtgatagaca ggctttacct ctcatctcac agaggtgtta tcgctgacaa 12300
tcaagcaaaa tgggctgtcc cgacaacacg aacagatgac aagttgcgaa tggagacatg 12360
cttccaacag gcgtgtaagg gtaaaatcca agcactctgc gagaatcccg agtgggcacc 12420
attgaaggat aacaggattc cttcatacgg ggtcttgtct gttgatctga gtctgacagt 12480
tgagcttaaa atcaaaattg cttcgggatt cgggccattg atcacacacg gttcagggat 12540
ggacctatac aaatccaacc acaacaatgt gtattggctg actatcccgc caatgaagaa 12600
cctagcctta ggtgtaatca acacattgga gtggataccg agattcaagg ttagtcccta 12660
cctcttcaat gtcccaatta aggaagcagg cgaagactgc catgccccaa catacctacc 12720
tgcggaggtg gatggtgatg tcaaactcag ttccaatctg gtgattctac ctggtcaaga 12780
tctccaatat gttttggcaa cctacgatac ttccagggtt gaacatgctg tggtttatta 12840
cgtttacagc ccaggccgct cattttctta cttttatcct tttaggttgc ctataaaggg 12900
ggtccccatc gaattacaag tggaatgctt cacatgggac caaaaactct ggtgccgtca 12960
cttctgtgtg cttgcggact cagaatctgg tggacatatc actcactctg ggatggtggg 13020
catgggagtc agctgcacag tcacccggga agatggaacc aatcgcagat agggctgcta 13080
gtgaaccaat ctcatgatgt cacccagaca tcaggcatac ccactagtgt gaaatagaca 13140
tcagaattaa gaaaaacgta gggtccaagt ggttccccgt tatggactcg ctatctgtca 13200
accagatctt ataccctgaa gttcacctag atagcccgat agttaccaat aagatagtag 13260
ccatcctgga gtatgctcga gtccctcacg cttacagcct ggaggaccct acactgtgtc 13320
agaacatcaa gcaccgccta aaaaacggat tttccaacca aatgattata aacaatgtgg 13380
aagttgggaa tgtcatcaag tccaagctta ggagttatcc ggcccactct catattccat 13440
atccaaattg taatcaggat ttatttaaca tagaagacaa agagtcaacg aggaagatcc 13500
gtgaactcct caaaaagggg aattcgctgt actccaaagt cagtgataag gttttccaat 13560
gcttaaggga cactaactca cggcttggcc taggctccga attgagggag gacatcaagg 13620
agaaagttat taacttggga gtttacatgc acagctccca gtggtttgag ccctttctgt 13680
tttggtttac agtcaagact gagatgaggt cagtgattaa atcacaaacc catacttgcc 13740
ataggaggag acacacacct gtattcttca ctggtagttc agttgagttg ctaatctctc 13800
gtgaccttgt tgctataatc agtaaagagt ctcaacatgt atattacctg acatttgaac 13860
tggttttgat gtattgtgat gtcatagagg ggaggttaat gacagagacc gctatgacta 13920
ttgatgctag gtatacagag cttctaggaa gagtcagata catgtggaaa ctgatagatg 13980
gtttcttccc tgcactcggg aatccaactt atcaaattgt agccatgctg gagcctcttt 14040
cacttgctta cctgcagctg agggatataa cagtagaact cagaggtgct ttccttaacc 14100
actgctttac tgaaatacat gatgttcttg accaaaacgg gttttctgat gaaggtactt 14160
atcatgagtt aattgaagct ctagattaca ttttcataac tgatgacata catctgacag 14220
gggagatttt ctcatttttc agaagtttcg gccaccccag acttgaagca gtaacggctg 14280
ctgaaaatgt taggaaatac atgaatcagc ctaaagtcat tgtgtatgag actctgatga 14340
aaggtcatgc catattttgt ggaatcataa tcaacggcta tcgtgacagg cacggaggca 14400
gttggccacc gctgaccctc cccctgcatg ctgcagacac aatccggaat gctcaagctt 14460
caggtgaagg gttaacacat gagcagtgcg ttgataactg gagatctttt gctggagtga 14520
aatttggctg ctttatgcct cttagcctgg atagtgatct gacaatgtac ctaaaggaca 14580
aggcacttgc tgctctccaa agggaatggg attcagttta cccgaaagag ttcctgcgtt 14640
acgaccctcc caagggaacc gggtcacgga ggcttgtaga tgttttcctt aatgattcga 14700
gctttgaccc atatgatgtg ataatgtatg ttgtaagtgg agcttacctc catgaccctg 14760
agttcaacct gtcttacagc ctgaaagaaa aggagatcaa ggaaacaggt agactttttg 14820
ctaaaatgac ttacaaaatg agggcatgcc aagtgattgc tgaaaatcta atctcaaacg 14880
ggattggcaa atattttaag gacaatggga tggccaagga tgagcacgat ttgactaagg 14940
cactccacac tctagctgtc tcaggagtcc ccaaagatct caaagaaagt cacagggggg 15000
ggccagtctt aaaaacctac tcccgaagcc cagtccacac aagtaccagg aacgtgagag 15060
cagcaaaagg gtttataggg ttccctcaag taattcggca ggaccaagac actgatcatc 15120
cggagaatat ggaagcttac gagacagtca gtgcatttat cacgactgat ctcaagaagt 15180
actgccttaa ttggagatat gagaccatca gcttgtttgc acagaggcta aatgagattt 15240
acggattgcc ctcatttttc cagtggctgc ataagaggct tgagacctct gtcctgtatg 15300
taagtgaccc tcattgcccc cccgaccttg acgcccatat cccgttatat aaagtcccca 15360
atgatcaaat cttcattaag taccctatgg gaggtataga agggtattgt cagaagctgt 15420
ggaccatcag caccattccc tatctatacc tggctgctta tgagagcgga gtaaggattg 15480
cttcgttagt gcaaggggac aatcagacca tagccgtaac aaaaagggta cccagcacat 15540
ggccctacaa ccttaagaaa cggaagctg ctagagtaac tagagattac tttgtaattc 15600
ttaggcaaag gctacatgat attggccatc acctcaaggc aaatgagaca attgtttcat 15660
cacatttttt tgtctattca aaaggaatat attatgatgg gctacttgtg tcccaatcac 15720
tcaagagcat cgcaagatgt gtattctggt cagagactat agttgatgaa acaagggcag 15780
catgcagtaa tattgctaca acaatggcta aaagcatcga gagaggttat gaccgttacc 15840
ttgcatattc cctgaacgtc ctaaaagtga tacagcaaat tctgatctct cttggcttca 15900
caatcaattc aaccatgacc cgggatgtag tcataccccct cctcacgaac aacgacctct 15960
taataaggat ggcactgttg cccgctccta ttggggggat gaattatctg aatatgagca 16020
ggctgtttgt cagaaacatc ggtgatccag taacatcatc aattgctgat ctcaagagaa 16080
tgattctcgc ctcactaatg cctgaagaga ccctccatca agtaatgaca caacaaccgg 16140
gggactcttc attcctagac tgggctagcg acccttactc agcaaatctt gtatgtgtcc 16200
agagcatcac tagactcctc aagaacataa ctgcaaggtt tgtcctgatc catagtccaa 16260
acccaatgtt aaaaggatta ttccatgatg acagtaaaga agaggacgag ggactggcgg 16320
cattcctcat ggacaggcat attatagtac ctagggcagc tcatgaaatc ctggatcata 16380
gtgtcacagg ggcaagagag tctattgcag gcatgctgga taccacaaaa ggcctgattc 16440
gagccagcat gaggaagggg gggttaacct ctcgagtgat aaccagattg tccaattatg 16500
actatgaaca attcagagca gggatggtgc tattgacagg aagaaagaga aatgtcctca 16560
ttgacaaaga gtcatgttca gtgcagctgg cgagagctct aagaagccat atgtgggcga 16620
ggctagctcg aggacggcct atttacggcc ttgaggtccc tgatgtacta gaatctatgc 16680
gaggccacct tattcggcgt catgagacat gtgtcatctg cgagtgtgga tcagtcaact 16740
acggatggtt ttttgtcccc tcgggttgcc aactggatga tattgacaag gaaacatcat 16800
ccttgagagt cccatatatt ggttctacca ctgatgagag aacagacatg aagcttgcct 16860
tcgtaagagc cccaagtcga tccttgcgat ctgctgttag aatagcaaca gtgtactcat 16920
gggcttacgg tgatgatgat agctcttgga acgaagcctg gttgttggct aggcaaaggg 16980
ccaatgtgag cctggaggag ctaagggtga tcactcccat ctcaacttcg actaatttag 17040
cgcataggtt gagggatcgt agcactcaag tgaaatactc aggtacatcc cttgtccgag 17100

-continued

```
tggcgaggta taccacaatc tccaacgaca atctctcatt tgtcatatca gataagaagg  17160
ttgatactaa ctttatatac caacaaggaa tgcttctagg gttgggtgtt ttagaaacat  17220
tgtttcgact cgagaaagat accggatcat ctaacacggt attacatctt cacgtcgaaa  17280
cagattgttg cgtgatcccg atgatagatc atcccaggat acccagctcc cgcaagctag  17340
agctgagggc agagctatgt accaacccat tgatatatga taatgcacct ttaattgaca  17400
gagatacaac aaggctatac acccagagcc ataggaggca ccttgtggaa tttgttacat  17460
ggtccacacc ccaactatat cacattttag ctaagtccac agcactatct atgattgacc  17520
tggtaacaaa atttgagaag gaccatatga atgaaatttc agctctcata ggggatgacg  17580
atatcaatag tttcataact gagtttctgc tcatagagcc aagattattc actatctact  17640
tgggccagtg tgcggccatc aattgggcat ttgatgtaca ttatcataga ccatcaggga  17700
aatatcagat gggtgagctg ttgtcatcgt tcctttctag aatgagcaaa ggagtgttta  17760
aggtgcttgt caatgctcta agccacccaa agatctacaa gaaattctgg cattgtggta  17820
ttatagagcc tatccatggt ccttcacttg atgctcaaaa cttgcacaca actgtgtgca  17880
acatggttta cacatgctat atgacctacc tcgacctgtt gttgaatgaa gagttagaag  17940
agttcacatt tctcttgtgt gaaagcgacg aggatgtagt accggacaga ttcgacaaca  18000
tccaggcaaa acacttatgt gttctggcag atttgtactg tcaaccaggg acctgcccac  18060
caattcgagg tctaagaccg gtagagaaat gtgcagttct aaccgaccat atcaaggcag  18120
aggctaggtt atctccagca ggatcttcgt ggaacataaa tccaattatt gtagaccatt  18180
actcatgctc tctgacttat ctccggcgag gatcgatcaa acagataaga ttgagagttg  18240
atccaggatt cattttcgac gccctcgctg aggtaaatgt cagtcagcca aagatcggca  18300
gcaacaacat ctcaaatatg agcatcaagg ctttcagacc cccacacgat gatgttgcaa  18360
aattgctcaa agatatcaac acaagcaagc acaatcttcc catttcaggg ggcaatctcg  18420
ccaattatga aatccatgct ttccgcagaa tcgggttgaa ctcatctgct tgctacaaag  18480
ctgttgagat atcaacatta attaggagat gccttgagcc aggggaggac ggcttgttct  18540
tgggtgaggg atcgggttcc atgttgatca cttataagga gatacttaaa ctaaacaagt  18600
gcttctataa tagtggggtt tccgccaatt ctagatctgg tcaaagggaa ttagcaccct  18660
atccctccga agttggcctt gtcgaacaca gaatgggagt aggtaatatt gtcaaagtgc  18720
tctttaacgg gaggcccgaa gtcacgtggg taggcagtgt agattgcttc aatttcatag  18780
ttagtaatat ccctacctct agtgtggggt ttatccattc agatatagag accttgccta  18840
acaaagatac tatagagaag ctagaggaat tggcagccat cttatcgatg gctctgctcc  18900
tgggcaaaat aggatcaata ctggtgatta agcttatgcc tttcagcggg gattttgttc  18960
agggatttat aagttatgta gggtcccatt atagagaagt gaaccttgta taccctagat  19020
acagcaactt catatctact gaatcttatt tggttatgac agatctcaag gctaaccggc  19080
taatgaatcc tgaaaagatt aagcagcaga taattgaatc atctgtgagg acttcacctg  19140
gacttatagg tcacatccta tccattaagc aactaagctg catacaagca attgtgggag  19200
acgcagttag tagaggtgat atcaatccta ctctgaaaaa acttacacct atagagcagg  19260
tgctgatcaa ttgcgggttg gcaattaacg gacctaagct gtgcaaagaa ttgatccacc  19320
atgatgttgc ctcagggcaa gatggattgc ttaattctat actcatcctc tacagggagt  19380
tggcaagatt caaagacaac caaagaagtc aacaagggat gttccacgct taccccgtat  19440
tggtaagtag caggcaacga gaacttatat ctaggatcac ccgcaaattt tgggggcaca  19500
```

```
ttcttcttta ctccgggaac agaaagttga taaataagtt tatccagaat ctcaagtccg  19560
gctatctgat actagactta caccagaata tcttcgttaa gaatctatcc aagtcagaga  19620
aacagattat tatgacgggg ggtttgaaac gtgagtgggt ttttaaggta acagtcaagg  19680
agaccaaaga atggtataag ttagtcggat acagtgccct gattaaggac taattggttg  19740
aactccggaa ccctaatcct gccctaggtg gttaggcatt atttgcaata gattaaagaa  19800
aactttgaaa atacgaagtt tctattccca gctttgtctg gtggccggca tggtcccagc  19860
ctcctcgctg gcgccggctg ggcaacattc cgaggggacc gtcccctcgg taatggcgaa  19920
tgggacgcgg ccgatccggc tgctaacaaa gcccgaaagg aagctgagtt ggctgctgcc  19980
accgctgagc aataactagc ataacccctt ggggcctcta aacgggtctt gaggggtttt  20040
ttgctgaaag gaggaactat atccggatgc ggccgatccg gctgctaaca aagcccgaaa  20100
ggaagctgag ttggctgctg ccaccgctga gcaataacta gcataacccc ttggggcctc  20160
taaacgggtc ttgaggggtt ttttgctgaa aggaggaact atatccggat ggccgccacc  20220
ggccggtggg ccttgcagca catcccccttt tcgccagctg gcgtaatagc gaagaggccc  20280
gcaccgatcg cccttcccaa cagttgcgca gcctgaatgg cgaatgggac gcgccctgta  20340
gcggcgcatt aagcgcggcg ggtgtggtgg ttacgcgcag cgtgaccgct acacttgcca  20400
gcgccctagc gcccgctcct ttcgctttct tcccttcctt tctcgccacg ttcgccggct  20460
ttccccgtca agctctaaat cgggggctcc ctttagggtt ccgatttagt gctttacggc  20520
acctcgaccc caaaaaactt gattagggtg atggttcacg tgggccatcg ccctgataga  20580
cggtttttcg ccctttgacg ttggagtcca cgttctttaa tagtggactc ttgttccaaa  20640
ctggaacaac actcaaccct atctcggtct attcttttga tttataaggg attttgccga  20700
tttcggccta ttggttaaaa aatgagctga tttaacaaaa atttaacgcg aattttaaca  20760
aaatattaac gcttacaatt taggtggcac ttttcgggga aatgtgcgcg gaacccctat  20820
ttgtttattt ttctaaatac attcaaatat gtatccgctc atgagacaat aaccctgata  20880
aatgcttcaa taatattgaa aaaggaagag tatgagtatt caacatttcc gtgtcgccct  20940
tattcccttt tttgcggcat tttgccttcc tgtttttgct cacccagaaa cgctggtgaa  21000
agtaaaagat gctgaagatc agttgggtgc acgagtgggt tacatcgaac tggatctcaa  21060
cagcggtaag atccttgaga gttttcgccc cgaagaacgt tttccaatga tgagcacttt  21120
taaagttctg ctatgtggcg cggtattatc ccgtattgac gccgggcaag agcaactcgg  21180
tcgccgcata cactattctc agaatgactt ggttgagtac tcaccagtca cagaaaagca  21240
tcttacggat ggcatgacag taagagaatt atgcagtgct gccataacca tgagtgataa  21300
cactgcggcc aacttacttc tgacaacgat cggaggaccg aaggagctaa ccgctttttt  21360
gcacaacatg ggggatcatg taactcgcct tgatcgttgg gaaccggagc tgaatgaagc  21420
cataccaaac gacgagcgtg acaccacgat gcctgtagca atggcaacaa cgttgcgcaa  21480
actattaact ggcgaactac ttacactagc ttcccggcaa caattaatag actggatgga  21540
ggcggataaa gttgcaggac cacttctgcg ctcggccctt ccggctggct ggtttattgc  21600
tgataaatct ggagccggtg agcgtgggtc tcgcggtatc attgcagcac tggggccaga  21660
tggtaagccc tcccgtatcg tagttatcta cacgacgggg agtcaggcaa ctatggatga  21720
acgaaataga cagatcgctg agataggtgc ctcactgatt aagcattggt aactgtcaga  21780
ccaagtttac tcatatatac tttagattga tttaaaactt catttttaat ttaaaaggat  21840
```

```
ctaggtgaag atcctttttg ataatctcat gaccaaaatc ccttaacgtg agttttcgtt  21900
ccactgagcg tcagaccccg tagaaaagat caaaggatct tcttgagatc cttttttct   21960
gcgcgtaatc tgctgcttgc aaacaaaaaa accaccgcta ccagcggtgg tttgtttgcc  22020
ggatcaagag ctaccaactc tttttccgaa ggtaactggc ttcagcagag cgcagatacc  22080
aaatactgtt cttctagtgt agccgtagtt aggccaccac ttcaagaact ctgtagcacc  22140
gcctacatac ctcgctctgc taatcctgtt accagtggct gctgccagtg gcgataagtc  22200
gtgtcttacc gggttggact caagacgata gttaccggat aaggcgcagc ggtcgggctg  22260
aacggggggt tcgtgcacac agcccagctt ggagcgaacg acctacaccg aactgagata  22320
cctacagcgt gagctatgag aaagcgccac gcttcccgaa gggagaaagg cggacaggta  22380
tccggtaagc ggcagggtcg gaacaggaga gcgcacgagg gagcttccag ggggaaacgc  22440
ctggtatctt tatagtcctg tcgggtttcg ccacctctga cttgagcgtc gatttttgtg  22500
atgctcgtca ggggggcgga gcctatggaa aaacgccagc aacgcggcct ttttacggtt  22560
cctggccttt tgctggcctt ttgctcacat gttctttcct gcgttatccc ctgattctgt  22620
ggataaccgt attaccgcct ttgagtgagc tgataccgct cgccgcagcc gaacgaccga  22680
gcgcagcgag tcagtgagcg aggaagcgga agagcgccca atacgcaaac cgcctctccc  22740
cgcgcgttgg ccgattcatt aatgcagctg gcacgacagg tttcccgact ggaaagcggg  22800
cagtgagcgc aacgcaatta atgtgagtta gctcactcat taggcacccc aggctttaca  22860
ctttatgctt ccggctcgta tgttgtgtgg aattgtgagc ggacaacaat ttcacacagg  22920
aaacagctat gaccatgatt acgccaagct cgggcggccg cttgtaatac gactcactat  22980
a                                                                  22981
```

<210> SEQ ID NO 21
<211> LENGTH: 22981
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(22981)
<223> OTHER INFORMATION: rMV-EZ-SARS-CoV-2-S-CO-AA-fneg

<400> SEQUENCE: 21

```
accaaacaaa gttgggtaag gatagttcaa tcaatgatca ttttctagtg cacttaggat     60
tcaagatcct attatcaggg acaagagcag gattaaggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtcaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcga gaacaaggaa atctcagata ttgaagtgca agaccctgag ggattcaaca    600
tgattctggg taccatccta gctcaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
```

-continued

```
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag gaccagaaca acatccgcct accctccatc attgttataa   1740
aaaacttagg aaccaggtcc acacagccgc cagcccatca accatccact cccacgattg   1800
gagccgatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc tccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
```

-continued ctaaagccga tcgggaaaaa gatgagctca gccgtcgggt ttgttcctga caccggccct 3180
gcatcacgca gtgtaatccg ctccattata aaatccagcc ggctagagga ggatcggaag 3240
cgttacctga tgactctcct tgatgatatc aaaggagcca atgatcttgc caagttccac 3300
cagatgctga tgaagataat aatgaagtag ctacagctca acttacctgc caaccccatg 3360
ccagtcgacc caactagtac aacctaaatc cattataaaa aacttaggag caaagtgatt 3420
gcctcccaag ttccacaggc gcgccatgtt cgtcttcctg gtcctgctgc ctctggtctc 3480
ctcacagtgc gtcaatctga caactcggac tcagctgcca cctgcttata ctaatagctt 3540
caccagaggc gtgtactatc ctgacaaggt gtttagaagc tccgtgctgc actctacaca 3600
ggatctgttt ctgccattct ttagcaacgt gacctggttc cacgccatcc acgtgagcgg 3660
caccaatggc acaaagcggt tcgacaatcc cgtgctgcct tttaacgatg gcgtgtactt 3720
cgcctctacc gagaagagca acatcatcag aggctggatc tttggcacca cactggactc 3780
caagacacag tctctgctga tcgtgaacaa tgccaccaac gtggtcatca aggtgtgcga 3840
gttccagttt tgtaatgatc ccttcctggg cgtgtactat cacaagaaca ataagagctg 3900
gatggagtcc gagtttagag tgtattctag cgccaacaac tgcacatttg agtacgtgag 3960
ccagcctttc ctgatggacc tggagggcaa gcagggcaat ttcaagaacc tgagggagtt 4020
cgtgtttaag aatatcgacg gctacttcaa aatctactct aagcacaccc ccatcaacct 4080
ggtgcgcgac ctgcctcagg gcttcagcgc cctggagccc ctggtggatc tgcctatcgg 4140
catcaacatc acccggtttc agacactgct ggccctgcac agaagctacc tgacacccgg 4200
cgactcctct agcggatgga ccgccggcgc tgccgcctac tatgtgggct acctccagcc 4260
ccggaccttc ctgctgaagt acaacgagaa tggcaccatc acagacgcag tggattgcgc 4320
cctggacccc ctgagcgaga caaagtgtac actgaagtcc tttaccgtgg agaagggcat 4380
ctatcagaca tccaatttca gggtgcagcc aaccgagtct atcgtgcgct ttcctaatat 4440
cacaaacctg tgcccatttg gcgaggtgtt caacgcaacc cgcttcgcca gcgtgtacgc 4500
ctggaatagg aagcggatca gcaactgcgt ggccgactat agcgtgctgt acaactccgc 4560
ctctttcagc acctttaagt gctatggcgt gtcccccaca aagctgaatg acctgtgctt 4620
taccaacgtc tacgccgatt ctttcgtgat caggggcgac gaggtgcgcc agatcgcccc 4680
cggccagaca ggcaagatcg cagactacaa ttataagctg ccagacgatt tcaccggctg 4740
cgtgatcgcc tggaacagca acaatctgga ttccaaagtg ggcggcaact acaattatct 4800
gtaccggctg tttagaaaga gcaatctgaa gcccttcgag agggacatct ctacagaaat 4860
ctaccaggcc ggcagcaccc cttgcaatgg cgtggagggc tttaactgtt atttcccact 4920
ccagtcctac ggcttccagc ccacaaacgg cgtgggctat cagccttacc gcgtggtggt 4980
gctgagcttt gagctgctgc acgccccagc aacagtgtgc ggccccaaga agtccaccaa 5040
tctggtgaag aacaagtgcg tgaacttcaa cttcaacggc ctgaccggca caggcgtgct 5100
gaccgagtcc aacaagaagt tcctgccatt tcagcagttc ggcagggaca tcgcagatac 5160
cacagacgcc gtgcgcgacc cacagaccct ggagatcctg gacatcacac cctgctcttt 5220
cggcggcgtg agcgtgatca cacccggcac caatacaagc aaccaggtgg ccgtgctgta 5280
tcaggacgtg aattgtaccg aggtgcccgt ggctatccac gccgatcagc tgaccccaac 5340
atggcgggtg tacagcaccg gctccaacgt cttccagaca agagccggat gcctgatcgg 5400
agcagagcac gtgaacaatt cctatgagtg cgacatccca atcggcgccg gcatctgtgc 5460
ctcttaccag acccagacaa actctcccgc atctgtgggc agcgtggcct cccagtctat 5520

-continued

```
catcgcctat accatgtccc tgggcgccga gaacagcgtg gcctactcta acaatagcat   5580
cgccatccca accaacttca caatctctgt gaccacagag atcctgcccg tgtccatgac   5640
caagacatct gtggactgca caatgtatat ctgtggcgat tctaccgagt gcagcaacct   5700
gctgctccag tacggcagct tttgtaccca gctgaataga gccctgacag gcatcgccgt   5760
ggagcaggat aagaacacac aggaggtgtt cgcccaggtg aagcaaatct acaagacccc   5820
ccctatcaag gactttggcg gcttcaattt ttcccagatc ctgcctgatc catccaagcc   5880
ttctaagcgg agctttatcg aggacctgct gttcaacaag gtgaccctgg ccgatgccgg   5940
cttcatcaag cagtatggcg attgcctggg cgacatcgca gccagggacc tgatctgcgc   6000
ccagaagttt aatggcctga ccgtgctgcc acccctgctg acagatgaga tgatcgcaca   6060
gtacacaagc gccctgctgg ccggcaccat cacatccgga tggaccttcg gcgcaggagc   6120
cgccctccag atcccctttg ccatgcagat ggcctatagg ttcaacggca tcggcgtgac   6180
ccagaatgtg ctgtacgaga accagaagct gatcgccaat cagtttaact ccgccatcgg   6240
caagatccag gacagcctgt cctctacagc cagcgccctg ggcaagctcc aggatgtggt   6300
gaatcagaac gcccaggccc tgaataccct ggtgaagcag ctgagcagca acttcggcgc   6360
catctctagc gtgctgaatg acatcctgag ccggctggac aaggtggagg cagaggtgca   6420
gatcgaccgg ctgatcaccg gccggctcca gagcctccag acctatgtga cacagcagct   6480
gatcagggcc gccgagatca gggccagcgc caatctggca gcaaccaaga tgtccgagtg   6540
cgtgctgggc cagtctaaga gagtggactt ttgtggcaag ggctatcacc tgatgtcctt   6600
ccctcagtct gccccacacg gcgtggtgtt tctgcacgtg acctacgtgc ccgcccagga   6660
gaagaacttc accacagccc ctgccatctg ccacgatggc aaggcccact ttccaaggga   6720
gggcgtgttc gtgtccaacg gcacccactg gtttgtgaca cagcgcaatt tctacgagcc   6780
ccagatcatc accacagaca acaccttcgt gagcggcaac tgtgacgtgg tcatcggcat   6840
cgtgaacaat accgtgtatg atccactcca gcccgagctg gacagcttta aggaggagct   6900
ggataagtat ttcaagaatc acacctcccc tgacgtggat ctgggcgaca tcagcggcat   6960
caatgcctcc gtggtgaaca tccagaagga gatcgaccgc ctgaacgagg tggctaagaa   7020
tctgaacgag agcctgatcg acctccagga gctgggcaag tatgagcagt acatcaagtg   7080
gccctggtac atctggctgg gcttcatcgc cggcctgatc gccatcgtga tggtgaccat   7140
catgctgtgc tgtatgacat cctgctgttc ttgcctgaag ggctgctgta gctgtggctc   7200
ctgctgtaag tttgacgagg atgactctga acctgtgctg aagggcgtgg cgctggctta   7260
cacctaacgc gcgacgtcct acagctcaac ttacctgcca accccatgcc agtcgaccca   7320
actagtacaa cctaaatcca ttataaaaaa cttaggagca aagtgattgc ctcccaagtt   7380
ccacaatgac agagatctac gacttcgaca agtcggcatg ggacatcaaa gggttgatcg   7440
ctccgataca acccaccacc tacagtgatg gcaggctggt gccccaggtc agagtcatag   7500
atcctggtct aggcgacagg aaggatgaat gctttatgta catgtttctg ctgggggttg   7560
ttgaggacag cgatccccta gggcctccaa tcgggcgagc atttgggtcc ctgcccttag   7620
gtgttggcag atccacagca aagcccgaaa aactcctcaa agaggccact gagcttgaca   7680
tagttgttag acgtacagca gggctcaatg aaaaactggt gttctacaac aacacccccac  7740
taactctcct cacaccttgg agaaaggtcc taacaacagg gagtgtcttc aacgcaaacc   7800
aagtgtgcaa tgcggttaat ctgataccgc tcgatacccc gcagaggttc cgtgttgttt   7860
```

-continued

```
atatgagcat cacccgtctt tcggataacg ggtattacac cgttcctaga agaatgctgg   7920
aattcagatc ggtcaatgca gtggccttca acctgctggt gacccttagg attgacaagg   7980
cgataggccc tgggaagatc atcgacaata cagagcaact tcctgaggca acatttatgg   8040
tccacatcgg gaacttcagg agaaagaaga gtgaagtcta ctctgccgat tattgcaaaa   8100
tgaaaatcga aaagatgggc ctggtttttg cacttggtgg gatagggggc accagtcttc   8160
acattagaag cacaggcaaa atgagcaaga ctctccatgc acaactcggg ttcaagaaga   8220
ccttatgtta cccgctgata gatatcaatg aagaccttaa tcgattactc tggaggagca   8280
gatgcaagat agtaagaatc caggcagttt tgcagccatc agttcctcaa gaattccgca   8340
tttacgacga cgtgatcata aatgatgacc aaggactatt caaagttctg tagaccgtag   8400
tgcccagcaa tgcccgaaaa cgacccccct cacaatgaca gccagaaggc ccggacaaaa   8460
aagcccccctc cgaaagactc cacggaccaa gcgagaggcc agccagcagc cgacggcaag   8520
cgcgaacacc aggcggcccc agcacagaac agccctgata caaggccacc accagccacc   8580
ccaatctgca tcctcctcgt gggacccccg aggaccaacc cccaaggctg cccccgatcc   8640
aaaccaccaa ccgcatcccc accacccccg ggaaagaaac ccccagcaat tggaaggccc   8700
ctccccctct tcctcaacac aagaactcca caaccgaacc gcacaagcga ccgaggtgac   8760
ccaaccgcag gcatccgact ccctagacag atcctctctc cccggcaaac taaacaaaac   8820
ttagggccaa ggaacataca cacccaacag aacccagacc ccggcccacg gcgccgcgcc   8880
cccaaccccc gacaaccaga gggagccccc aaccaatccc gccggctccc ccggtgccca   8940
caggcaggga caccaacccc cgaacagacc cagcacccaa ccatcgacaa tccaagacgg   9000
gggggccccc ccaaaaaaag gcccccaggg gccgacagcc agcaccgcga ggaagcccac   9060
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggaccccc   9240
gaaccgcaaa ggacatcagt atcccacagc ctctccaagt cccccggtct cctccccttc   9300
tcgaagggac caaaagatca atccaccaca cccgacgaca ctcaactccc caccccctaaa   9360
ggagacaccg ggaatcccag aatcaagact catccaatgt ccatcatggg tctcaaggtg   9420
aacgtctctg ccatattcat ggcagtactg ttaactctcc aaacacccac cggtcaaatc   9480
cattggggca atctctctaa gatagggggtg gtaggaatag gaagtgcaag ctacaaagtt   9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcaatgacc cagaatataa gaccggttca gagtgtagct   9720
tcaagtagga gacacaagag atttgcggga gtagtcctgg caggtgcggc cctaggcgtc   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg gccagaagct cgggctcaaa  10020
ttgctcagat actatacaga aatcctgtca ttatttggcc ccagcttacg ggaccccata  10080
tctgcggaga tatctatcca ggctttgagc tatgcgcttg gaggagacat caataaggtg  10140
ttagaaaagc tcggatacag tggaggtgat ttactgggca tcttagagag cagaggaata  10200
aaggcccgga taactcacgt cgacacagag tcctacttca ttgtcctcag tatagcctat  10260
```

```
ccgacgctgt ccgagattaa gggggtgatt gtccaccggc tagagggggt ctcgtacaac  10320
ataggctctc aagagtggta taccactgtg cccaagtatg ttgcaaccca agggtacctt  10380
atctcgaatt ttgatgagtc atcgtgtact ttcatgccag aggggactgt gtgcagccaa  10440
aatgccttgt acccgatgag tcctctgctc caagaatgcc tccgggggtc caccaagtcc  10500
tgtgctcgta cactcgtatc cgggtctttt gggaaccggt tcattttatc acaagggaac  10560
ctaatagcca attgtgcatc aatcctttgc aagtgttaca caacaggaac gatcattaat  10620
caagaccctg acaagatcct aacatacatt gctgccgatc actgcccggt agtcgaggtg  10680
aacggcgtga ccatccaagt cgggagcagg aggtatccag atgctgtgta cttgcacaga  10740
attgacctcg gtcctcccat atcattggag aggttggacg tagggacaaa tctggggaat  10800
gcaattgcta agttggagga tgccaaggaa ttgttggagt catcggacca gatattgagg  10860
agtatgaaag gtttatcgag cactagcata gtctacatcc tgattgcagt gtgtcttgga  10920
gggttgatag ggatccccgc tttaatatgt tgctgcaggg ggcgttgtaa caaaaaggga  10980
gaacaagttg gtatgtcaag accaggccta aagcctgatc ttacgggaac atcaaaatcc  11040
tatgtaaggt cgctctgatc ctctacaact cttgaaacac aaatgtccca caagtctcct  11100
cttcgtcatc aagcaaccac cgcacccagc atcaagccca cctgaaatta tctccggctt  11160
ccctctggcc gaacaatatc ggtagttaat taaaacttag ggtgcaagat catccacaat  11220
gtcaccacaa cgagaccgga taaatgcctt ctacaaagat aacccccatc ccaagggaag  11280
taggatagtc attaacagag aacatcttat gattgataga ccttatgttt tgctggctgt  11340
tctgtttgtc atgtttctga gcttgatcgg gttgctagcc attgcaggca ttagacttca  11400
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
tgaagtgggc ctgaggacac ctcagagatt cactgaccta gtgaaattca tctctgacaa  11580
gattaaattc cttaatccgg atagggagta cgacttcaga gatctcactt ggtgtatcaa  11640
cccgccagag agaatcaaat tggattatga tcaatactgt gcagatgtgg ctgctgaaga  11700
gctcatgaat gcattggtga actcaactct actggagacc agaacaacca atcagttcct  11760
agctgtctca aagggaaact gctcagggcc cactacaatc agaggtcaat tctcaaacat  11820
gtcgctgtcc ctgttagact tgtatttagg tcgaggttac aatgtgtcat ctatagtcac  11880
tatgacatcc cagggaatgt atgggggaac ttacctagtg gaaaagccta atctgagcag  11940
caaaaggtca gagttgtcac aactgagcat gtaccgagtg tttgaagtag gtgttatcag  12000
aaatccgggt ttgggggctc cggtgttcca tatgacaaac tatcttgagc aaccagccag  12060
taatgatctc agcaactgta tggtggcttt gggggagctc aaactcgcag ccctttgtca  12120
cggggaagat tctatcacaa ttccctatca gggatcaggg aaaggtgtca gcttccagct  12180
cgtcaagcta ggtgtctgga aatccccaac cgacatgcaa tcctgggtcc ccttatcaac  12240
ggatgatcca gtgatagaca ggctttacct ctcatctcac agaggtgtta tcgctgacaa  12300
tcaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
```

cctagcctta ggtgtaatca acacattgga gtggataccg agattcaagg ttagtcccta 12660
cctcttcaat gtcccaatta aggaagcagg cgaagactgc catgccccaa catacctacc 12720
tgcggaggtg gatggtgatg tcaaactcag ttccaatctg gtgattctac ctggtcaaga 12780
tctccaatat gttttggcaa cctacgatac ttccagggtt gaacatgctg tggtttatta 12840
cgtttacagc ccaggccgct cattttctta cttttatcct tttaggttgc ctataaaggg 12900
ggtccccatc gaattacaag tggaatgctt cacatgggac caaaaactct ggtgccgtca 12960
cttctgtgtg cttgcggact cagaatctgg tggacatatc actcactctg ggatggtggg 13020
catgggagtc agctgcacag tcacccggga agatggaacc aatcgcagat agggctgcta 13080
gtgaaccaat ctcatgatgt cacccagaca tcaggcatac ccactagtgt gaaatagaca 13140
tcagaattaa gaaaaacgta gggtccaagt ggttccccgt tatggactcg ctatctgtca 13200
accagatctt ataccctgaa gttcacctag atagcccgat agttaccaat aagatagtag 13260
ccatcctgga gtatgctcga gtccctcacg cttacagcct ggaggaccct acactgtgtc 13320
agaacatcaa gcaccgccta aaaaacggat tttccaacca aatgattata aacaatgtgg 13380
aagttgggaa tgtcatcaag tccaagctta ggagttatcc ggcccactct catattccat 13440
atccaaattg taatcaggat ttatttaaca tagaagacaa agagtcaacg aggaagatcc 13500
gtgaactcct caaaaagggg aattcgctgt actccaaagt cagtgataag gttttccaat 13560
gcttaaggga cactaactca cggcttggcc taggctccga attgagggag gacatcaagg 13620
agaaagttat taacttggga gtttacatgc acagctccca gtggtttgag ccctttctgt 13680
tttggtttac agtcaagact gagatgaggt cagtgattaa atcacaaacc catacttgcc 13740
ataggaggag acacacacct gtattcttca ctggtagttc agttgagttg ctaatctctc 13800
gtgaccttgt tgctataatc agtaaagagt ctcaacatgt atattacctg acatttgaac 13860
tggttttgat gtattgtgat gtcatagagg ggaggttaat gacagagacc gctatgacta 13920
ttgatgctag gtatacagag cttctaggaa gagtcagata catgtggaaa ctgatagatg 13980
gtttcttccc tgcactcggg aatccaactt atcaaattgt agccatgctg gagcctcttt 14040
cacttgctta cctgcagctg agggatataa cagtagaact cagaggtgct ttccttaacc 14100
actgctttac tgaaatacat gatgttcttg accaaaacgg gttttctgat gaaggtactt 14160
atcatgagtt aattgaagct ctagattaca ttttcataac tgatgacata catctgacag 14220
gggagatttt ctcatttttc agaagtttcg gccaccccag acttgaagca gtaacggctg 14280
ctgaaaatgt taggaaatac atgaatcagc ctaaagtcat tgtgtatgag actctgatga 14340
aaggtcatgc catattttgt ggaatcataa tcaacggcta tcgtgacagg cacggaggca 14400
gttggccacc gctgaccctc cccctgcatg ctgcagacac aatccggaat gctcaagctt 14460
caggtgaagg gttaacacat gagcagtgcg ttgataactg gagatctttt gctggagtga 14520
aatttggctg ctttatgcct cttagcctgg atagtgatct gacaatgtac ctaaaggaca 14580
aggcacttgc tgctctccaa agggaatggg attcagttta cccgaaagag ttcctgcgtt 14640
acgaccctcc caagggaacc gggtcacgga ggcttgtaga tgttttcctt aatgattcga 14700
gctttgaccc atatgatgtg ataatgtatg ttgtaagtgg agcttacctc catgaccctg 14760
agttcaacct gtcttacagc ctgaaagaaa aggagatcaa ggaaacaggt agacttttttg 14820
ctaaaatgac ttacaaaatg agggcatgcc aagtgattgc tgaaaatcta atctcaaacg 14880
ggattggcaa atattttaag gacaatggga tggccaagga tgagcacgat ttgactaagg 14940
cactccacac tctagctgtc tcaggagtcc ccaaagatct caaagaaagt cacaggggggg 15000 ggccagtctt aaaaacctac tcccgaagcc cagtccacac aagtaccagg aacgtgagag 15060
cagcaaaagg gtttataggg ttccctcaag taattcggca ggaccaagac actgatcatc 15120
cggagaatat ggaagcttac gagacagtca gtgcatttat cacgactgat ctcaagaagt 15180
actgccttaa ttggagatat gagaccatca gcttgtttgc acagaggcta aatgagattt 15240
acggattgcc ctcatttttc cagtggctgc ataagaggct tgagacctct gtcctgtatg 15300
taagtgaccc tcattgcccc cccgaccttg acgcccatat cccgttatat aaagtcccca 15360
atgatcaaat cttcattaag taccctatgg gaggtataga agggtattgt cagaagctgt 15420
ggaccatcag caccattccc tatctatacc tggctgctta tgagagcgga gtaaggattg 15480
cttcgttagt gcaaggggac aatcagacca tagccgtaac aaaaagggta cccagcacat 15540
ggccctacaa ccttaagaaa cgggaagctg ctagagtaac tagagattac tttgtaattc 15600
ttaggcaaag gctacatgat attggccatc acctcaaggc aaatgagaca attgtttcat 15660
cacatttttt tgtctattca aaaggaatat attatgatgg gctacttgtg tcccaatcac 15720
tcaagagcat cgcaagatgt gtattctggt cagagactat agttgatgaa acaagggcag 15780
catgcagtaa tattgctaca acaatggcta aaagcatcga gagaggttat gaccgttacc 15840
ttgcatattc cctgaacgtc ctaaaagtga tacagcaaat tctgatctct cttggcttca 15900
caatcaattc aaccatgacc cgggatgtag tcatacccct cctcacgaac aacgacctct 15960
taataaggat ggcactgttg cccgctccta ttggggggat gaattatctg aatatgagca 16020
ggctgtttgt cagaaacatc ggtgatccag taacatcatc aattgctgat ctcaagagaa 16080
tgattctcgc ctcactaatg cctgaagaga ccctccatca agtaatgaca caacaaccgg 16140
gggactcttc attcctagac tgggctagcg acccttactc agcaaatctt gtatgtgtcc 16200
agagcatcac tagactcctc aagaacataa ctgcaaggtt tgtcctgatc catagtccaa 16260
acccaatgtt aaaaggatta ttccatgatg acagtaaaga agaggacgag ggactggcgg 16320
cattcctcat ggacaggcat attatagtac ctagggcagc tcatgaaatc ctggatcata 16380
gtgtcacagg ggcaagagag tctattgcag gcatgctgga taccacaaaa ggcctgattc 16440
gagccagcat gaggaagggg gggttaacct ctcgagtgat aaccagattg tccaattatg 16500
actatgaaca attcagagca gggatggtgc tattgacagg aagaaagaga aatgtcctca 16560
ttgacaaaga gtcatgttca gtgcagctgg cgagagctct aagaagccat atgtgggcga 16620
ggctagctcg aggacggcct atttacggcc ttgaggtccc tgatgtacta gaatctatgc 16680
gaggccacct tattcggcgt catgagacat gtgtcatctg cgagtgtgga tcagtcaact 16740
acggatggtt ttttgtcccc tcgggttgcc aactggatga tattgacaag gaaacatcat 16800
ccttgagagt cccatatatt ggttctacca ctgatgagag aacagacatg aagcttgcct 16860
tcgtaagagc cccaagtcga tccttgcgat ctgctgttag aatagcaaca gtgtactcat 16920
gggcttacgg tgatgatgat agctcttgga acgaagcctg gttgttggct aggcaaaggg 16980
ccaatgtgag cctggaggag ctaagggtga tcactcccat ctcaacttcg actaatttag 17040
cgcataggtt gagggatcgt agcactcaag tgaaatactc aggtacatcc cttgtccgag 17100
tggcgaggta taccacaatc tccaacgaca atctctcatt tgtcatatca gataagaagg 17160
ttgatactaa ctttatatac caacaaggaa tgcttctagg gttgggtgtt ttagaaacat 17220
tgtttcgact cgagaaagat accggatcat ctaacacggt attacatctt cacgtcgaaa 17280
cagattgttg cgtgatcccg atgatagatc atcccaggat acccagctcc cgcaagctag 17340

-continued

```
agctgagggc agagctatgt accaacccat tgatatatga taatgcacct ttaattgaca  17400
gagatacaac aaggctatac acccagagcc ataggaggca ccttgtggaa tttgttacat  17460
ggtccacacc ccaactatat cacattttag ctaagtccac agcactatct atgattgacc  17520
tggtaacaaa atttgagaag gaccatatga atgaaatttc agctctcata ggggatgacg  17580
atatcaatag tttcataact gagtttctgc tcatagagcc aagattattc actatctact  17640
tgggccagtg tgcggccatc aattgggcat ttgatgtaca ttatcataga ccatcaggga  17700
aatatcagat gggtgagctg ttgtcatcgt tcctttctag aatgagcaaa ggagtgttta  17760
aggtgcttgt caatgctcta agccacccaa agatctacaa gaaattctgg cattgtggta  17820
ttatagagcc tatccatggt ccttcacttg atgctcaaaa cttgcacaca actgtgtgca  17880
acatggttta cacatgctat atgacctacc tcgacctgtt gttgaatgaa gagttagaag  17940
agttcacatt tctcttgtgt gaaagcgacg aggatgtagt accggacaga ttcgacaaca  18000
tccaggcaaa acacttatgt gttctggcag atttgtactg tcaaccaggg acctgcccac  18060
caattcgagg tctaagaccg gtagagaaat gtgcagttct aaccgaccat atcaaggcag  18120
aggctaggtt atctccagca ggatcttcgt ggaacataaa tccaattatt gtagaccatt  18180
actcatgctc tctgacttat ctccggcgag gatcgatcaa acagataaga ttgagagttg  18240
atccaggatt cattttcgac gccctcgctg aggtaaatgt cagtcagcca aagatcggca  18300
gcaacaacat ctcaaatatg agcatcaagg ctttcagacc cccacacgat gatgttgcaa  18360
aattgctcaa agatatcaac acaagcaagc acaatcttcc catttcaggg ggcaatctcg  18420
ccaattatga aatccatgct ttccgcagaa tcgggttgaa ctcatctgct tgctacaaag  18480
ctgttgagat atcaacatta attaggagat gccttgagcc aggggaggac ggcttgttct  18540
tgggtgaggg atcgggttcc atgttgatca cttataagga gatacttaaa ctaaacaagt  18600
gcttctataa tagtggggtt tccgccaatt ctagatctgg tcaaagggaa ttagcaccct  18660
atccctccga agttggcctt gtcgaacaca gaatgggagt aggtaatatt gtcaaagtgc  18720
tctttaacgg gaggcccgaa gtcacgtggg taggcagtgt agattgcttc aatttcatag  18780
ttagtaatat ccctacctct agtgtggggt ttatccattc agatatagag accttgccta  18840
acaaagatac tatagagaag ctagaggaat tggcagccat cttatcgatg gctctgctcc  18900
tgggcaaaat aggatcaata ctggtgatta agcttatgcc tttcagcggg gattttgttc  18960
agggatttat aagttatgta gggtcccatt atagagaagt gaaccttgta taccctagat  19020
acagcaactt catatctact gaatcttatt tggttatgac agatctcaag gctaaccggc  19080
taatgaatcc tgaaaagatt aagcagcaga taattgaatc atctgtgagg acttcacctg  19140
gacttatagg tcacatccta tccattaagc aactaagctg catacaagca attgtgggag  19200
acgcagttag tagaggtgat atcaatccta ctctgaaaaa acttacacct atagagcagg  19260
tgctgatcaa ttgcgggttg gcaattaacg gacctaagct gtgcaaagaa ttgatccacc  19320
atgatgttgc ctcagggcaa gatggattgc ttaattctat actcatcctc tacagggagt  19380
tggcaagatt caaagacaac caaagaagtc aacaagggat gttccacgct taccccgtat  19440
tggtaagtag caggcaacga gaacttatat ctaggatcac ccgcaaattt tgggggcaca  19500
ttcttcttta ctccgggaac agaaagttga taaataagtt tatccagaat ctcaagtccg  19560
gctatctgat actagactta caccagaata tcttcgttaa gaatctatcc aagtcagaga  19620
aacagattat tatgacgggg ggtttgaaac gtgagtgggt ttttaaggta acagtcaagg  19680
agaccaaaga atggtataag ttagtcggat acagtgccct gattaaggac taattggttg  19740
```

aactccggaa ccctaatcct gccctaggtg gttaggcatt atttgcaata gattaaagaa 19800
aactttgaaa atacgaagtt tctattccca gctttgtctg gtggccggca tggtcccagc 19860
ctcctcgctg gcgccggctg ggcaacattc cgaggggacc gtcccctcgg taatggcgaa 19920
tgggacgcgg ccgatccggc tgctaacaaa gcccgaaagg aagctgagtt ggctgctgcc 19980
accgctgagc aataactagc ataacccctt ggggcctcta aacgggtctt gaggggtttt 20040
ttgctgaaag gaggaactat atccggatgc ggccgatccg gctgctaaca aagcccgaaa 20100
ggaagctgag ttggctgctg ccaccgctga gcaataacta gcataacccc ttggggcctc 20160
taaacgggtc ttgaggggtt ttttgctgaa aggaggaact atatccggat ggccgccacc 20220
ggccggtggg ccttgcagca catcccccctt tcgccagctg gcgtaatagc gaagaggccc 20280
gcaccgatcg cccttcccaa cagttgcgca gcctgaatgg cgaatgggac gcgccctgta 20340
gcggcgcatt aagcgcggcg ggtgtggtgg ttacgcgcag cgtgaccgct acacttgcca 20400
gcgccctagc gcccgctcct ttcgctttct tcccttcctt tctcgccacg ttcgccggct 20460
ttccccgtca agctctaaat cgggggctcc ctttagggtt ccgatttagt gctttacggc 20520
acctcgaccc caaaaaactt gattagggtg atggttcacg tgggccatcg ccctgataga 20580
cggtttttcg ccctttgacg ttggagtcca cgttctttaa tagtggactc ttgttccaaa 20640
ctggaacaac actcaaccct atctcggtct attcttttga tttataaggg attttgccga 20700
tttcggccta ttggttaaaa aatgagctga tttaacaaaa atttaacgcg aattttaaca 20760
aaatattaac gcttacaatt taggtggcac ttttcgggga aatgtgcgcg gaacccctat 20820
ttgtttattt ttctaaatac attcaaatat gtatccgctc atgagacaat aaccctgata 20880
aatgcttcaa taatattgaa aaaggaagag tatgagtatt caacatttcc gtgtcgccct 20940
tattcccttt tttgcggcat tttgccttcc tgtttttgct cacccagaaa cgctggtgaa 21000
agtaaaagat gctgaagatc agttgggtgc acgagtgggt tacatcgaac tggatctcaa 21060
cagcggtaag atccttgaga gttttcgccc cgaagaacgt tttccaatga tgagcacttt 21120
taaagttctg ctatgtggcg cggtattatc ccgtattgac gccgggcaag agcaactcgg 21180
tcgccgcata cactattctc agaatgactt ggttgagtac tcaccagtca cagaaaagca 21240
tcttacggat ggcatgacag taagagaatt atgcagtgct gccataacca tgagtgataa 21300
cactgcggcc aacttacttc tgacaacgat cggaggaccg aaggagctaa ccgctttttt 21360
gcacaacatg ggggatcatg taactcgcct tgatcgttgg gaaccggagc tgaatgaagc 21420
cataccaaac gacgagcgtg acaccacgat gcctgtagca atggcaacaa cgttgcgcaa 21480
actattaact ggcgaactac ttacactagc ttcccggcaa caattaatag actggatgga 21540
ggcggataaa gttgcaggac cacttctgcg ctcggccctt ccggctggct ggtttattgc 21600
tgataaatct ggagccggtg agcgtgggtc tcgcggtatc attgcagcac tggggccaga 21660
tggtaagccc tcccgtatcg tagttatcta cacgacgggg agtcaggcaa ctatggatga 21720
acgaaataga cagatcgctg agataggtgc ctcactgatt aagcattggt aactgtcaga 21780
ccaagtttac tcatatatac tttagattga tttaaaactt catttttaat ttaaaaggat 21840
ctaggtgaag atcctttttg ataatctcat gaccaaaatc ccttaacgtg agttttcgtt 21900
ccactgagcg tcagaccccg tagaaaagat caaaggatct tcttgagatc cttttttttct 21960
gcgcgtaatc tgctgcttgc aaacaaaaaa accaccgcta ccagcggtgg tttgtttgcc 22020
ggatcaagag ctaccaactc tttttccgaa ggtaactggc ttcagcagag cgcagatacc 22080
aaatactgtt cttctagtgt agccgtagtt aggccaccac ttcaagaact ctgtagcacc 22140
gcctacatac ctcgctctgc taatcctgtt accagtggct gctgccagtg gcgataagtc 22200
gtgtcttacc gggttggact caagacgata gttaccggat aaggcgcagc ggtcgggctg 22260
aacggggggt tcgtgcacac agcccagctt ggagcgaacg acctacaccg aactgagata 22320
cctacagcgt gagctatgag aaagcgccac gcttcccgaa gggagaaagg cggacaggta 22380
tccggtaagc ggcagggtcg gaacaggaga gcgcacgagg gagcttccag ggggaaacgc 22440
ctggtatctt tatagtcctg tcgggtttcg ccacctctga cttgagcgtc gatttttgtg 22500
atgctcgtca ggggggcgga gcctatggaa aaacgccagc aacgcggcct ttttacggtt 22560
cctggccttt tgctggcctt ttgctcacat gttctttcct gcgttatccc ctgattctgt 22620
ggataaccgt attaccgcct ttgagtgagc tgataccgct cgccgcagcc gaacgaccga 22680
gcgcagcgag tcagtgagcg aggaagcgga agagcgccca atacgcaaac cgcctctccc 22740
cgcgcgttgg ccgattcatt aatgcagctg gcacgacagg tttcccgact ggaaagcggg 22800
cagtgagcgc aacgcaatta atgtgagtta gctcactcat taggcacccc aggctttaca 22860
ctttatgctt ccggctcgta tgttgtgtgg aattgtgagc ggacaacaat ttcacacagg 22920
aaacagctat gaccatgatt acgccaagct cgggcggccg cttgtaatac gactcactat 22980
a 22981

<210> SEQ ID NO 22
<211> LENGTH: 3822
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3822)
<223> OTHER INFORMATION: Non-codon optimized SARS-CoV-2 Spike
from rMV-EZ-SARS-CoV-2-S clone 3
<220> FEATURE:
<221> NAME/KEY: misc_feature
<222> LOCATION: (3713)..(3713)
<223> OTHER INFORMATION: mutation that arose during cloning
<220> FEATURE:
<221> NAME/KEY: misc_feature
<222> LOCATION: (3805)..(3807)
<223> OTHER INFORMATION: mutation that disrupts ER retention signal
<220> FEATURE:
<221> NAME/KEY: misc_feature
<222> LOCATION: (3811)..(3813)
<223> OTHER INFORMATION: mutation that disrupts ER retention signal

<400> SEQUENCE: 22
atgtttgttt ttcttgtttt attgccacta gtctctagtc agtgtgttaa tcttacaacc 60
agaactcaat taccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600

-continued

```
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
```

cttcaaagtt tgcagacata tgtgactcaa caattaatta gagctgcaga aatcagagct 3060
tctgctaatc ttgctgctac taaaatgtca gagtgtgtac ttggacaatc aaaaagagtt 3120
gatttttgtg gaaagggcta tcatcttatg tccttccctc agtcagcacc tcatggtgta 3180
gtcttcttgc atgtgactta tgtccctgca caagaaaaga acttcacaac tgctcctgcc 3240
atttgtcatg atggaaaagc acactttcct cgtgaaggtg tctttgtttc aaatggcaca 3300
cactggtttg taacacaaag gaatttttat gaaccacaaa tcattactac agacaacaca 3360
tttgtgtctg gtaactgtga tgttgtaata ggaattgtca acaacacagt ttatgatcct 3420
ttgcaacctg aattagactc attcaaggag gagttagata aatattttaa gaatcataca 3480
tcaccagatg ttgatttagg tgacatctct ggcattaatg cttcagttgt aaacattcaa 3540
aaagaaattg accgcctcaa tgaggttgcc aagaatttaa atgaatctct catcgatctc 3600
caagaacttg gaaagtatga gcagtatata aaatggccat ggtacatttg gctaggtttt 3660
atagctggct tgattgccat agtaatggtg acaattatgc tttgctgtat gaacagttgc 3720
tgtagttgtc tcaagggctg ttgttcttgt ggatcctgct gcaaatttga tgaagacgac 3780
tctgagccag tgctcaaagg agtcgcatta gcttacacat aa 3822

<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23

Ala Ser Val Gly
1

<210> SEQ ID NO 24
<211> LENGTH: 53
<212> TYPE: DNA
<213> ORGANISM: Artificial Sequence
<220> FEATURE:
<223> OTHER INFORMATION: Synthetic

<400> SEQUENCE: 24
caaagtgatt gcctcccaag ttccacaggc gcgccatgtt cgtcttcctg gtc 53

<210> SEQ ID NO 25
<211> LENGTH: 56
<212> TYPE: DNA
<213> ORGANISM: Artificial Sequence
<220> FEATURE:
<223> OTHER INFORMATION: Synthetic

<400> SEQUENCE: 25
gttggcaggt aagttgagct gtaggacgtc gcgcgttagg tgtaatgcag cttcac 56

<210> SEQ ID NO 26
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (47)..(48)
<223> OTHER INFORMATION: mutation that disrupts the ER retention signal
<220> FEATURE:
<221> NAME/KEY: misc_feature -continued

```
<222> LOCATION: (53)..(54)
<223> OTHER INFORMATION: mutation that disrupts the ER retention signal

<400> SEQUENCE: 26

ggttggcagg taagttgagc tgtaggacgt cgcgcgttag gtgtaagcca gcgccacgcc      60
```

MEASLES VIRUS VACCINE EXPRESSING SARS-COV-2 PROTEIN(S)

CROSS-REFERENCE TO RELATED APPLICATIONS

This patent application claims the benefit of U.S. Provisional Patent Application No. 63/039,275, filed Jun. 15, 2020, and U.S. Provisional Patent Application No. 63/071,479, filed Aug. 28, 2020, each of which is incorporated by reference herein in its entirety.

SEQUENCE LISTING

Incorporated by reference in its entirety herein is a nucleotide/amino acid sequence listing submitted concurrently herewith and identified as follows: One 337,215 Byte ASCII (Text) file named "750663.TXT," created on Aug. 31, 2020.

BACKGROUND OF THE INVENTION

In December 2019, a novel coronavirus (Severe Acute Respiratory Syndrome Coronavirus 2 or SARS-CoV-2) belonging to the betacoronavirus family emerged. All human betacoronaviruses are unique from one another, however, they do share a certain degree of genetic and structural homology. SARS-CoV-2 genome sequence homology with SARS-CoV and MERS-CoV is 77% and 50%, respectively.

In contrast to the relatively smaller outbreaks of SARS-CoV in 2002 and MERS-CoV in 2012, SARS-CoV-2 is exhibiting an unprecedented scale of infection, resulting in a global pandemic declaration of Coronavirus Infectious Disease (COVID-19) by the World Health Organization (WHO). COVID-19 has a high infection rate and long incubation period. Similar to influenza, COVID-19 has the potential to become a seasonal disease.

Therefore, there is a desire for a COVID-19 vaccine.

BRIEF SUMMARY OF THE INVENTION

An embodiment of the invention provides a recombinant measles viral vector (rMV) (e.g., Edmonston Zagreb (EZ) MV) comprising a nucleic acid sequence encoding a Severe Acute Respiratory Syndrome Coronavirus 2 (SARS-CoV-2) spike (S) glycoprotein.

An embodiment of the invention provides a pharmaceutical composition comprising the recombinant measles viral vector, as well as methods for preventing, inhibiting, reducing, eliminating, protecting, or delaying the onset of an infection or an infectious clinical condition caused by coronavirus in a subject and methods for inducing an immune response against a coronavirus in a subject.

An embodiment of the invention also provides a polypeptide comprising an amino acid sequence selected from the group consisting of the amino acid sequences of SEQ ID NO: 8 (S6), SEQ ID NO: 9 (S-CO), SEQ ID NO: 10 (S-CO-AA), SEQ ID NO: 11 (S), SEQ ID NO: 12 (S-CO-AA-PP), SEQ ID NO: 13 (S-CO-AA-fneg-PP), and SEQ ID NO: 14 (S-CO-AA-fneg), as well as related nucleic acids, recombinant vectors, compositions, and methods.

BRIEF DESCRIPTION OF THE SEVERAL VIEWS OF THE DRAWINGS

1A is a schematic representation of parental virus $rMV^{EZ}$EGFP(3), the cDNA clone of which was used to generate cDNA plasmids for viruses $rMV^{EZ}$SARS-CoV-2-S3, $rMV^{EZ}$SARS-CoV-2-S6, $rMV^{EZ}$SARS-CoV-2-S-CO and $rMV^{EZ}$SARS-CoV-2-S-COAA. Amino acid differences in the spike between the four viruses are shown, wherein underlined residues differ from wild-type spike sequence. Residues K and H in the cytoplasmic tail region were altered to A and A to disrupt a endoplasmic reticulum (ER) retention signal (KxHxx) sequence in viruses $rMV^{EZ}$SARS-CoV-2-S3, $rMV^{EZ}$SARS-CoV-2-S6 and $rMV_{EZ}$SARS-CoV-2-S-COAA. RBD; receptor binding domain, TM; transmembrane domain. FIG. 1B is a phase image of Vero cell monolayer infected with $rMV^{EZ}$SARS-CoV-2-S6 (shown as a representative image of a primary rescue). FIG. 1C are images of an immunoplaque assay of Vero cell monolayers infected with a 10-fold dilution of rescued $rMV^{EZ}$SARS-CoV-2-S6. Plaques were stained using anti-SARS-CoV-2-S antibody. Dilutions $10^{-6}$ and $10^{-7}$ are shown as representatives.

FIG. 3A is a schematic describing the experiment. Groups of 5 mice were infected with either $rMV^{EZ}$SARS-CoV-2-S3, $rMV^{EZ}$SARS-CoV-2-S6, $rMV^{EZ}$SARS-CoV-2-S-CO, $rMV^{EZ}$SARS-CoV-2-S-COAA, or $rMV^{EZ}$EGFP(3). Serum was collected on days 21 and 42, and splenocytes were collected on day 42. FIG. 3B is table showing neutralization of SARS-CoV-2 using the harvested mice serum, indicating that SARS-CoV-2 neutralizing antibodies were produced in mice vaccinated with $rMV^{EZ}$SARS-CoV-2-S-CO and $rMV^{EZ}$SARS-CoV-2-S-COAA viruses.

FIG. 11A is a schematic describing the experiment. Groups of 2 or 3 African green monkeys (AGMs) were vaccinated with $rMV^{EZ}$SARS-CoV-2-S-CO or $rMV^{EZ}$ and then challenged with SARS-CoV-2. FIG. 11B is a table with neutralization titers of serum against SARS-CoV-2, which were determined as described in Klimstra et al., 2020: PMID: 32821033, and MV as described in de Swart et al., 2017: PMID: 29263877. The results support that primates produce antibodies which neutralize both SARS-CoV-2 and measles virus following vaccination.

DETAILED DESCRIPTION OF THE INVENTION

An embodiment of the invention provides a recombinant measles viral vector that encodes one or more (e.g., two, three, four, or five) SARS-CoV-2 spike glycoproteins, wherein the SARS-CoV-2 spike glycoproteins may be the same or different. The recombinant measles viral vector or a composition thereof can be administered to a subject to prevent, inhibit, reduce, eliminate, protect, or delay the onset of an infection or an infectious clinical condition caused by coronavirus (e.g., SARS-CoV-2) in a subject. The recombinant measles viral vector or a composition thereof also can be administered to a subject to induce an immune response against a coronavirus (e.g., SARS-CoV-2) in a subject.

The recombinant measles viral vector can be any suitable recombinant measles viral vector. For example, the measles viral vector can be an Edmonston wild-type virus or vaccine strains of the Edmonston lineage, such as the AIK-C, Moraten, Rubeovax, Schwarz, or Zagreb strains (Bankamp et al., *J. Infect. Dis.,* 204 Suppl. 1: 5533-5548 (2011)). Alternatively, the measles viral vector can be selected from the group consisting of CAM-70, Changchun-47, Leningrad-4, Shanghai-191 (Bankamp et al., *J. Infect. Dis.,* 204 Suppl. 1: 5533-5548 (2011)), Leningrad-16, Moscow-5 (Sinitsyna et al., *Res. Virol.,* 141(5): 517-31 (1990)), 9301B (Takeda et al., *J Virol.,* 72(11): 8690-8696 (1998)), ATTENUVAX®, and those described in Schneider-Schaulies et al., *PNAS,* 92(2): 3943-7 (1995).

Measles viruses and recombinant measles viral vectors are described in WO 98/13501, which provides the sequence of a DNA copy of the positive strand (antigenomic) message sense RNA of various wild-type of vaccine measles strains, including Edmonston wild-type strain, Moraten strain, and Schwarz strain, and WO 97/06270, which discloses the production of recombinant measles vectors.

Figure 4:
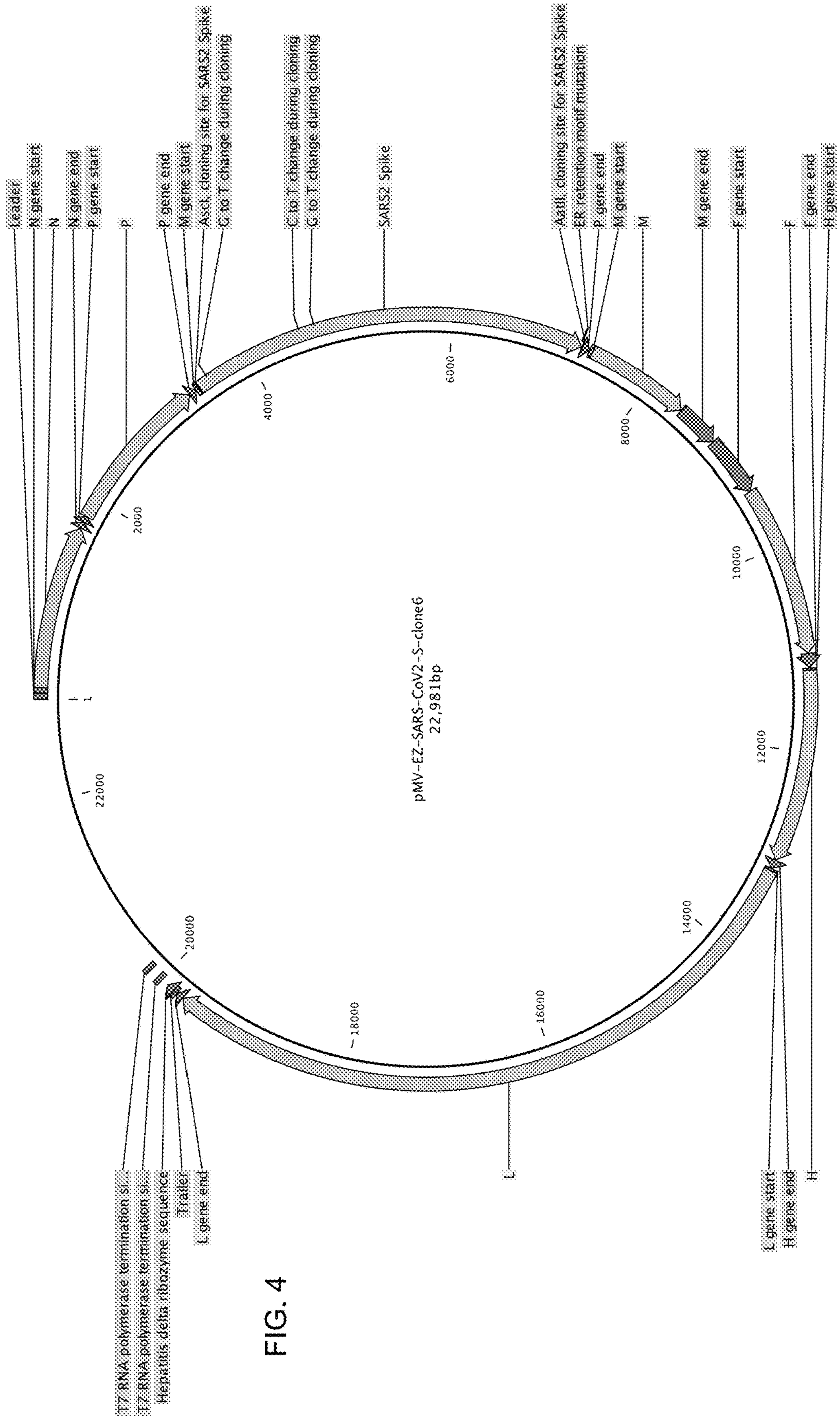
FIG. 4 is a vector map of $rMV^{EZ}$SARS-CoV-2-S6.
Figure 5:
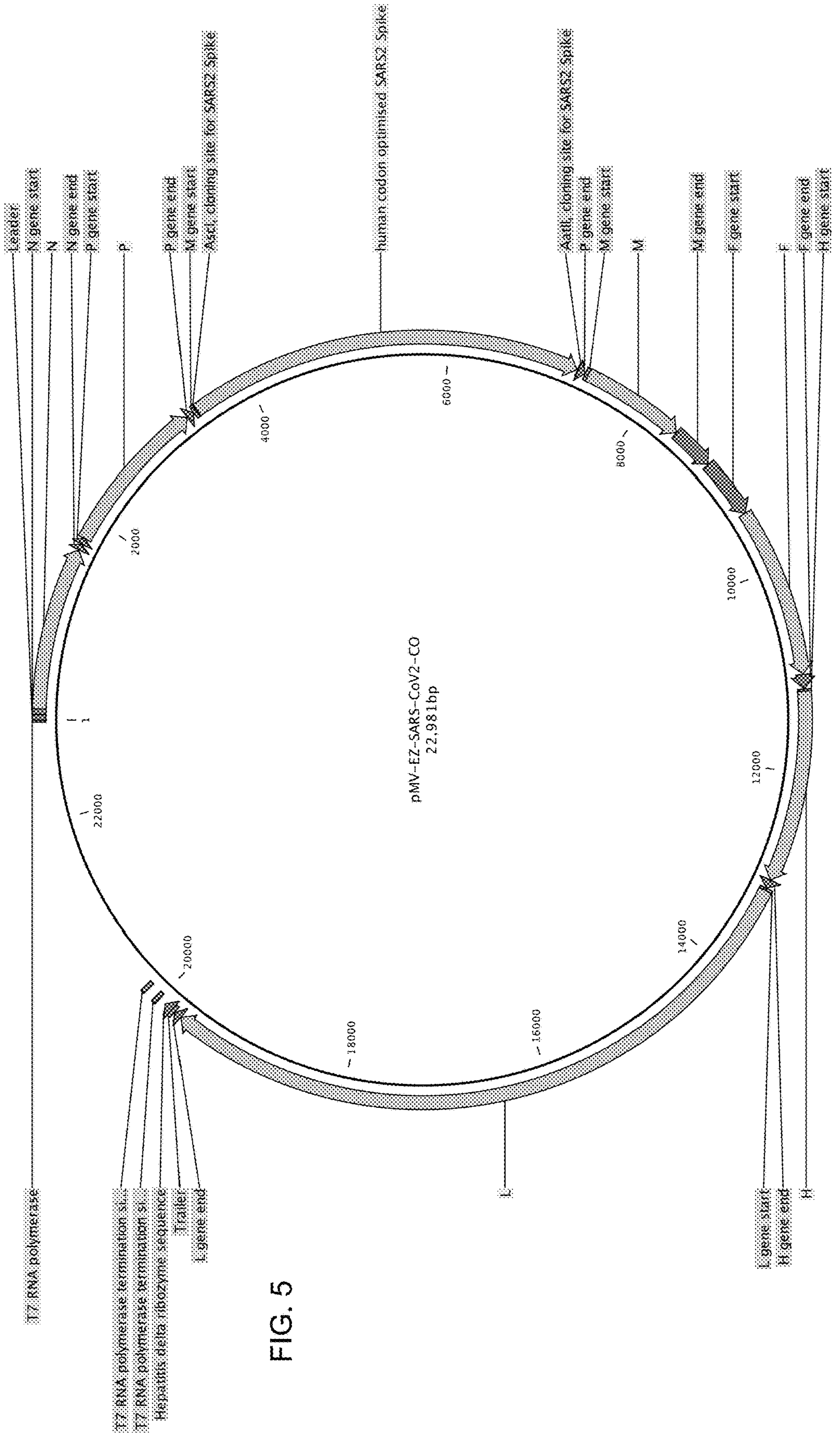
FIG. 5 is a vector map of $rMV^{EZ}$SARS-CoV-2-S-CO.
Figure 6:
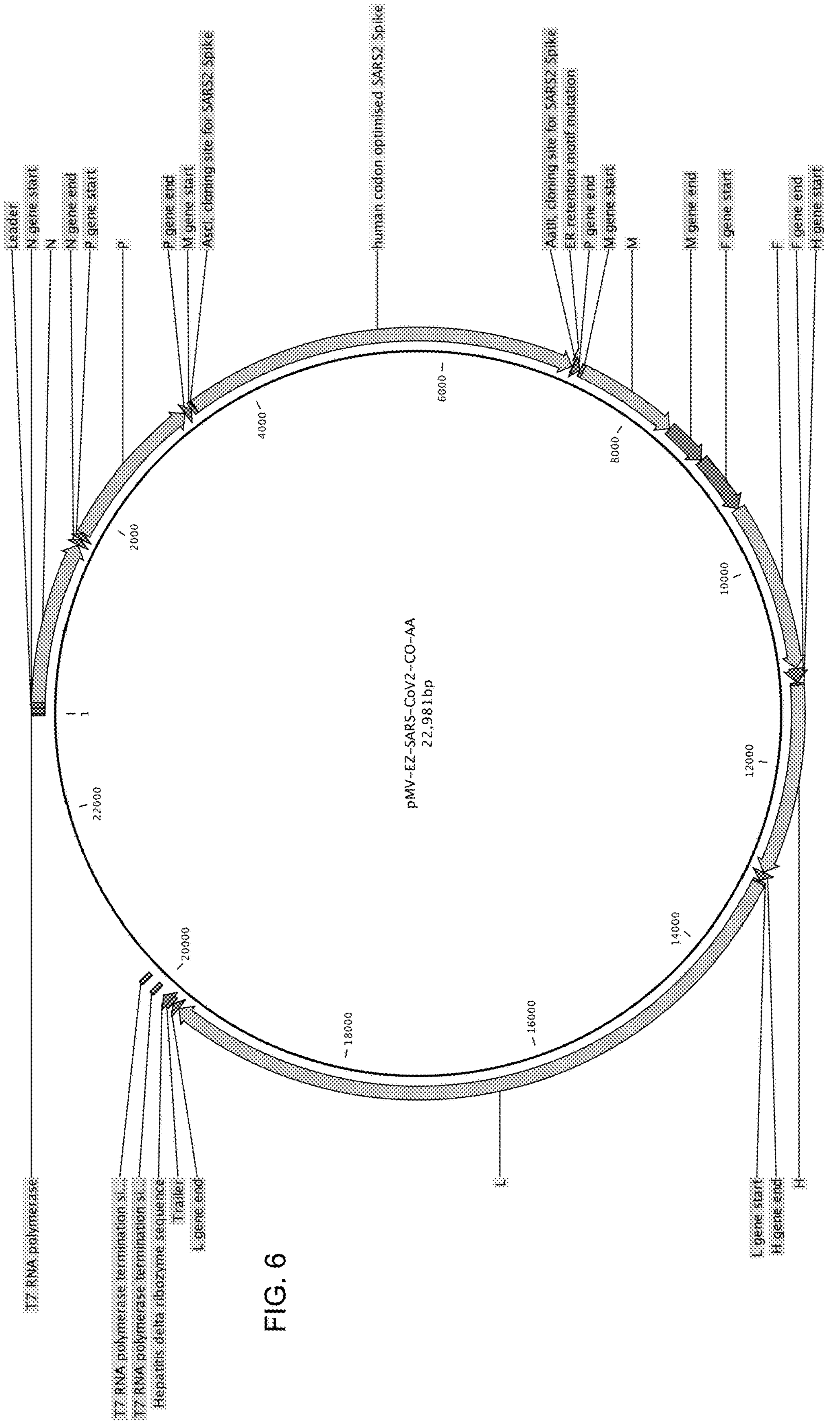
FIG. 6 is a vector map of $rMV^{EZ}$SARS-CoV-2-S-COAA.
Figure 7:
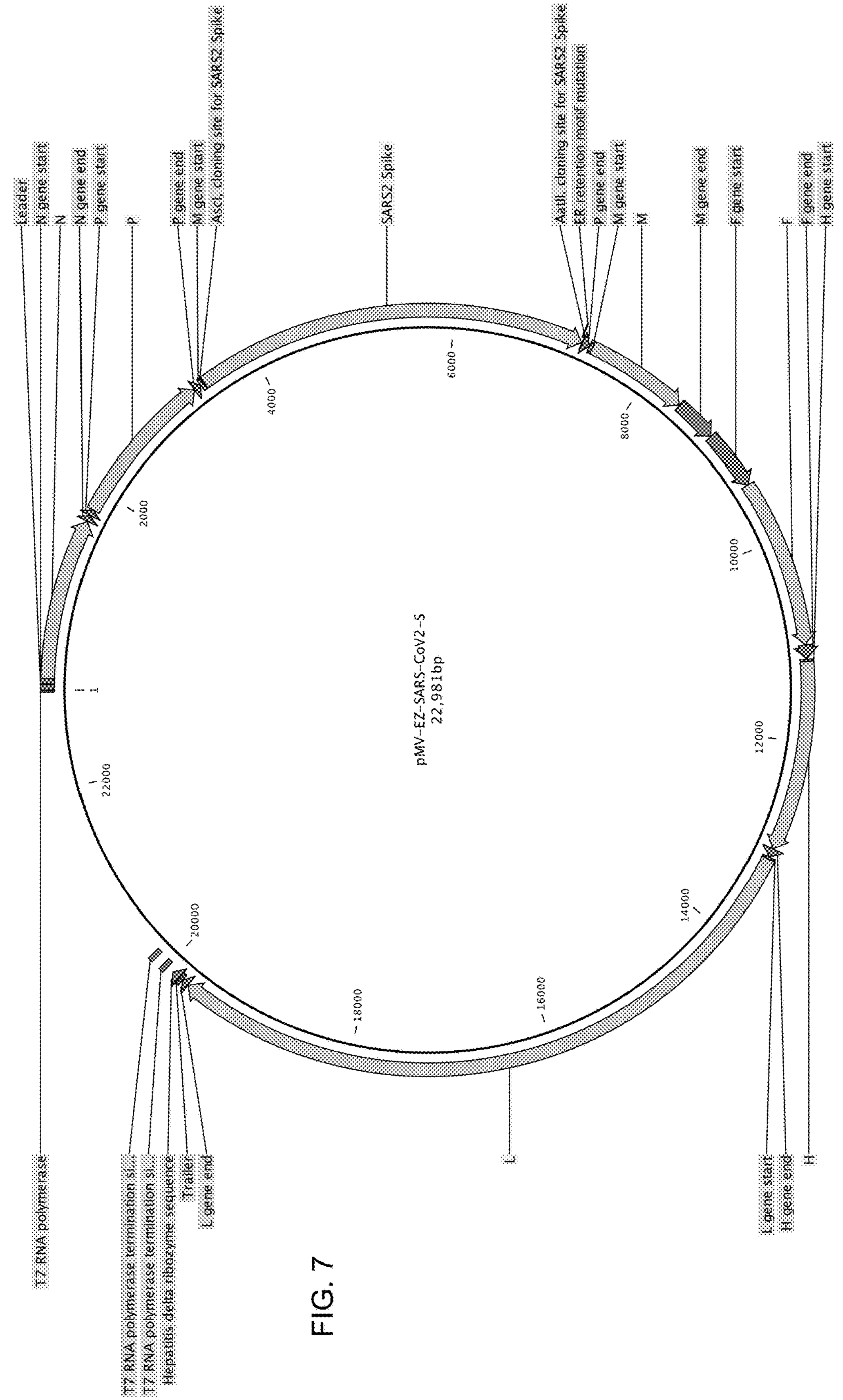
FIG. 7 is a vector map of $rMV^{EZ}$SARS-CoV-2-S.
Figure 8:
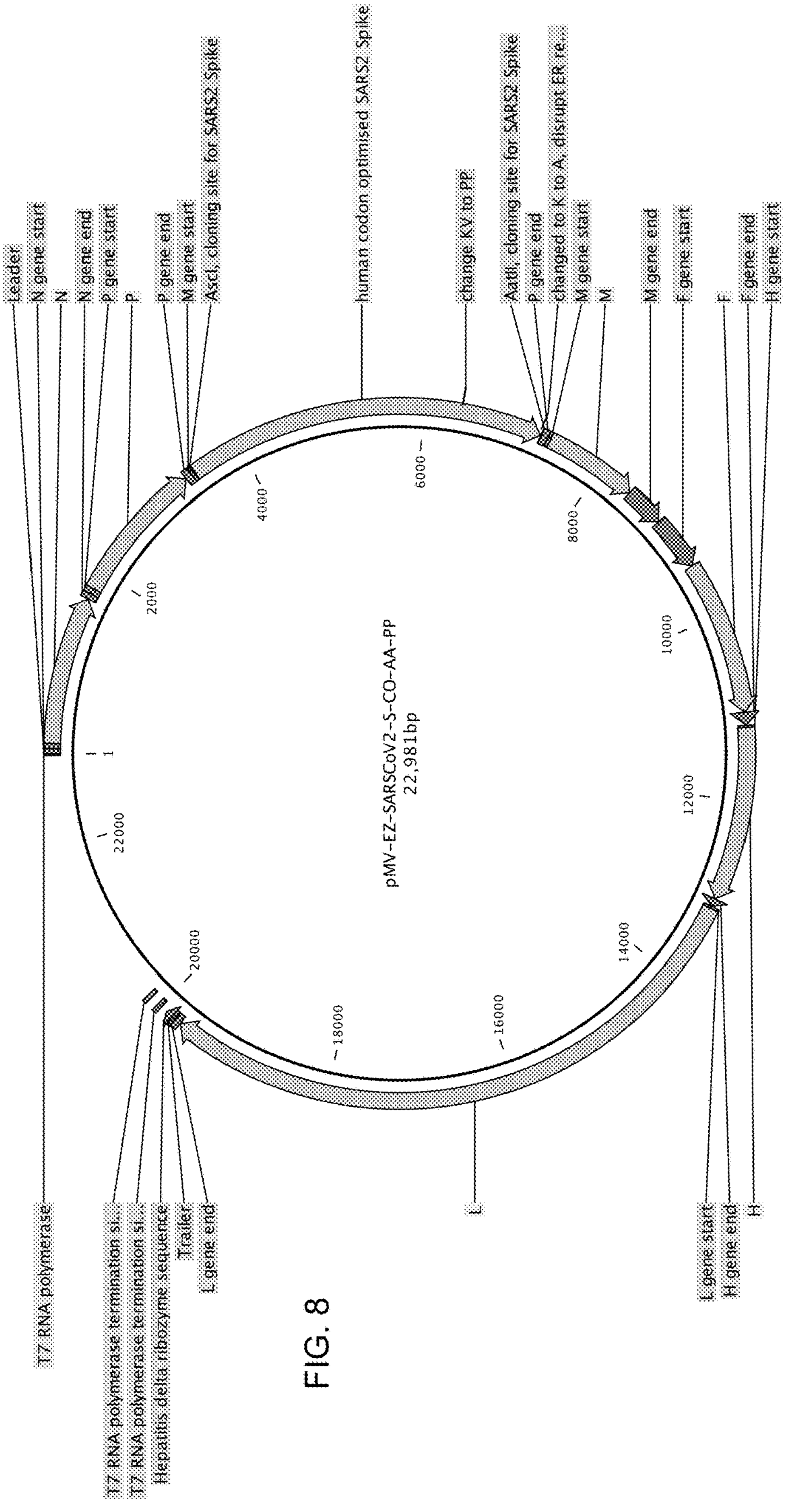
FIG. 8 is a vector map of $rMV^{EZ}$SARS-CoV-2-S-COAA-PP.
Figure 9:
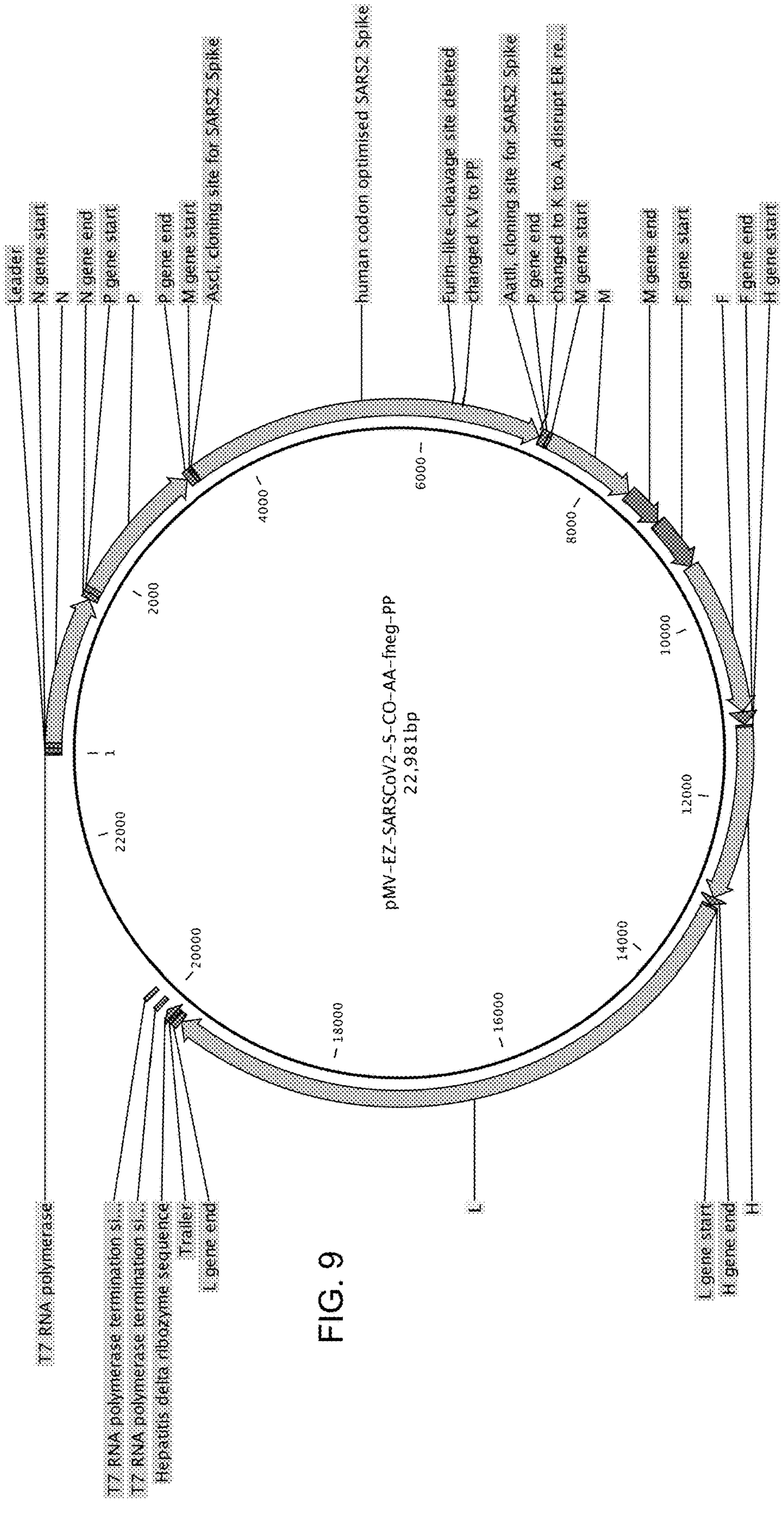
FIG. 9 is a vector map of $rMV^{EZ}$SARS-CoV-2-S-COAA-fneg-PP.
Figure 10:
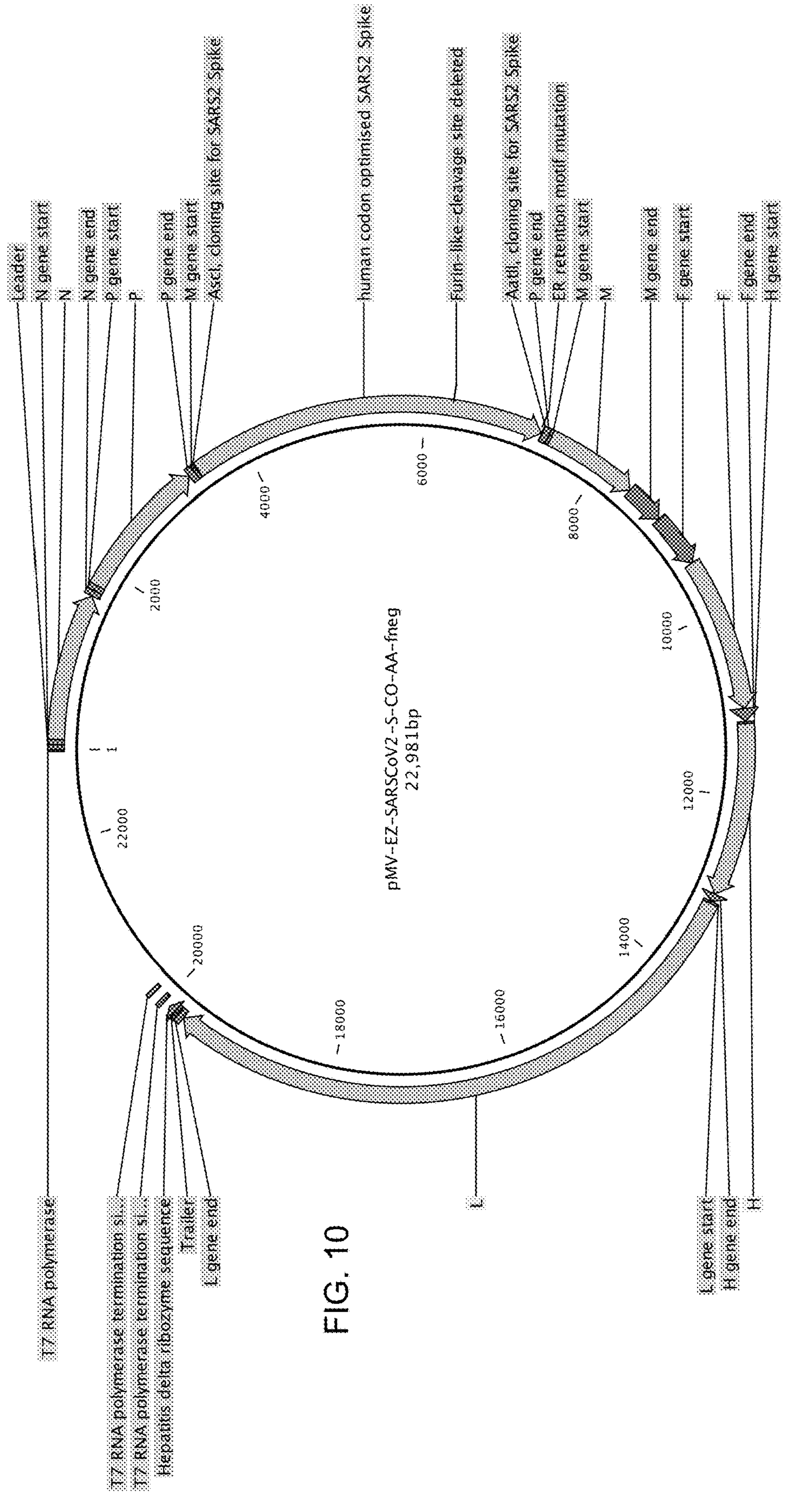
FIG. 10 is a vector map of and $rMV^{EZ}$SARS-CoV-2-S-COAA-fneg.

In one embodiment, the measles viral vector is an Edmonston-Zagreb (EZ) measles viral vector. Particular recombinant measles viral vectors of the Edmonston-Zagreb (EZ) strain include the following: $rMV^{EZ}$SARS-CoV-2-S6 (FIG. 4), $rMV^{EZ}$SARS-CoV-2-S-CO (FIG. 5), $rMV^{EZ}$SARS-CoV-2-S-COAA (FIG. 6), $rMV^{EZ}$SARS-CoV-2-S (FIG. 7), $rMV^{EZ}$SARS-CoV-2-S-COAA-PP (FIG. 8), $rMV^{EZ}$SARS-CoV-2-S-COAA-fneg-PP (FIG. 9), and $rMV^{EZ}$SARS-CoV-2-S-COAA-fneg (FIG. 10).

The recombinant measles vector comprises a nucleic acid encoding the SARS-CoV-2 spike glycoprotein, wherein the nucleic acid sequence encoding the SARS-CoV-2 spike glycoprotein can be any suitable nucleic acid sequence.

In one embodiment, the nucleic acid sequence encoding the SARS-CoV-2 spike glycoprotein is codon optimized. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by ribosomes using tRNAs that are more readily available within a cell, thus increasing translation efficiency and overall protein production. Optimization of the nucleotide sequence may also reduce secondary mRNA structures that would interfere with translation, thus increasing translation efficiency. $rMV^{EZ}$SARS-CoV-2-S-CO, $rMV^{EZ}$SARS-CoV-2-S-COAA, $rMV^{EZ}$SARS-CoV-2-S-COAA-PP, $rMV^{EZ}$SARS-CoV-2-S-COAA-fneg-PP, and $rMV^{EZ}$SARS-CoV-2-S-COAA-fneg each contain codon optimized SARS-CoV-2 spike glycoprotein sequences. Techniques for codon optimization are known in the art.

The nucleic acid sequence encoding the SARS-CoV-2 spike glycoprotein can contain at least one modification that disrupts the endoplasmic reticulum (ER) retention sequence of the SARS-CoV-2 spike glycoprotein. For example, the modification can result in an ER retention sequence of the SARS-CoV-2 spike glycoprotein containing AxAxx rather than KxHxx in the cytoplasmic tail (as described in Case et al., *bioRxiv* (2020). doi:10.1101/2020.05.18.102038 and Example 2). $rMV^{EZ}$SARS-CoV2-S6, $rMV^{EZ}$SARS-CoV-2-S, $rMV^{EZ}$SARS-CoV-2-S-COAA, $rMV^{EZ}$SARS-CoV-2-S-COAA-PP, $rMV^{EZ}$SARS-CoV-2-S-COAA-fneg-PP, and $rMV^{EZ}$SARS-CoV-2-S-COAA-fneg each contain modifications to ablate the ER retention signal. In particular, the amino acid sequences of the SARS-CoV-2 spike glycoproteins encoded by $rMV^{EZ}$SARS-CoV2-S6, $rMV^{EZ}$SARS-CoV-2-S, $rMV^{EZ}$SARS-CoV-2-S-COAA, $rMV^{EZ}$SARS-CoV2-S, $rMV^{EZ}$SARS-CoV-2-S-COAA-PP, $rMV^{EZ}$SARS-CoV-2-S-COAA-fneg-PP, and $rMV^{EZ}$SARS-CoV-2-S-COAA-fneg each contain two alanine substitutions at residues 1269 and 1271 of SEQ ID NOs: 8 and 10-14, respectively.

The nucleic acid encoding the SARS-CoV-2 spike glycoprotein can contain at least one modification that locks in the prefusion conformation. The spike (S) glycoprotein is a trimeric class I fusion protein that exists in a metastable prefusion conformation that undergoes a substantial structural rearrangement to fuse the viral membrane with the host cell membrane (Wrapp et al., *Science,* 13: 1260-1263 (2020)). This process is triggered when the S1 subunit binds to a host cell receptor. Receptor binding destabilizes the prefusion trimer, resulting in shedding of the S1 subunit and transition of the S2 subunit to a stable postfusion conformation. To engage a host cell receptor, the receptor-binding domain (RBD) of 51 undergoes hinge-like conformational movements that transiently hide or expose the determinants of receptor binding. The amino acid sequences of the SARS-CoV-2 spike glycoproteins encoded by $rMV^{EZ}$SARS-CoV-2-S-COAA-PP and $rMV^{EZ}$SARS-CoV-2-S-COAA-fneg-PP each contain two proline modifications (PP) at residues 986 and 987 of SEQ ID NOs: 9 and 10, respectively, which lock in the prefusion conformation.

The nucleic acid encoding the SARS-CoV-2 spike glycoprotein can contain at least one modification that ablates the furin cleavage signal, such as by modifying the furin cleavage site so that furin no longer cleaves the sequence. The furin cleavage site can be any polypeptide site cleavable by furin. The minimal cleavage site typically is, in the single letter code for amino acid residues, R-X-X-R, with cleavage occurring after the second "R" (Duckert et al., *Protein Engineering, Design & Selection,* 17(1):107-112 (2004); and WO 2009/032954). Whether or not any particular sequence is cleavable by furin can be determined by methods known in the art. For example, whether or not a sequence is cleavable by furin can be tested by incubating the sequence with furin.

rMV$^{EZ}$SARS-CoV-2-S-COAA-fneg-PP and rMV$^{EZ}$SARS-CoV-2-S-COAA-fneg each contain modifications to ablate the furin cleavage signal. In particular, the amino acid sequences of the SARS-CoV-2 spike glycoproteins encoded by rMV$^{EZ}$SARS-CoV2-S-COAA-fneg-PP and rMV$^{EZ}$SARS-CoV-2-S-COAA-fneg each contain four amino acid changes (ASVG; SEQ ID NO: 23) at residues 682-685 of SEQ ID NOs: 13 and 14, respectively, that ablate the furin cleavage signal.

In one embodiment, the nucleic acid encoding the SARS-CoV-2 spike glycoprotein encodes an amino acid sequence selected from the group consisting of SEQ ID NO: 8 (S6 spike glycoprotein), SEQ ID NO: 9 (S-CO spike glycoprotein), SEQ ID NO: 10 (S-CO-AA spike glycoprotein), SEQ ID NO: 11 (S spike glycoprotein), SEQ ID NO: 12 (S-CO-AA-PP spike glycoprotein), SEQ ID NO: 13 (S-CO-AA-fneg-PP spike glycoprotein), and SEQ ID NO: 14 (S-CO-AA-fneg spike glycoprotein).

In another embodiment, the nucleic acid encoding the SARS-CoV-2 spike glycoprotein is selected from the group consisting of SEQ ID NO: 1 (S6), SEQ ID NO: 2 (S-CO), SEQ ID NO: 3 (S-CO-AA), SEQ ID NO: 4 (S), SEQ ID NO: 5 (S-CO-AA-PP), SEQ ID NO: 6 (S-CO-AA-fneg-PP), and SEQ ID NO: 7 (S-CO-AA-fneg).

The recombinant measles viral vector comprising a nucleic acid sequence encoding a SARS-CoV-2 spike glycoprotein can have any suitable nucleic acid sequence. For example, the recombinant measles viral vector can comprise, consist essentially of, or consist of a nucleic acid sequence selected from the group consisting of SEQ ID NO: 15 (rMV$^{EZ}$SARS-CoV-2-S6), SEQ ID NO: 16 (rMV$^{EZ}$SARS-CoV-2-S-CO), SEQ ID NO: 17 (rMV$^{EZ}$SARS-CoV-2-S-COAA), SEQ ID NO: 18 (rMV$^{EZ}$SARS-CoV-2-S), SEQ ID NO: 19 (rMV$^{EZ}$SARS-CoV-2-S-COAA-PP), SEQ ID NO: 20 (rMV$^{EZ}$SARS-CoV-2-S-COAA-fneg-PP), and SEQ ID NO: 21 (rMV$^{EZ}$SARS-CoV-2-S-COAA-fneg). The vector sequences can comprise one or more nucleic acid sequences encoding the N, P, S, M, F, H, and L genes as described in GenBank Accession Nos. AY486083.1 and AY486084.1.

An embodiment of the invention also provides a polypeptide comprising, consisting essentially of, or consisting of an amino acid sequence selected from the group consisting of SEQ ID NO: 8 (S6), SEQ ID NO: 9 (S-CO), SEQ ID NO: 10 (S-CO-AA), SEQ ID NO: 11 (S), SEQ ID NO: 12 (S-CO-AA-PP), SEQ ID NO: 13 (S-CO-AA-fneg-PP), and SEQ ID NO: 14 (S-CO-AA-fneg), corresponding a SARS-CoV-2 spike glycoprotein.

The polypeptide can be prepared by any of a number of conventional techniques. In this respect, the polypeptide sequence can be synthetic, recombinant, isolated, and/or purified.

The polypeptide can be isolated or purified from a recombinant source. For instance, a DNA fragment encoding a desired polypeptide can be subcloned into an appropriate vector using well-known molecular genetic techniques. The fragment can be transcribed and the polypeptide subsequently translated in vitro. Commercially available kits also can be employed. The polymerase chain reaction optionally can be employed in the manipulation of nucleic acids.

The polypeptide also can be synthesized using an automated peptide synthesizer in accordance with methods known in the art. Alternately, the polypeptide can be synthesized using standard peptide synthesizing techniques well-known to those of skill in the art. In particular, the polypeptide can be synthesized using the procedure of solid-phase synthesis. If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The protein-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the polypeptide, further purification (e.g., using HPLC) optionally can be performed in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation or through genetic means, such as are known to those skilled in the art. In this regard, an embodiment of the invention also provides a fusion protein comprising the polypeptide and one or more other protein(s) having any desired properties or functions, such as to facilitate isolation, purification, analysis, or stability of the fusion protein.

An embodiment of the invention also provides a nucleic acid encoding the polypeptide. In one embodiment, the nucleic acid comprises, consists essentially of, or consists of a nucleic acid sequence selected from the group consisting of SEQ ID NO: 1 (S6), SEQ ID NO: 2 (S-CO), SEQ ID NO: 3 (S-CO-AA), SEQ ID NO: 4 (SARS-CoV2-S), SEQ ID NO: 5 (S-CO-AA-PP), SEQ ID NO: 6 (S-CO-AA-fneg-PP), and SEQ ID NO: 7 (S-CO-AA-fneg).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acid is recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acid (e.g., DNA, RNA, cDNA, and the like) can be produced in any suitable matter including, but not limited to recombinant production and commercial synthesis. In this respect, the nucleic acid sequence can be synthetic, recombinant, isolated, and/or purified.

The nucleic acid can be constructed based on chemical synthesis and/or enzymatic ligation reactions using procedures known in the art. See, for example, Green et al. (eds.), *Molecular Cloning, A Laboratory Manual,* $4^{th}$ Edition, Cold Spring Harbor Laboratory Press, New York (2012). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid encoding the polypeptide can be provided as part of a construct comprising the nucleic acid and elements that enable delivery of the nucleic acid to a cell, and/or expression of the nucleic acid in a cell. For example, the polynucleotide sequence encoding the polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG/AUG) in front of a protein-encoding gene, splicing signal for introns, maintenance of the correct reading frame of that gene to permit proper translation of mRNA, and stop codons.

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system, the Ecdysone inducible system, the T-REX™ system (Invitrogen, Carlsbad, Calif.), LACSWITCH™ System (Stratagene, San Diego, Calif.), and the Cre-ERT tamoxifen inducible recombinase system.

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. For example, the nucleic acid encoding the polypeptide can be operably linked to a CMV enhancer/chicken β-actin promoter (also referred to as a "CAG promoter").

A nucleic acid encoding the polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the polypeptide can be isolated by polymerase chain reaction of cDNA using primers based on the DNA sequence of the molecule. A wide variety of cloning and in vitro amplification methodologies are well known to persons skilled in the art.

An embodiment of the invention also provides a recombinant vector comprising the nucleic acid. Examples of suitable vectors include plasmids (e.g., DNA plasmids), bacterial vectors, and viral vectors, such as poxvirus, retrovirus, adenovirus, adeno-associated virus, herpes virus, poliovirus, alphavirus, baculovirus, measles virus, and Sindbis virus. When the vector is a plasmid (e.g., DNA plasmid), the plasmid can be complexed with chitosan.

The polypeptide, nucleic acid, or vector (e.g., recombinant measles virus vector) can be formulated as a composition (e.g., pharmaceutical composition) comprising the polypeptide, nucleic acid, or vector (e.g., recombinant measles virus vector) and a carrier (e.g., a pharmaceutically or physiologically acceptable carrier). Furthermore, the polypeptide, nucleic acid, vector (e.g., recombinant measles virus vector), or composition can be used in the methods described herein alone or as part of a pharmaceutical formulation.

The composition (e.g., pharmaceutical composition) can comprise more than one polypeptide, nucleic acid, vector (e.g., recombinant measles virus vector), or composition of the invention. Alternatively, or in addition, the composition can comprise one or more (e.g., one, two, three, or more) additional pharmaceutically active agents or drugs, such as corticosteroids, antibiotics, and antivirals.

The carrier can be any of those conventionally used and is limited only by physio-chemical considerations, such as solubility and lack of reactivity with the active compound(s) and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular polypeptide, nucleic acid, vector, or composition thereof of the invention and other active agents or drugs used, as well as by the particular method used to administer the polypeptide, nucleic acid, vector (e.g., recombinant measles virus vector), or composition thereof.

The composition also can be formulated to enhance transduction efficiency. In addition, a person of ordinary skill in the art will appreciate that the one or more of the polypeptides, nucleic acids, or vectors (e.g., recombinant measles virus vectors) can be present in a composition with other therapeutic or biologically-active agents. For example, factors that control inflammation, such as ibuprofen or steroids, can be part of the composition to reduce swelling and inflammation associated with in vivo administration of one or more of the polypeptides, nucleic acids, or vectors (e.g., recombinant measles virus vector). Antibiotics, i.e., microbicides and fungicides, can be present to treat existing infection and/or reduce the risk of future infection.

The invention provides a method for preventing, inhibiting, reducing, eliminating, protecting, or delaying the onset of an infection or an infectious clinical condition caused by coronavirus in a subject comprising administering the polypeptide, nucleic acid, vector (e.g., recombinant measles virus vector), or composition thereof to a subject. The invention also provides a method for inducing an immune response against a coronavirus in a subject comprising administering the polypeptide, nucleic acid, vector (e.g., recombinant measles virus vector), or composition thereof to the subject.

Administration of the polypeptide, nucleic acid, vector (e.g., recombinant measles virus vector), or composition thereof to the subject can be used to protect against one or more strains of coronavirus (e.g., SARS-CoV-2), thereby treating, preventing, and/or protecting against coronavirus-based pathologies.

Administration of the polypeptide, nucleic acid, vector (e.g., recombinant measles virus vector), or composition thereof can significantly induce an immune response of a subject administered the polypeptide, nucleic acid, vector (e.g., recombinant measles virus vector), or composition thereof, thereby protecting against and treating coronavirus (e.g., SARS-CoV-2) infection.

Administration of the polypeptide, nucleic acid, vector (e.g., recombinant measles virus vector), or composition thereof can induce a humoral immune response in a subject. The induced humoral immune response can be specific for the SARS-CoV-2 spike glycoprotein. The humoral immune response can be induced in the subject administered the vaccine by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

The induced humoral immune response can include an increased level of neutralizing antibodies as compared to a subject not administered the polypeptide, nucleic acid, vector (e.g., recombinant measles virus vector), or composition thereof. The neutralizing antibodies can be specific for the SARS-CoV-2 spike glycoprotein. The neutralizing antibodies can provide protection against and/or treatment of SARS-CoV-2 infection and its associated pathologies in the subject administered the polypeptide, nucleic acid, vector (e.g., recombinant measles virus vector), or composition thereof.

The induced humoral immune response can include an increased level of IgG antibodies as compared to a subject not administered the polypeptide, nucleic acid, vector (e.g., recombinant measles virus vector), or composition thereof. These IgG antibodies can be specific for the SARS-CoV-2 antigens. The level of IgG antibody can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

The induced humoral immune response can include an increased level of IgM and/or IgA antibodies as compared to a subject not administered the polypeptide, nucleic acid, vector (e.g., recombinant measles virus vector), or composition thereof. These IgM and or IgA antibodies can be specific for the SARS-CoV-2 antigen. The level of IgM/IgA antibody can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 16.5-fold, at least about 17-fold, at least about 17.5-fold, at least about 18-fold, at least about 18.5-fold, at least about 19-fold, at least about 19.5-fold, at least about 20-fold, or ranges of any combination of these values as compared to a subject not administered the polypeptide, nucleic acid, vector (e.g., recombinant measles virus vector), or composition thereof.

Administration of the polypeptide, nucleic acid, vector (e.g., recombinant measles virus vector), or composition thereof can induce a cellular immune response in the subject. The induced cellular immune response can be specific for the SARS-CoV-2 antigen.

The induced cellular immune response can include eliciting a CD8+ T cell response, which can include eliciting a CD8+ T cell response in which the CD8+ T cells produce interferon-gamma (IFN-γ), tumor necrosis factor alpha (TNF-α), interleukin-2 (IL-2), or a combination thereof (e.g., a combination of IFN-γ and TNF-α).

The CD8+ T cell response can be increased by at least about 1.5-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 10.5-fold, at least about 11-fold, at least about 11.5-fold, at least about 12-fold, at least about 12.5-fold, at least about 13-fold, at least about 13.5-fold, at least about 14-fold, at least about 14.5-fold, at least about 15-fold, at least about 15.5-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, at least about 30-fold, or ranges of any combination of these values as compared to the subject not administered the polypeptide, nucleic acid, vector (e.g., recombinant measles virus vector), or composition thereof.

Administration of the polypeptide, nucleic acid, vector (e.g., recombinant measles virus vector), or composition thereof can also include eliciting a CD4+ T cell response, which can include eliciting a CD4+ T cell response in which the CD4+ T cells produce IFN-γ, TNF-α, IL-2, or a combination thereof (e.g., a combination of IFN-γ and TNF-α).

The polypeptide, nucleic acid, vector (e.g., recombinant measles virus vector), or composition thereof can be administered to the subject by various routes including, but not limited to, oral, sublingual, buccal, intradermal, topical, parenteral (using single or arrays of dissolvable and hybrid microneedles, in lyophilized or solution), subcutaneous, intravenous, intramuscular, intraarterial, intrathecal, interperitoneal, intranasal, large and/or small particle aerosol, dry-powder aerosols or intratracheal administration, or subretinal injection or intravitreal injection.

The invention includes a prime and boost protocol. In particular, the protocol includes an initial "prime" with the polypeptide, nucleic acid, vector (e.g., recombinant measles virus vector), or composition thereof, followed by one or preferably multiple "boosts" with the polypeptide, nucleic acid, vector (e.g., recombinant measles virus vector), or composition thereof. The boosts can be administered 1-3 times (e.g., 1, 2, or 3 times) at any suitable time period (e.g., every 3-4 weeks, every six months, or once a year) for any suitable length of time.

The polypeptide, nucleic acid, vector (e.g., recombinant measles virus vector), or composition thereof can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The polypeptide, nucleic acid, vector (e.g., recombinant measles virus vector), or composition thereof can be administered prophylactically or therapeutically. In prophylactic administration, the polypeptide, nucleic acid, vector (e.g., recombinant measles virus vector), or composition thereof are administered in an amount sufficient to induce an immune response. In therapeutic applications, the polypeptide, nucleic acid, vector (e.g., recombinant measles virus vector), or composition thereof are administered to a subject in need thereof in an amount sufficient to elicit a therapeutic effect. An amount adequate to accomplish this is defined as "therapeutically effective dose." Amounts effective for this use will depend on, e.g., the particular composition of the polypeptide, nucleic acid, vector (e.g., recombinant measles virus vector), or composition thereof administered to a subject, the manner of administration, the stage and severity of the infection, the general state of health of the patient, and the judgment of the prescribing physician.

The following examples further illustrate the invention but, of course, should not be construed as in any way limiting its scope.

Example 1

This example provides materials and methods for the studies described in Example 2.

Cell Lines, Viruses and Plasmids

Vero cells (African green monkey kidney cells; ATCC CCL-81) purchased from ATCC (Manassas, Va., USA) were grown in advanced Dulbecco's modified Eagle medium (DMEM; Gibco) supplemented with 10% (V/V) fetal bovine serum (HI FBS heat inactivated, Gibco) and GlutaMAX-I (Gibco). Cells were grown and maintained at 37° C. and 5% (V/V) $CO_2$, and tested negative for *mycoplasma* contamination prior to use in virus rescue experiments. MV plasmids expressing N, P and L, $pMV^{EZ}$EGFP(3), as well as $rMV^{EZ}$EGFP(3) virus have been described previously (Rennick et al., *J. Virol.* (2015). doi:10.1128/jvi.02924-14).

Construction of $MV^{EZ}$ cDNA Plasmids Expressing SARS-CoV-2 Spike Glycoprotein As described in Rennick et al., *J. Virol.* (2015). doi: 10.1128/jvi.02924-14), three recombinant viruses were generated that contained the open reading frame encoding enhanced green fluorescent protein (EGFP) within an additional transcriptional unit (ATU) at various positions within the genome. $rMV^{EZ}$EGFP(1), $rMV^{EZ}$EGFP(3), and $rMV^{EZ}$EGFP(6) contained the ATU upstream of the N gene, following the P gene, and following the H gene, respectively. The viruses were compared in vitro by growth curves, which indicated that $rMV^{EZ}$EGFP(1) was over-attenuated. Intratracheal infection of cynomolgus macaques with these recombinant viruses revealed differences in immunogenicity. $rMV^{EZ}$EGFP(1) and $rMV^{EZ}$EGFP(6) did not induce satisfactory serum antibody responses, whereas both in vitro and in vivo $rMV^{EZ}$EGFP(3) was functionally equivalent to the commercial $MV^{EZ}$-containing vaccine. Intramuscular vaccination of macaques with $rMV^{EZ}$EGFP(3) resulted in the identification of $EGFP^{+}$ cells in the muscle at days 3, 5, and 7 post-vaccination. Therefore, $rMV^{EZ}$EGFP(3) was selected for further experiments.

pMV$^{EZ}$ versions expressing SARS-CoV-2 spike glycoprotein (Accession number MN908947) were generated by replacing the open reading frame of EGFP in pMV$^{EZ}$EGFP (3) (Rennick et al., *J. Virol.* (2015). doi:10.1128/jvi.02924-14).

Plasmid pMV$^{EZ}$EGFP(3) was linearized using restriction sites Asc I at genome position 3439 and Aat II at genome position 4176. These restriction sites were originally designed into pMV$^{EZ}$EGFP(3) to allow easy replacement of foreign genes in place of EGFP. SARS-CoV-2 spike with mutations in the endoplasmic reticulum (ER) retention signal sequence as previously described (Case et al., *bioRxiv* (2020). doi:10.1101/2020.05.18.102038) were obtained in two gene fragments. These fragments were ligated into the linearized pMV$^{EZ}$EGFP(3) using Gibson Assembly (NEBuilder® HiFi DNA assembly, NEB). This generated two versions pMV$^{EZ}$SARS-CoV-2-S and pMV$^{EZ}$SARS-CoV-2-S6.

A human codon optimized SARS-CoV-2 spike glycoprotein expressing plasmid was obtained from GenScript (Piscataway, N.J., USA). Spike was amplified from the plasmid using oligonucleotides that contained a 35 nucleotide homology (lower case sequence) to the linearized pMV$^{EZ}$EGFP(3) (Forward primer: 5'caaagtgattgcctcccaagttccacaggcgcgccATGTTCGTCTTCCTGGTC3' (SEQ ID NO: 24) and reverse primer: 5'gttggcaggtaagttgagctgtaggacgtcgcgcgTTAGGTGTAATGCAGCTTCAC3' (SEQ ID NO: 25)). The amplified product was then ligated into linearized pMV$^{EZ}$EGFP(3) using Gibson Assembly (NEBuilder® HiFi DNA assembly, NEB). This generated pMV$^{EZ}$SARSCoV2-S-CO. pMV$^{EZ}$SARS-CoV-2-S-COAA was generated the same way, but using a reverse primer (5'ggttggcaggtaagttgagctgtaggacgtcgcgcgT-TAGGTGTAAGCCAGCGCCACGCC3' (SEQ ID NO: 26) with nucleotide changes (in bold) to disrupt the ER retention signal.

The spike sequence in all plasmids were sequence confirmed via Sanger sequencing (Genewiz, NJ, USA).

Generation of Recombinant rMV$^{EZ}$-SARS-CoV-2-Spike Glycoprotein Viruses

Vero cell monolayers in 6-well trays were infected with a recombinant vaccinia virus expressing T7 polymerase (MVA-T7) in Opti-MEM (Gibco) for 30 mins at 37° C. and then spinoculated at room temperature for another 30 mins. Virus inoculum was removed and 1 ml fresh Opti-MEM was added onto cells. Cells were then transfected with 5 μg of pMV$^{EZ}$SARS-CoV-2-S, pMV$^{EZ}$SARS-CoV-2-S6, pMV$^{EZ}$SARS-CoV-2-S-CO, or pMV$^{EZ}$SARS-CoV-2-S-COAA. MV plasmids expressing nucleoprotein (N), phosphoprotein (P) and polymerase (L) at 1 μg, 0.6 μg and 0.4 μg respectively, were also transfected into the cells. 24 hours post-transfection (h.p.t.), medium was removed from the cells and DMEM/2% (V/V) fetal bovine serum (FBS) was added. Cells were monitored daily for approximately 14 days post-transfection (d.p.t.) for syncytium formation. Plaque picked viruses were then grown in Vero cells and harvested by free-thaw when complete cytopathic effect was visible. Virus titers were determined by endpoint titration and expressed as 50% tissue culture infectious ($TCID_{50}$) units.

Reverse Transcription Polymerase Chain Reaction (RT/PCR) and Sequencing

Total RNA from working virus stocks was extracted using TRIzol LS reagent (ThermoFisher) according to manufacturer's recommendations and RNA pellet resuspended in 40 μl nuclease-free water (Invitrogen). cDNA was generated with 5 μl of resuspended RNA using SuperScript™ III First-strand synthesis system (Thermo Fisher Scientific) and random primers. 3 μl of the resultant cDNA was then used to amplify MV-spike fragments with primers using Phusion high-fidelity DNA polymerase (NEB) in a total volume of 50 μl (using a touch-down PCR amplification protocol). Amplified PCR products were analyzed on a 1% agarose gel and bands gel purified using QIAquick gel extraction kit (Qiagen). Products were sequenced confirmed via Sanger sequencing (Genewiz, NJ, USA).

Immunofluorescence

Confluent Vero cells in 24-well trays were infected with rMV$^{EZ}$SARS-CoV2-S6 or rMV$^{EZ}$SARS-CoV-2-S-CO at a multiplicity of infection (MOI) of 0.01. At 2 days post infection, cells were fixed with 4% paraformaldehyde for 10 minutes at room temperature. Cells were washed twice in PBS and permeabilized (0.1% Triton-X in PBS) at 37° C. for 30 minutes before incubating with primary antibody (Rabbit anti-SARS2-S, Sino biologicals 40150-R007; 1:500) made in PBS with 0.1% (V/V) Triton-X at 37° C. for 1 hour. Cells were then washed three times in PBS before incubating with secondary antibody (Chicken anti-rabbit Alexa Fluor 488, Invitrogen; 1:400) at 37° C. for 1 hour. Cells were washed three times in PBS and stained with DAPI nuclei stain (Invitrogen; 300 nM DAPI stain solution) for 10 minutes at room temperature in the dark. Images were obtained using a fluorescent microscope (Leica).

Virus Growth Kinetics

Vero cell monolayers at $2\times10^5$ cells in 24-well trays were infected with rMV$^{EZ}$EGFP(3), rMV$^{EZ}$SARS-CoV-2-S3, rMV$^{EZ}$SARS-CoV-2-S6, rMV$^{EZ}$SARS-CoV-2-S-CO, or rMV$^{EZ}$SARS-CoV-2-S-COAA at a 0.05 MOI. Cell monolayers were infected for 1 hour at 37° C. after which virus inoculum was removed and cell monolayers washed twice using phosphate-buffered saline (PBS; Gibco). DMEM/2% (V/V) FBS was added onto the cells and at the desired time points cells were scraped into culture medium and placed at −80° C. After freeze-thawing the cells and medium, cell debris were clarified and total virus measured by $TCID_{50}$.

Immunoplaque Assay

Confluent Vero cell monolayers in 6-well trays were infected with a 10-fold serial dilution of virus prepared in Opti-MEM. Cells were incubated for 1 h at 37° C. and then overlaid with 0.6% Avicel (FMC Biopolymer) supplemented with 2×MEM (10×MEM, no glutamine, Gibco) and 2% FBS. Cells were incubated for 5 days and then fixed using 4% paraformaldehyde for 30 minutes at room temperature. Cells were permeabilized (0.5% Triton X-100, 20 mM sucrose in PBS; 1 ml) for 30 minutes at room temperature and then washed (0.1% Tween-20 in PBS; 1 ml) once before incubating with primary antibody (Rabbit anti-SARS2-S, Sino biologicals 40150-R007; 1:1000) in blocking buffer (4% dried milk/0.1% Tween-20 in PBS) for 1 hour at room temperature. Cells were washed three times and incubated with secondary antibody (Goat anti-rabbit HRP, Abcam, ab6721; 1:1000) for 1 hour at room temperature. Plaques were visualized using KPL TrueBlue Peroxidase Substrate solution (Sera Care, 5510-0050). Plates were digitalized using a scanner.

Animal Study Design

All animal experiments were conducted in compliance with all applicable U.S. Federal policies and regulations and AAALAC International standards for the humane care and use of animals. All protocols were approved by the University of Pittsburgh Institutional Animal Care and Use Committee (IACUC).

Twenty-five IFNar1 knockout mice in groups of five were infected with $10^4$ $TCID_{50}$ of rMV$^{EZ}$EGFP(3), rMV$^{EZ}$SARS- CoV-2-S3, rMV$^{EZ}$SARS-CoV-2-S6, rMV$^{EZ}$SARS-CoV-2-S-CO, or rMV$^{EZ}$SARS-CoV-2-S-COAA viruses via the intraperitoneal (IP) route. 21 days post-infection, mice were bled for serum, and then boosted with $10^5$ $TCID_{50}$ of the respective virus.

African green monkeys were immunized with either measles vaccine or rMV$^{EZ}$SARS-CoV-2-S-CO (in groups of 2 or 3) with $10^5$ $TCID_{50}$ of candidate vaccine. In our proof of principle study we focused on a prime/boost (day 0 and 21 days). Animals were challenged 42 days after immunization with $10^6$ plaque forming units of SARS-CoV-2.

All animals seroconverted generating antibodies to both measles and SARS-CoV-2. These antibodies neutralized both viruses, some at levels higher than what is seen in human convalescent serum.

Statistical Analysis

Statistical analyses were performed using GraphPad Prism software (La Jolla, Calif.).

Vector Maps

Vector maps are provided in FIGS. 4-10 for each of rMV$^{EZ}$SARS-CoV-2-S6, rMV$^{EZ}$SARS-CoV-2-S-CO, rMV$^{EZ}$SARS-CoV-2-S-COAA, rMV$^{EZ}$SARS-CoV-2-S, rMV$^{EZ}$SARS-CoV-2-S-COAA-PP, rMV$^{EZ}$SARS-CoV-2-S-COAA-fneg-PP, and rMV$^{EZ}$SARS-CoV-2-S-COAA-fneg, wherein the spike glycoprotein is inserted after the measles virus N and P genes (in the third (3) position).

Example 2

This example demonstrates the generation and characterization of recombinant MV vaccine strain viruses expressing SARS-CoV-2 spike glycoprotein.

Based on previously generated reverse genetics system for live-attenuated measles virus (MV) vaccine strain Edmonston-Zagreb (EZ) that expresses an enhanced green fluorescent protein (EGFP; rMV$^{EZ}$ EGFP(3)), recombinant MV vaccine viruses encoding SARS-CoV-2 spike glycoprotein were generated and rescued. The open reading frame for the spike glycoprotein lies within an additional transcriptional unit at position 3 in the MV genome in place of EGFP. These viruses were compared in vitro for replication and expression of the spike glycoprotein. The growth kinetics of all tested viruses were equivalent to rMV$^{EZ}$ EGFP(3).

pMV$^{EZ}$EGFP(3) (Rennick et al., *J. Virol.* (2015). doi: 10.1128/jvi.02924-14) was modified to express SARS-CoV-2 spike glycoprotein in place of EGFP. In a manner similar to that described in Case et al, *bioRxiv* (2020). doi:10.1101/2020.05.18.102038, an endoplasmic reticulum (ER) retention signal sequence present in the cytoplasmic tail (CT) of the spike was altered from KxHxx to AxAxx-COOH, and anti-genomic plasmids expressing a non-codon and human codon optimized version (pMV$^{EZ}$SARS-CoV2-S and pMV$^{EZ}$SARS-CoV-2-COAA, respectively) were generated. An additional human codon optimized version with the authentic KxHxx-COOH sequence was also generated (pMV$^{EZ}$SARS-CoV-2-CO).

Recovery of a plasmid with the correct spike sequence proved challenging for the non-codon optimized version, and as a result two plasmids were generated: one with the authentic sequence (pMV$^{EZ}$SARS-CoV-2-S) and one with three nucleotide changes, one of which does not cause an amino acid change (pMV$^{EZ}$SARS-CoV-2-S6).

To recover recombinant viruses, Vero cells were transfected with either pMV$^{EZ}$SARS-CoV-2-S, pMV$^{EZ}$SARS-CoV-2-S6, pMV$^{EZ}$SARS-CoV-2-CO or pMV$^{EZ}$SARS-CoV-2-COAA along with expression plasmids for nucleoprotein (N), phosphoprotein (P) and polymerase (L) proteins. Sequence confirmation of the virus generated from clone pMV$^{EZ}$SARS-CoV-2-S revealed an amino acid change in the CT tail. This virus was subsequently named rMV$^{EZ}$SARS-CoV-2-S3 (FIG. 1A).

Figure 1A:
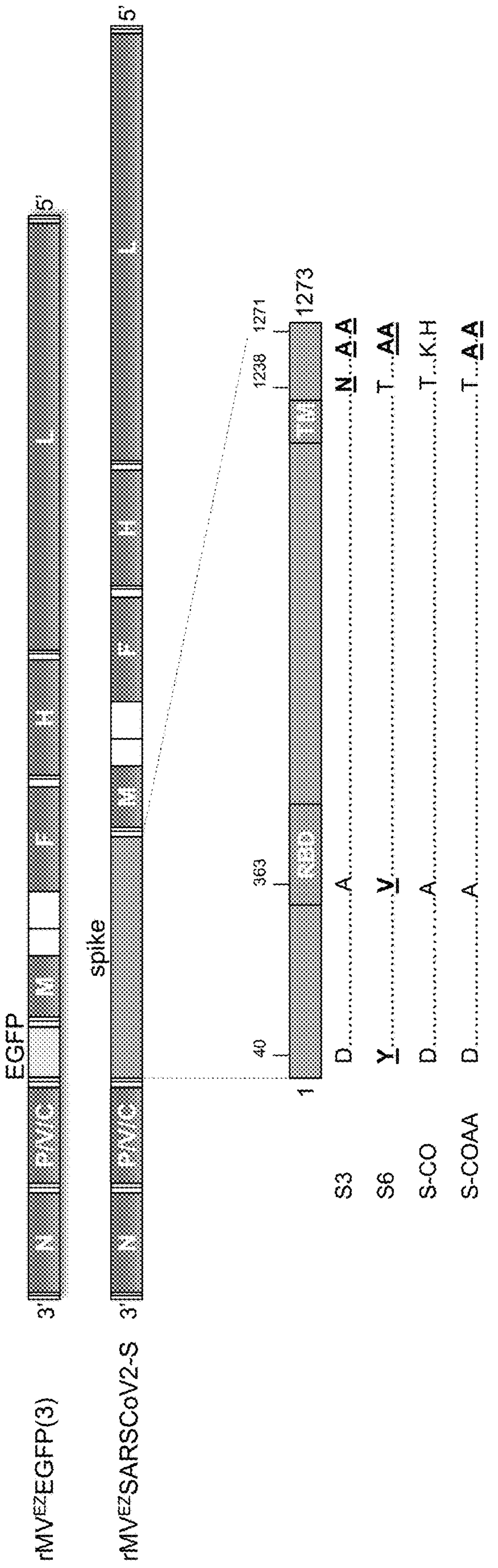
FIGS. 1A-1C demonstrate the generation of $rMV^{EZ}$ viruses expressing SARS-CoV-2 spike glycoprotein. FIG.
Figure 1C:
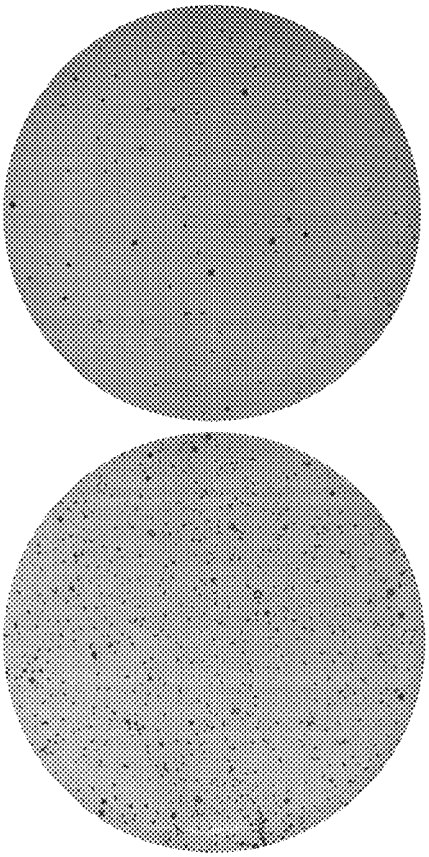
Figure 1B:
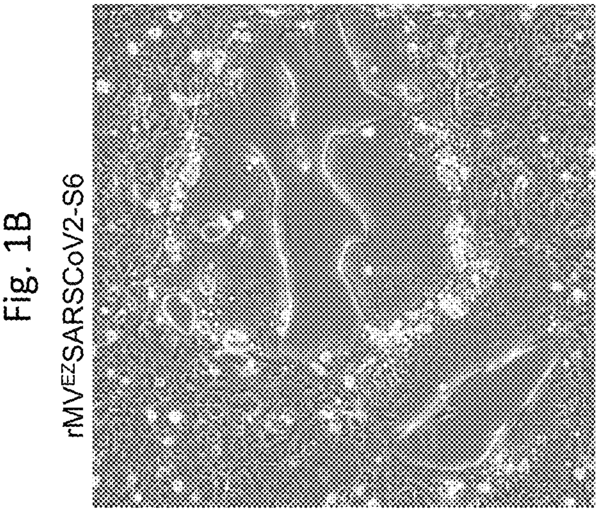

The spike glycoprotein sequences in rMV$^{EZ}$SARS-CoV-2-S6, rMV$^{EZ}$SARS-CoV-2-CO, and rMV$^{EZ}$SARS-CoV-2-COAA correspond to their cDNA clones (FIG. 1A). Rescue experiments were reproducible with syncytium formation about 14 days post transfection (FIG. 1B).

To test if the spike glycoprotein was expressed, Vero cells were infected and fixed and stained at 48 hours post-infection using an anti-SARS2-S antibody. Substantial amounts of spike expression were detectable in the infected cells, especially for rMV$^{EZ}$SARS-CoV-2-CO (FIG. 1C). Expression was further confirmed by staining viral plaques with anti-SARS2-S antibody (FIG. 1D).

Figure 2:
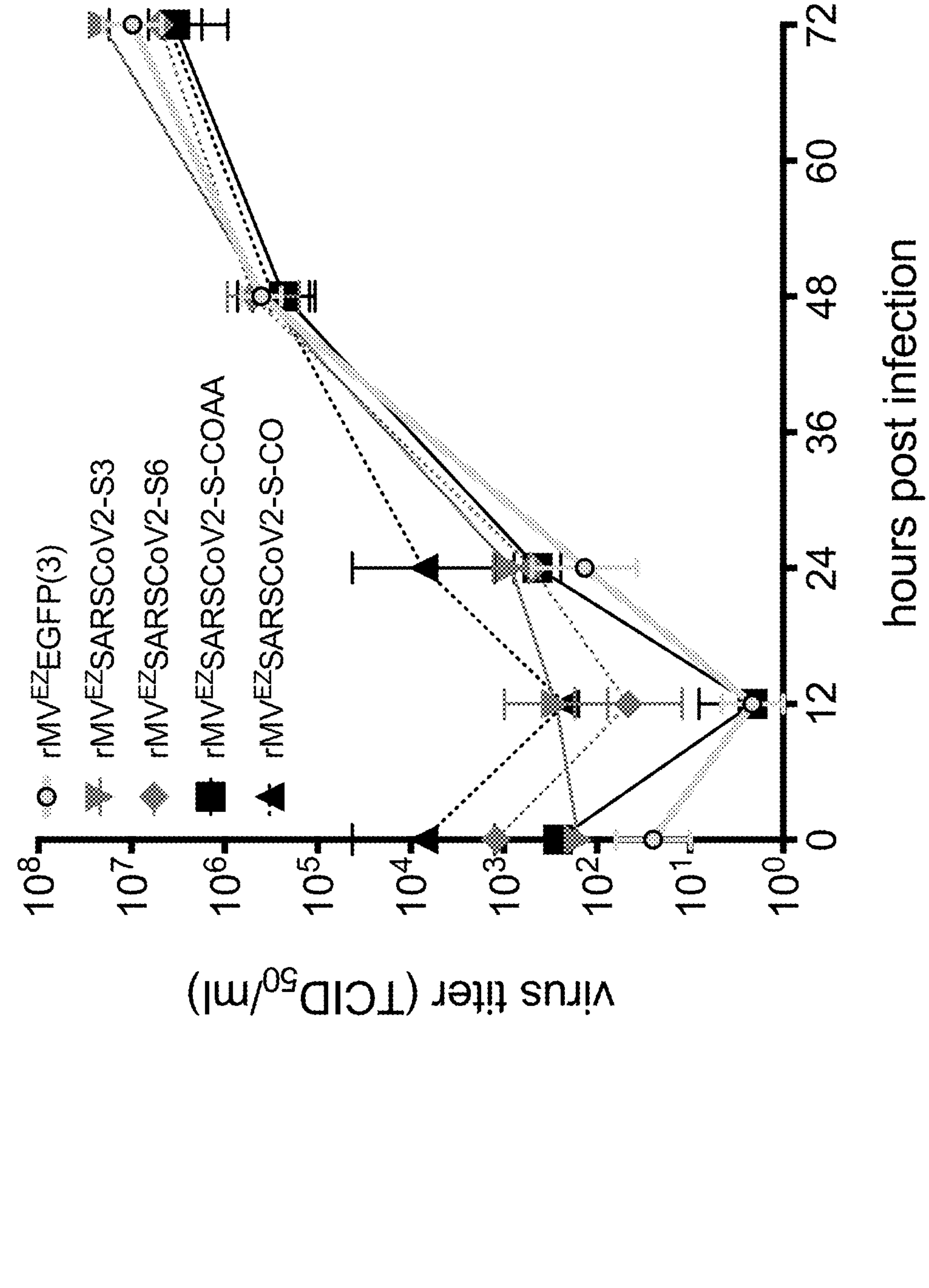
FIG. 2 demonstrates that growth kinetics of $rMV^{EZ}$SARS-CoV-2-S3, $rMV^{EZ}$SARS-CoV-2-S6, $rMV^{EZ}$SARS-CoV-2-S-CO, and $rMV^{EZ}$SARS-CoV-2-S-COAA compared to $rMV^{EZ}$EGFP(3). Vero cells were infected at a multiplicity of infections (MOI) of 0.05. Samples were harvested at the indicated time points and titrated on Vero cells. Error bars indicate standard deviation (n=3).

Growth analysis of rMV$^{EZ}$SARS-CoV-2-S3, rMV$^{EZ}$SARS-CoV-2-S6, rMV$^{EZ}$SARS-CoV-2-CO, and rMV$^{EZ}$SARS-CoV-2-COAA were compared to rMV$^{EZ}$EGFP(3) in Vero cells over a 3 day period. Viruses replicated similar to rMV$^{EZ}$EGFP(3) by reaching a titers close to $10^7$ $TCID_{50}$/ml (FIG. 2).

Additional vectors were generated with modifications to ablate the furin cleavage signal (rMV$^{EZ}$SARS-CoV-2-S-COAA-fneg and rMV$^{EZ}$SARS-CoV-2-S-COAA-fneg-PP), and to lock in the prefusion conformation by substitution of two proline residues (rMV$^{EZ}$SARS-CoV-2-S-COAA-PP and S-CO-AA-fneg-PP).

rMV$^{EZ}$SARS-CoV-2-S3 and rMV$^{EZ}$SARS-CoV-2-S6 encode a spike glycoprotein with nucleotide changes that arose during virus rescue and plasmid generation, respectively.

rMV$^{EZ}$SARS-CoV-2-S-CO, rMV$^{EZ}$SARS-CoV-2-S-COAA, rMV$^{EZ}$SARS-CoV-2-S-COAA-PP, rMV$^{EZ}$SARS-CoV-2-S-COAA-fneg, and rMV$^{EZ}$SARS-CoV-2-S-COAA-fneg-PP encode a human codon optimized spike glycoprotein.

rMV$^{EZ}$SARS-CoV-2-S3, rMV$^{EZ}$SARS-CoV-2-S6, rMV$^{EZ}$SARS-CoV-2-S, rMV$^{EZ}$SARS-CoV-2-S-COAA, rMV$^{EZ}$SARS-CoV-2-S-COAA-PP, rMV$^{EZ}$SARS-CoV-2-S-COAA-fneg-PP, and rMV$^{EZ}$SARS-CoV-2-S-COAA-fneg contain mutations in the spike glycoprotein to disrupt the endoplasmic reticulum (ER) retention sequence that has been described as essential for SARS-CoV-2 virion assembly via the ER-Golgi compartment.

The nucleic acid sequence encoding the spike glycoprotein of rMV$^{EZ}$SARS-CoV-2-S3 corresponds to SEQ ID NO: 22.

The following table summarizes the sequence information for each of the vectors and the corresponding nucleic acid and amino acid sequences of the spike glycoprotein.

| Vector Designation | Nucleic Acid Sequence of Spike Glycoprotein | Amino Acid Sequence of Spike Glycoprotein | Nucleic Acid Sequence of Vector | Modifications |
|---|---|---|---|---|
| rMV$^{EZ}$SARS-CoV-2-S6 | 1 | 8 | 15 | modifications to ablate ER retention signal |
| rMV$^{EZ}$SARS-CoV-2-CO | 2 | 9 | 16 | codon optimized |
| rMV$^{EZ}$SARS-CoV-2-S-COAA | 3 | 10 | 17 | codon optimized;<br>modifications to ablate ER retention signal |

-continued

| Vector Designation | Nucleic Acid Sequence of Spike Glycoprotein | Amino Acid Sequence of Spike Glycoprotein | Nucleic Acid Sequence of Vector | Modifications |
|---|---|---|---|---|
| rMV$^{EZ}$SARS-CoV-2-S | 4 | 11 | 18 | modifications to ablate ER retention signal |
| rMV$^{EZ}$SARS-CoV-2-S-COAA-PP | 5 | 12 | 19 | codon optimized; modifications to ablate ER retention signal; modifications to lock in prefusion conformation |
| rMV$^{EZ}$SARS-CoV-2-S-COAA-fneg-PP | 6 | 13 | 20 | codon optimized; modifications to ablate ER retention signal; modifications to lock in prefusion conformation; modifications to ablate furin cleavage signal |
| rMV$^{EZ}$SARS-CoV-2-S-COAA-fneg | 7 | 14 | 21 | codon optimized; modifications to ablate ER retention signal; modifications to ablate furin cleavage signal |
| rMV$^{EZ}$SARS-CoV-2-S3 | 22 | | | modifications to ablate ER retention signal |

Example 3

This example describes vaccination/challenge studies with recombinant MV vaccine strain viruses expressing SARS-CoV-2 spike glycoprotein.

Mice

Figures 3A, 3B:
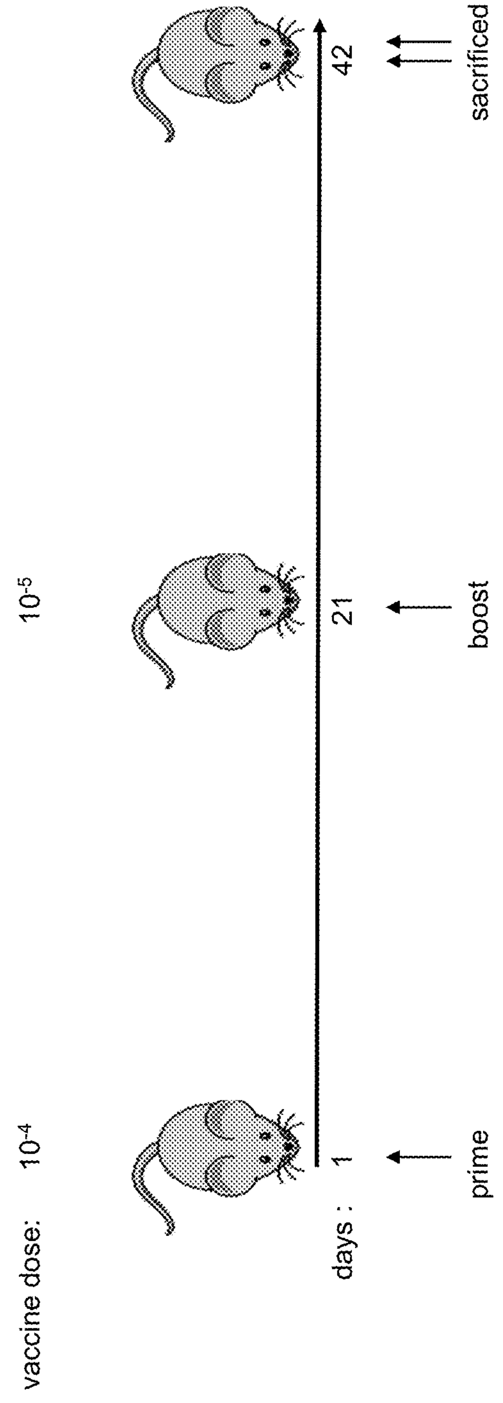
FIGS. 3A-3B demonstrate an experimental set-up for mice immunized with recombinant viruses.

The experimental set-up for mice immunized with recombinant viruses is described in FIG. 3A. Groups of 5 mice were infected with either rMV$^{EZ}$SARS-CoV-2-S3, rMV$^{EZ}$SARS-CoV-2-S6, rMV$^{EZ}$SARS-CoV-2-S-CO, rMV$^{EZ}$SARS-CoV-2-S-COAA, or rMV$^{EZ}$EGFP(3). Serum was collected on days 21 and 42, and splenocytes were collected on day 42. Neutralization of SARS-CoV-2 using the harvested mice serum indicates that SARS-CoV-2 neutralizing antibodies were produced in mice vaccinated with rMV$^{EZ}$SARS-CoV-2-S-CO and rMV$^{EZ}$SARS-CoV-2-S-COAA viruses (FIG. 3B).

Figure 12:
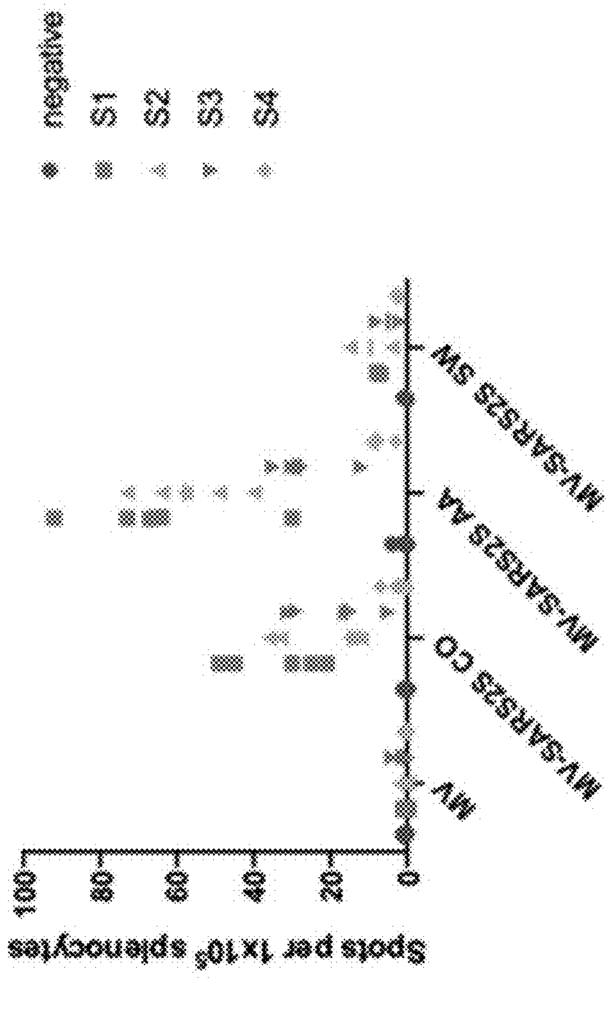
FIG. 12 is a graph demonstrating the secretion of IFN-γ in spleens from mice immunized with recombinant measles virus expressing SARS-CoV-2 codon-optimized spike protein. Splenocytes prepared from $rMV^{EZ}$, $rMV^{EZ}$SARS-CoV-2-CO, $rMV^{EZ}$SARS-CoV-2-S6, and $rMV^{EZ}$SARS-CoV-2-COAA immunized mice were used in an ELISPOT assay to detect the secretion of proinflammatory cytokine IFN-γ. Mice splenocytes were re-stimulated for 24 hours with four pools of synthetic peptides (S1, S2, S3 and S4) designed to span the entire SARS-CoV-2 spike protein. Unstimulated splenocytes (medium) served as negative controls and splenocytes treated with PMA/ionomycin confirmed splenocyte re-stimulation. Dots represent individual animals (n=5) for each vaccinated group. The number of cells expressing IFN-γ after re-stimulation are represented as $1\times10^5$ cells.

Splenocytes prepared from rMV$^{EZ}$, rMV$^{EZ}$SARS-CoV-2-CO, rMV$^{EZ}$SARS-CoV-2-S6, and rMV$^{EZ}$SARS-CoV-2-COAA immunized mice were used in an ELISPOT assay to detect the secretion of proinflammatory cytokine IFN-γ. Mice splenocytes were re-stimulated for 24 hours with four pools of synthetic peptides (51, S2, S3 and S4) designed to span the entire SARS-CoV-2 spike protein. Unstimulated splenocytes (medium) served as negative controls and splenocytes treated with PMA/ionomycin confirmed splenocyte re-stimulation. The number of cells expressing IFN-γ after re-stimulation are represented as $1\times10^5$ cells in FIG. 12. The results demonstrate that IFN-γ is secreted in spleens from mice immunized with recombinant measles virus expressing SARS-CoV-2 codon-optimized spike protein.

Figure 13A:
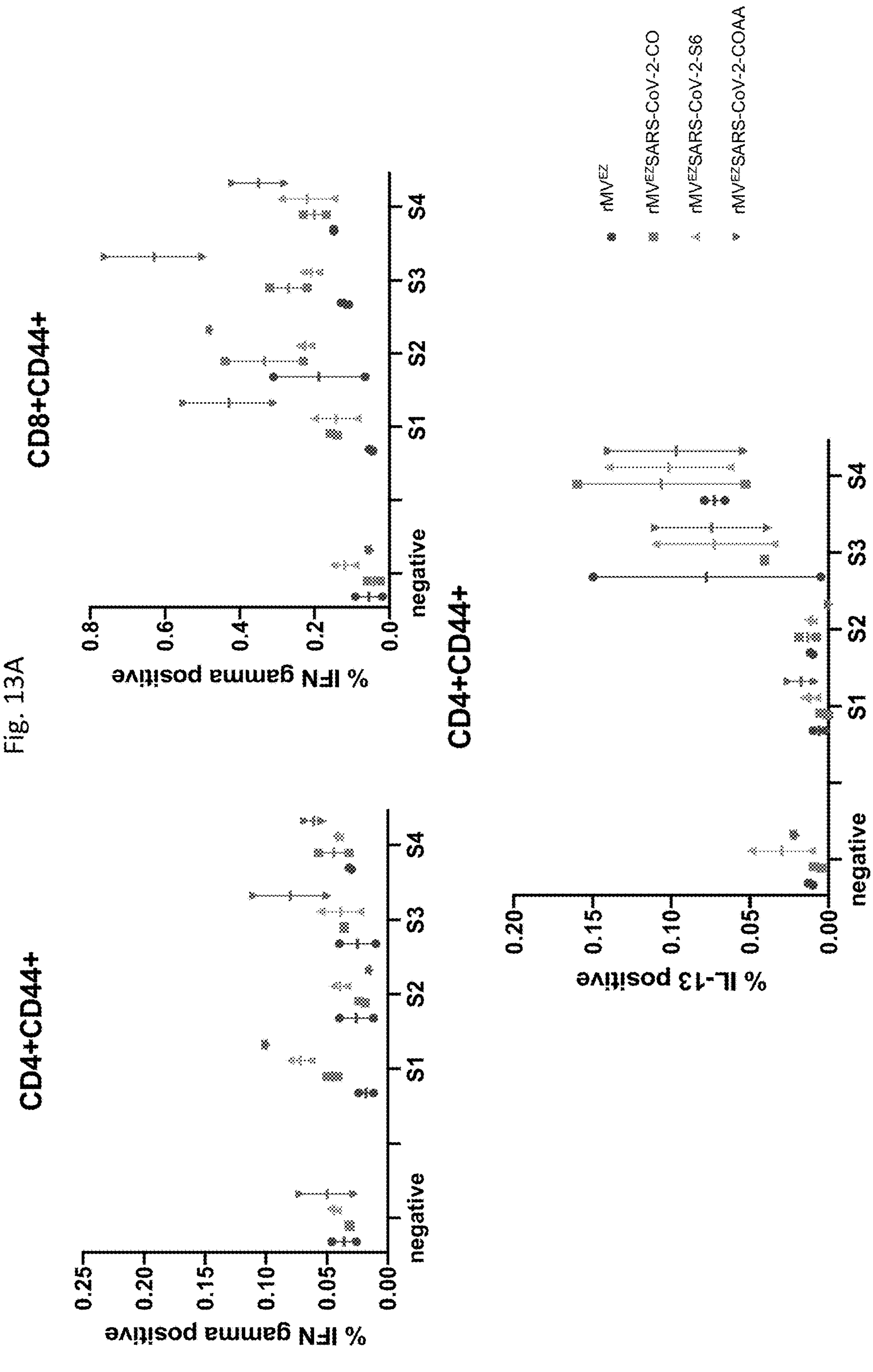
FIGS. 13A and 13B demonstrate the T cell responses in immunized mice. Flow cytometry was used to determine the proportion of $CD4^+/CD44^+$ and $CD8^+/CD44^+$ T cells in the spleens of mice immunized with $rMV^{EZ}$, $rMV^{EZ}$SARS-CoV-2-CO, $rMV^{EZ}$SARS-CoV-2-S6, and $rMV^{EZ}$SARS-CoV-2-COAA. To determine the optimal re-stimulation period splenocytes from two mice from each immunized group were first re-stimulated for 6 hours (FIG. 13A) while the remaining three mice spleens were re-stimulated for 12-hours (FIG. 13B). Cells were re-stimulated with spike specific peptide pools S1, S2, S3 and S4, or left unstimulated (negative control; medium). Re-stimulation was confirmed with a cell activation cocktail containing PMA/ionomycin and brefaldin-A. Intracellular cytokine staining for IFN-γ and IL-13 were then carried out to determine Th1 and Th2 responses, respectively. Dots represent individual animals.
Figure 13B:
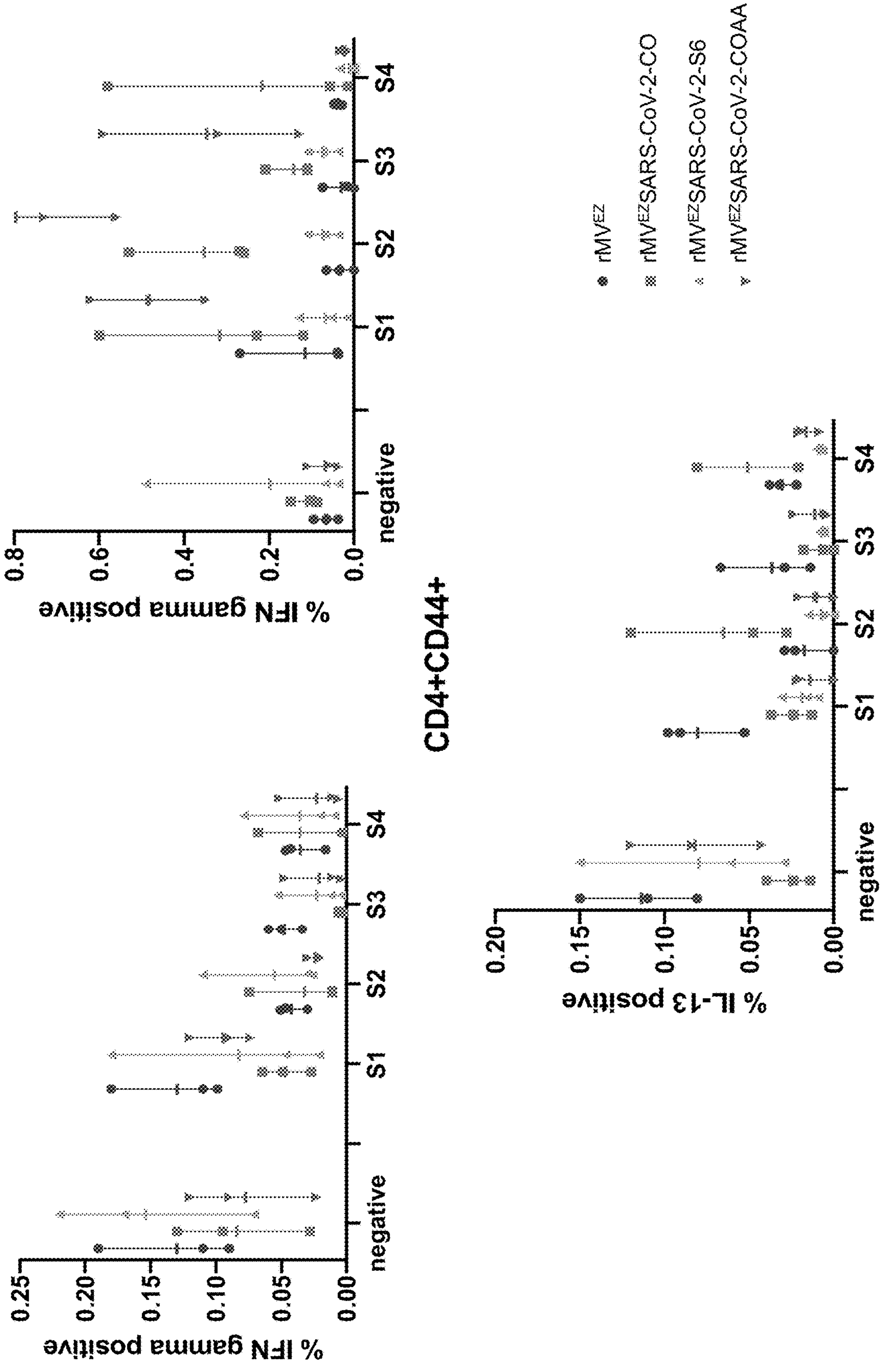

Flow cytometry was used to determine the proportion of $CD4^+/CD44^+$ and CD8+/CD44+ T cells in the spleens of mice immunized with rMV$^{EZ}$, rMV$^{EZ}$SARS-CoV-2-CO, rMV$^{EZ}$SARS-CoV-2-S6, and rMV$^{EZ}$SARS-CoV-2-COAA. To determine the optimal re-stimulation period splenocytes from two mice from each immunized group were first re-stimulated for 6 hours (FIG. 13A) while the remaining three mice spleens were re-stimulated for 12-hours (FIG. 13B). Cells were re-stimulated with spike specific peptide pools S1, S2, S3 and S4, or left unstimulated (negative control; medium). Re-stimulation was confirmed with a cell activation cocktail containing PMA/ionomycin and Brefaldin-A. Intracellular cytokine staining for IFN-γ and IL-13 were then carried out to determine Th1 and Th2 responses, respectively. The results in FIGS. 13A and 13B demonstrate the T cell responses in immunized mice.

Non-Human Primates

Multi-route delivery and challenge testing for natural measles is described in de Swart et al., *NPJ vaccines,* 2(1), pp. 1-11 (2017). Specifically, infection of rhesus macaques with rMV$^{EZ}$EGFP(3) vaccine via the intramuscular, intranasal, and aerosol routes, along with the intratracheal route as a control matching the usual experimental inoculation route, has been described. Serum antibody responses were detected by enzyme linked immunosorbent assay (ELISA), virus neutralization, or indirect immunofluorescence for MV fusion (MV-F) or hemagglutinin (MV-H) glycoprotein-specific antibodies. Animals vaccinated by the intramuscular (IM) route produced similar antibody responses to those inoculated via the aerosol route. In all assays, lowest serum antibody levels were consistently observed in animals immunized by intranasal instillation. All animals were protected from challenge after intratracheal instillation of a wild-type strain of MV.

For this study, African green monkeys (AGMs) were used since a SARS-CoV-2 challenge model has been established (Hartman et al., doi: https://doi.org/10.1101/2020.06.20.137687 (2020)—in press *PLoS Pathogens*). In this challenge model, AGMs were inoculated via a multi-route mucosal (oral, nasal, and ocular) exposure with a low passage, clinical isolate of SARS-CoV-2. The experimental design is detailed in FIGS. 11A and 11B.

All AGMs develop mild disease with pulmonary lesions detectable by PET/CT in the acute phase which subsequently resolve. All AGMs exhibit prolonged shedding of infectious virus from oral, nasal, conjunctival, and rectal mucosal surfaces with viral RNA (vRNA) detectable throughout the respiratory and gastrointestinal tissues at later timepoints in the absence of replication-competent virus.

Animals (maximum group size n=6) were vaccinated (IM) with the recombinant measles viral vector of the invention. Two animals were vaccinated with the standard measles virus Edmonston Zagreb vaccine strain. Some animals received a boost at 3 or 4 weeks post-vaccination. Animals were sampled before vaccination and then weekly over 6 or 8 weeks for the development of SARS-CoV-2 and MV serum antibody responses (IgG, IgM, IgA and neutralizing antibodies and T cell responses).

Development of MV-specific immune response will be compared to historical controls using banked samples from the studies analyzing intramuscular, aerosol, intranasal, and intratracheal administration of MV vaccine (de Swart et al., *NPJ vaccines,* 2(1), pp. 1-11 (2017)). EDTA blood samples will be collected in Vacuette tubes containing $K_3EDTA$ as an anticoagulant. A sample of whole blood will be used directly for hematology analysis. Plasma will be separated from blood cells by low speed centrifugation and used in a commercial ELISA classic Measles Virus IgG assay (Serion) to assess anti-MV IgG alongside an in house MV-N-specific IgG ELISA.

Development of anti SARS-CoV-2 specific IgG and IgM will be determined using an in house ELISA that detects antibodies against the SARS-CoV-2 spike protein receptor binding domain (RBD). ELISA plates will be coated with 50 ng/well of SARS-CoV-2 RBD and subsequently blocked in 5% (V/V) FBS, 5% (W/V) skim milk in PBS with 0.1% (V/V) Tween-20 (PBS T) for 1 hour at 37° C. Serial dilutions of plasma will be made in block solution and incubated on the blocked plates for 2 h at 37° C. After washing with PBS T, bound antibodies will be detected by incubation with goat-anti-monkey IgM(μ)-HRP (Seracare/KPL #5220-0334) or goat-anti-rhesus IgG (H+L)-HRP (Southern Biotech #6200-05), both used at a 1:5,000 dilution in blocking solution for 1 hour at 37° C. After washing with PBS T the assay will be developed by incubation with TMB (Seracare) for 7 min prior to the addition of TMB stop solution (Seracare). Absorbance values will be determined at 450 nm.

PBMC are isolated from the residual blood cell pellet by layering diluted whole blood onto Lymphoprep and subsequent density gradient centrifugation. A sample of PBMC will be used for MV virus isolation by plating dilutions of PBMC with Vero cells expressing human CD150 (Vero hCD150 cells). Assays are incubated at 37° C. for 3-5 days and then scored for cytopathic effect. A portion of PBMC will also be used for RNA extraction and subsequent RT/PCR analysis for detection of viral genome.

Figures 11A, 11B:
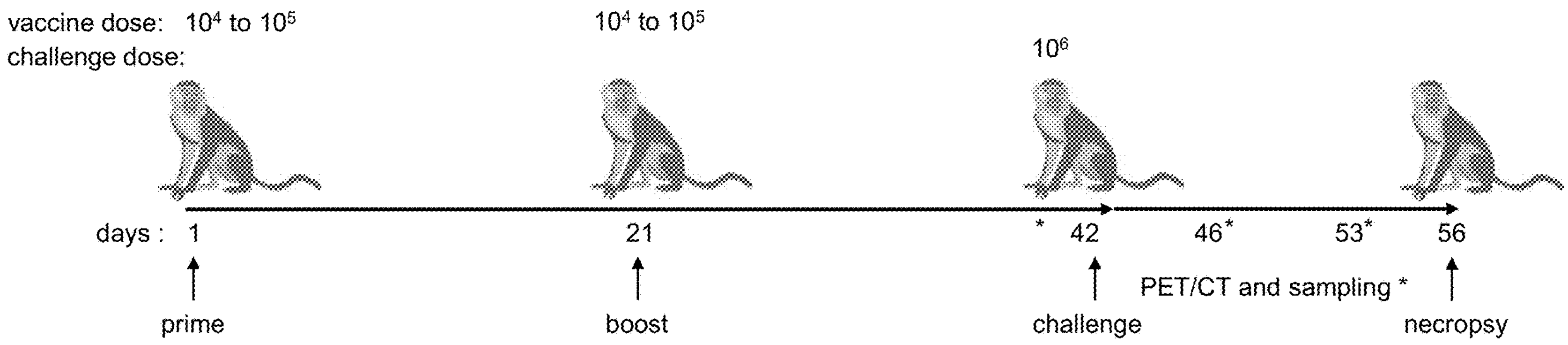
FIGS. 11A-B demonstrates an experimental set-up for non-human primates vaccinated (prime and/or boost) with any of the candidates.

Blood samples for serum will be collected in Vacuette tubes (FIG. 11B). After coagulation, low speed centrifugation will be used to remove the clot from the serum supernatant. A sample will be used for serum biochemistry and the rest will be available for neutralizing antibody analysis. Virus neutralizing antibodies will be detected using a fluorescent focus reduction neutralization test (FRNT) for MV and a plaque reduction neutralization test (PRNT) for SARS-CoV-2. The FRNT uses a MV that expresses EGFP during replication; this facilitates rapid screening of assays. Detection of fluorescence indicates virus replication and seronegativity while lack of fluorescence indicates the presence of neutralizing antibodies which prevent virus infection. Serum dilutions will be mixed with 100 plaque forming units (plu.) of MV and incubated at 37° C. for 1 hour. After addition of Vero cells expressing the MV receptor human CD150, assays will be incubated at 37° C. for 3-5 days before screening for fluorescence as a measure of virus replication. For the PRNT, serum dilutions will be mixed with 100 p.f.u. of SARS-CoV-2 and incubated at 37° C. for 1 hour after which they will be added to confluent Vero E6 cell monolayers. After incubation at 37° C. for 1 hour, medium will be replaced by immunodiffusion agarose. After incubation at 37° C. for 72 hours, the agarose overlay will be removed and the cell monolayer fixed and stained with crystal violet. Plaques will be enumerated and the $PRNT_{80}$ calculated. The SARS-CoV-2 molecular, virological and immunological assays are described in Klimstra et al., *J. Gen. Virol*., doi: 10.1099/jgv.0.001481 (2020).

The vaccinated and sham vaccinated animals will be challenged via multi route mucosal exposure with $10^6$ plu. of SARS-CoV-2. Protection will be assessed by sampling oral, ocular, rectal and nasal swabs for decreases in infectious virus and viral RNA copies following challenge, decreased PET/CT signals in lungs and lymph nodes and secondary immune responses. Brushes will be used to collect throat and rectal samples and swabs will be used to collect nasal and ocular samples into virus transport medium. After vortexing the brush/swab is removed and the remaining liquid is used directly for SARS-CoV-2 virus isolation by adding to VeroE6 cell monolayers, and for RNA isolation for RTqPCR analysis. For virus isolations, after incubation at 37° C. for 1 hour, medium will be replaced by immunodiffusion agarose. After incubation at 37° C. for 72 hours, the agarose overlay will be removed and the cell monolayer fixed and stained with crystal violet to allow visualization of plaques. After RNA isolation, one-step RT-qPCR will be performed using a One-Step Multiplex RT-qPCR Supermix (BioRad), and primers and probe targeting the SARS-CoV-2 N gene sequence. Quantitation of virus genome copies will be determined by comparing the cycle threshold values from the unknown samples to cycle threshold values from a positive-sense SARS-CoV-2 vRNA standard curve generated from 10-fold serial dilutions of in house synthesized template.

Serial PET/CT images will be acquired pre-infection and at 3 or 4 and 10 or 11 dpi. The scans will be performed on a MultiScan LFER 150 (Mediso Medical Imaging Systems). CT acquisition will be performed using the following parameters: Semi-circular single field-of-view, 360 projections, 80 kVp, 670 μA, exposure time 90 ms, binning 1:4, voxel size of final image: 500×500 μm. PET acquisition will be performed 55 min after intravenous injection of 18F-fluoro-2-deoxy-D-glucose (FDG) with the following parameters: 10 min acquisition, single field-of-view, 1-9 coincidence mode, 5 ns coincidence time window. PET images will be reconstructed with the following parameters: Tera-Tomo 3D reconstruction, 400-600 keV energy window, 1-9 coincidence mode, median filter on, spike filter on, voxel size 0.7 mm, 8 iterations, 9 subsets, scatter correction on, attenuation correction based on CT material map segmentation. Images will be analyzed using OsiriX MD or 64-bit (v.11, Pixmeo, Geneva, Switzerland). Before analysis, PET images will be Gaussian smoothed in OsiriX and smoothing will be applied to raw data with a 3×3 matrix size and a matrix normalization value of 24. Whole lung FDG uptake will be measured by first creating a whole lung region-of-interest (ROI) on the lung in the CT scan by creating a 3D growing region highlighting every voxel in the lungs between −1024 and −500 Hounsfield units. This whole lung ROI will be copied and pasted to the PET scan and gaps within the ROI will be filled in using a closing ROI brush tool with a structuring element radius of 3. All voxels within the lung ROI with a standard uptake value (SUV) below 1.5 will be set to zero and the SUVs of the remaining voxels will be summed for a total lung FDG uptake (total inflammation) value. Thoracic lymph nodes will be analyzed by measuring the maximum SUV within each lymph node using an oval drawing tool. Both total FDG uptake and lymph node uptake values will be normalized to back muscle FDG uptake measured by drawing cylinder ROIs on the back muscles adjacent to the spine at the same axial level as the carina (SUVCMR; cylinder-muscle-ratio). PET quantification values will be organized in Microsoft Excel and graphed using GraphPad Prism.

Blood samples will be collected and processed as for the vaccination phase of the study and the secondary immune response to SARS-CoV-2 will be measured as before using the SARS-CoV-2 spike protein receptor binding domain ELISA for detection of IgG and IgM, and the PRNT for detection of neutralizing antibodies and the T cells assays already established in the IFNAR mice (FIGS. 13A and 13B) to assess cellular immune responses.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A recombinant measles viral vector comprising a nucleic acid sequence encoding a Severe Acute Respiratory Syndrome Coronavirus 2 (SARS-CoV-2) spike glycoprotein, wherein the nucleic acid sequence contains at least one modification that disrupts the endoplasmic reticulum (ER) retention sequence of the SARS-CoV-2 spike glycoprotein.

2. The recombinant measles viral vector of claim 1, wherein the ER retention sequence of the SARS-CoV-2 spike glycoprotein contains AxAxx rather than KxHxx in the cytoplasmic tail.

3. The recombinant measles viral vector of claim 1, wherein the nucleic acid sequence encoding the SARS-CoV-2 spike glycoprotein is SEQ ID NO: 3 (S-CO-AA).

4. The recombinant measles viral vector of claim 1, wherein the amino acid sequence of the SARS-CoV-2 spike glycoprotein is SEQ ID NO: 10 (S-CO-AA).

5. The recombinant measles viral vector of claim 1, comprising the nucleic acid sequence of SEQ ID NO: 17 (SARS-CoV-2-S-CO-AA).

6. A pharmaceutical composition comprising the recombinant measles viral vector of claim 1 and a pharmaceutically acceptable carrier.

7. A nucleic acid encoding a polypeptide comprising the amino acid sequence of SEQ ID NO: 10 (S-CO-AA).

8. A nucleic acid comprising the nucleic acid sequence of SEQ ID NO: 3 (S-CO-AA).

9. A recombinant vector comprising the nucleic acid of claim 7.

10. A pharmaceutical composition comprising (i) the nucleic acid of claim 7 and (ii) a pharmaceutically acceptable carrier.

* * * * *

UNITED STATES PATENT AND TRADEMARK OFFICE
CERTIFICATE OF CORRECTION

| | |
|---|---|
| PATENT NO. | : 11,103,576 B1 |
| APPLICATION NO. | : 17/010591 |
| DATED | : August 31, 2021 |
| INVENTOR(S) | : William Paul Duprex |

It is certified that error appears in the above-identified patent and that said Letters Patent is hereby corrected as shown below:

On the Title Page

Item (12), should read:
William Paul Duprex et al.

Item (72) Inventors, please add the following inventors:
Natasha Louise Tilston-Lunel, Pittsburgh, PA (US)
Shamkumar Nambulli, Bridgeville, PA (US)

Signed and Sealed this
Sixth Day of September, 2022

*Katherine Kelly Vidal*

Katherine Kelly Vidal
*Director of the United States Patent and Trademark Office*